US008129504B2

(12) United States Patent
Prior et al.

(10) Patent No.: US 8,129,504 B2
(45) Date of Patent: Mar. 6, 2012

(54) ORAL DELIVERY OF MODIFIED TRANSFERRIN FUSION PROTEINS

(75) Inventors: Christopher P. Prior, King of Prussia, PA (US); Homayoun Sadeghi, King of Prussia, PA (US); Andrew Turner, King of Prussia, PA (US)

(73) Assignee: Biorexis Technology, Inc., Wilmington, DE (US)

( * ) Notice: Subject to any disclaimer, the term of this patent is extended or adjusted under 35 U.S.C. 154(b) by 1747 days.

(21) Appl. No.: 10/515,232

(22) PCT Filed: Aug. 28, 2003

(86) PCT No.: PCT/US03/26778
§ 371 (c)(1),
(2), (4) Date: Feb. 22, 2006

(87) PCT Pub. No.: WO2004/019872
PCT Pub. Date: Mar. 11, 2004

(65) Prior Publication Data
US 2011/0091543 A1    Apr. 21, 2011

Related U.S. Application Data

(60) Provisional application No. 60/406,977, filed on Aug. 30, 2002, provisional application No. 60/460,829, filed on Apr. 8, 2003.

(51) Int. Cl.
*A61K 38/40* (2006.01)
*A61K 38/00* (2006.01)

(52) U.S. Cl. ............... 530/387.3; 530/394; 530/530; 424/1.69

(58) Field of Classification Search .......... None
See application file for complete search history.

(56) References Cited

U.S. PATENT DOCUMENTS

| | | | |
|---|---|---|---|
| 4,289,689 A | 9/1981 | Friesen et al. ............ 530/351 |
| 4,738,931 A | 4/1988 | Sugano et al. ............ 435/320.1 |
| 4,816,449 A | 3/1989 | Hahn ............ 514/17 |
| 5,026,651 A | 6/1991 | Bowman et al. ............ 435/320.1 |
| 5,091,513 A | 2/1992 | Huston et al. ............ 530/387.3 |
| 5,262,177 A | 11/1993 | Brown et al. ............ 435/35.1 |
| 5,292,869 A * | 3/1994 | Schryvers ............ 530/413 |
| 5,336,603 A * | 8/1994 | Capon et al. ............ 435/69.7 |
| 5,432,018 A | 7/1995 | Dower et al. |
| 5,442,043 A | 8/1995 | Fukuta et al. ............ 530/303 |
| 5,455,030 A | 10/1995 | Ladner et al. ............ 424/135.1 |
| 5,464,933 A | 11/1995 | Bolognesi et al. ............ 530/324 |
| 5,518,889 A | 5/1996 | Ladner et al. ............ 435/7.93 |
| 5,571,691 A | 11/1996 | Conneely et al. ............ 435/69.1 |
| 5,571,896 A | 11/1996 | Conneely et al. ............ 530/400 |
| 5,656,272 A | 8/1997 | Le et al. ............ 424/133.1 |
| 5,672,683 A | 9/1997 | Friden et al. ............ 530/350 |
| 5,817,780 A * | 10/1998 | Fleche et al. ............ 536/18.6 |
| 5,817,789 A | 10/1998 | Heartlein et al. ............ 536/23.4 |
| 5,876,969 A | 3/1999 | Fleer et al. ............ 435/69.7 |
| 5,948,613 A | 9/1999 | Teng et al. ............ 435/6 |
| 5,977,307 A | 11/1999 | Friden et al. ............ 530/350 |
| 5,986,067 A * | 11/1999 | Funk et al. ............ 530/394 |
| 6,027,921 A | 2/2000 | Heartlein et al. ............ 435/69.7 |
| 6,066,469 A | 5/2000 | Kruzel et al. ............ 435/69.1 |
| 6,069,193 A | 5/2000 | Vargas et al. |
| 6,245,737 B1 | 6/2001 | Boyd et al. ............ 514/2 |
| 6,262,026 B1 | 7/2001 | Heartlein et al. ............ 514/12 |
| 6,277,817 B1 | 8/2001 | Kruzel et al. ............ 514/8 |
| 6,329,336 B1 | 12/2001 | Bridon et al. |
| 6,348,568 B1 | 2/2002 | Barney et al. ............ 530/300 |
| 6,355,270 B1 * | 3/2002 | Ferrari et al. ............ 424/489 |
| 6,380,362 B1 | 4/2002 | Watson et al. ............ 530/350 |
| 6,420,346 B1 | 7/2002 | Karin ............ 514/44 |
| 6,455,494 B1 * | 9/2002 | Jefferies et al. ............ 424/85.1 |
| 6,455,687 B1 | 9/2002 | Kruzel et al. ............ 536/23.5 |
| 6,458,924 B2 | 10/2002 | Knudsen et al. |
| 7,094,577 B2 * | 8/2006 | Fleer et al. ............ 435/69.7 |
| 2001/0025026 A1 | 9/2001 | Heartlein et al. ............ 514/12 |
| 2002/0019350 A1 * | 2/2002 | Levine et al. ............ 514/12 |
| 2002/0034805 A1 * | 3/2002 | Gilbert et al. ............ 435/193 |
| 2002/0049153 A1 | 4/2002 | Bridon et al. |
| 2003/0199672 A1 | 10/2003 | Knudsen et al. |
| 2003/0221201 A1 | 11/2003 | Prior et al. ............ 800/7 |
| 2003/0226155 A1 | 12/2003 | Sadeghi et al. ............ 800/7 |
| 2004/0023334 A1 | 2/2004 | Prior ............ 435/69.7 |
| 2006/0105387 A1 | 5/2006 | Prior et al. |
| 2006/0130158 A1 | 6/2006 | Turner et al. |
| 2006/0205037 A1 | 9/2006 | Sadeghi et al. |
| 2008/0020942 A1 * | 1/2008 | Raines et al. ............ 506/18 |

FOREIGN PATENT DOCUMENTS

| | | |
|---|---|---|
| EP | 0314317 A1 | 5/1989 |
| EP | 0413622 A2 | 2/1991 |
| EP | 0978565 A1 | 2/2000 |
| EP | 1408050 A1 | 4/2004 |
| WO | WO 91/09967 A1 | 7/1991 |
| WO | WO 95/02421 A1 | 1/1995 |
| WO | WO 99/43707 A1 | 9/1999 |

(Continued)

OTHER PUBLICATIONS

Mason et al., 1993, Biochemistry, 32: 5472-5479.*
Ali et al. (1999) Transferrin trojan horses as a rational approach for the biological delivery of therapeutic peptide domains, J. Biol. Chem., vol. 274, No. 34, pp. 24066-24073.*
Lin et al. (1993) Calorimetric studies of the N-terminal half-molecule of transferrin and mutant forms modified near the Fe(3+)-binding site, Biochem. J., 293, 517-522L.*
Lin et al. (1993) Calorimetric studies of the N-terminal half-molecule of transferrin and mutant forms modified near the Fe(3+)-binding site, Biochem. J., vol. 293, Pa.2, pp. 517-522.*

(Continued)

*Primary Examiner* — Anand Desai
*Assistant Examiner* — Samuel Liu
(74) *Attorney, Agent, or Firm* — Pfizer Inc.

(57) ABSTRACT

Pharmaceutical compositions containing modified fusion proteins of transferrin and therapeutic proteins or peptides with increased serum half-life or increased serum stability are disclosed. Preferred fusion proteins include those modified so that the transferrin moiety exhibits no or reduced glycosylation, but does exhibit binding to iron and/or the transferrin receptor. Such fusion proteins may be administered orally.

2 Claims, 6 Drawing Sheets

FOREIGN PATENT DOCUMENTS

| WO | WO 99/46283 A1 | 9/1999 |
|---|---|---|
| WO | WO 01/04156 A1 | 1/2001 |
| WO | WO 01/36643 A1 | 5/2001 |
| WO | WO 01/46254 | 6/2001 |
| WO | WO 01/79258 | 10/2001 |
| WO | WO 02/46227 | 6/2002 |
| WO | WO 03/016349 A1 | 2/2003 |
| WO | WO 03/20746 | 3/2003 |
| WO | WO 03/082898 | 10/2003 |
| WO | WO 2004/019872 | 3/2004 |
| WO | WO 2004/020404 | 3/2004 |
| WO | WO 2004/020405 | 3/2004 |
| WO | WO 2004/020454 | 3/2004 |
| WO | WO 2004/020588 | 3/2004 |
| WO | WO 2004/078777 | 9/2004 |
| WO | WO 2005/021579 | 3/2005 |
| WO | WO 2006/017688 | 2/2006 |
| WO | WO 2006/049983 | 5/2006 |
| WO | WO 2006/096515 | 9/2006 |

OTHER PUBLICATIONS

MacGillivray et al. (1983) The primary structure of human serum transferrin. The structures of seven cyanogen bromide fragments and the assembly of the complete structure, J, Biol, Chem., vol. 258, No. 6, pp. 3543-3553.*

Xia et al. (2000) Hypoglycemic effect of insulin-transferrin conjugate in streptozotocin-induced diabetic rats, J. Pharmacol. Exp. Ther., vol. 295, No. 2, pp. 594-600.*

Baker et al. (2003 Structural and functional consequences of binding site mutations in transferrin: crystal structures of the Asp63Glu and Arg124Ala mutants of the N-lobe of human transferrin, Biochemistry, vol. 42, No. 23, pp. 7084-7089.*

Mason et al. (1993) Expression of glycosylated and nonglycosylated human transferrin in mammalian cells. Characterization of the recombinant proteins with comparison to three commercially available transferrs, Biochemistry, vol. 32, No. 20, pp. 5472-5479.*

Adelhorst et al., "Structure-Activity Studies of Glucagon-like Peptide-1," *J. Biol. Chem.* 269(9):6275-6278 (1994).

Amit et al., "Three-Dimensional Structure of an Antigen-Antibody Complex at 2.8 Å Resolution," *Science* 233:747-753 (1986).

Bowie et al., "Deciphering the Message in Protein Sequences: Tolerance to Amino Acid Substitutions," *Science* 247:1306-1310 (1990).

Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," *J. Cell. Biol.* 111:2129-2138 (1990).

Carlson, "International Search Report," from PCT/US05/38531, 2 pages (mailed Oct. 19, 2006).

Duksin and Mahoney, "Relationship of the Structure and Biological Activity of the Natural Homologues of Tunicamycin," *J. Biol. Chem.* 257:3105-3109 (1982).

Eigler et al., "Taming TNF: strategies to restrain this proinflammatory cytokine," *Immunol. Today* 18:487-492 (1997).

Holliger et al., "'Diabodies': Small bivalent and bispecific antibody fragments," *Proc. Natl. Acad. Sci. USA* 90:6444-6448 (1993).

Johnson, D.L., and L.K. Jolliffe, "Erythropoietin mimetic peptides and the future," *Nephrol. Dial. Transplant* 15:1274-1277 (2000).

Kawai et al., "The Biological Effects of Glucagon-Like Peptide-1 (GLP-1) and its Structure-Activity Relationship," *Biomed. Res.* 9(Suppl. 3):213-217 (1988).

Kieffer et al., "Degradation of Glucose-Dependent Insulinotropic Polypeptide and Truncated Glucagon-Like Peptide 1 in Vitro and in Vivo by Dipeptidyl Peptidase IV," *Endocrinology* 136(8):3585-3596 (1995).

Knudsen et al., "Potent Derivatives of Glucagon-like Peptide-1 with Pharmacokinetic Properties Suitable for Once Daily Administration," *J. Med. Chem.* 43:1664-1669 (2000).

Lazar et al., "Transforming Growth Factor α: Mutation of Aspartic Acid 47 and Leucine 48 Results in Different Biological Activities," *Mol. Cell. Biol.* 8:1247-1252 (1988).

Li, Hongyan and Qian, Zhong Ming, "Transferrin/Transferrin Receptor-Mediated Drug Delivery," *Medicinal Research Reviews.* 22(3):225-250 (2002).

Liu, "International Search Report," from PCT/US04/06462, 7 pages (mailed Nov. 15, 2005).

Liu, "International Search Report," from PCT/US06/07617, 6 pages (mailed Sep. 20, 2006).

Liu, "PCT Written Opinion," from PCT/US03/26818 (mailed Oct. 19, 2006).

Livnah, O., et al., "Functional Mimicry of a Protein hormone by a Peptide Agonist: The EPO Receptor Complex at 2.8 Å," *Science* 273:464-471 (1996).

Mayer, S.Z., "International Search Report," 5 pages, from International Patent Application No. PCT/US04/27949, United States Patent and Trademark Office, Alexandria, Virginia USA (mailed Jun. 8, 2005).

Mojsov, "Structural requirements for biological activity of glucagon-like peptide-I," *Int'l. J. Pept. Prot. Res.* 40(3/4):333-343 (1992).

Mossier, "Partial European Search Report," from EP 03791808.3, 6 pages, European Patent Office, Munich, Germany (mailed Apr. 18, 2006).

Mossier, "Supplementary Partial European Search Report," from EP 04717362.0, 12 pages, European Patent Office, Munich, Germany (mailed Aug. 8, 2006).

Ngo et al., "Computational Complexity, Protein Structure Prediction, and the Levinthal Paradox," in *The Protein Folding Problem and Tertiary Structure Prediction*, Merz, Jr. and Le Grand, Eds. Birkhauser, Boston, Mass., USA, pp. 433, and 492-495 (1994).

Ohneda et al., "The Structure-Function Relationship of GLP-1 Related Peptides in the Endocrine Function of Canine Pancreas," *Tohoku J. Exp. Med.* 165:209-221 (1991).

Panka et al., "Variable region framework differences result in decreased or increased affinity of variant anti-digoxin antibodies," *Proc. Natl. Acad. Sci. USA* 85:3080-3084 (1982).

Parise, F., et al., "Construction and in Vitro Functional Evaluation of a Low-Density Lipoprotein Receptor/Transferrin Fusion Protein as a Therapeutic Tool for Familial Hypercholesterolemia," *Human Gene Therapy* 10:1219-1228 (1999).

Parker et al., "Agonist internalization by cloned Y1 neuropeptide Y (NPY) receptor in Chinese hamster ovary cells shows strong preference for NPY, endosome-linked entry and fast receptor recycling," *Reg. Peptides* 107:49-62 (2002).

Qureshi, S.A., et al., "Mimicry of erythropoietin by a nonpeptide molecule," *Proc. Natl. Acad. Sci. USA* 96:12156-12161 (1999).

Rudikoff et al., "Single amino acid substitution altering antigen-binding specificity," *Proc. Natl. Acad. Sci. USA* 79:1979-1983 (1982).

Seffernick et al., "Melamine Deaminase and Atrazine Chlorohydrase: 98% Identical but Functionally Different," *J. Bacteriol.* 183:2405-2410 (2001).

Skolnick and Fetrow, "From genes to protein structure and function: novel applications of computational approaches in the genomic era," *TIBTECH* 18:34-39 (2000).

Sommer, B., "Supplementary Partial European Search Report," from EP 03749159.4, 4 pages, European Patent Office, Munich, Germany (mailed May 30, 2006).

Vogt, "Communication pursuant to Article 96(2) EPC," from EP 02757486.2, 7 pages, European Patent Office, Munich, Germany (mailed Jun. 1, 2006).

Vogt, "Supplementary European Search Report," from EP 02757486.2, 2 pages, European Patent Office, Munich, Germany (mailed Dec. 6, 2005).

Wagner et al., "Delivery of drugs, proteins and genes into cells using transferrin as a ligand for receptor-mediated endocytosis," *Adv. Drug. Deliv. Rev.* 14:113-135 (1994).

Wells, "Additivity of Mutational Effects in Proteins," *Biochemistry* 29:8509-8517 (1990).

Aldred et al., "Synthesis of rat transferrin in *Escherichia coli* containing a recombinant bacteriophage," *Biochem. Biophys. Res. Commun.* 122:960-965, 1984.

Ah et al., "High-yield production of functionally active human serum transferrin using a baculovirus expression system, and its structural characterization," *Biochem. J.* 319:191-195, 1996.

Deacon et al., "Dipeptidyl peptidase IV resistant analogues of glucagon-like peptide-1 which have extended metabolic stability and improved biological activity," *Diabetologia* 41:271-278, 1998.

Hoefkens et al., "influence of transferrin glycans on receptor binding and iron-donation," *Glycoconjugate J.* 14:289-295, 1997.

O'Harte et al., "NH$_2$-Terminally Modified Gastric Inhibitory Polypeptide Exhibits Amino-Peptidase Resistance and Enhanced Antihyperglycemic Activity," *Diabetes* 48:758-765, 1999.

Pedersen et al., "Removal of N-terminal Polyhjistidine Tags from recombinant Proteins Using Engineered Aminopeptidases," *Protein Express. Purif.* 15:389-400, 1999.

Siegel et al., "Biological activity of GLP-1-analogues with N-terminal modifications," *Regulatory Peptides* 79:93-102, 1999.

Xiao et al., "Biological Activities of Glucagon-Like Peptide-1 Analogues in Vitro and in Vivo," *Biochemistry* 40:2860-2869, 2001.

Zhao et al., "Inhibition of Dipeptidyl Peptidase IV (DPP IV) by 2-(2-Amino-1-fluoro-propylidene)-cyclopentanecarbonitrile, a Fluoroolefin Containing Peptidomimetic,"*Bioorg. Med. Chem.* 11:207-215, 2003.

Adrian et al. "Human transferrin: Expression and iron modulation of chimeric genes intransgenic mice" J. Biol. Chem. 265(22): 13344-13350, 1990.

Ali et al., "Transferrin Trojan Horses as a Rational Approach for the Biological Delivery of Therapeutic Peptide Domains," J Biol Chem 274(34):24066-24073, 1999.

Arndt, T., "Carbohydrate-Deficient Transferrin as a Marker of Chronic Alcohol Abuse: A Critical Review of Preanalysis, Analysis, and Interpretation," Clinical Chemistry, 47:13-27, 2001.

Batra et al., "Single Chain Immunotoxins Directed at the Human Transferrin Receptor Containing Pseudomonas Exotoxin A or Diphtheria Toxin: Anti-TFR(Fv)-PE40 and DT 388-Anti-TFR(Fv)", Mol. Cell. Biol., 11:2200-2205, 1991.

Batra et al., "Recombinant anti-erbB2 immunotoxins containing Pseudomonas exotoxin", Proc. Nat. Acad. Sci. USA, vol. 89, pp. 5867-5871, Jul. 1992.

Bradley et al., "Anthrax toxin receptor proteins," Biochemical Pharmacology 65:309-314, 2003.

Bradley et al., "Identification of the cellular receptor for anthrax toxin," Nature 414:225-229, 2001.

Brinkman et al., "A recombinant immunotoxiin that is active on prostate cancer cells and that is composed of the Fv region of monoclonal antibody PR1 and a truncated form of Pseudomonas exotoxin", Proc. Natl. Sci. Acad. Sci. USA, vol. 90, pp. 547-551, Jan. 1993.

Cha et al., "Receptor-based antidote for diphtheria," Infection and Immunity 70(5):2344-2350, 2002.

Chaudhary et al., "A recombinant immunotoxin consisting of two antibody variable domains fused to Pseudomonas exotoxin", Nature, 339:394-397, 1989.

Database A GENESEQ (Compugen LTD), Accession No. AAR66492, (Jacobs et al), Nov. 25, 1994.

Drucker, "Biological actions and therapeutic potential of the glucagon-like peptides," Gastroenterology 122:531-544, 2002.

Gallop et al. "Applications of combinatorial technologies to drug discovery. 1. Background and peptide combinatorial libraries" J. Med. Chem. 37(9): 1234-1251, 1994.

Gallwitz B et al. "GLP-1/GIP chimeric peptides define the structural requirements for specific ligand-receptor interaction of GLP-1" Regul Pept. 63(1):17-22, 1996.

Hoo et al., "Characterization of a single-chain T-cell receptor expressed in *Escherichia coli*", Proc. Nat. Acad. Sci. USA, 89:4759-4763, 1993.

Hosoi et al., "Structural Characterization of Fibroblast Human Interferon-1," Journal of Interferon Research 8:375-384, 1988.

Huston et al., "Protein engineering of antibody binding sites: Recovery of specific activity in an anti-digoxin single-chain Fv analogue produced in *Escherichia coli*", Proc. Nat. Acad. Sci. USA; 85 (16): 5879-5883, 1988.

Johnson et al., "Identification of a 13 Amino Acid Peptide Mimetic of Erythropoietin and Description of Amino Acids Critical for the Mimetic Activity of EMP1," Biochemistry 37:3699-3710, 1998.

Kozaki et al., "Characterization of *Clostridium botulinum* type B neurotoxin associated with infant botulism in Japan," Infection and Immunity 66(10):4811-4816, 1998.

Li et al., "Isolation of synaptotagmin as a receptor for types A and E botulinum neurotoxin and analysis of their comparative binding using a new microtiter plate assay," J Natural Toxins 7(3):215-226, 1998.

Liang et al., "Production and Characterization of Monoclonal Antibodies Against Recombinant Human Tumor Necrosis, Factor/Cachetin", Biochem Biophys Res. Comm. 137:847-854, 1986.

MacGillivray et al. "The primary structure of human serum transferrin" J. Biol. Chem. 258(6): 3543-3553, 1983.

Naglich et al., "Expression Cloning of a Diphtheria Toxin Receptor: Identity with a Heparin-Binding EGF-like Growth Factor Precursor," Cell 69:1051-1061, 1993.

Newton et al., "Antitransferrin receptor antibody-RNase Fusion Protein Expressed in the Mammary Gland of transgenic mice," J. Immunological Methods 231:159-167, 1999.

Nicholls, "Characterization of Single-chain Antibody (sFv)-Toxin Fusion Proteins Produced in Vitro in Rabbit Reticulocyte Lysate", J. Biological Chem., 268: 5302-5308, 1993.

Nishiki et al., "Identification of protein receptor for *Clostridium botulinum* type B neurotoxin in rat brain synaptosomes," J Biol Chem 269(14):10498-10503, 1994.

Park et al., "Production and characterization of Fusion Proteins Containing Transferrin and Nerve Growth Factor," J Drug Targeting 6(1):53-64, 1998.

Prince et al., "Efficient Endocytosis of the Cystic Fibrosis Transmembrane Conductance Regulator Requires a Tyrosine-Based signal," J Biol Chem 274(6):3602-3609, 1999.

Regoeczi et al., "Rat Aglycotransferrin and Human Monoglycotransferrin: Production and Metabolic Properties," Archives of Biochemistry and Biophysics 268(2): 637-642, 1989.

Salmon et al. "Production of human lactoferrin in transgenic tobacco plants" Protein Expr. Purif. 13: 127-135, 1998.

Sheridan et al., "Solid-phase Synthesis and Cyclization of a Large Branched Peptide from IgG Fc with Affinity for FcRI", J. Pept. Sci, 1999, 5(12):555-562.

Shin et al., "Transferrin-Antibody Fusion Proteins are Effective in Brain Targeting," Proc Natl Acad Sci USA 92:2820-2824, 1995.

Traunecker et al., "Bispecific single chain molecules (Janusins) target cytotoxic lymphocytes on HIV infected cells", EMBO J., 10(12):3655-3659, 1991.

Ward et al. "A system for production of commercial quantities of human lactoferrin: a broad spectrum natural antibiotic" Biotechnology 13:498-503, 1995.

Wrighton et al., "Small peptides as potent mimetics of the protein hormone erythropoietin," Science 273(5274):458-464, 1996.

Xia et al., "Hypoglycemic effect of insulin-transferrin conjugate in streptozotocin-induced diabetic rats," J Pharmacology and Experimental Therapeutics 295(2);594-600, 2000.

\* cited by examiner

FIG. 1

```
N  --VPD---KTVRWCAVSEHEATKCQSFRDHMKSVIPSDGPSVACVKKASYLDCIRAIAAN
C  PEAPTDECKPVKWCALSHHERLKCDEWS------VNSVGKIECVSAETTEDCIAKIMNG
                    *                              *
N  EADAVTLDAGLVYDAYLAPNNLKPVVAEFYG----SKEDPQTFYYAVAVVKK-DSGFQMN
C  EADAMSLDGGFVYIAGKCG--LMPVLAENYNKSDNCEDTPEAGYFAVAVVKKSASDLTWD
            ‡  ‡‡‡
N  QLRGKKSCHTGLGRSAGWNIPIGLLYCDLPEPRKPLEKAVANFFSGSCAPCADGTDFPQL
C  NLKGKKSCHTAVGRTAGWNIPMGLLYNKINHCR--FD----EEFSEGCAPGSKKD--SSL
                         *
N  CQLCPGCG---CSTLN--QYFGYSGAFKCLKDGAGDVAFVKHSTIFEN-------LANK
C  CKLCMGSGLNLCEPNNKEGYYGYTGAFRCLVEKGDVAFVKHQTVPDNTGGKNPDPWAKN
                                *
N  ADRDQYELLCLDNTRKPVDEYKDCHLAQVPSHTVVARSMGGKEDLIWELLNDAQEHFGK-
C  LNEKDYELLCLDGTRKPVEEYANCHLARAPNHAVVTR--KDKEACVHKILRQQQHLFGSN
                                  ‡
N  --DKSKEFQLFSSPHGKDLLFKDSAHGFLKVPPRMDAKMYLGYEYVTAIRNLREGTC---
C  VTDCSGNFCLFRSET-KDLLFRDDTVCLAKLHDRNTYEKYLGEEYVKAVGNLRKCSTSSL

N  ---------
C  LEACTFRRP
```

☐ : similarity
▨ : identity

FIG. 2A-1
Alignment of Tf Sequences

```

Human    1  -VPDKTVRWCAVSEHEATKCQSFRDHMKSVIPSDGPSVACVKKASYLDCIRAIAANEADA   59
Rabbit   1  -VTEKTVRWCAVNDHEASKCANFRDSMKKVLPEDGPRIICVKKASYLDCIKAIAAHEADA   59
Rat      1  -VPDKTVKWCAVSEHENTKCISFRDHMKTVLPADGPRLPCVKGTSYQDCIKAISGGEADA   59
Mouse    1  -VPDKTVKWCAVSEHENTKCISFRDHMKTVLPPDGPRLACVKKTSYPDCIKAISASEADA   59
Horse    1  --AEQTVRWCTVSNHEVSKCASFRLSVKSIVPA-PLVACVKRTSYLECIKAIADNEADA   57
Bovine   1  -DPERTVRWCTISTHEANKCASFRENVLRILES-GPLVACVKRTSHMDCIRAITSNNEADA  58
Pig      1  -VAQKTVRWCTISNQEANKCSSFRENMSKAVKN-GPLVSCVKKSSYLDCIKAIANNEADA   58
Chicken  1  APPKSVIRWCTISSPEEKCNNLRDLTQQERIS----LTCVQKATYLDCIKAITSCH     56

Human    60 VTLDAGLVYDAYLAPNNLKPVVAEFYGSKEDPQTFYYAVAVVKKDSGFQMNQLRGKKSCH  119
Rabbit   60 VTLDGGAIYEAGLHPYKLKPVAAEFYGSKENPKICVAALIEEGLRQLEIGQSCH       119
Rat      60 ITLDGGWIYDAGITPNNLKPVAAEFYGSLEHPQTHYLAVAVVKKGTDFQLNQLEGKSS-H  119
Mouse    60 MTLDGGWIYDAGITPNNLKPVAAEFYGSKTEPQTHYYAVAVVKKGTDFQLNQLQGKKSCH  119
Horse    58 VTLDAGLVFEAGLSPYNLKPVAAEFYGSKTEPQTHYYAVAVVKKNSNFQLNQLQGKKSCH  117
Bovine   59 VTLDGGLVYEAGLAPIKDLKPVAAEFYGSKTKDNPQTHYYAVAVVKKDTDFKLDELRGK-SH 118
Pig      59 VTLDAGLVFEAGLAPYKLKPVAAEFHGTKDNPQDHYYAVAVVKKGSNFQLNQLQGKRSCH  118
Chicken  57 ISLDLQAFELAGLARYKLRPIALEIVYEHTEGSTTSYYAVAVVAKKGIEFTVLDLQGKTTSCH 116

Human   120 TGLGRSAGWNIPIGLLYCDLPEPRK-----PLEKAVANFFSGSCAPCADGTDFPQLCQLC  174
Rabbit  120 TGLGRSAGWNIPIGLLYCDLPEPRK-----PLEKAVASFFSGSCVPCADGAPDPVAVPV  174
Rat     120 TGLGRSAGWNIPIGLLFCNLPEPRK-----PLEKAVASFFSGSCVPCADGPVAVPVA-  174
Mouse   120 IGLGRSAGWVIPIGLLFCKLSEPRS-----PLEKAVSSFFSGSCVPCADGRTAVPNL-  174
Horse   118 VGLGRSAGWVIPIGLLYWQLPEPRE----SLQKAVSNFFTAGSCAPCADQSSPKLCQL-  172
Bovine  119 MAKIIYKELPDPQE-----SIQRATANFFSASCAPCAGPQDSVPVNKLCQ-         173
Pig     119 IGLGRSAGWNIPMGLLYDQLPEPRK-----PIEKAVASFFSASCVPCADPVNKTLCQ-   173
Chicken 117 IGLGRSAGWNIELHTLLHRGAIEWEGIESGSVGIEQKAVGA--TIEQKLCRQC        174
```

FIG. 2A-2
Alignment of Tf Sequences

FIG. 2B-1

```
Human     345 CALSHERLKCDEWSVNSVGKTECVSAETTEEDCAKTMNGEADASTEEDCG FVYTAGKCG 404
Rabbit    345 CALSHERLKCDEWSVTSGGLIECESAETPEDCAKTINGEAEASIEEDCG YVVTAGQCGI 404
Rat       341 CALSHOERACDEWSVTGNGQIECEAESETTPGDCDTVINGEDSEDCG HAYTAGQCGI 400
Mouse     344 CALSHLERTCDEESIISEGKIECESAEFTEEDCDXIVNGEADITEDGGHAITDGGHA 403
Horse.    348 CAIGHERKVCDEJVNSGGNIECEGAAQSIEQCIAKTMRGEADASEGGFIVVIAGKCG 407
Bovine    348 CAIGHQERTCDEFVNSGFSGGALECETTAENIEECIAKTMRGEADASEGGYIVIAGKCG 407
Pig       349 CAIGHEETQCCKDAJSINSGGKIECVSAENLEDCIAKVKGEADASEDGYIVLAGKCG 408
Chicken   348 CAVGKDEKSKCDRMSVVSNGDVECTVVDEIKDICIIITKIMKGEADAVALDGGLVITTAAGVCG 407

Human     405 AGYFAVAIVK--KSASDLTVDILKGSSHTAVGR 456
Rabbit    405 VPLLAENYNKS---DNCEDTPE----AGYFAVAIVK--KSNPDINMIEGKSSHTAVGR 455
Rat       401 VPLLAENIYEST--D-KKAPE----EGLSLAAIYK--ASDSSINKGSSHIAVDR 455
Mouse     404 VPLMAEMYIVDIS--S-CTNP-QSDVFPK-YVYAAIAANK--ASDTSITAIFKGSHIGVDR 459
Horse     408 VPLMAEYIVESS--N-CAIPSQQGIFFPK-LIYAAAIK--SSSDPDLIS LKGGNHTGVDR 462
Bovine    408 VPLLAENYETRSGSACVDTPE----EGYHAAVAIVK--TSDANINKLKDKSSHTAVDR 460
Pig       409 VPLLAEYKTE-GESCKNTPE----KGYLAAAYK--KSSGPDLNIVLKGSSHIAVGR 462
Chicken   408 MAERVDDE--SOCSKTDER----PASLYFAVAIAR--KDSNVNLGKSCHIAVGR 460

Human     457 TAGVNVTPNGLTYNKI HCRFQEEFFSEGCAPGSKKDSSLCKTMGSGL---NLCEPMKKEG 513
Rabbit    456 TAGVNTPNGLTYNKI HCRFDEEFFSEGFRQGCAPGSQKVSSICECLCIGP---SVCAPIYKREG 510
Rat       456 LAGVNTPNGLDYNRLIHCRFDEEFFSQGCAPGYEKISTLCDELCAP---AKCAPIKLEE 510
Mouse     460 LAGVNVTPNGMLYNRLIHCKEEFFSQGCAPGYEKTLCTCAP---LKCAPIKIEE 514
Horse     463 IAGVNTPNGLDYSEIKIVNCFFQKIEFQKFEKIAGCASGPGRECEPIHER 522
Bovine    461 IAGVNTPNGLTYYSKINNCSCKF UQLEFQIFEEGACAIGLQCGSEKGTGKEVDSNEK 520
Pig       463 IAGVIVPNGLIYNKLLSGCAPGSQRRSSLCACAIGSERAPGRECLAIHER 522
Chicken   461 IAGIVLPMGLIHNRTGTCNEDEYESEGCAPGSPPISRLQLOGSGGIPPEKCVASSHEK 520
```

FIG. 2B-2

ORAL DELIVERY OF MODIFIED TRANSFERRIN FUSION PROTEINS

RELATED APPLICATIONS

This application claims the benefit of U.S. Provisional Application 60/460,829, filed on Apr. 8, 2003, U.S. application Ser. No. 10/378,094, filed Mar. 4, 2003, and U.S. Provisional Application 60/406,977, filed Aug. 30, 2002, all of which are herein incorporated by reference in their entirety.

FIELD OF THE INVENTION

The present invention relates to orally administerable therapeutic proteins or peptides with extended serum stability or serum half-life, particularly to therapeutic proteins or peptides fused to or inserted in a transferrin molecule modified to reduce or inhibit glycosylation.

BACKGROUND OF THE INVENTION

Therapeutic proteins or peptides in their native state or when recombinantly produced are typically labile molecules exhibiting short periods of serum stability or short in vivo circulatory half-lives. In addition, these molecules are often extremely labile when formulated, particularly when formulated in aqueous solutions for diagnostic and therapeutic purposes.

Few practical solutions exist to extend or promote the stability in vivo or in vitro of proteinaceous therapeutic molecules. Polyethylene glycol (PEG) is a substance that can be attached to a protein, resulting in longer-acting, sustained activity of the protein. If the activity of a protein is prolonged by the attachment to PEG, the frequency that the protein needs to be administered may be decreased. PEG attachment, however, often decreases or destroys the protein's therapeutic activity. While in some instance PEG attachment can reduce immunogenicity of the protein, in other instances it may increase immunogenicity.

Therapeutic proteins or peptides have also been stabilized by fusion to a protein capable of extending the in vivo circulatory half-life of the therapeutic protein. For instance, therapeutic proteins fused to albumin or to antibody fragments may exhibit extended in vivo circulatory half-life when compared to the therapeutic protein in the unfused state. See U.S. Pat. Nos. 5,876,969 and 5,766,883.

Another serum protein, glycosylated human transferrin (Tf) has also been used to make fusions with therapeutic proteins to target delivery to the interior of cells or to carry agents across the blood-brain barrier. These fusion proteins comprising glycosylated human Tf have been used to target nerve growth factor (NGF) or ciliary neurotrophic factor (CNTF) across the blood-brain barrier by fusing full-length Tf to the agent. See U.S. Pat. Nos. 5,672,683 and 5,977,307. In these fusion proteins, the Tf portion of the molecule is glycosylated and binds to two atoms of iron, which is required for Tf binding to its receptor on a cell and, according to the inventors of these patents, to target delivery of the NGF or CNTF moiety across the blood-brain barrier. Transferrin fusion proteins have also been produced by inserting an HIV-1 protease target sequence into surface exposed loops of glycosylated transferrin to investigate the ability to produce another form of Tf fusion for targeted delivery to the inside of a cell via the Tf receptor (Ali et al. (1999) J. Biol. Chem. 274(34):24066-24073).

Serum transferrin (Tf) is a monomeric glycoprotein with a molecular weight of 80,000 daltons that binds iron in the circulation and transports it to various tissues via the transferrin receptor (TfR) (Aisen et al. (1980) Ann. Rev. Biochem. 49: 357-393; MacGillivray et al. (1981) J. Biol. Chem. 258: 3543-3553, U.S. Pat. No. 5,026,651). Tf is one of the most common serum molecules, comprising up to about 5-10% of total serum proteins. Carbohydrate deficient transferrin occurs in elevated levels in the blood of alcoholic individuals and exhibits a longer half life (approximately 14-17 days) than that of glycosylated transferrin (approximately 7-10 days). See van Eijk et al. (1983) Clin. Chim. Acta 132:167-171, Stibler (1991) Clin. Chem. 37:2029-2037 (1991), Arndt (2001) Clin. Chem. 47(1):13-27 and Stibler et al. in "Carbohydrate-deficient consumption", Advances in the Biosciences, (Ed Nordmann et al.), Pergamon, 1988, Vol. 71, pages 353-357).

The structure of Tf has been well characterized and the mechanism of receptor binding, iron binding and release and carbonate ion binding have been elucidated (U.S. Pat. Nos. 5,026,651, 5,986,067 and MacGillivray et al. (1983) J. Biol. Chem. 258(6):3543-3546).

Transferrin and antibodies that bind the transferrin receptor have also been used to deliver or carry toxic agents to tumor cells as cancer therapy (Baselga and Mendelsohn, 1994), and transferrin has been used as a non-viral gene therapy vector to deliver DNA to cells (Frank et al., 1994; Wagner et al., 1992). The ability to deliver proteins to the central nervous system (CNS) using the transferrin receptor as the entry point has been demonstrated with several proteins and peptides including CD4 (Walus et al., 1996), brain derived neurotrophic factor (Pardridge et al., 1994), glial derived neurotrophic factor (Albeck et al.), a vasointestinal peptide analogue (Bickel et al., 1993), a beta-amyloid peptide (Saito et al., 1995), and an antisense oligonucleotide (Pardridge et al., 1995).

Transferrin fusion proteins have not, however, been modified or engineered to extend the in vivo circulatory half-life of a therapeutic protein nor peptide or to increase bioavailability by reducing or inhibiting glycosylation of the Tf moiety nor to reduce or prevent iron and/or Tf receptor binding.

SUMMARY OF THE INVENTION

As described in more detail below, the present invention includes orally administerable modified Tf fusion proteins comprising at least one therapeutic protein, polypeptide or peptide entity, wherein the Tf portion is engineered to extend the serum half-life or bioavailability of the molecule. The invention also includes pharmaceutical formulations and compositions formulated for oral administration comprising the fusion proteins, methods of extending the serum stability, serum half-life and bioavailability of a therapeutic protein by fusion to modified transferrin, nucleic acid molecules encoding the modified Tf fusion proteins, and the like. Moreover, the present invention relates to methods of treating a patient with a modified Tf fusion protein by oral administration. Further, the present invention relates to methods of treating a patient with a modified Tf fusion protein by intranasal administration. Additionally, the present invention relates to methods of treating a patient with a modified Tf fusion protein by pulmonary administration.

BRIEF DESCRIPTION OF THE DRAWINGS

FIG. 1 shows the alignment of the N and C Domains of Human (Hu) transferrin (Tf) (SEQ ID NO: 3) with similarities and identities highlighted. Amino acid residues involved in iron binding are marked with (*). In the N terminus domain, these are Asp63, Tyr95, Tyr188, and His249. In the C terminus domain, these are Asp392, Tyr426, Tyr514, and His585. Amino acid residues indirectly involved in iron binding are marked with (†). These are Lys296 in the N terminus domain and Arg632 in the C terminus domain. Amino acid residues involved in the binding of carbonate ion are marked with (‡). In the N terminus domain, these are Thr120, Arg124, Ala126, and Gly127. In the C terminus domain, these are Thr452, Arg456, Ala458, and Gly459.

Figure 2A-2:
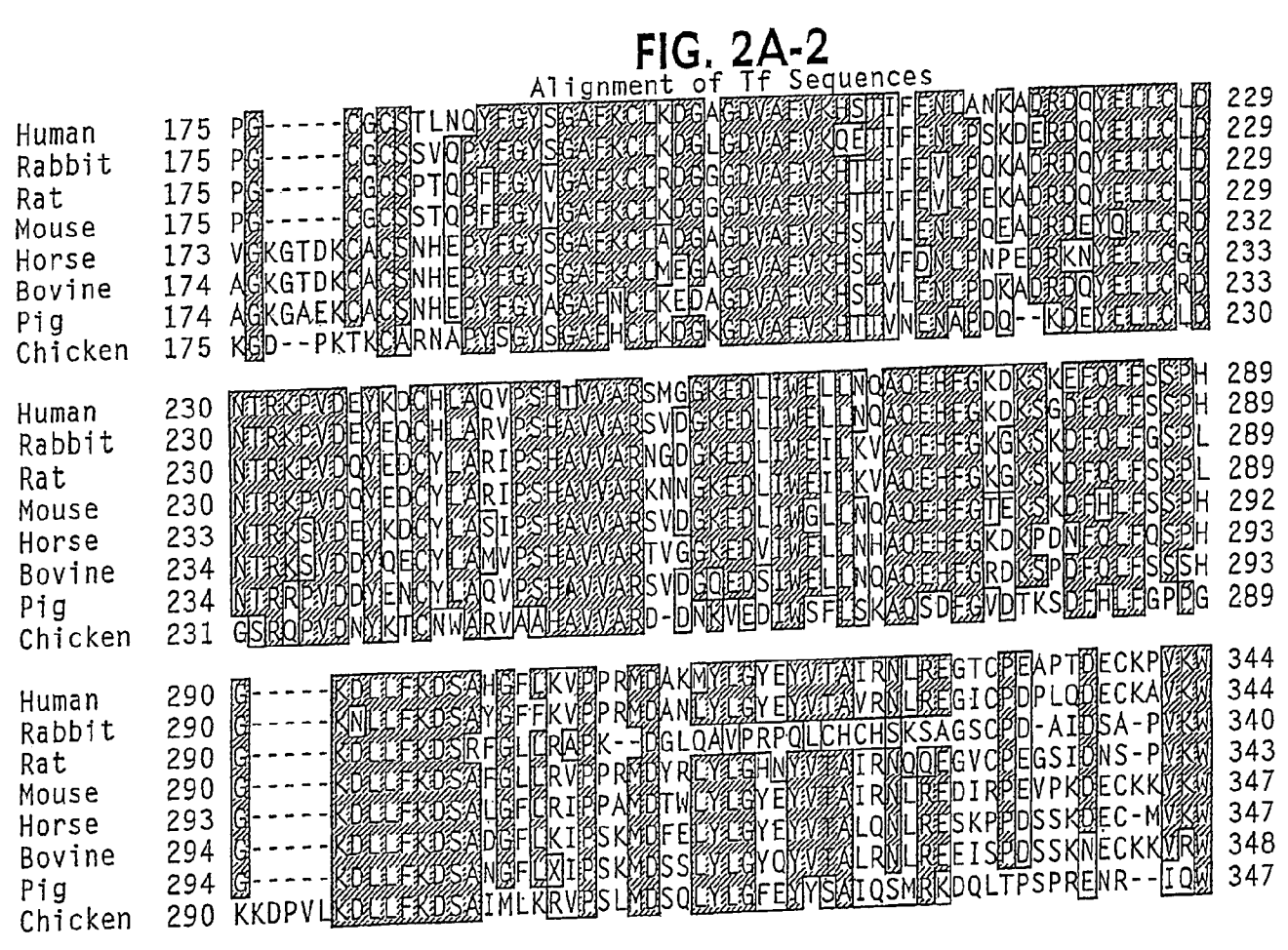
Figure 2B-2:
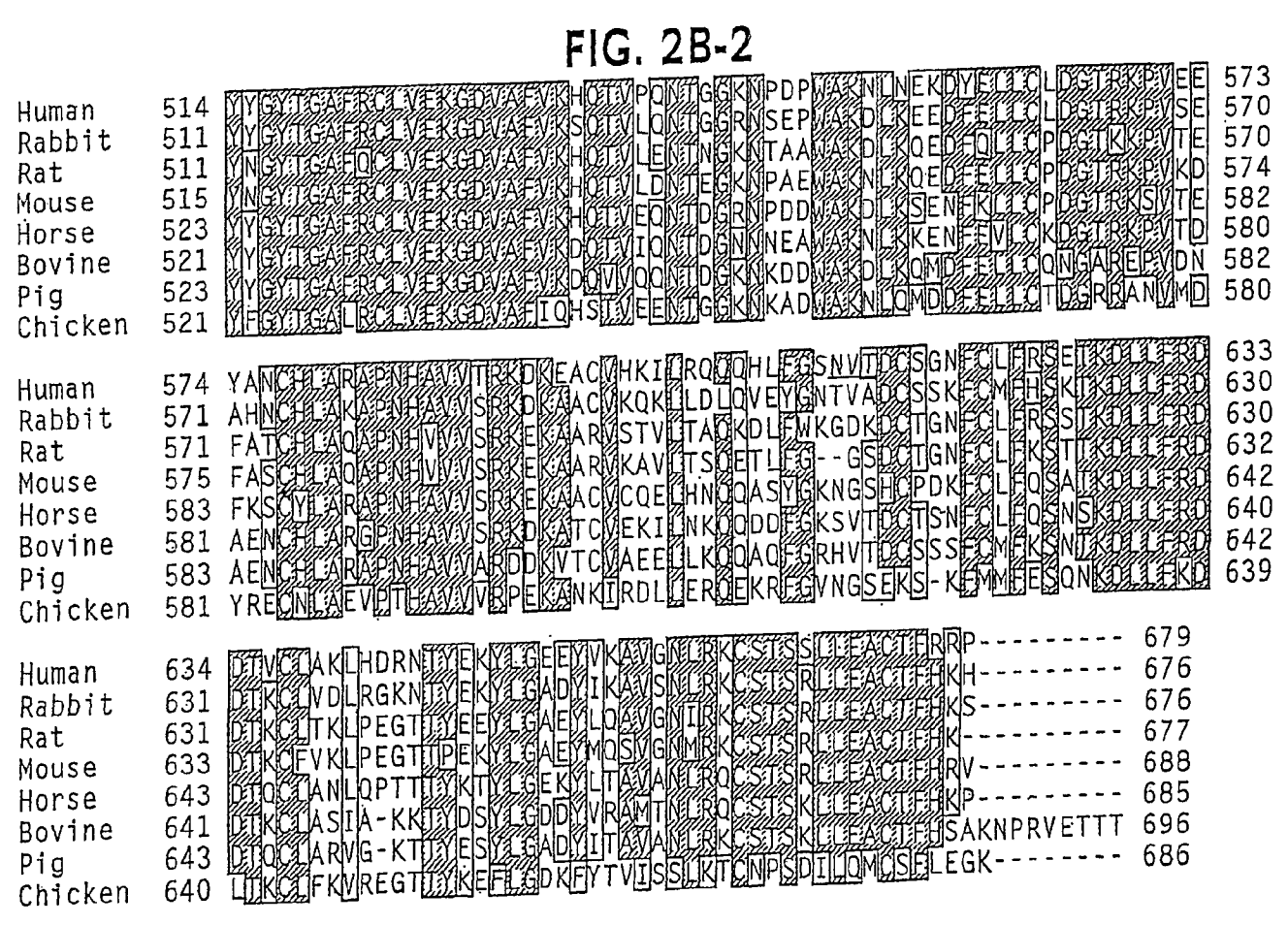

FIG. 2A-2B shows an alignment of transferrin sequences from different species (SEQ ID NOs: 3 and 48-54). Light shading: Similarity; Dark shading: Identity.

DETAILED DESCRIPTION

General Description

Figure 3:
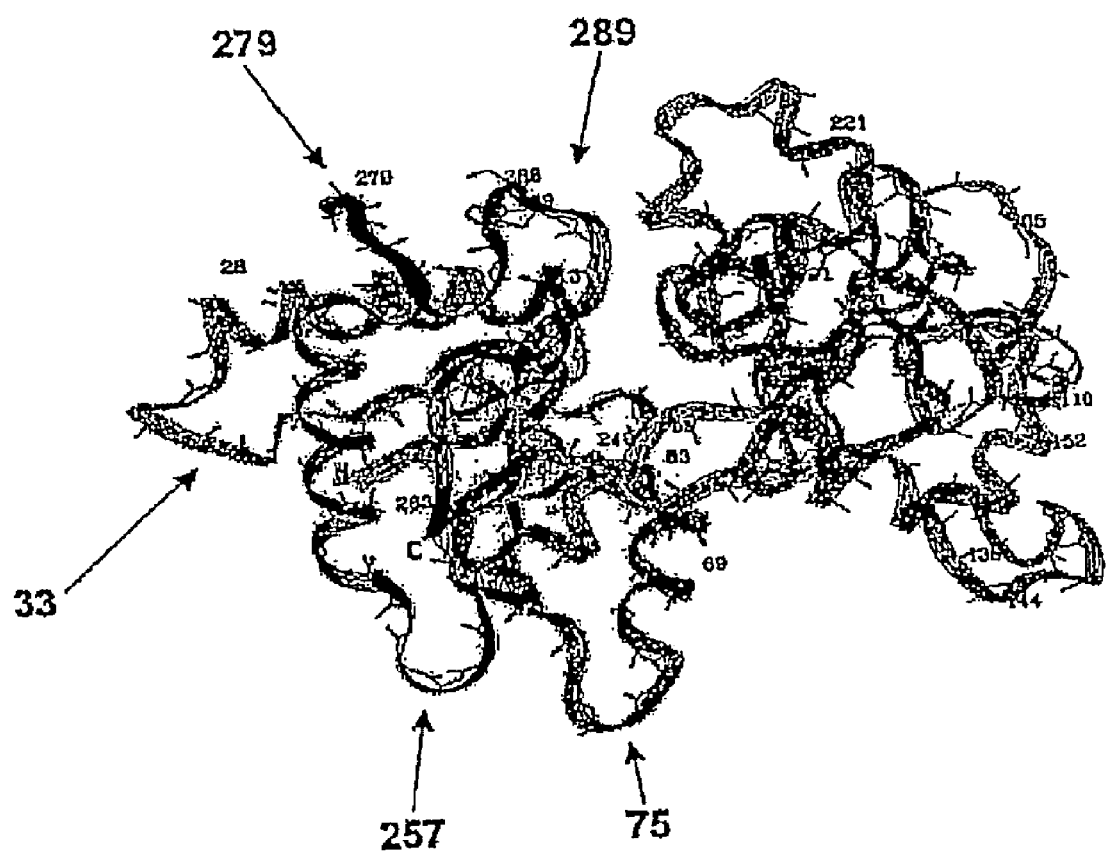
FIG. 3 shows the location of a number of Tf surface exposed insertion sites for therapeutic proteins, polypeptides or peptides.

It has been discovered that a therapeutic protein (e.g., a polypeptide, antibody, or peptide, or fragments and variants thereof) can be stabilized to extend the in vivo circulatory half-life and/or retain the therapeutic protein's activity for extended periods of time in vivo by genetically fusing or chemically conjugating the therapeutic protein, polypeptide or peptide to all or a portion of modified transferrin sufficient to extend its half life in serum. The modified transferrin fusion proteins include a transferrin protein or domain covalently linked to a therapeutic protein or peptide, wherein the transferrin portion is modified to contain one or more amino acid substitutions, insertions or deletions compared to a wild-type transferrin sequence. In one embodiment, Tf fusion proteins are engineered to reduce or prevent glycosylation within the Tf or a Tf domain. In other embodiments, the Tf protein or Tf domain(s) is modified to exhibit reduced or no binding to iron or carbonate ion, or to have a reduced affinity or not bind to a Tf receptor (TfR).

The present invention therefore includes transferrin fusion proteins, therapeutic compositions comprising the fusion proteins, and methods of treating, preventing, or ameliorating diseases or disorders by administering the fusion proteins. A transferrin fusion protein of the invention includes at least a fragment or variant of a therapeutic protein and at least a fragment or variant of modified transferrin, which are associated with one another, preferably by genetic fusion (i.e., the transferrin fusion protein is generated by translation of a nucleic acid in which a polynucleotide encoding all or a portion of a therapeutic protein is joined in-frame with a polynucleotide encoding all or a portion of modified transferrin) or chemical conjugation to one another. The therapeutic protein and transferrin protein, once part of the transferrin fusion protein, may be referred to as a "portion", "region" or "moiety" of the transferrin fusion protein (e.g., a "therapeutic protein portion' or a "transferrin protein portion").

In one embodiment, the invention provides a transferrin fusion protein comprising, or alternatively consisting of, a therapeutic protein and a modified serum transferrin protein. In other embodiments, the invention provides a transferrin fusion protein comprising, or alternatively consisting of, a biologically active and/or therapeutically active fragment of a therapeutic protein and a modified transferrin protein. In other embodiments, the invention provides a transferrin fusion protein comprising, or alternatively consisting of, a biologically active and/or therapeutically active variant of a therapeutic protein and modified transferrin protein. In further embodiments, the invention provides a transferrin fusion protein comprising a therapeutic protein, and a biologically active and/or therapeutically active fragment of modified transferrin. In another embodiment, the therapeutic protein portion of the transferrin fusion protein is the active form of the therapeutic protein.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

Definitions

As used herein, an "amino acid corresponding to" or an "equivalent amino acid" in a transferrin sequence is identified by alignment to maximize the identity or similarity between a first transferrin sequence and at least a second transferrin sequence. The number used to identify an equivalent amino acid in a second transferrin sequence is based on the number used to identify the corresponding amino acid in the first transferrin sequence. In certain cases, these phrases may be used to describe the amino acid residues in human transferrin compared to certain residues in rabbit serum transferrin.

As used herein, the term "biological activity" refers to a function or set of activities performed by a therapeutic molecule, protein or peptide in a biological context (i.e., in an organism or an in vitro facsimile thereof). Biological activities may include but are not limited to the functions of the therapeutic molecule portion of the claimed fusion proteins, such as, but not limited to, the induction of extracellular matrix secretion from responsive cell lines, the induction of hormone secretion, the induction of chemotaxis, the induction of mitogenesis, the induction of differentiation, or the inhibition of cell division of responsive cells. A fusion protein or peptide of the invention is considered to be biologically active if it exhibits one or more biological activities of its therapeutic protein's native counterpart.

As used herein, "binders" are agents used to impart cohesive qualities to the powdered material. Binders, or "granulators" as they are sometimes known, impart a cohesiveness to the tablet formulation, which insures the tablet remaining intact after compression, as well as improving the free-flowing qualities by the formulation of granules of desired hardness and size. Materials commonly used as binders include starch; gelatin; sugars, such as sucrose, glucose, dextrose, molasses, and lactose; natural and synthetic gums, such as acacia, sodium alginate, extract of Irish moss, panwar gum, ghatti gum, mucilage of isapol husks, carboxymethylcellulose, methylcellulose, polyvinylpyrrolidone, Veegum, microcrystalline cellulose, microcrystalline dextrose, amylose, and larch arabogalactan, and the like.

As used herein, the term "carrier" refers to a diluent, adjuvant, excipient, or vehicle with which a composition is administered. Such pharmaceutical carriers can be sterile liquids, such as water and oils, including those of petroleum, animal, vegetable or synthetic origin, such as peanut oil, soybean oil, mineral oil, sesame oil and the like.

As used herein, "coloring agents" are agents that give tablets a more pleasing appearance, and in addition help the manufacturer to control the product during its preparation and help the user to identify the product. Any of the approved certified water-soluble FD&C dyes, mixtures thereof, or their corresponding lakes may be used to color tablets. A color lake is the combination by adsorption of a water-soluble dye to a hydrous oxide of a heavy metal, resulting in an insoluble form of the dye.

As used herein, "diluents" are inert substances added to increase the bulk of the formulation to make the tablet a practical size for compression. Commonly used diluents include calcium phosphate, calcium sulfate, lactose, kaolin, mannitol, sodium chloride, dry starch, powdered sugar, silica, and the like.

As used herein, "disintegrators" or "disintegrants" are substances that facilitate the breakup or disintegration of tablets after administration. Materials serving as disintegrants have been chemically classified as starches, clays, celluloses, algins, or gums. Other disintegrators include Veegum HV, methylcellulose, agar, bentonite, cellulose and wood products, natural sponge, cation-exchange resins, alginic acid, guar gum, citrus pulp, cross-linked polyvinylpyrrolidone, carboxymethylcellulose, and the like.

As used herein, the term "dispersibility" or "dispersible" means a dry powder having a moisture content of less than about 10% by weight (% w) water, usually below about 5% w and preferably less than about 3% w; a particle size of about 1.0-5.0 μm mass median diameter (MMD), usually 1.0-4.0 μm MMD, and preferably 1.0-3.0 μm MMD; a delivered dose of about >30%, usually >40%, preferably >50%, and most preferred >60%; and an aerosol particle size distribution of 1.0-5.0 μm mass median aerodynamic diameter (MMAD), usually 1.5-4.5 μm MMAD, and preferably 1.5-4.0 μm MMAD.

As used herein, the term "dry" means that the composition has a moisture content such that the particles are readily dispersible in an inhalation device to form an aerosol. This moisture content is generally below about 10% by weight (% w) water, usually below about 5% w and preferably less than about 3% w.

As used herein, "effective amount" means an amount of a drug or pharmacologically active agent that is sufficient to provide the desired local or systemic effect and performance at a reasonable benefit/risk ratio attending any medical treatment.

As used herein, "flavoring agents" vary considerably in their chemical structure, ranging from simple esters, alcohols, and aldehydes to carbohydrates and complex volatile oils. Synthetic flavors of almost any desired type are now available.

As used herein, the terms "fragment of a Tf protein" or "Tf protein," or "portion of a Tf protein" refer to an amino acid sequence comprising at least about 5%, 10%, 20%, 30%, 40%, 50%, 60%, 70%, 80%, 90%, 95%, 96%, 97%, 98%, 99% or 100% of a naturally occurring Tf protein or mutant thereof.

As used herein, the term "gene" refers to any segment of DNA associated with a biological function. Thus, genes include, but are not limited to, coding sequences and/or the regulatory sequences required for their expression. Genes can also include non-expressed DNA segments that, for example, form recognition sequences for other proteins. Genes can be obtained from a variety of sources, including cloning from a source of interest or synthesizing from known or predicted sequence information, and may include sequences designed to have desired parameters.

As used herein, a "heterologous polynucleotide" or a "heterologous nucleic acid" or a "heterologous gene" or a "heterologous sequence" or an "exogenous DNA segment" refers to a polynucleotide, nucleic acid or DNA segment that originates from a source foreign to the particular host cell, or, if from the same source, is modified from its original form. A heterologous gene in a host cell includes a gene that is endogenous to the particular host cell, but has been modified. Thus, the terms refer to a DNA segment which is foreign or heterologous to the cell, or homologous to the cell but in a position within the host cell nucleic acid in which the element is not ordinarily found. As an example, a signal sequence native to a yeast cell but attached to a human Tf sequence is heterologous.

As used herein, an "isolated" nucleic acid sequence refers to a nucleic acid sequence which is essentially free of other nucleic acid sequences, e.g., at least about 20% pure, preferably at least about 40% pure, more preferably about 60% pure, even more preferably about 80% pure, most preferably about 90% pure, and even most preferably about 95% pure, as determined by agarose gel electrophoresis. For example, an isolated nucleic acid sequence can be obtained by standard cloning procedures used in genetic engineering to relocate the nucleic acid sequence from its natural location to a different site where it will be reproduced. The cloning procedures may involve excision and isolation of a desired nucleic acid fragment comprising the nucleic acid sequence encoding the polypeptide, insertion of the fragment into a vector molecule, and incorporation of the recombinant vector into a host cell where multiple copies or clones of the nucleic acid sequence will be replicated. The nucleic acid sequence may be of genomic, cDNA, RNA, semi-synthetic, synthetic origin, or any combinations thereof.

As used herein, two or more DNA coding sequences are said to be "joined" or "fused" when, as a result of in-frame fusions between the DNA coding sequences, the DNA coding sequences are translated into a fusion polypeptide. The term "fusion" in reference to Tf fusions includes, but is not limited to, attachment of at least one therapeutic protein, polypeptide or peptide to the N-terminal end of Tf, attachment to the C-terminal end of Tf, and/or insertion between any two amino acids within Tf.

As used herein, "lubricants" are materials that perform a number of functions in tablet manufacture, such as improving the rate of flow of the tablet granulation, preventing adhesion of the tablet material to the surface of the dies and punches, reducing interparticle friction, and facilitating the ejection of the tablets from the die cavity. Commonly used lubricants include talc, magnesium stearate, calcium stearate, stearic acid, and hydrogenated vegetable oils. Typical amounts of lubricants range from about 0.1% by weight to about 5% by weight.

As used herein, "Modified transferrin" as used herein refers to a transferrin molecule that exhibits at least one modification of its amino acid sequence, compared to wild-type transferrin.

As used herein, "Modified transferrin fusion protein" as used herein refers to a protein formed by the fusion of at least one molecule of modified transferrin (or a fragment or variant thereof) to at least one molecule of a therapeutic protein (or fragment or variant thereof).

As used herein, the terms "nucleic acid" or "polynucleotide" refer to deoxyribonucleotides or ribonucleotides and polymers thereof in either single- or double-stranded form. Unless specifically limited, the terms encompass nucleic acids containing analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g. degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al. (1991) Nucleic Acid Res. 19:5081; Ohtsuka et al. (1985) J. Biol. Chem. 260:2605-2608; Cassol et al. (1992); Rossolini et al. (1994) Mol. Cell. Probes 8:91-98). The term nucleic acid is used interchangeably with gene, cDNA, and mRNA encoded by a gene.

As used herein, a DNA segment is referred to as "operably linked" when it is placed into a functional relationship with another DNA segment. For example, DNA for a signal sequence is operably linked to DNA encoding a fusion protein of the invention if it is expressed as a preprotein that participates in the secretion of the fusion protein; a promoter or enhancer is operably linked to a coding sequence if it stimulates the transcription of the sequence. Generally, DNA sequences that are operably linked are contiguous, and in the case of a signal sequence or fusion protein both contiguous and in reading phase. However, enhancers need not be contiguous with the coding sequences whose transcription they control. Linking, in this context, is accomplished by ligation at convenient restriction sites or at adapters or linkers inserted in lieu thereof.

As used herein, "pharmaceutically acceptable" refers to materials and compositions that are physiologically tolerable and do not typically produce an allergic or similar untoward reaction, such as gastric upset, dizziness and the like, when administered to a human. Typically, as used herein, the term "pharmaceutically acceptable" means approved by a regulatory agency of the Federal or a state government or listed in the U.S. Pharmacopeia or other generally recognized pharmacopeia for use in animals, and more particularly in humans.

As used herein, "physiologically effective amount" is that amount delivered to a subject to give the desired palliative or curative effect. This amount is specific for each drug and its ultimate approved dosage level.

As used herein, the term "powder" means a composition that consists of finely dispersed solid particles that are free flowing and capable of being readily dispersed in an inhalation device and subsequently inhaled by a subject so that the particles reach the lungs to permit penetration into the alveoli. Thus, the powder is said to be "respirable." Preferably the average particle size is less than about 10 microns (μm) in diameter with a relatively uniform spheroidal shape distribution. More preferably the diameter is less than about 7.5 μm and most preferably less than about 5.0 μm. Usually the particle size distribution is between about 0.1 μm and about 5 μm in diameter, particularly about 0.3 μm to about 5 μm.

As used herein, the term "promoter" refers to a region of DNA involved in binding RNA polymerase to initiate transcription.

As used herein, the term "recombinant" refers to a cell, tissue or organism that has undergone transformation with a new combination of genes or DNA.

As used herein, the term "subject" can be a human, a mammal, or an animal. The subject being treated is a patient in need of treatment.

As used herein, a targeting entity, protein, polypeptide or peptide refers to a molecule that binds specifically to a particular cell type [normal (e.g., lymphocytes) or abnormal e.g., (cancer cell)] and therefore may be used to target a Tf fusion protein or compound (drug, or cytotoxic agent) to that cell type specifically.

As used herein, "tablets" are solid pharmaceutical dosage forms containing drug substances with or without suitable diluents and prepared either by compression or molding methods well known in the art. Tablets have been in widespread use since the latter part of the 19$^{th}$ century and their popularity continues. Tablets remain popular as a dosage form because of the advantages afforded both to the manufacturer (e.g., simplicity and economy of preparation, stability; and convenience in packaging, shipping, and dispensing) and the patient (e.g., accuracy of dosage, compactness, portability, blandness of taste, and ease of administration). Although tablets are most frequently discoid in shape, they may also be round, oval, oblong, cylindrical, or triangular. They may differ greatly in size and weight depending on the amount of drug substance present and the intended method of administration. They are divided into two general classes, (1) compressed tablets, and (2) molded tablets or tablet triturates. In addition to the active or therapeutic ingredient or ingredients, tablets contain a number or inert materials or additives. A first group of such additives includes those materials that help to impart satisfactory compression characteristics to the formulation, including diluents, binders, and lubricants. A second group of such additives helps to give additional desirable physical characteristics to the finished tablet, such as disintegrators, colors, flavors, and sweetening agents.

As used herein, the term "therapeutically effective amount" refers to that amount of the transferrin fusion protein comprising a therapeutic molecule which, when administered to a subject in need thereof, is sufficient to effect treatment. The amount of transferrin fusion protein which constitutes a "therapeutically effective amount" will vary depending on the therapeutic protein used, the severity of the condition or disease, and the age and body weight of the subject to be treated, but can be determined routinely by one or ordinary skill in the art having regard to his/her own knowledge and to this disclosure.

As used herein, "therapeutic protein" refers to proteins, polypeptides, peptides or fragments or variants thereof, having one or more therapeutic and/or biological activities. Therapeutic proteins encompassed by the invention include but are not limited to proteins, polypeptides, peptides, antibodies, and biologics. The terms peptides, proteins, and polypeptides are used interchangeably herein. Additionally, the term "therapeutic protein" may refer to the endogenous or naturally occurring correlate of a therapeutic protein. By a polypeptide displaying a "therapeutic activity" or a protein that is "therapeutically active" is meant a polypeptide that possesses one or more known biological and/or therapeutic activities associated with a therapeutic protein such as one or more of the therapeutic proteins described herein or otherwise known in the art. As a non-limiting example, a "therapeutic protein" is a protein that is useful to treat, prevent or ameliorate a disease, condition or disorder. Such a disease, condition or disorder may be in humans or in a non-human animal, e.g., veterinary use.

As used herein, the term "transformation" refers to the transfer of nucleic acid (i.e., a nucleotide polymer) into a cell. As used herein, the term "genetic transformation" refers to the transfer and incorporation of DNA, especially recombinant DNA, into a cell.

As used herein, the term "transformant" refers to a cell, tissue or organism that has undergone transformation.

As used herein, the term "transgene" refers to a nucleic acid that is inserted into an organism, host cell or vector in a manner that ensures its function.

As used herein, the term "transgenic" refers to cells, cell cultures, organisms, bacteria, fungi, animals, plants, and progeny of any of the preceding, which have received a foreign or modified gene and in particular a gene encoding a modified Tf fusion protein by one of the various methods of transformation, wherein the foreign or modified gene is from the same or different species than the species of the organism receiving the foreign or modified gene.

As used herein, the term "Variants or variant" refers to a polynucleotide or nucleic acid differing from a reference nucleic acid or polypeptide, but retaining essential properties thereof. Generally, variants are overall closely similar, and, in many regions, identical to the reference nucleic acid or polypeptide. As used herein, "variant" refers to a therapeutic protein portion of a transferrin fusion protein of the invention, differing in sequence from a native therapeutic protein but retaining at least one functional and/or therapeutic property thereof as described elsewhere herein or otherwise known in the art.

As used herein, the term "vector" refers broadly to any plasmid, phagemid or virus encoding an exogenous nucleic acid. The term is also be construed to include non-plasmid, non-phagemid and non-viral compounds which facilitate the transfer of nucleic acid into virions or cells, such as, for example, polylysine compounds and the like. The vector may be a viral vector that is suitable as a delivery vehicle for delivery of the nucleic acid, or mutant thereof, to a cell, or the vector may be a non-viral vector which is suitable for the same purpose. Examples of viral and non-viral vectors for delivery of DNA to cells and tissues are well known in the art and are described, for example, in Ma et al. (1997, *Proc. Natl. Acad. Sci.* U.S.A. 94:12744-12746). Examples of viral vectors include, but are not limited to, a recombinant vaccinia virus, a recombinant adenovirus, a recombinant retrovirus, a recombinant adeno-associated virus, a recombinant avian pox virus, and the like (Cranage et al., 1986, EMBO 3. 5:3057-3063; International Patent Application No. WO94/17810, published Aug. 18, 1994; International Patent Application No. WO94/23744, published Oct. 27, 1994). Examples of non-viral vectors include, but are not limited to, liposomes, polyamine derivatives of DNA, and the like.

As used herein, the term "wild type" refers to a polynucleotide or polypeptide sequence that is naturally occurring.

Transferrin and Transferrin Modifications

Any transferrin may be used to make modified Tf fusion proteins of the invention. As an example, the wild-type human Tf (Tf) is a 679 amino acid protein of approximately 75 kDa (not accounting for glycosylation), with two main domains, N (about 330 amino acids) and C (about 340 amino acids), which appear to originate from a gene duplication. See GenBank accession numbers NM001063, XM002793, M12530, XM039845, XM 039847 and S95936 (www.ncbi.nlm.nih.gov/), all of which are herein incorporated by reference in their entirety, as well as SEQ ID NOS 1, 2 and 3. The two domains have diverged over time but retain a large degree of identity/similarity (FIG. 1).

Each of the N and C domains is further divided into two subdomains, N1 and N2, C1 and C2. The function of Tf is to transport iron to the cells of the body. This process is mediated by the Tf receptor (TfR), which is expressed on all cells, particularly actively growing cells. TfR recognizes the iron bound form of Tf (two molecules of which are bound per receptor), endocytosis then occurs whereby the TfR/Tf complex is transported to the endosome, at which point the localized drop in pH results in release of bound iron and the recycling of the TfR/Tf complex to the cell surface and release of Tf (known as apoTf in its un-iron bound form). Receptor binding is through the C domain of Tf. The two glycosylation sites in the C domain do not appear to be involved in receptor binding as unglycosylated iron bound Tf does bind the receptor.

Each Tf molecule can carry two iron ions ($Fe^{3+}$). These are complexed in the space between the N1 and N2, C1 and C2 sub domains resulting in a conformational change in the molecule. Tf crosses the blood brain barrier (BBB) via the Tf receptor.

In human transferrin, the iron binding sites comprise at least amino acids Asp 63 (Asp 82 of SEQ ID NO: 2 which includes the native Tf signal sequence), Asp 392 (Asp 411 of SEQ ID NO: 2), Tyr 95 (Tyr 114 of SEQ ID NO: 2), Tyr 426 (Tyr 445 of SEQ ID NO: 2), Tyr 188 (Tyr 207 of SEQ ID NO: 2), Tyr 514 or 517 (Tyr 533 or Tyr 536 SEQ ID NO: 2), His 249 (His 268 of SEQ ID NO: 2), and His 585 (His 604 of SEQ ID NO: 2) of SEQ ID NO: 3. The hinge regions comprise at least N domain amino acid residues 94-96, 245-247 and/or 316-318 as well as C domain amino acid residues 425-427, 581-582 and/or 652-658 of SEQ ID NO: 3. The carbonate binding sites comprise at least amino acids Thr 120 (Thr 139 of SEQ ID NO: 2), Thr 452 (Thr 471 of SEQ ID NO: 2), Arg 124 (Arg 143 of SEQ ID NO: 2), Arg 456 (Arg 475 of SEQ ID NO: 2), Ala 126 (Ala 145 of SEQ ID NO: 2), Ala 458 (Ala 477 of SEQ ID NO: 2), Gly 127 (Gly 146 of SEQ ID NO: 2), and Gly 459 (Gly 478 of SEQ ID NO: 2) of SEQ ID NO: 3.

In one embodiment of the invention, the modified transferrin fusion protein includes a modified human transferrin, although any animal Tf molecule may be used to produce the fusion proteins of the invention, including human Tf variants, cow, pig, sheep, dog, rabbit, rat, mouse, hamster, echnida, platypus, chicken, frog, hornworm, monkey, as well as other bovine, canine and avian species. All of these Tf sequences are readily available in GenBank and other public databases. The human Tf nucleotide sequence is available (see SEQ ID NOS 1, 2 and 3 and the accession numbers described above and available at www.ncbi.nlm.nih.gov/) and can be used to make genetic fusions between Tf or a domain of Tf and the therapeutic molecule of choice. Fusions may also be made from related molecules such as lacto transferrin (lactoferrin) GenBank Acc: NM_002343) or melanotransferrin (GenBank Acc. NM_013900, murine melanotransferrin).

Melanotransferrin is a glycosylated protein found at high levels in malignant melanoma cells and was originally named human melanoma antigen p97 (Brown et al., 1982, Nature, 296: 171-173). It possesses high sequence homology with human serum transferrin, human lactoferrin, and chicken transferrin (Brown et al., 1982, Nature, 296: 171-173; Rose et al., Proc. Natl. Acad. Sci. USA, 1986, 83: 1261-1265). However, unlike these receptors, no cellular receptor has been identified for melanotransferrin. Melanotransferrin reversibly binds iron and it exists in two forms, one of which is bound to cell membranes by a glycosyl phosphatidylinositol anchor while the other form is both soluble and actively secreted (Baker et al., 1992, FEBS Lett, 298: 215-218; Alemany et al., 1993, J. Cell Sci., 104: 1155-1162; Food et al., 1994, J. Biol. Chem. 274: 7011-7017).

Lactoferrin (Lf), a natural defense iron-binding protein, has been found to possess antibacterial, antimycotic, antiviral, antineoplastic and anti-inflammatory activity. The protein is present in exocrine secretions that are commonly exposed to normal flora: milk, tears, nasal exudate, saliva, bronchial mucus, gastrointestinal fluids, cervico-vaginal mucus and seminal fluid. Additionally, Lf is a major constituent of the secondary specific granules of circulating polymorphonuclear neutrophils (PMNs). The apoprotein is released on degranulation of the PMNs in septic areas. A principal function of Lf is that of scavenging free iron in fluids and inflamed areas so as to suppress free radical-mediated damage and decrease the availability of the metal to invading microbial and neoplastic cells. In a study that examined the turnover rate of $^{125}$I Lf in adults, it was shown that Lf is rapidly taken up by the liver and spleen, and the radioactivity persisted for several weeks in the liver and spleen (Bennett et al. (1979), *Clin. Sci. (Lond.)* 57: 453-460).

In one embodiment, the transferrin portion of the transferrin fusion protein of the invention includes a transferrin splice

| N domain (1-330) | 4-24 | 36-72 75-88 | 94-136 | 138-139 | 149-164 | 168-173 | 178-198 200-214 | 219-255 | 259-260 | 263-268 | 271-275 | 279-280 | 283-288 290-304 | 309-327 |
|---|---|---|---|---|---|---|---|---|---|---|---|---|---|---|
| C domain (340-679) | 340-361 | 365-415 | 425-437 439-468 | 470-471 | 475-490 | 492-497 | 507-542 | 555-591 | 593-594 | 597-602 | 605-609 | 614-615 | 620-640 | 645-663 | variant. In one example, a transferrin splice variant can be a splice variant of human transferrin. In one specific embodiment, the human transferrin splice variant can be that of Genbank Accession AAA61140.

In another embodiment, the transferrin portion of the transferrin fusion protein of the invention includes a lactoferrin splice variant. In one example, a human serum lactoferrin splice variant can be a novel splice variant of a neutrophil lactoferrin. In one specific embodiment, the neutrophil lactoferrin splice variant can be that of Genbank Accession AAA59479. In another specific embodiment, the neutrophil lactoferrin splice variant can comprise the following amino acid sequence EDCIALKGEADA (SEQ ID NO: 8), which includes the novel region of splice-variance.

In another embodiment, the transferrin portion of the transferrin fusion protein of the invention includes a melanotransferrin variant.

Modified Tf fusions may be made with any Tf protein, fragment, domain, or engineered domain. For instance, fusion proteins may be produced using the full-length Tf sequence, with or without the native Tf signal sequence. Tf fusion proteins may also be made using a single Tf domain, such as an individual N or C domain or a modified form of Tf comprising 2N or 2C domains (see U.S. Provisional Application 60/406,977, filed Aug. 30, 2002, which is herein incorporated by reference in its entirety). In some embodiments, fusions of a therapeutic protein to a single C domain may be produced, wherein the C domain is altered to reduce, inhibit or prevent glycosylation. In other embodiments, the use of a single N domain is advantageous as the Tf glycosylation sites reside in the C domain and the N domain, on its own. A preferred embodiment is the Tf fusion protein having a single N domain which is expressed at a high level.

As used herein, a C terminal domain or lobe modified to function as an N-like domain is modified to exhibit glycosylation patterns or iron binding properties substantially like that of a native or wild-type N domain or lobe. In a preferred embodiment, the C domain or lobe is modified so that it is not glycosylated and does not bind iron by substitution of the relevant C domain regions or amino acids to those present in the corresponding regions or sites of a native or wild-type N domain.

As used herein, a Tf moiety comprising "two N domains or lobes" includes a Tf molecule that is modified to replace the native C domain or lobe with a native or wild-type N domain or lobe or a modified N domain or lobe or contains a C domain that has been modified to function substantially like a wild-type or modified N domain. Analysis of the two domains by overlay of the two domains (Swiss PDB Viewer 3.7b2, Iterative Magic Fit) and by direct amino acid alignment (ClustalW multiple alignment) reveals that the two domains have diverged over time. Amino acid alignment shows 42% identity and 59% similarity between the two domains. However, approximately 80% of the N domain matches the C domain for structural equivalence. The C domain also has several extra disulfide bonds compared to the N domain.

Alignment of molecular models for the N and C domain reveals the following structural equivalents:

The disulfide bonds for the two domains align as follows:

| N | C |
|---|---|
|  | C339-C596 |
| C9-C48 | C345-C377 |
| C19-C39 | C355-C368 |
|  | C402-C674 |
|  | C418-C637 |
| C118-C194 | C450-C523 |
| *C137-C331* |  |
|  | C474-C665 |
| C158-C174 | C484-C498 |
| C161-C179 |  |
| C171-C177 | C495-C506 |
| C227-C241 | C563-C577 |
|  | C615-C620 |

Bold aligned disulfide bonds
*Italics* bridging peptide

In one embodiment, the transferrin portion of the transferrin fusion protein includes at least two N terminal lobes of transferrin. In further embodiments, the transferrin portion of the transferrin fusion protein includes at least two N terminal lobes of transferrin derived from human serum transferrin.

In another embodiment, the transferrin portion of the transferrin fusion protein includes, comprises, or consists of at least two C terminal lobes of transferrin. In further embodiments, the transferrin portion of the transferrin fusion protein includes at least two C terminal lobes of transferrin derived from human serum transferrin.

In a further embodiment, the C terminal lobe mutant further includes a mutation of at least one of Asn413 and Asn611 of SEQ ID NO: 3 which does not allow glycosylation.

In some embodiments, the Tf or Tf portion will be of sufficient length to increase the in vivo circulatory half-life, serum stability, in vitro solution stability or bioavailability of the therapeutic protein compared to the in vivo circulatory half-life, serum stability, in vitro solution stability or bioavailability of the therapeutic protein in an unfused state. Such an increase in stability, serum half-life or bioavailability may be about a 30%, 50%, 70%, 80%, 90% or more increase over the unfused therapeutic protein. In some cases, the modified transferrin fusion proteins exhibit a serum half-life of about 10-20 or more days, about 12-18 days or about 14-17 days.

When the C domain of Tf is part of the fusion protein, the two N-linked glycosylation sites, amino acid residues corresponding to N413 and N611 of SEQ ID NO:3 may be mutated for expression in a yeast system to prevent glycosylation or hypermannosylation and extend the serum half-life of the fusion protein and/or therapeutic protein (to produce asialo-, or in some instances, monosialo-Tf or disialo-Tf). In addition to Tf amino acids corresponding to N413 and N611, mutations may be to the adjacent residues within the N-X-S/T glycosylation site to prevent or substantially reduce glycosylation. See U.S. Pat. No. 5,986,067 of Funk et al. It has also been reported that the N domain of Tf expressed in *Pichia pastoris* becomes O-linked glycosylated with a single hexose at S32 which also may be mutated or modified to prevent such glycosylation.

Accordingly, in one embodiment of the invention, the transferrin fusion protein includes a modified transferrin molecule wherein the transferrin exhibits reduced glycosylation, including but not limited to asialo-monosialo- and disialoforms of Tf. In another embodiment, the transferrin portion of the transferrin fusion protein includes a recombinant transferrin mutant that is mutated to prevent glycosylation. In another embodiment, the transferrin portion of the transferrin fusion protein includes a recombinant transferrin mutant that is fully glycosylated. In a further embodiment, the transferrin portion of the transferrin fusion protein includes a recombinant human serum transferrin mutant that is mutated to prevent glycosylation, wherein at least one of Asn413 and Asn611 of SEQ ID NO:3 are mutated to an amino acid which does not allow glycosylation. In another embodiment, the transferrin portion of the transferrin fusion protein includes a recombinant human serum transferrin mutant that is mutated to prevent or substantially reduce glycosylation, wherein mutations may be to the adjacent residues within the N-X-S/T glycosylation site. Moreover, glycosylation may be reduced or prevented by mutating the serine or threonine residue. Further, changing the X to proline is known to inhibit glycosylation.

In other embodiments of the invention, the iron binding is retained and the iron binding ability of Tf may be used to deliver a therapeutic protein or peptide(s) to the inside of a cell, across an epithelial or endothelial cell membrane and/or across the BBB. These embodiments that bind iron and/or the Tf receptor will often be engineered to reduce or prevent glycosylation to extend the serum half-life of the therapeutic protein. The N domain alone will not bind to TfR when loaded with iron, and the iron bound C domain will bind TfR but not with the same affinity as the whole molecule.

In another embodiment, the transferrin portion of the transferrin fusion protein includes a recombinant transferrin mutant having a mutation wherein the mutant does not retain the ability to bind metal ions. In an alternate embodiment, the transferrin portion of the transferrin fusion protein includes a recombinant transferrin mutant having a mutation wherein the mutant has a weaker binding avidity for metal ions than wild-type serum transferrin. In an alternate embodiment, the transferrin portion of the transferrin fusion protein includes a recombinant transferrin mutant having a mutation wherein the mutant has a stronger binding avidity for metal ions than wild-type serum transferrin.

In another embodiment, the transferrin portion of the transferrin fusion protein includes a recombinant transferrin mutant having a mutation wherein the mutant does not retain the ability to bind to the transferrin receptor. In an alternate embodiment, the transferrin portion of the transferrin fusion protein includes a recombinant transferrin mutant having a mutation wherein the mutant has a weaker binding avidity for the transferrin receptor than wild-type serum transferrin. In an alternate embodiment, the transferrin portion of the transferrin fusion protein includes a recombinant transferrin mutant having a mutation wherein the mutant has a stronger binding avidity for the transferrin receptor than wild-type serum transferrin.

In another embodiment, the transferrin portion of the transferrin fusion protein includes a recombinant transferrin mutant having a mutation wherein the mutant does not retain the ability to bind to carbonate ions. In an alternate embodiment, the transferrin portion of the transferrin fusion protein includes a recombinant transferrin mutant having a mutation wherein the mutant has a weaker binding avidity for carbonate ions than wild-type serum transferrin. In an alternate embodiment, the transferrin portion of the transferrin fusion protein includes a recombinant transferrin mutant having a mutation wherein the mutant has a stronger binding avidity for carbonate ions than wild-type serum transferrin.

In another embodiment, the transferrin portion of the transferrin fusion protein includes a recombinant human serum transferrin mutant having a mutation in at least one amino acid residue selected from the group consisting of Asp63, Gly65, Tyr95, Tyr188, His249, Asp392, Tyr426, Tyr514, Tyr517 and His585 of SEQ ID NO:3, wherein the mutant retains the ability to bind metal ions. In an alternate embodiment, a recombinant human serum transferrin mutant having a mutation in at least one amino acid residue selected from the group consisting of Asp63, Gly65, Tyr95, Tyr188, His249, Asp392, Tyr426, Tyr514, Tyr517 and His585 of SEQ ID NO:3, wherein the mutant has a reduced ability to bind metal ions. In another embodiment, a recombinant human serum transferrin mutant having a mutation in at least one amino acid residue selected from the group consisting of Asp63, Gly65, Tyr95, Tyr188, His249, Asp392, Tyr426, Tyr517 and His585 of SEQ ID NO:3, wherein the mutant does not retain the ability to bind metal ions.

In another embodiment, the transferrin portion of the transferrin fusion protein includes a recombinant human serum transferrin mutant having a mutation at Lys206 or His207 of SEQ ID NO:3, wherein the mutant has a stronger binding avidity for metal ions than wild-type human serum transferrin (see U.S. Pat. No. 5,986,067, which is herein incorporated by reference in its entirety). In an alternate embodiment, the transferrin portion of the transferrin fusion protein includes a recombinant human serum transferrin mutant having a mutation at Lys206 or His207 of SEQ ID NO:3, wherein the mutant has a weaker binding avidity for metal ions than wild-type human serum transferrin. In a further embodiment, the transferrin portion of the transferrin fusion protein includes a recombinant human serum transferrin mutant having a mutation at Lys206 or His207 of SEQ ID NO:3, wherein the mutant does not bind metal ions.

Any available technique may be used to make the fusion proteins of the invention, including but not limited to molecular techniques commonly available, for instance, those disclosed in Sambrook et al. Molecular Cloning: A Laboratory Manual, 2nd Ed., Cold Spring Harbor Laboratory Press, 1989. When carrying out nucleotide substitutions using techniques for accomplishing site-specific mutagenesis that are well known in the art, the encoded amino acid changes are preferably of a minor nature, that is, conservative amino acid substitutions, although other, non-conservative, substitutions are contemplated as well, particularly when producing a modified transferrin portion of a Tf fusion protein, e.g., a modified Tf fusion protein exhibiting reduced glycosylation, reduced iron binding and the like. Specifically contemplated are amino acid substitutions, small deletions or insertions, typically of one to about 30 amino acids; insertions between transferrin domains; small amino- or carboxyl-terminal extensions, such as an amino-terminal methionine residue, or small linker peptides of less than 50, 40, 30, 20 or 10 residues between transferrin domains or linking a transferrin protein and a therapeutic protein or peptide; or a small extension that facilitates purification, such as a poly-histidine tract, an antigenic epitope or a binding domain.

Examples of conservative amino acid substitutions are substitutions made within the same group such as within the group of basic amino acids (such as arginine, lysine, histidine), acidic amino acids (such as glutamic acid and aspartic acid), polar amino acids (such as glutamine and asparagine), hydrophobic amino acids (such as leucine, isoleucine, valine), aromatic amino acids (such as phenylalanine, tryptophan, tyrosine) and small amino acids (such as glycine, alanine, serine, threonine, methionine).

Non-conservative substitutions encompass substitutions of amino acids in one group by amino acids in another group. For example, a non-conservative substitution would include the substitution of a polar amino acid for a hydrophobic amino acid. For a general description of nucleotide substitution, see e.g. Ford et al. (1991), *Prot. Exp. Pur.* 2: 95-107. Non-conservative substitutions, deletions and insertions are particularly useful to produce TF fusion proteins of the invention that exhibit no or reduced binding of iron, no or reduced binding of the fusion protein to the Tf receptor.

In the polypeptide and proteins of the invention, the following system is followed for designating amino acids in accordance with the following conventional list:

TABLE OF AMINO ACIDS

| AMINO ACID | ONE-LETTER SYMBOL | THREE-LETTER SYMBOL |
|---|---|---|
| Alanine | A | Ala |
| Arginine | R | Arg |
| Asparagine | N | Asn |
| Aspartic Acid | D | Asp |
| Cysteine | C | Cys |
| Glutamine | Q | Gln |
| Glutamic Acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |

Iron binding and/or receptor binding may be reduced or disrupted by mutation, including deletion, substitution or insertion into, amino acid residues corresponding to one or more of Tf N domain residues Asp63, Tyr95, Tyr188, His249 and/or C domain residues Asp 392, Tyr 426, Tyr 514 and/or His 585 of SEQ ID NO: 3. Iron binding may also be affected by mutation to amino acids Lys206, His207 or Arg632 of SEQ ID NO: 3. Carbonate binding may be reduced or disrupted by mutation, including deletion, substitution or insertion into, amino acid residues corresponding to one or more of Tf N domain residues Thr120, Arg124, Ala126, Gly 127 and/or C domain residues Thr 452, Arg 456, Ala 458 and/or Gly 459 of SEQ ID NO: 3. A reduction or disruption of carbonate binding may adversely affect iron and/or receptor binding.

Binding to the Tf receptor may be reduced or disrupted by mutation, including deletion, substitution or insertion into, amino acid residues corresponding to one or more of Tf N domain residues described above for iron binding.

As discussed above, glycosylation may be reduced or prevented by mutation, including deletion, substitution or insertion into, amino acid residues corresponding to one or more of Tf C domain residues around the N-X-S/T sites corresponding to C domain residues N413 and/or N611 (See U.S. Pat. No. 5,986,067). For instance, the N413 and/or N611 may be mutated to Glu residues.

In instances where the Tf fusion proteins of the invention are not modified to prevent glycosylation, iron binding, carbonate binding and/or receptor binding, glycosylation, iron and/or carbonate ions may be stripped from or cleaved off of the fusion protein. For instance, available deglycosylases may be used to cleave glycosylation residues from the fusion protein, in particular the sugar residues attached to the Tf portion, yeast deficient in glycosylation enzymes may be used to prevent glycosylation and/or recombinant cells may be grown in the presence of an agent that prevents glycosylation, e.g., tunicamycin.

The carbohydrates on the fusion protein may also be reduced or completely removed enzymatically by treating the fusion protein with deglycosylases. Deglycosylases are well known in the art. Examples of deglycosylases include but are not limited to galactosidase, PNGase A, PNGase F, glucosidase, mannosidase, fucosidase, and Endo H deglycosylase.

Nevertheless, in certain circumstances, it may be preferable for oral delivery that the Tf portion of the fusion protein be fully glycosylated Additional mutations may be made with Tf to alter the three dimensional structure of Tf, such as modifications to the hinge region to prevent the conformational change needed for iron biding and Tf receptor recognition. For instance, mutations may be made in or around N domain amino acid residues 94-96, 245-247 and/or 316-318 as well as C domain amino acid residues 425-427, 581-582 and/or 652-658. In addition, mutations may be made in or around the flanking regions of these sites to alter Tf structure and function.

In one aspect of the invention, the transferrin fusion protein can function as a carrier protein to extend the half life or bioavailability of the therapeutic protein as well as, in some instances, delivering the therapeutic protein inside a cell and/or across the blood brain barrier. In an alternate embodiment, the transferrin fusion protein includes a modified transferrin molecule wherein the transferrin does not retain the ability to cross the blood brain barrier.

In another embodiment, the transferrin fusion protein includes a modified transferrin molecule wherein the transferrin molecule retains the ability to bind to the transferrin receptor and transport the therapeutic peptide inside cells. In an alternate embodiment, the transferrin fusion protein includes a modified transferrin molecule wherein the transferrin molecule does not retain the ability to bind to the transferrin receptor and transport the therapeutic peptide inside cells.

In further embodiments, the transferrin fusion protein includes a modified transferrin molecule wherein the transferrin molecule retains the ability to bind to the transferrin receptor and transport the therapeutic peptide inside cells and retains the ability to cross the blood brain barrier. In an alternate embodiment, the transferrin fusion protein includes a modified transferrin molecule wherein the transferrin molecule retains the ability to cross the blood brain barrier, but does not retain the ability to bind to the transferrin receptor and transport the therapeutic peptide inside cells.

Modified Transferrin Fusion Proteins

The fusion proteins of the invention may contain one or more copies of the therapeutic protein or polypeptide attached to the N-terminus and/or the C-terminus of the Tf protein. In some embodiments, the therapeutic protein or polypeptide is attached to both the N- and C-terminus of the Tf protein and the fusion protein may contain one or more equivalents of the therapeutic protein or polypeptide on either or both ends of Tf. In other embodiments, the therapeutic protein or polypeptide is inserted into known domains of the Tf protein, for instance, into one or more of the loops of Tf (see Ali et al. (1999) J. Biol. Chem. 274(34):24066-24073). In other embodiments, the therapeutic protein or therapeutic peptide is inserted between the N and C domains of Tf.

Generally, the transferrin fusion protein of the invention may have one modified transferrin-derived region and one therapeutic protein-derived region. Multiple regions of each protein, however, may be used to make a transferrin fusion protein of the invention. Similarly, more than one therapeutic protein may be used to make a transferrin fusion protein of the invention, thereby producing a multi-functional modified Tf fusion protein.

The present invention provides transferrin fusion protein containing a therapeutic protein or polypeptide or portion thereof fused to a transferrin molecule or portion thereof. In one embodiment, the transferrin fusion protein of the invention contains a therapeutic protein or polypeptide fused to the N terminus of a transferrin molecule. In an alternate embodiment, the transferrin fusion protein of the invention contains a therapeutic protein fused to the C terminus of a transferrin molecule. The present invention also provides transferrin fusion protein containing a therapeutic protein or polypeptide or protion thereof fused to a modified transferrin molecule or portion thereof.

In other embodiments, the transferrin fusion protein of the inventions contains a therapeutic protein fused to both the N-terminus and the C-terminus of modified transferrin. In another embodiment, the therapeutic proteins fused at the N- and C-termini are the same therapeutic proteins. In an alternate embodiment, the therapeutic proteins fused at the N- and C-termini are different therapeutic proteins. In another alternate embodiment, the therapeutic proteins fused to the N- and C-termini are different therapeutic proteins which may be used to treat or prevent the same disease, disorder, or condition. In another embodiment, the therapeutic proteins fused at the N- and C-termini are different therapeutic proteins which may be used to treat or prevent diseases or disorders which are known in the art to commonly occur in patients simultaneously.

In addition to modified transferrin fusion protein of the inventions in which the modified transferrin portion is fused to the N terminal and/or C-terminal of the therapeutic protein portion, transferrin fusion protein of the inventions of the invention may also be produced by inserting the therapeutic protein or peptide of interest (e.g., a therapeutic protein or peptide as disclosed herein, or, for instance, a single chain antibody that binds a therapeutic protein or a fragment or variant thereof) into an internal region of the modified transferrin. Internal regions of modified transferrin include, but are not limited to, the iron binding sites, the hinge regions, the bicarbonate binding sites, or the receptor binding domain.

Within the protein sequence of the modified transferrin molecule a number of loops or turns exist, which are stabilized by disulfide bonds. These loops are useful for the insertion, or internal fusion, of therapeutically active peptides, particularly those requiring a secondary structure to be functional, or therapeutic proteins to generate a modified transferrin molecule with specific biological activity.

When therapeutic proteins or peptides are inserted into or replace at least one loop of a Tf molecule, insertions may be made within any of the surface exposed loop regions, in addition to other areas of Tf. For instance, insertions may be made within the loops comprising Tf amino acids 32-33, 74-75, 256-257, 279-280 and 288-289 (Ali et al., supra) (See FIG. 3). As previously described, insertions may also be made within other regions of Tf such as the sites for iron and bicarbonate binding, hinge regions, and the receptor binding domain as described in more detail below. The loops in the Tf protein sequence that are amenable to modification/replacement for the insertion of proteins or peptides may also be used for the development of a screenable library of random peptide inserts. Any procedures may be used to produce nucleic acid inserts for the generation of peptide libraries, including available phage and bacterial display systems, prior to cloning into a Tf domain and/or fusion to the ends of Tf. In other embodiments, the library is made directly in or on the ends of a Tf peptide as described below.

The N-terminus of Tf is free and points away from the body of the molecule. Fusions of proteins or peptides on the N-terminus may therefore be a preferred embodiment. Such fusions may include a linker region, such as but not limited to a poly-glycine stretch, to separate the therapeutic protein or peptide from Tf. Attention to the junction between the leader sequence, the choice of leader sequence, and the structure of the mRNA by codon manipulation/optimization (no major stem loops to inhibit ribosome progress) will increase secretion and can be readily accomplished using standard recombinant protein techniques.

The C-terminus of Tf appears to be more buried and secured by a disulfide bond 6 amino acids from the C-terminus. In human Tf, the C-terminal amino acid is a proline which, depending on the way that it is orientated, will either point a fusion away or into the body of the molecule. A linker or spacer moiety at the C-terminus may be used in some embodiments of the invention. There is also a proline near the N-terminus. In one aspect of the invention, the proline at the N- and/or the C-termini may be changed out. In another aspect of the invention, the C-terminal disulfide bond may be eliminated to untether the C-terminus.

In yet other embodiments, small molecule therapeutics may be complexed with iron and loaded on a modified Tf protein fusion for delivery to the inside of cells and across the BBB. The addition of a targeting peptide or, for example, a single chain antibody (SCA) can be used to target the payload to a particular cell type, e.g., a cancer cell.

Nucleic Acids

Nucleic acid molecules are also provided by the present invention. These encode a modified Tf fusion protein comprising a transferrin protein or a portion of a transferrin protein covalently linked or joined to a therapeutic protein. As discussed in more detail below, any therapeutic protein may be used. The fusion protein may further comprise a linker region, for instance a linker less than about 50, 40, 30, 20, or 10 amino acid residues. The linker can be covalently linked to and between the transferrin protein or portion thereof and the therapeutic protein. Nucleic acid molecules of the invention may be purified or not.

Host cells and vectors for replicating the nucleic acid molecules and for expressing the encoded fusion proteins are also provided. Any vectors or host cells may be used, whether prokaryotic or eukaryotic, but eukaryotic expression systems, in particular yeast expression systems, may be preferred. Many vectors and host cells are known in the art for such purposes. It is well within the skill of the art to select an appropriate set for the desired application.

DNA sequences encoding transferrin, portions of transferrin and therapeutic proteins of interest may be cloned from a variety of genomic or cDNA libraries known in the art. The techniques for isolating such DNA sequences using probe-based methods are conventional techniques and are well known to those skilled in the art. Probes for isolating such DNA sequences may be based on published DNA or protein sequences (see, for example, Baldwin, G. S. (1993) Comparison of Transferrin Sequences from Different Species. Comp. Biochem. Physiol. 106B/1:203-218 and all references cited therein, which are hereby incorporated by reference in their entirety). Alternatively, the polymerase chain reaction (PCR) method disclosed by Mullis et al. (U.S. Pat. No. 4,683,195) and Mullis (U.S. Pat. No. 4,683,202), incorporated herein by reference may be used. The choice of library and selection of probes for the isolation of such DNA sequences is within the level of ordinary skill in the art.

As known in the art, "similarity" between two polynucleotides or polypeptides is determined by comparing the nucleotide or amino acid sequence and its conserved nucleotide or amino acid substitutes of one polynucleotide or polypeptide to the sequence of a second polynucleotide or polypeptide. Also known in the art is "identity" which means the degree of sequence relatedness between two polypeptide or two polynucleotide sequences as determined by the identity of the match between two strings of such sequences. Both identity and similarity can be readily calculated (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991).

While there exist a number of methods to measure identity and similarity between two polynucleotide or polypeptide sequences, the terms "identity" and "similarity" are well known to skilled artisans (Sequence Analysis in Molecular Biology, von Heinje, G., Academic Press, 1987; Sequence Analysis Primer, Gribskov, M. and Devereux, J., eds., M Stockton Press, New York, 1991; and Carillo, H., and Lipman, D., SIAM J. Applied Math., 48: 1073 (1988). Methods commonly employed to determine identity or similarity between two sequences include, but are not limited to those, disclosed in Guide to Huge Computers, Martin J. Bishop, ed., Academic Press, San Diego, 1994, and Carillo, H., and Lipman, D., SIAM J. Applied Math. 48:1073 (1988).

Preferred methods to determine identity are designed to give the largest match between the two sequences tested. Methods to determine identity and similarity are codified in computer programs. Preferred computer program methods to determine identity and similarity between two sequences include, but are not limited to, GCG program package (Devereux, et al., Nucl. Acid Res. 12(1):387 (1984)), BLASTP, BLASTN, FASTA (Atschul, et al., J. Mol. Biol. 215:403 (1990)). The degree of similarity or identity referred to above is determined as the degree of identity between the two sequences, often indicating a derivation of the first sequence from the second. The degree of identity between two nucleic acid sequences may be determined by means of computer programs known in the art such as GAP provided in the GCG program package (Needleman and Wunsch J. Mol. Biol. 48:443-453 (1970)). For purposes of determining the degree of identity between two nucleic acid sequences for the present invention, GAP is used with the following settings: GAP creation penalty of 5.0 and GAP extension penalty of 0.3.

Codon Optimization

The degeneracy of the genetic code permits variations of the nucleotide sequence of a transferrin protein and/or therapeutic protein of interest, while still producing a polypeptide having the identical amino acid sequence as the polypeptide encoded by the native DNA sequence. The procedure, known as "codon optimization" (described in U.S. Pat. No. 5,547,871 which is incorporated herein by reference in its entirety) provides one with a means of designing such an altered DNA sequence. The design of codon optimized genes should take into account a variety of factors, including the frequency of codon usage in an organism, nearest neighbor frequencies, RNA stability, the potential for secondary structure formation, the route of synthesis and the intended future DNA manipulations of that gene. In particular, available methods may be used to alter the codons encoding a given fusion protein with those most readily recognized by yeast when yeast expression systems are used.

The degeneracy of the genetic code permits the same amino acid sequence to be encoded and translated in many different ways. For example, leucine, serine and arginine are each encoded by six different codons, while valine, proline, threonine, alanine and glycine are each encoded by four different codons. However, the frequency of use of such synonymous codons varies from genome to genome among eukaryotes and prokaryotes. For example, synonymous codon-choice patterns among mammals are very similar, while evolutionarily distant organisms such as yeast (such as *S. cerevisiae*), bacteria (such as *E. coli*) and insects (such as *D. melanogaster*) reveal a clearly different pattern of genomic codon use frequencies (Grantham, R., et al., Nucl. Acid Res., 8, 49-62 (1980); Grantham, R., et al., Nucl. Acid Res., 9, 43-74 (1981); Maroyama, T., et al., Nucl. Acid Res., 14, 151-197 (1986); Aota, S., et al., Nucl. Acid Res., 16, 315-402 (1988); Wada, K., et al., Nucl. Acid Res., 19 Supp., 1981-1985 (1991); Kurland, C. G., FEBS Lett., 285, 165-169 (1991)). These differences in codon-choice patterns appear to contribute to the overall expression levels of individual genes by modulating peptide elongation rates. (Kurland, C. G., FEBS Lett., 285, 165-169 (1991); Pedersen, S., EMBO J., 3, 2895-2898 (1984); Sorensen, M. A., J. Mol. Biol., 207, 365-377 (1989); Randall, L. L., et al., Eur. J. Biochem., 107, 375-379 (1980); Curran, J. F., and Yarus, M., J. Mol. Biol., 209, 65-77 (1989); Varenne, S., et al., J. Mol. Biol., 180, 549-576 (1984), Varenne, S., et al., J. Mol, Biol., 180, 549-576 (1984); Garel, J.-P., J. Theor. Biol., 43, 211-225 (1974); Ikemura, T., J. Mol. Biol., 146, 1-21 (1981); Ikemura, T., J. Mol. Biol., 151, 389-409 (1981)).

The preferred codon usage frequencies for a synthetic gene should reflect the codon usages of nuclear genes derived from the exact (or as closely related as possible) genome of the cell/organism that is intended to be used for recombinant protein expression, particularly that of yeast species. As discussed above, in one preferred embodiment the human Tf sequence is codon optimized, before or after modification as herein described for yeast expression as may be the therapeutic protein nucleotide sequence(s).

Vectors

Expression units for use in the present invention will generally comprise the following elements, operably linked in a 5' to 3' orientation: a transcriptional promoter, a secretory signal sequence, a DNA sequence encoding a modified Tf fusion protein comprising transferrin protein or a portion of a transferrin protein joined to a DNA sequence encoding a therapeutic protein or peptide of interest and a transcriptional terminator. As discussed above, any arrangement of the therapeutic protein or peptide fused to or within the Tf portion may be used in the vectors of the invention. The selection of suitable promoters, signal sequences and terminators will be determined by the selected host cell and will be evident to one skilled in the art and are discussed more specifically below.

Suitable yeast vectors for use in the present invention are described in U.S. Pat. No. 6,291,212 and include YRp7 (Struhl et al., Proc. Natl. Acad. Sci. USA 76: 1035-1039, 1978), YEp13 (Broach et al., Gene 8: 121-133, 1979), pJDB249 and pJDB219 (Beggs, Nature 275:104-108, 1978), pPPC0005, pSeCHSA, pScNHSA, pC4 and derivatives thereof. Useful yeast plasmid vectors also include pRS403-406, pRS413-416 and the *Pichia* vectors available from Stratagene Cloning Systems, La Jolla, Calif. 92037, USA. Plasmids pRS403, pRS404, pRS405 and pRS406 are Yeast Integrating plasmids (YIps) and incorporate the yeast selectable markers HIS3, TRP1, LEU2 and URA3. Plasmids pRS413-41.6 are Yeast Centromere plasmids (YCps).

Such vectors will generally include a selectable marker, which may be one of any number of genes that exhibit a dominant phenotype for which a phenotypic assay exists to enable transformants to be selected. Preferred selectable markers are those that complement host cell auxotrophy, provide antibiotic resistance or enable a cell to utilize specific carbon sources, and include LEU2 (Broach et al. ibid.), URA3 (Botstein et al., Gene 8: 17, 1979), HIS3 (Struhl et al., ibid.) or POT1 (Kawasaki and Bell, EP 171,142). Other suitable selectable markers include the CAT gene, which confers chloramphenicol resistance on yeast cells. Preferred promoters for use in yeast include promoters from yeast glycolytic genes (Hitzeman et al., J Biol. Chem. 225: 12073-12080, 1980; Alber and Kawasaki, J. Mol. Appl. Genet. 1: 419-434, 1982; Kawasaki, U.S. Pat. No. 4,599,311) or alcohol dehydrogenase genes (Young et al., in Genetic Engineering of Microorganisms for Chemicals, Hollaender et al., (eds.), p. 355, Plenum, N.Y., 1982; Ammerer, Meth. Enzymol. 101: 192-201, 1983). In this regard, particularly preferred promoters are the TPI1 promoter (Kawasaki, U.S. Pat. No. 4,599, 311) and the ADH2-4$^C$ (see U.S. Pat. No. 6,291,212 promoter (Russell et al., Nature 304: 652-654, 1983). The expression units may also include a transcriptional terminator. A preferred transcriptional terminator is the TPI1 terminator (Alber and Kawasaki, ibid.). Other preferred vectors and preferred components such as promoters and terminators of a yeast expression system are disclosed in European Patents EP 0258067, EP 0286424, EP0317254, EP 0387319, EP 0386222, EP 0424117, EP 0431880, and EP 1002095; European Patent Publications EP 0828759, EP 0764209, EP 0749478, and EP 0889949; PCT Publication WO 00/44772 and WO 94/04687; and U.S. Pat. Nos. 5,739,007; 5,637,504; 5,302,697; 5,260,202; 5,667,986; 5,728,553; 5,783,423; 5,965,386; 6150,133; 6,379,924; and 5,714,377; which are herein incorporated by reference in their entirety.

In addition to yeast, modified fusion proteins of the present invention can be expressed in filamentous fungi, for example, strains of the fungi Aspergillus. Examples of useful promoters include those derived from *Aspergillus nidulans* glycolytic genes, such as the adh3 promoter (McKnight et al., EMBO J. 4: 2093-2099, 1985) and the tpiA promoter. An example of a suitable terminator is the adh3 terminator (McKnight et al., ibid.). The expression units utilizing such components may be cloned into vectors that are capable of insertion into the chromosomal DNA of *Aspergillus*, for example.

Mammalian expression vectors for use in carrying out the present invention will include a promoter capable of directing the transcription of the modified Tf fusion protein. Preferred promoters include viral promoters and cellular promoters. Preferred viral promoters include the major late promoter from adenovirus 2 (Kaufman and Sharp, Mol. Cell. Biol. 2: 1304-13199, 1982) and the SV40 promoter (Subramani et al., Mol. Cell. Biol. 1: 854-864, 1981). Preferred cellular promoters include the mouse metallothionein 1 promoter (Palmiter et al., Science 222: 809-814, 1983) and a mouse Vκ (see U.S. Pat. No. 6,291,212) promoter (Grant et al., Nuc. Acids Res. 15: 5496, 1987). A particularly preferred promoter is a mouse $V_H$ (see U.S. Pat. No. 6,291,212) promoter (Loh et al., ibid.). Such expression vectors may also contain a set of RNA splice sites located downstream from the promoter and upstream from the DNA sequence encoding the transferrin fusion protein. Preferred RNA splice sites may be obtained from adenovirus and/or immunoglobulin genes.

Also contained in the expression vectors is a polyadenylation signal located downstream of the coding sequence of interest. Polyadenylation signals include the early or late polyadenylation signals from SV40 (Kaufman and Sharp, ibid.), the polyadenylation signal from the adenovirus 5 E1B region and the human growth hormone gene terminator (De-Noto et al., Nucl. Acid Res. 9: 3719-3730, 1981). A particularly preferred polyadenylation signal is the $V_H$ (see U.S. Pat. No. 6,291,212) gene terminator (Loh et al., ibid.). The expression vectors may include a noncoding viral leader sequence, such as the adenovirus 2 tripartite leader, located between the promoter and the RNA splice sites. Preferred vectors may also include enhancer sequences, such as the SV40 enhancer and the mouse (see U.S. Pat. No. 6,291,212) enhancer (Gillies, Cell 33: 717-728, 1983). Expression vectors may also include sequences encoding the adenovirus VA RNAs.

Transformation

Techniques for transforming fungi are well known in the literature, and have been described, for instance, by Beggs (ibid.), Hinnen et al. (Proc. Natl. Acad. Sci. USA 75: 1929-1933, 1978), Yelton et al., (Proc. Natl. Acad. Sci. USA 81: 1740-1747, 1984), and Russell (Nature 301: 167-169, 1983). Other techniques for introducing cloned DNA sequences into fungal cells, such as electroporation (Becker and Guarente, Methods in Enzymol. 194: 182-187, 1991) may be used. The genotype of the host cell will generally contain a genetic defect that is complemented by the selectable marker present on the expression vector. Choice of a particular host and selectable marker is well within the level of ordinary skill in the art.

Cloned DNA sequences comprising modified Tf fusion proteins of the invention may be introduced into cultured mammalian cells by, for example, calcium phosphate-mediated transfection (Wigler et al., Cell 14: 725, 1978; Corsaro and Pearson, Somatic Cell Genetics 7: 603, 1981; Graham and Van der Eb, Virology 52: 456, 1973.) Other techniques for introducing cloned DNA sequences into mammalian cells, such as electroporation (Neumann et al., EMBO J. 1: 841-845, 1982), or lipofection may also be used. In order to identify cells that have integrated the cloned DNA, a selectable marker is generally introduced into the cells along with the gene or cDNA of interest. Preferred selectable markers for use in cultured mammalian cells include genes that confer resistance to drugs, such as neomycin, hygromycin, and methotrexate. The selectable marker may be an amplifiable selectable marker. A preferred amplifiable selectable marker is the DHFR gene. A particularly preferred amplifiable marker is the DHFR$^r$ (see U.S. Pat. No. 6,291,212) cDNA (Simonsen and Levinson, Proc. Natl. Acad. Sci. USA 80: 2495-2499, 1983). Selectable markers are reviewed by Thilly (Mammalian Cell Technology, Butterworth Publishers, Stoneham, Mass.) and the choice of selectable markers is well within the level of ordinary skill in the art.

Host Cells

The present invention also includes a cell, preferably a yeast cell transformed to express a modified transferrin fusion protein of the invention. In addition to the transformed host cells themselves, the present invention also includes a culture of those cells, preferably a monoclonal (clonally homogeneous) culture, or a culture derived from a monoclonal culture, in a nutrient medium. If the polypeptide is secreted, the medium will contain the polypeptide, with the cells, or without the cells if they have been filtered or centrifuged away. Host cells for use in practicing the present invention include eukaryotic cells, and in some cases prokaryotic cells, capable of being transformed or transfected with exogenous DNA and grown in culture, such as cultured mammalian, insect, fungal, plant and bacterial cells.

Fungal cells, including species of yeast (e.g., *Saccharomyces* spp., *Schizosaccharomyces* spp., *Pichia* spp.) may be used as host cells within the present invention. Examples of fungi including yeasts contemplated to be useful in the practice, of the present invention as hosts for expressing the transferrin fusion protein of the inventions are *Pichia* (some species of which were formerly classified as *Hansenula*), *Saccharomyces, Kluyveromyces spergillus, Candida, Torulopsis, Torulaspora, Schizosaccharomyces, Citeromyces, Pachysolen, Zygosaccharomyces, Debaromyces, Trichoderma, Cephalosporium, Humicola, Mucor, Neurospora, Yarrowia, Metschunikowia, Rhodosporidium, Leucosporidiunz, Botryoascus, Sporidiobolus, Endomycopsis*, and the like. Examples of *Saccharomyces* spp. are *S. cerevisiae, S. italicus* and *S. rouxii*. Examples of *Kluyveromyces* spp. are *K. fragilis, K. lactis* and *K. marxianus*. A suitable *Torulaspora* species is *T. delbrueckii*. Examples of *Pichia* spp. are *P. angusta* (formerly *H. polymorpha*), *P. anomala* (formerly *H. anomala*) and *P. pastoris*.

Particularly useful host cells to produce the Tf fusion proteins of the invention are the methylotrophic *Pichia pastoris* (Steinlein et al. (1995) *Protein Express. Purif.* 6:619-624). *Pichia pastoris* has been developed to be an outstanding host for the production of foreign proteins since its alcohol oxidase promoter was isolated and cloned; its transformation was first reported in 1985. *P. pastoris* can utilize methanol as a carbon source in the absence of glucose. The *P. pastoris* expression system can use the methanol-induced alcohol oxidase (AOX1) promoter, which controls the gene that codes for the expression of alcohol oxidase, the enzyme which catalyzes the first step in the metabolism of methanol. This promoter has been characterized and incorporated into a series of *P. pastoris* expression vectors. Since the proteins produced in *P. pastoris* are typically folded correctly and secreted into the medium, the fermentation of genetically engineered *P. pastoris* provides an excellent alternative to *E. coli* expression systems. A number of proteins have been produced using this system, including tetanus toxin fragment, *Bordatella pertussis* pertactin, human serum albumin and lysozyme.

Strains of the yeast *Saccharomyces cerevisiae* are another preferred host. In a preferred embodiment, a yeast cell, or more specifically, a *Saccharomyces cerevisiae* host cell that contains a genetic deficiency in a gene required for asparagine-linked glycosylation of glycoproteins is used. *S. cerevisiae* host cells having such defects may be prepared using standard techniques of mutation and selection, although many available yeast strains have been modified to prevent or reduce glycosylation or hypermannosylation. Ballou et al. (J. Biol. Chem. 255: 5986-5991, 1980) have described the isolation of mannoprotein biosynthesis mutants that are defective in genes which affect asparagine-linked glycosylation. Gentzsch and Tanner (Glycobiology 7:481-486, 1997) have described a family of at least six genes (PMT1-6) encoding enzymes responsible for the first step in O-glycosylation of proteins in yeast. Mutants defective in one or more of these genes show reduced O-linked glycosylation and/or altered specificity of O-glycosylation.

To optimize production of the heterologous proteins, it is also preferred that the host strain carries a mutation, such as the *S. cerevisiae* pep4 mutation (Jones, Genetics 85: 23-33, 1977), which results in reduced proteolytic activity. Host strains containing mutations in other protease encoding regions are particularly useful to produce large quantities of the Tf fusion proteins of the invention.

Host cells containing DNA constructs of the present invention are grown in an appropriate growth medium. As used herein, the term "appropriate growth medium" means a medium containing nutrients required for the growth of cells. Nutrients required for cell growth may include a carbon source, a nitrogen source, essential amino acids, vitamins, minerals and growth factors. The growth medium will generally select for cells containing the DNA construct by, for example, drug selection or deficiency in an essential nutrient which is complemented by the selectable marker on the DNA construct or co-transfected with the DNA construct. Yeast cells, for example, are preferably grown in a chemically defined medium, comprising a carbon source, e.g. sucrose, a non-amino acid nitrogen source, inorganic salts, vitamins and essential amino acid supplements. The pH of the medium is preferably maintained at a pH greater than 2 and less than 8, preferably at pH 5.5-6.5. Methods for maintaining a stable pH include buffering and constant pH control. Preferred buffering agents include succinic acid and Bis-Tris (Sigma Chemical Co., St. Louis, Mo.). Yeast cells having a defect in a gene required for asparagine-linked glycosylation are preferably grown in a medium containing an osmotic stabilizer. A preferred osmotic stabilizer is sorbitol supplemented into the medium at a concentration between 0.1 M and 1.5 M., preferably at 0.5 M or 1.0 M.

Cultured mammalian cells are generally grown in commercially available serum-containing or serum-free media. Selection of a medium appropriate for the particular cell line used is within the level of ordinary skill in the art. Transfected mammalian cells are allowed to grow for a period of time, typically 1-2 days, to begin expressing the DNA sequence(s) of interest. Drug selection is then applied to select for growth of cells that are expressing the selectable marker in a stable fashion. For cells that have been transfected with an amplifiable selectable marker the drug concentration may be increased in a stepwise manner to select for increased copy number of the cloned sequences, thereby increasing expression levels.

Baculovirus/insect cell expression systems may also be used to produce the modified Tf fusion proteins of the invention. The BacPAK™ Baculovirus Expression System (BD Biosciences (Clontech)) expresses recombinant proteins at high levels in insect host cells. The target gene is inserted into a transfer vector, which is cotransfected into insect host cells with the linearized BacPAK6 viral DNA. The BacPAK6 DNA is missing an essential portion of the baculovirus genome. When the DNA recombines with the vector, the essential element is restored and the target gene is transferred to the baculovirus genome. Following recombination, a few viral plaques are picked and purified, and the recombinant phenotype is verified. The newly isolated recombinant virus can then be amplified and used to infect insect cell cultures to produce large amounts of the desired protein.

Tf fusion proteins of the present invention may also be produced using transgenic plants and animals. For example, sheep and goats can make the therapeutic protein in their milk. Or tobacco plants can include the protein in their leaves. Both transgenic plant and animal production of proteins comprises adding a new gene coding the fusion protein into the genome of the organism. Not only can the transgenic organism produce a new protein, but it can also pass this ability onto its offspring.

Secretory Signal Sequences

The terms "secretory signal sequence" or "signal sequence" or "secretion leader sequence" are used interchangeably and are described, for example in U.S. Pat. No. 6,291,212 and U.S. Pat. No. 5,547,871, both of which are herein incorporated by reference in their entirety. Secretory signal sequences or signal sequences or secretion leader sequences encode secretory peptides. A secretory peptide is an amino acid sequence that acts to direct the secretion of a mature polypeptide or protein from a cell. Secretory peptides are generally characterized by a core of hydrophobic amino acids and are typically (but not exclusively) found at the amino termini of newly synthesized proteins. Very often the secretory peptide is cleaved from the mature protein during secretion. Secretory peptides may contain processing sites that allow cleavage of the signal peptide from the mature protein as it passes through the secretory pathway. Processing sites may be encoded within the signal peptide or may be added to the signal peptide by, for example, in vitro mutagenesis.

Secretory peptides may be used to direct the secretion of modified Tf fusion proteins of the invention. One such secretory peptide that may be used in combination with other secretory peptides is the alpha mating factor leader sequence. Secretory signal sequences or signal sequences or secretion leader sequences are required for a complex series of post-translational processing steps which result in secretion of a protein. If an intact signal sequence is present, the protein being expressed enters the lumen of the rough endoplasmic reticulum and is then transported through the Golgi apparatus to secretory vesicles and is finally transported out of the cell. Generally, the signal sequence immediately follows the initiation codon and encodes a signal peptide at the amino-terminal end of the protein to be secreted. In most cases, the signal sequence is cleaved off by a specific protease, called a signal peptidase. Preferred signal sequences improve the processing and export efficiency of recombinant protein expression using viral, mammalian or yeast expression vectors. In some cases, the native Tf signal sequence may be used to express and secrete fusion proteins of the invention.

Linkers

The Tf moiety and therapeutic protein moiety(s) of the modified transferrin fusion proteins of the invention can be fused directly or using a linker peptide of various lengths to provide greater physical separation and allow more spatial mobility between the fused proteins and thus maximize the accessibility of the therapeutic protein portion, for instance, for binding to its cognate receptor. The linker peptide may consist of amino acids that are flexible or more rigid. For example, a linker such as but not limited to a poly-glycine stretch. The linker can be less than about 50, 40, 30, 20, or 10 amino acid residues. The linker can be covalently linked to and between the transferrin protein or portion thereof and the therapeutic protein.

Detection of Tf Fusion Proteins

Assays for detection of biologically active modified transferrin-therapeutic protein fusions may include Western transfer, protein blot or colony filter as well as activity based assays that detect the fused therapeutic protein. A Western transfer filter may be prepared using the method described by Towbin et al. (*Proc. Natl. Acad. Sci. USA* 76: 4350-4354, 1979). Briefly, samples are electrophoresed in a sodium dodecylsulfate polyacrylamide gel. The proteins in the gel are electrophoretically transferred to nitrocellulose paper. Protein blot filters may be prepared by filtering supernatant samples or concentrates through nitrocellulose filters using, for example, a Minifold (Schleicher & Schuell, Keene, N. H.). Colony filters may be prepared by growing colonies on a nitrocellulose filter that has been laid across an appropriate growth medium. In this method, a solid medium is preferred. The cells are allowed to grow on the filters for at least 12 hours. The cells are removed from the filters by washing with an appropriate buffer that does not remove the proteins bound to the filters. A preferred buffer comprises 25 mM Tris-base, 19 mM glycine, pH 8.3, 20% methanol.

Fusion proteins of the invention may also be detected by assaying for the activity of the therapeutic protein moiety. Such assays are readily available, including but not limited to, those assays described in Table 1. Specifically, transferrin fusion proteins of the invention may be assayed for functional activity (e.g., biological activity or therapeutic activity) using the assay referenced in the "Exemplary Activity Assay" column of Table 1. Additionally, one of skill in the art may routinely assay fragments of a therapeutic protein corresponding to a therapeutic protein portion of a fusion protein of the invention, for activity using assays referenced in its corresponding row of Table 1. Further, one of skill in the art may routinely assay fragments of a modified transferrin protein for activity using assays known in the art.

For example, in one embodiment where one is assaying for the ability of a transferrin fusion protein of the invention to bind or compete with a therapeutic protein for binding to an anti-therapeutic polypeptide antibody and/or anti-transferrin antibody, various immunoassays known in the art can be used, including but not limited to, competitive and non-competitive assay systems using techniques such as radioimmunoassays, ELISA (enzyme linked immunosorbent assay), sandwich immunoassays, immunoradiometric assays, gel diffusion precipitation reactions, immunodiffusion assays, in situ immunoassays (using colloidal gold, enzyme or radio-isotope labels, for example), western blots, precipitation reactions, agglutination assays (e.g., gel agglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention.

In a further embodiment, where a binding partner (e.g., a receptor or a ligand) of a therapeutic protein is identified, binding to that binding partner by a transferrin fusion protein containing that therapeutic protein as the therapeutic protein portion of the fusion can be assayed, e.g., by means well-known in the art, such as, for example, reducing and non-reducing gel chromatography, protein affinity chromatography, and affinity blotting. Other methods will be known to the skilled artisan and are within the scope of the invention.

Isolation/Purification of Modified Transferrin Fusion Proteins

Secreted, biologically active, modified transferrin fusion proteins may be isolated from the medium of host cells grown under conditions that allow the secretion of the biologically active fusion proteins. The cell material is removed from the culture medium, and the biologically active fusion proteins are isolated using isolation techniques known in the art. Suitable isolation techniques include precipitation and fractionation by a variety of chromatographic methods, including gel filtration, ion exchange chromatography and affinity chromatography.

A particularly preferred purification method is affinity chromatography on an iron binding or metal chelating column or an immunoaffinity chromatography using an antibody directed against the transferrin or therapeutic protein or peptide portion of the polypeptide fusion. The antibody is preferably immobilized or attached to a solid support or substrate. A particularly preferred substrate is CNBr-activated Sepharose (Pharmacia LKB Technologies, Inc., Piscataway, N.J.). By this method, the medium is combined with the antibody/substrate under conditions that will allow binding to occur. The complex may be washed to remove unbound material, and the transferrin fusion protein is released or eluted through the use of conditions unfavorable to complex formation. Particularly useful methods of elution include changes in pH, wherein the immobilized antibody has a high affinity for the ligand at a first pH and a reduced affinity at a second (higher or lower) pH; changes in concentration of certain chaotropic agents; or through the use of detergents.

Labeled Modified Transferrin Fusion Proteins

Transferrin fusion proteins of the present invention may also be labeled with a radioisotope or other imaging agent and used for in vivo diagnostic purposes. Preferred radioisotope imaging agents include iodine-125 and technetium-99, with technetium-99 being particularly preferred. Methods for producing protein-isotope conjugates are well known in the art, and are described by, for example, Eckelman et al. (U.S. Pat. No. 4,652,440), Parker et al. (WO 87/05030) and Wilber et al. (EP 203,764). Alternatively, the transferrin fusion proteins may be bound to spin label enhancers and used for magnetic resonance (MR) imaging. Suitable spin label enhancers include stable, sterically hindered, free radical compounds such as nitroxides. Methods for labeling ligands for MR imaging are disclosed by, for example, Coffman et al. (U.S. Pat. No. 4,656,026). For administration, the labeled transferrin fusion proteins are combined with a pharmaceutically acceptable carrier or diluent, such as sterile saline or sterile water. Administration is preferably by bolus injection, preferably intravenously.

Production of Fusion Proteins

The present invention further provides methods for producing a modified fusion protein of the invention using nucleic acid molecules herein described. In general terms, the production of a recombinant form of a protein typically involves the following steps.

A nucleic acid molecule is first obtained that encodes a transferrin fusion protein of the invention. The nucleic acid molecule is then preferably placed in operable linkage with suitable control sequences, as described above, to form an expression unit containing the protein open reading frame. The expression unit is used to transform a suitable host and the transformed host is cultured under conditions that allow the production of the recombinant protein. Optionally the recombinant protein is isolated from the medium or from the cells; recovery and purification of the protein may not be necessary in some instances where some impurities may be tolerated.

Each of the foregoing steps can be accomplished in a variety of ways. For example, the construction of expression vectors that are operable in a variety of hosts is accomplished using appropriate replicons and control sequences, as set forth above. The control sequences, expression vectors, and transformation methods are dependent on the type of host cell used to express the gene and were discussed in detail earlier and are otherwise known to persons skilled in the art. Suitable restriction sites can, if not normally available, be added to the ends of the coding sequence so as to provide an excisable gene to insert into these vectors. A skilled artisan can readily adapt any host/expression system known in the art for use with the nucleic acid molecules of the invention to produce a desired recombinant protein.

As discussed above, any expression system may be used, including yeast, bacterial, animal, plant, eukaryotic and prokaryotic systems. In some embodiments, yeast, mammalian cell culture and transgenic animal or plant production systems are preferred. In other embodiments, yeast systems that have been modified to reduce native yeast glycosylation, hyper-glycosylation or proteolytic activity may be used.

Therapeutic Molecules

Any therapeutic molecule may be used as the fusion partner to Tf according to the methods and compositions of the present invention. As used herein, a therapeutic molecule is typically a protein or peptide capable of exerting a beneficial biological effect in vitro or in vivo and includes proteins or peptides that exert a beneficial effect in relation to normal homeostasis, physiology or a disease state. Therapeutic molecules do not include, fusion partners commonly used as markers or protein purification aids, such as bacterial galactosidases (see for example, U.S. Pat. No. 5,986,067 and Aldred et al. (1984) *Biochem. Biophys. Res. Commun.* 122: 960-965). For instance, a beneficial effect as related to a disease state includes any effect that is advantageous to the treated subject, including disease prevention, disease stabilization, the lessening or alleviation of disease symptoms or a modulation, alleviation or cure of the underlying defect to produce an effect beneficial to the treated subject.

A modified transferrin fusion protein of the invention includes at least a fragment or variant of a therapeutic protein and at least a fragment or variant of modified serum transferrin, which are associated with one another, preferably by genetic fusion.

In one embodiment, the transferrin fusion protein includes a modified transferrin molecule linked to a neuropharmaceutical agent. In another embodiment, the modified transferrin fusion protein includes transferrin at the carboxyl terminus linked to a neuropharmaceutical agent at the amino terminus. In an alternate embodiment, the modified transferrin fusion protein includes transferrin at the amino terminus linked to a neuropharmaceutical agent at the carboxy terminus. In specific embodiments, the neuropharmaceutical agent is either nerve growth factor or ciliary neurotrophic factor.

In further embodiments, a modified transferrin fusion protein of the invention may contain at least a fragment or variant of a therapeutic protein, and/or at least a fragment or variant of an antibody. In a further embodiment, the transferrin fusion proteins can contain peptide fragments or peptide variants of proteins or antibodies wherein the variant or fragment retains at least one biological or therapeutic activity. The transferrin fusion proteins can contain therapeutic proteins that can be peptide fragments or peptide variants at least about 4, at least 5, at least 6, at least 7, at least 8, at least 9, at least 10, at least 11, at least 12, at least 13, at least 14, at least 15, at least 20, at least 25, at least 30, at least 35, or at least about 40, at least about 50, at least about 55, at least about 60 or at least about 70 or more amino acids in length fused to the N and/or C termini, inserted within, or inserted into a loop of a modified transferrin.

In another embodiment, the modified transferrin fusion molecules contain a therapeutic protein portion that can be fragments of a therapeutic protein that include the full length protein as well as polypeptides having one or more residues deleted from the amino terminus of the amino acid sequence.

In another embodiment, the modified transferrin fusion molecules contain a therapeutic protein portion that can be fragments of a therapeutic protein that include the full length protein as well as polypeptides having one or more residues deleted from the carboxy terminus of the amino acid sequence.

In another embodiment, the modified transferrin fusion molecules contain a therapeutic protein portion that can have one or more amino acids deleted from both the amino and the carboxy termini.

In another embodiment, the modified transferrin fusion molecules contain a therapeutic protein portion that is at least about 80%, 85%, 90%, 95%, 96%, 97%, 98% or 99% identical to a reference therapeutic protein set forth herein, or fragments thereof. In further embodiments, the transferrin fusion molecules contain a therapeutic protein portion that is at least about 80%, 85%, 90%, 95%, 96%, 97%, 98% or 99% identical to reference polypeptides having the amino acid sequence of N- and C-terminal deletions as described above.

In another embodiment, the modified transferrin fusion molecules contain the therapeutic protein portion that is at least about 80%, 85%, 90%, 95%, 96%, 97%, 98%, 99% or 100%, identical to, for example, the native or wild-type amino acid sequence of a therapeutic protein. Fragments, of these polypeptides are also provided.

The therapeutic proteins corresponding to a therapeutic protein portion of a modified transferrin fusion protein of the invention, such as cell surface and secretory proteins, can be modified by the attachment of one or more oligosaccharide groups. The modification referred to as glycosylation can significantly affect the physical properties of proteins and can be important in protein stability, secretion, and localization. Glycosylation occurs at specific locations along the polypeptide backbone. There are usually two major types of glycosylation: glycosylation characterized by O-linked oligosaccharides, which are attached to serine or threonine residues; and glycosylation characterized by N-linked oligosaccharides, which are attached to asparagine residues in an Asn-X-Ser/Thr sequence, where X can be an amino acid except proline. Variables such as protein structure and cell type influence the number and nature of the carbohydrate units within the chains at different glycosylation sites. Glycosylation isomers are also common at the same site within a given cell type. For example, several types of human interferon are glycosylated.

Therapeutic proteins corresponding to a therapeutic protein portion of a transferrin fusion protein of the invention, as well as analogs and variants thereof, may be modified so that glycosylation at one or more sites is altered as a result of manipulation(s) of their nucleic acid sequence by the host cell in which they are expressed, or due to other conditions of their expression. For example, glycosylation isomers may be produced by abolishing or introducing glycosylation sites, e.g., by substitution or deletion of amino acid residues, such as substitution of glutamine for asparagine, or unglycosylated recombinant proteins may be produced by expressing the proteins in host cells that will not glycosylate them, e.g. in glycosylation-deficient yeast. These approaches are known in the art.

Therapeutic proteins and their nucleic acid sequences are well known in the art and available in public databases such as Chemical Abstracts Services Databases (e.g., the CAS Registry), GenBank, and GenSeq. The Accession Numbers and sequences referred to below are herein incorporated by reference in their entirety.

In other embodiments, the transferrin fusion proteins of the invention are capable of a therapeutic activity and/or biologic activity, corresponding to the therapeutic activity and/or biologic activity of the therapeutic protein listed in the corresponding row of Table 1 and elsewhere in this application. (See, e.g., the "Biological Activity" and "Therapeutic Protein X" columns of Table 1.) In further embodiments, the therapeutically active protein portions of the transferrin fusion proteins of the invention are fragments or variants of the reference sequences cited herein.

The present invention is further directed to modified Tf fusion proteins comprising fragments of the therapeutic proteins herein described. Even if deletion of one or more amino acids from the N-terminus of a protein results in modification or loss of one or more biological functions of the therapeutic protein portion, other therapeutic activities and/or functional activities (e.g., biological activities, ability to multimerize, ability to bind a ligand) may still be retained. For example, the ability of polypeptides with N-terminal deletions to induce and/or bind to antibodies which recognize the complete or mature forms of the polypeptides generally will be retained with less than the majority of the residues of the complete polypeptide removed from the N-terminus. Whether a particular polypeptide lacking N-terminal residues of a complete polypeptide retains such immunologic activities can be assayed by routine methods described herein and otherwise known in the art. It is not unlikely that a mutant with a large number of deleted N-terminal amino acid residues may retain some biological or immunogenic activities. In fact, peptides composed of as few as six amino acid residues may often evoke an immune response.

Also as mentioned above, even if deletion of one or more amino acids from the N-terminus or C-terminus of a therapeutic protein results in modification or loss of one or more biological functions of the protein, other functional activities (e.g., biological activities, ability to multimerize, ability to bind a ligand) and/or therapeutic activities may still be retained. For example the ability of polypeptides with C-terminal deletions to induce and/or bind to antibodies which recognize the complete or mature forms of the polypeptide generally will be retained when less than the majority of the residues of the complete or mature polypeptide are removed from the C-terminus. Whether a particular polypeptide lacking the N-terminal and/or, C-terminal residues of a reference polypeptide retains therapeutic activity can readily be determined by routine methods described herein and/or otherwise known in the art.

Peptide fragments of the therapeutic proteins can be fragments comprising, or alternatively, consisting of, an amino acid sequence that displays a therapeutic activity and/or functional activity (e.g. biological activity) of the polypeptide sequence of the therapeutic protein of which the amino acid sequence is a fragment.

The peptide fragments of the therapeutic protein may comprise only the N- and C-termini of the protein, i.e., the central portion of the therapeutic protein has been deleted. Alternatively, the peptide fragments may comprise non-adjacent and/or adjacent portions of the central part of the therapeutic protein.

Other polypeptide fragments are biologically active fragments. Biologically active fragments are those exhibiting activity similar, but not necessarily identical, to an activity of a therapeutic protein used in the present invention. The biological activity of the fragments may include an improved desired activity, or a decreased undesirable activity.

Generally, variants of proteins are overall very similar, and, in many regions, identical to the amino acid sequence of the therapeutic protein corresponding to a therapeutic protein portion of a transferrin fusion protein of the invention. Nucleic acids encoding these variants are also encompassed by the invention.

Further therapeutic polypeptides that may be used in the invention are polypeptides encoded by polynucleotides which hybridize to the complement of a nucleic acid molecule encoding an amino-acid sequence of a therapeutic protein under stringent hybridization conditions which are known to those of skill in the art. (see, for example, Ausubel, F. M. et al., eds., 1989 Current protocol in Molecular Biology, Green Publishing Associates, Inc., and John Wiley & Sons Inc., New. York). Polynucleotides encoding these polypeptides are also encompassed by the invention.

By a polypeptide-having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted, or substituted with another amino acid. These alterations of the reference sequence may occur at the amino- or carboxy-terminal positions of the reference amino acid sequence or anywhere between those terminal positions, interspersed either individually among residues in the reference sequence, or in one or more contiguous groups within the reference sequence.

As a practical matter, whether any particular polypeptide is at least about 80%, 85%, 90%, 95%, 96%, 97%, 98% or 99% identical to, for instance, the amino acid sequence of a transferrin fusion protein of the invention or a fragment thereof (such, as the therapeutic protein portion of the transferrin fusion protein or the transferrin portion of the transferrin fusion protein), can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brufiag et al. (Comp. App. Biosci 245 (1990)).

The polynucleotide variants of the invention may contain alterations in the coding regions, non-coding regions, or both. Polynucleotide variants containing alterations which produce silent substitutions, additions, or deletions, but do not alter the properties or activities of the encoded polypeptide may be used to produce modified Tf fusion proteins. Nucleotide variants produced by silent substitutions due to the degeneracy of the genetic code can be utilized. Moreover, polypeptide variants in which less than about 50, less than 40, less than 30, less than 20, less than 10, or 5-50, 5-25, 5-10, 1-5, or 1-2 amino acids are substituted, deleted, or added in any combination can also be utilized. Polynucleotide variants can be produced for a variety of reasons, e.g., to optimize codon expression for a particular host (change codons in the human mRNA to those preferred by a host, such as, yeast or E. coli as described above).

In other embodiments, the therapeutic protein moiety has conservative substitutions compared to the wild-type sequence. By "conservative substitutions" is intended swaps within groups such as replacement of the aliphatic or hydrophobic amino acids Ala, Val, Leu and Ile; replacement of the hydroxyl residues Ser and Thr; replacement of the acidic residues Asp and Glu; replacement of the amide residues Asn and Gln, replacement of the basic residues Lys, Arg, and His; replacement of the aromatic residues Phe, Tyr, and Trp, and replacement of the small-sized amino acids Ala, Ser, Thr, Met, and Gly. Guidance concerning how to make phenotypically silent amino acid substitutions is provided, for example, in Bowie et al., "Deciphering the Message in Protein Sequences: Tolerance to Amino Acid Substitutions," Science 247:1306-1310 (1990). In specific embodiments, the polypeptides of the invention comprise, or alternatively, consist of, fragments or variants of the amino acid sequence of a therapeutic protein described herein and/or serum transferrin, and/or modified transferrin protein of the invention, wherein the fragments or variants have 1-5, 5-10, 5-25, 5-50, 10-50 or 50-150 amino acid residue additions, substitutions, and/or deletions when compared to the reference amino acid sequence. In further embodiments, the amino acid substitutions are conservative. Nucleic acids encoding these polypeptides are also encompassed by the invention.

The modified fusion proteins of the present invention can be composed of amino-acids joined to each other by peptide bonds or modified peptide bonds and may contain amino acids other than the 20 gene-encoded amino acids. The polypeptides may be modified by either natural processes, such as post-translational processing, or by chemical modification techniques which are well known in the art. Such modifications are well described in basic texts and in more detailed monographs, as well as in a voluminous research literature.

Modifications can occur anywhere in a polypeptide, including the peptide backbone, the amino acid side-chains and the amino or carboxy termini. It will be appreciated that the same type of modification may be present in the same or varying degrees at several sites in a given polypeptide. Also, a given polypeptide may contain many types of modifications. Polypeptides may be branched, for example, as a result of ubiquitination, and they may be cyclic, with or without branching. Cyclic, branched, and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, glycosylation, GPI anchor formation, hydroxylation, iodination, methylation, myristylation, oxidation, pegylation, proteolytic processing, phosphorylation, prenylation, racemization, sulfation, transfer-RNA mediated addition of amino acids to proteins such as arginylation, and ubiquitination. (See, for instance, PROTEINS—STRUCTURE AND MOLECULAR PROPERTIES, 2nd Ed., T. E. Creighton, W.H. Freeman and Company, New York (1993); POST-TRANSLATIONAL COVALENT MODIFICATION OF PROTEINS, B. C. Johnson, Ed., Academic Press, New York, pgs. 1-12 (1983); Seifter et al. (1990) Meth. Enzymol. 182:626-646; Rattan et al., Ann. N.Y. Acad. Sci. 663:48-62.

Therapeutic molecules that may be fused to or inserted into Tf include, but are not limited to, hormones, matrix proteins, immunosuppressants, bronchodilators, cardiovascular agents, enzymes, CNS agents, neurotransmitters, receptor proteins or peptides, growth hormones, growth factors, antiviral peptides, fusogenic inhibitor peptides, cytokines, lymphokines, monokines, interleukins, colony stimulating factors, differentiation factors, angiogenic factors, receptor ligands, cancer-associated proteins, antineoplastics, viral peptides, antibiotic peptides, blood proteins, antagonist proteins, transcription factors, anti-angiogenic factors, antagonist proteins or peptides, receptor antagonists, antibodies, single chain antibodies and cell adhesion molecules. Different therapeutic molecules may be combined into a single fusion protein to produce a bi or multi-functional therapeutic molecule. Different molecules may also be used in combination to produce a fusion protein with a therapeutic entity and a targeting entity.

Cytokines are soluble proteins released by cells of the immune system, which act nonenzymatically through specific receptors to regulate immune responses. Cytokines resemble hormones in that they act at low concentrations bound with high affinity to a specific receptor. The term "cytokine" is used herein to describe naturally occurring or recombinant proteins, analogs thereof, and fragments thereof which elicit a specific biological response in a cell which has a receptor for that cytokine. Cytokines preferably include interleukins such as interleukin-2 (IL-2) (GenBank Acc. No. S77834), IL-3 (GenBank Acc. No. M14743), IL-4 (GenBank Acc. No. M23442), IL-5 (GenBank Acc. No. J03478), IL-6 (GenBank Acc. No. M14584), IL-7 (GenBank Acc. No. NM_000880), IL-10 (GenBank Acc. No. NM_000572), IL-12 (GenBank Acc. No. AF180562 and GenBank Acc. No. AF180563), IL-13 (GenBank Acc. No. U10307), IL-14 (GenBank Acc. No. XM_170924), IL-15 (GenBank Acc. No. X91233), IL-16 (GenBank Acc. No. NM_004513), IL-17 (GenBank Acc. No. NM_002190) and IL-18 (GenBank Acc. No. NM_001562), hematopoietic factors such as granulocyte-macrophage colony stimulating factor (GM-CSF) (GenBank Acc. No. X03021), granulocyte colony stimulating factor (G-CSF) (GenBank Acc. No. X03656), platelet activating factor (GenBank Acc. No. NM_000437) and erythropoietin (GenBank Acc. No. X02158), tumor necrosis factors (TNF) such as TNFα (GenBank Acc. No. X02910), lymphokines such as lymphotoxin-α (GenBank Acc. No. X02911), lymphotoxin-β (GenBank Acc. No. L11016), leukoregulin, macrophage migration inhibitory factor (GenBank Acc. No. M25639), and neuroleukin (GenBank Acc. No. K03515), regulators of metabolic processes such as leptin (GenBank Acc. No. U43415), interferons such as interferon α (IFNα) (GenBank Acc. No. M54886), IFNβ (GenBank Acc. No. V00534), IFNγ (GenBank Acc. No. J00219), IFNα (GenBank Acc. No. NM_002177), thrombospondin 1 (THBS1) (GenBank Acc. No. NM_003246), THBS2 (GenBank Acc. No. L12350), THBS3 (GenBank Acc. No. L38969), THBS4 (GenBank Acc. No. NM_003248), and chemokines. Preferably, the modified transferrin-cytokine fusion protein of the present invention displays cytokine biological activity.

The term "hormone" is used herein to describe any one of a number of biologically active substances that are produced by certain cells or tissues and that cause specific biological changes or activities to occur in another cell or tissue located elsewhere in the body. Hormones preferably include GLP-1 of glucagon preproprotein (GenBank Acc. No. NM_002045), proinsulin (GenBank Acc. No. V00565), insulin (GenBank Acc. No. NM_000207), growth hormone 1 (GenBank Acc. No. V00520), growth hormone 2 (GenBank Acc. No. F006060), growth hormone release factor (GenBank Acc. No. NM_021081), insulin-like growth factor I (GenBank Acc. No. M27544), insulin-like growth factor II (GenBank Acc. No. NM_000612), insulin-like growth factor binding protein 1 (IGFBP-1) (GenBank Acc. No. M59316), IGFBP-2 (GenBank Acc. No. X16302), IGFBP-3 (GenBank Acc. No. NM_000598), IGFBP-4 (GenBank Acc. No. Y12508), IGFBP-5 (GenBank Acc. No. M65062), IGFBP-6 (GenBank Acc. No. NM_002178), IGFBP-7 (GenBank Acc. No. NM_001553), chorionic gonadotropin β chain (GenBank Acc. No. NM_033142), chorionic gonadotropin α chain (GenBank Acc. No. NM_000735), luteinizing hormone β (GenBank Acc. No. X00264), follicle-stimulating hormone β (GenBank Acc. No. NM_000510), thyroid-stimulating hormone β (GenBank Acc. No. NM_000549), prolactin (GenBank Acc. No. NM_000948), pro-opiomelanocortin (GenBank Acc. No. V01510), corticotropin (ACTH), β-lipotropin, α-melanocyte stimulating hormone (α-MSH), γ-lipotropin, β-MSH, β-endorphin, and corticotropin-like intermediate lobe peptide (CLIP).

The term "growth factor" is used herein to describe any protein or peptide that binds to a receptor to stimulate cell proliferation. Growth factors preferably include platelet-derived growth factor-α (PDGF-α) (GenBank Acc. No. X03795); PDGF-β (GenBank Acc. No. X02811), steroid hormones, epidermal growth factor (EGF) (GenBank Acc. No. NM_001963), fibroblast growth factors such as fibroblast growth factor 1 (FGF1) (GenBank Acc. No. NM_000800), FGF2 (GenBank Acc. No. NM_002006), FGF3 (GenBank Acc. No. NM_005247), FGF4 (GenBank Acc. No. NM_002007), FGF5 (GenBank Acc. No. M37825), FGF6 (GenBank Acc. No. X57075), FGF7 (GenBank Acc. No. NM_002009), FGF8 (GenBank Acc. No. AH006649), FGF9 (GenBank Acc. No. NM_002010), FGF10 (GenBank Acc. No. AB002097), FGF11 (GenBank Acc. No. NM_004112), FGF12 (GenBank Acc. No. NM_021032), FGF13 (GenBank Acc. No. NM_004114), FGF14 (GenBank Acc. No. NM_004115), FGF16 (GenBank Acc. No. AB009391), FGF17 (GenBank Acc. No. NM_003867), FGF18 (GenBank Acc. No. AF075292), FGF19 (GenBank Acc. No. NM_005117), FGF20 (GenBank Acc. No. NM_019851), FGF21 (GenBank Acc. No. NM_019113), FGF22 (GenBank Acc. No. NM_020637), and FGF23 (GenBank Acc. No. NM_020638), angiogenin (GenBank Acc. No. M11567), brain-derived neurotrophic factor (GenBank Acc. No. M61176), ciliary neurotrophic growth factor (GenBank Acc. No. X60542), transforming growth factor-α (TGF-α) (GenBank Acc. No. X70340), TGF-β (GenBank Acc. No. X02812), nerve growth factor-α (NGF-α) (GenBank Acc. No. NM_010915), NGF-β (GenBank Acc. No. X52599), tissue inhibitor of metalloproteinase 1 (TIMP1) (GenBank Acc. No. NM_003254), TIMP2 (GenBank Acc. No. NM_003255), TIMP3 (GenBank Acc. No. U02571), TIMP4 (GenBank Acc. No. U76456) and macrophage stimulating 1 (GenBank Acc. No. L11924).

The term "matrix protein" is used herein to describe proteins or peptides that are normally found in the extracellular matrix. These proteins may be functionally important for strength, filtration, or adhesion. Matrix proteins preferably include collagens such as collagen I (GenBank Acc. No. Z74615), collagen II (GenBank Acc. No. X16711), collagen III (GenBank Acc. No. X14420), collagen IV (GenBank Acc. No. NM_001845), collagen V (GenBank Acc. No. NM_000393), collagen VI (GenBank Acc. No. NM_058175), collagen VII (GenBank Acc. No. L02870), collagen VIII (GenBank Acc. No. NM_001850), collagen IX (GenBank Acc. No. X54412), collagen X (GenBank Acc. No. X60382), collagen XI (GenBank Acc. No. J04177), and collagen XII (GenBank Acc. No. U73778), laminin proteins such as LAMA2 (GenBank Acc. No. NM_000426), LAMA3 (GenBank Acc. No. L34155), LAMA4 (GenBank Acc. No. NM_002290), LAMB1 (GenBank Acc. No. NM_002291), LAMB3 (GenBank Acc. No. L25541), LAMC1 (GenBank Acc. No. NM_002293), nidogen (GenBank Acc. No. NM_002508), α-tectorin (GenBank Acc. No. NM_005422), β-tectorin (GenBank Acc. No. NM_058222), and fibronectin (GenBank Acc. No. X02761).

The term "blood proteins" are traditionally defined as those sourced from plasma, many now commonly produced by recombinant means, and include, but are not limited to native serum proteins, derivatives, fragments and mutants or variants thereof, blood clotting factors, derivatives, mutants, variants and fragments (including factors VII, VIII, IX, X), protease inhibitors (antithrombin 3, alpha-1 antitrypsin), urokinase-type plasminogen activator, immunoglobulins, von Willebrand factor and von Willebrand mutants, fibronectin, fibrinogen, thrombin and hemoglobin.

The term "enzyme" is used herein to describe any protein or proteinaceous substance which catalyzes a specific reaction without itself being permanently altered or destroyed. Enzymes preferably include coagulation factors such as F2 (GenBank Acc. No. XM_170688), F7 (GenBank Acc. No. XM_027508), F8 (GenBank Acc. No. XM_013124), F9 (GenBank Acc. No. NM_000133), F10 (GenBank Acc. No. AF503510) and others, matrix metalloproteinases such as matrix metalloproteinase I (GenBank Acc. No. MMP1) (GenBank Acc. No. NM_002421), MMP2 (GenBank Acc. No. NM_004530), MMP3 (GenBank Acc. No. NM_002422), MMP7 (GenBank Acc. No. NM_002423), MMP8 (GenBank Acc. No. NM_002424), MMP9 (GenBank Acc. No. NM_004994), MMP10 (GenBank Acc. No. NM_002425), MMP12 (GenBank Acc. No. NM_002426), MMP13 (GenBank Acc. No. X75308), MMP20 (GenBank Acc. No. NM_004771), adenosine deaminase (GenBank Acc. No. NM_000022), mitogen activated protein kinases such as MAPK3 (GenBank Acc. No. XM_055766), MAP2K2 (GenBank Acc. No. NM_030662), MAP2K1 (GenBank Acc. No. NM_002755), MAP2K4 (GenBank Acc. No. NM_003010), MAP2K7 (AF013588), and MAPK12 (NM_002969), kinases such as JNKK1 (GenBank Acc. No. U17743), JNKK2 (GenBank Acc. No. AF014401), JAK1 (M64174), JAK2 (NM_004972), and JAK3 (NM_000215), and phosphatases such as PPM1A (GenBank Acc. No. NM_021003) and PPM1D (GenBank Acc. No. NM_003620).

The term "transcription factors" is used herein to describe any protein or peptide involved in the transcription of protein-coding genes. Transcription factors may include Sp1, Sp2 (GenBank Acc. No. NM_003110), Sp3 (GenBank Acc. No. AY070137), Sp4 (GenBank Acc. No. NM_003112) NFYB (GenBank Acc. No. NM_006166), Hap2 (GenBank Acc. No. M59079), GATA-1 (GenBank Acc. No. NM_002049), GATA-2 (GenBank Acc. No. NM_002050), GATA-3 (GenBank Acc. No. X55122), GATA-4 (GenBank Acc. No. L34357), GATA-5, GATA-6 (GenBank Acc. No. NM_005257), FOG2 (NM_012082), Eryf1 (GenBank Acc. No. X17254), TRPS1 (GenBank Acc. No. NM_014112), NF-E2 (GenBank Acc. No. NM_006163), NF-E3, NF-E4, TFCP2 (GenBank Acc. No. NM_005653), Oct-1 (GenBank Acc. No. X13403), homeobox proteins such as HOXB2 (GenBank Acc. No. NM_002145), HOX2H (GenBank Acc. No. X16665), hairless homolog (GenBank Acc. No. NM_005144), mothers against decapentaplegic proteins such as MADH1 (GenBank Acc. No. NM_005900), MADH2 (GenBank Acc. No. NM_005901), MADH3 (GenBank Acc. No. NM_005902), MADH4 (GenBank Acc. No. NM_005359), MADH5 (GenBank Acc. No. AF009678), MADH6 (GenBank Acc. No. NM_005585), MADH7 (GenBank Acc. No. NM_005904), MADH9 (GenBank Acc. No. NM_005905), and signal transducer and activator of transcription proteins such as STAT1 (GenBank Acc. No. XM_010893), STAT2 (GenBank Acc. No. NM_005419), STAT3 (GenBank Acc. No. AJ012463), STAT4 (GenBank Acc. No. NM_003151), STAT5 (GenBank Acc. No. L41142), and STAT6 (GenBank Acc. No. NM_003153).

In yet another embodiment of the invention, the therapeutic molecule is a non-human or non-mammalian protein. For example, HIV gp120, HIV Tat, surface proteins of other viruses such as hepatitis, herpes, influenza, adenovirus and RSV, other HIV components, parasitic surface proteins such as malarial antigens, and bacterial surface proteins are preferred. These non-human proteins may be used, for example, as antigens, or because they have useful activities. For example, the therapeutic molecule may be streptokinase, staphylokinase, asparaginase, or other proteins with useful enzymatic activities.

In an alternative embodiment, the therapeutic molecule is a ligand-binding protein with biological activity. Such ligand-binding proteins may, for example, (1) block receptor-ligand interactions at the cell surface; or (2) neutralize the biological activity of a molecule in the fluid phase of the blood, thereby preventing it from reaching its cellular target. In some embodiments, the modified transferrin fusion proteins include a modified transferrin molecule fused to a ligand-binding domain of a receptor selected from the group consisting of, but not limited to, a low density lipoprotein (LDL) receptor, an acetylated LDL receptor, a tumor necrosis factor α receptor, a transforming growth factor β receptor, a cytokine receptor, an immunoglobulin Fc receptor, a hormone receptor, a glucose receptor, a glycolipid receptor, and a glycosaminoglycan receptor. In other embodiments, ligand-binding proteins include CD2 (M14362), CD3G (NM_000073), CD3D (NM_000732), CD3E (NM_000733), CD3Z (J04132), CD28 (NM_006139), CD4 (GenBank Acc. No. NM_000616), CD1A (GenBank Acc. No. M28825), CD1B (GenBank Acc. No. NM_001764), CD1C (GenBank Acc. No. NM_001765), CD1D (GenBank Acc. No. NM_001766), CD80 (GenBank Acc. No. NM_005191), GNB3 (GenBank Acc. No. AF501884), CTLA-4 (GenBank Acc. No. NM_005214), intercellular adhesion molecules such as ICAM-1 (NM_000201), ICAM-2 (NM_000873), and ICAM-3 (NM_002162), tumor necrosis factor receptors such as TNFRSF1A (GenBank Acc. No. X55313), TNFR1SFB (GenBank Acc. No. NM_001066), TNFRSF9 (GenBank Acc. No. NM_001561), TNFRSF10B (GenBank Acc. No. NM_003842), TNFRSF11B (GenBank Acc. No. NM_002546), and TNFRSF13B (GenBank Acc. No. NM_006573), and interleukin receptors such as IL2RA (GenBank Acc. No. NM_000417), IL2RG (GenBank Acc. No. NM_000206), IL4R (GenBank Acc. No. AF421855), IL7R (GenBank Acc. No. NM_002185), IL9R (GenBank Acc. No. XM_015989), and IL13R (GenBank Acc. No. X95302). Preferably, the Tf-ligand-binding protein fusion of the present invention displays the biological activity of the ligand-binding protein.

The term "cancer-associated proteins" is used herein to describe proteins or polypeptides whose expression is associated with cancer or the maintenance of controlled cell growth, such as proteins encoded by tumor suppressor genes or oncogenes. Cancer-associated proteins may include p16 (GenBank Acc. No. AH005371), p53 (GenBank Acc. No. NM_000546), p63 (GenBank Acc. No. NM_003722), p73 (GenBank Acc. No. NM_05427), BRCA1 (GenBank Acc. No. U14680), BRCA2 (GenBank Acc. No. NM_000059), CTBP interacting protein (GenBank Acc. No. U72066), DMBT1 (GenBank Acc. No. NM_004406), HRAS (GenBank Acc. No. NM_005343), NCYM (GenBank Acc. No. NM_006316), FGR (GenBank Acc. No. NM_005248), myb (GenBank Acc. No. AF104863), raf1 (GenBank Acc. No. NM_002880), erbB2 (GenBank Acc. No. NM_004448), VAV (GenBank Acc. No. X16316), c-fos (V GenBank Acc. No. 01512), c-fes (GenBank Acc. No. X52192), c-jun (Gen- Bank Acc. No. NM_002228), MAS1 (GenBank Acc. No. M13150), pim-1 (GenBank Acc. No. M16750), TIF1 (GenBank Acc. No. NM_003852), c-fms (GenBank Acc. No. X03663), EGFR (GenBank Acc. No. NM_005228), erbA (GenBank Acc. No. X04707), c-src tyrosine kinase (GenBank Acc. No. XM_044659), c-abl (GenBank Acc. No. M14752), N-ras (GenBank Acc. No. X02751), K-ras (GenBank Acc. No. M54968), jun-B (GenBank Ace. No. M29039), c-myc (GenBank Acc. No. AH001511), RB1 (GenBank Acc. No. M28419), DCC (GenBank Acc. No. X76132), APC (GenBank Acc. No. NM_000038), NF1 (GenBank Acc. No. M89914), NF2 (GenBank Acc. No. Y18000), and bcl-2 (GenBank Acc. No. M13994).

"Fusogenic inhibitor peptides" is used herein to describe peptides that show antiviral activity, anti-membrane fusion capability, and/or an ability to modulate intracellular processes, for instance, those involving coiled-coil peptide structures. Antiviral activity includes, but is not limited to, the inhibition of HIV-1, HIV-2, RSV, SIV, EBV, measles virus, influenza virus, or CMV transmission to uninfected cells. Additionally, the antifusogenic capability, antiviral activity or intracellular modulatory activity of the peptides merely requires the presence of the peptides and specifically does not require the stimulation of a host immune response directed against such peptides. Antifusogenic refers to a peptide's ability to inhibit or reduce the level of membrane fusion events between two or more moieties relative to the level of membrane fusion which occurs between said moieties in the absence of the peptide. The moieties may be, for example, cell membranes or viral structures, such as viral envelopes or pili. The term "antiviral peptide", as used herein, refers to the peptide's ability to inhibit viral infection of cells or some viral activity required for productive viral infection and/or viral pathogenesis, via, for example, cell-cell fusion or free virus infection. Such infection may involve membrane fusion, as occurs in the case of enveloped viruses, or some other fusion event involving a viral structure and a cellular structure. Fusogenic inhibitor peptides and antiviral peptides often have amino acid sequences that are derived from greater than one viral protein (e.g., an HIV-1, HIV-2, RSV, and SIV-derived polypeptide).

Examples of fusogenic inhibitor peptides and antiviral peptides can be found in WO 94/2820, WO 96/19495, WO 96/40191, WO 01/64013 and U.S. Pat. Nos. 6,333,395, 6,258, 782, 6,228,983, 6,133,418, 6,093,794, 6,068,973, 6,060,065, 6,054,265, 6,020,459, 6,017,536, 6,013,263, 5,464,933, 5,346,989, 5,603,933, 5,656,480, 5,759,517, 6,245,737; 6,326,004, and 6,348,568; all of which are herein incorporated by reference. In a preferred embodiment, antifusogenic peptides are selected from the group consisting of HIV T-20 (FWNWLSAWKDLELLEQENKEQQNQSEEILSHILSTY, SEQ ID NO: 4), HIV T-1249, RSV T786 (VYPSDEYDASISQVNEEINQALAYIRKADELLENV, SEQ ID NO: 5), RSV T1584 (AVSKVLHLEGEVNKIKSALLSTNKAVVSLSNGVSVLTSKVLDLKNYIDKQL, SEQ ID NO: 6) and RSV T112 (VFPSDEFDASISQVNEKINQSLAFIRESDELLHNV, SEQ ID NO: 7).

Examples of other types of peptides, include fragments of therapeutic proteins as described herein, in particular, fragments of human proteins that retain at least one activity of the parent molecule. Peptides that may be used to produce modified Tf fusion proteins of the invention also include mimetic peptides and peptides that exhibit a biological activity of a therapeutic protein but differ in sequence or three-dimensional structure from a full-length therapeutic protein. As a non-limited example, peptides include erythropoietin mimetic peptides disclosed by Johnson et al. (2000) *Nephrol.* *Dial. Transplant* 15(9): 1274-7, Kuai et al. (2000) *J. Pept. Res.* 56(2):59-62, Barbone et al. (1999) *Nephrol. Dial. Transplant.* 14 Supp 2:80-4, Middleton et al. (1999) *J. Biol. Chem.* 274(20):14163-9, Johnson et al. (1998) *Biochemistry* 37(10: 3699-710, Johnson et al. (1997) *Chem. Biol.* 12:939-50, Wrighton et al. (1997) *Nat. Biotechnol.* 15(12):1261-5, Livnah et al. (1996) *Science* 273:464-71, and Wrighton et al., (1996) *Science* 273:458-64.

Therapeutic molecules also include allergenic proteins and digested fragments thereof. These include pollen allergens from ragweed, rye, June grass, orchard grass, sweet vernal grass, red top grass, timothy grass, yellow dock, wheat, corn, sagebrush, blue grass, California annual grass, pigweed, Bermuda grass, Russian thistle, mountain cedar, oak, box elder, sycamore, maple, elm, etc., dust mites, bee venom, food allergens, animal dander, and other insect venoms.

Other therapeutic molecules include microbial vaccines which include viral, bacterial and protozoal vaccines and their various components such as surface antigens. These include vaccines which contain glycoproteins, proteins or peptides derived from these proteins. Such vaccines are prepared from *Staphylococcus aureus, Streptococcus pyogenes, Streptococcus pneumoniae, Neisseria meningitidis, Neisseria gonorrhoeae, Salmonella* spp., *Shigella* spp., *Escherichia coli, Klebsiella* spp., *Proteus* spp., *Vibrio cholerae, Campylobacter pylori, Pseudomonas aeruginosa, Haemophilus influenzae, Bordetella pertussis, Mycobacterium tuberculosis, Legionella pneumophila, Treponema pallidum*, chlamydia, tetanus toxoid, diphtheria toxoid, influenza viruses, adenoviruses, paramyxoviruses (mumps, measles), rubella viruses, polio viruses, hepatitis viruses, herpes viruses, rabies virus, HIV-1, HIV-2, RSV and papilloma viruses.

Preferred fusion molecules may contain anti-HIV viral peptides, anti-RSV peptides, human growth hormone, α and/or β interferons, erythropoietin (EPO), EPO like peptides, granulocyte-colony stimulating factor (GCSF), granulocyte-macrophage colony-stimulating factor (GMCSF), insulin, insulin-like growth factor (IGF), thrombopoeitin, peptides corresponding to the CDR of an antibody, Islet Neogenesis Associated Protein (INGAP), calcitonin, angiostatin, endostatin, interleukin-2, growth hormone releasing factor, human parathyroid hormone, anti-tumor necrosis factor (TNF) peptides, interleukin-1 (IL-1) receptor and/or single chain antibodies.

Fusion proteins of the invention may also be prepared to include peptides or polypeptides derived from peptide libraries to screen for molecules with new or novel functions. Such peptide libraries may include those commercially or publicly available, e.g., American Peptide Co. Inc., Cell Sciences Inc., Invitrogen Corporation, Phoenix Pharmaceuticals Inc., United States Biological, as well as those produced by available technologies, e.g., bacteriophage and bacterial display libraries made using standard procedures.

In yet other embodiments of the invention, Tf fusion proteins may be prepared by using therapeutic protein moieties as known in the art and exemplified by the peptides and proteins currently approved by the Food and Drug Administration at (www.fda.gov/cber/efoi/approve.htm) as well as PCT Patent Publication Nos. WO 01/79258, WO 01/77137, WO 01/79442, WO 01/79443, WO 01/79444 and WO 01/79480, all of which are herein incorporated by reference in their entirety.

Table 1 (adapted from PCT International Publication No. WO 01/79444) provides a non-exhaustive list of therapeutic proteins that correspond to a therapeutic protein portion of a modified transferrin fusion protein of the invention. The "Therapeutic Protein X" column discloses therapeutic protein molecules followed by parentheses containing scientific and brand names that comprise or alternatively consist of that therapeutic protein molecule or a fragment or variant thereof. "Therapeutic protein X" as used herein may refer either to an individual therapeutic protein molecule (as defined by the amino acid sequence obtainable from the CAS and Genbank accession numbers), or to the entire group of therapeutic proteins associated with a given therapeutic protein molecule disclosed in this column. The 'Exemplary Identifier' column provides Chemical Abstracts Services (CAS) Registry Numbers (published by the American Chemical Society) and/or Genbank Accession Numbers (e.g., Locus ID, NP-XXXXX (Reference Sequence Protein), and XP-XXXXX (Model Protein) identifiers available through the National Center for Biotechnology Information (NCBI) webpage (www.ncbi.nlm.nih.gov) that correspond to entries in the CAS Registry or Genbank database which contain an amino acid sequence of the protein molecule or of a fragment or variant of the therapeutic protein molecule. In addition GenSeq Accession numbers and/or journal publication citations are given to identify the exemplary amino acid sequence for some polypeptides.

The summary pages associated with each of these CAS and Genbank and GenSeq Accession Numbers as well as the cited journal publications are available (e.g., PubMed ID number (PMID)) and are herein incorporated by reference in their entirety. The PCT/Patent Reference column provides U.S. patent numbers, or PCT International Publication Numbers corresponding to patents and/or published patent-applications that describe the therapeutic protein molecule all of which are herein incorporated by reference in their entirety. The Biological Activity column describes biological activities associated with the therapeutic protein molecule. The Exemplary Activity Assay column provides references that describe assays which may be used to test the therapeutic and/or biological activity of a therapeutic protein or a transferrin fusion protein of the invention comprising a therapeutic protein X portion. These references are also herein incorporated by reference in their entirety. "The Preferred Indication Y" column describes disease, disorders, and/or conditions that may be treated, prevented, diagnosed, or ameliorated by therapeutic protein X or a transferrin fusion protein of the invention comprising a therapeutic protein X portion.

TABLE 1

| Therapeutic Protein X | Exemplary Identifier | PCT/Patent Reference | Biological Activity | Exemplary Activity Assay | Preferred Indication Y |
|---|---|---|---|---|---|
| BMP-1 | GeneSeq Acession P80618 | WO8800205 | BMP1 belongs to the transforming growth factor-beta (TGFB) superfamily. Bone morphogenic proteins induce cartilage and bone formation, play an important role in nephrogesis, and play a role in the development of many organs, including lung, heart, teeth, gut, skin, and particularly the kidney. | BMP-1 activity can be determined using the following assays known in the art: Nat Genet. 2001 January; 27(1): 84-8; Eur J Biochem 1996 Apr. 1; 237(1): 295-302; J Biol Chem, Vol. 274, Issue 16, 10897-10902, Apr. 16, 1999; and Hogan, B. L. M. (1996) Genes Dev. 10, 1580-1594. | Induction of Cartilage, Tissue and Bone Growth, and Diabetes |
| BMP-2 | GeneSeq Acession P80619 | WO8800205 | BMP-2 belongs to the transforming growth factor-beta (TGFB) superfamily. Bone morphogenic protein induces bone formation. | BMP-2 activity can be determined using the following assays known in the art: Nat Genet. 2001 January; 27(1): 84-8; Eur J Biochem 1996 Apr. 1; 237(1): 295-302; J Biol Chem, Vol. 274, Issue 16, 10897-10902, Apr. 16, 1999; and Hogan, B. L. M. (1996) Genes Dev. 10, 1580-1594. | Induction of Cartilage, Tissue and Bone Growth, and Diabetes |
| BMP-2B | GeneSeq Acession W24850 | U.S. Pat. No. 5,631,142 | BMP-2b belongs to the transforming growth factor-beta (TGFB) superfamily. Bone morphogenic protein induces bone formation. | BMP-2b activity can be determined using the following assays known in the art: Nat Genet. 2001 January; 27(1): 84-8; Eur J Biochem 1996 Apr. 1; 237(1): 295-302; J Biol Chem, Vol. 274, Issue 16, 10897-10902, Apr. 16, 1999; and Hogan, B. L. M. (1996) Genes Dev. 10, 1580-1594. | Induction of Cartilage, Tissue and Bone Growth, and Diabetes |
| BMP-4 | GeneSeq Acession B02796 | WO0020591 | BMP-4 belongs to the transforming growth factor-beta (TGFB) superfamily. Bone morphogenic protein induces bone formation. | BMP-4 activity can be determined using the following assays known in the art: Nat Genet. 2001 January; 27(1): 84-8; Eur J Biochem 1996 Apr. 1; 237(1): 295-302; J Biol Chem, Vol. 274, Issue 16, 10897-10902, Apr. 16, 1999; and Hogan, B. L. M. (1996) Genes Dev. 10, 1580-1594. | Induction of Cartilage, Tissue and Bone Growth, and Diabetes |
| BMP-5 | GeneSeq Acession B02797 | WO0020591 | BMP-5 belongs to the transforming growth factor-beta (TGFB) superfamily. Bone morphogenic protein induces bone formation. | BMP-5 activity can be determined using the following assays known in the art: Nat Genet. 2001 January; 27(1): 84-8; Eur J Biochem 1996 Apr. 1; 237(1): 295-302; J Biol Chem, Vol. 274, Issue 16, 10897-10902, Apr. 16, 1999; and Hogan, B. L. M. (1996) Genes Dev. 10, 1580-1594. | Induction of Cartilage, Tissue and Bone Growth, and Diabetes |
| BMP-6 | GeneSeq Acession R32904 | U.S. Pat. No. 5,187,076 | BMP-6 belongs to the transforming growth factor-beta (TGFB) superfamily. Bone morphogenic protein induces bone formation. | BMP-6 activity can be determined using the following assays known in the art: Nat Genet. 2001 January; 27(1): 84-8; Eur J Biochem 1996 Apr. 1; 237(1): 295-302; J Biol Chem, Vol. 274, Issue 16, 10897-10902, Apr. 16, 1999; and Hogan, B. L. M. (1996) Genes Dev. 10, 1580-1594. | Induction of Cartilage, Tissue and Bone Growth, and Diabetes |

TABLE 1-continued

| Therapeutic Protein X | Exemplary Identifier | PCT/Patent Reference | Biological Activity | Exemplary Activity Assay | Preferred Indication Y |
|---|---|---|---|---|---|
| Osteogenic Protein-1; OP-1; BMP-7 | GeneSeq Accession W34783 | WO973462 | OP-1 belongs to the transforming growth factor-beta (TGFB) superfamily. Bone morphogenic protein induces bone formation. | OP-1 activity can be determined using the following assays known in the art: Nat Genet. 2001 January; 27(1): 84-8; Eur J Biochem 1996 Apr. 1; 237(1): 295-302; J Biol Chem, Vol. 274, Issue 16, 10897-10902, Apr. 16, 1999; and Hogan, B. L. M. (1996) Genes Dev. 10, 1580-1594. | Induction of Cartilage, Tissue and Bone Growth, and Diabetes |
| Osteogenic Protein-2 | GeneSeq Accession R57973 | WO9406399 | OP-2 belongs to the transforming growth factor-beta (TGFB) superfamily. Bone morphogenic Protein induces bone formation. | OP-2 activity can be determined using the following assays known in the art: Nat Genet. 2001 January; 27(1): 84-8; Eur J Biochem 1996 Apr. 1; 237(1): 295-302; J Biol Chem, Vol. 274, Issue 16, 10897-10902, Apr. 16, 1999; and Hogan, B. L. M. (1996) Genes Dev. 10, 1580-1594. | Induction of Cartilage, Tissue and Bone Growth, and Diabetes |
| GDF-1 | GeneSeq Accession R60961 | WO9406449 | Members of the TGF-beta family of proteins initiate cell signaling by binding to heteromeric receptor complexes of type I (TbetaRI) and type II (TbetaRII) serine/threonine kinase receptors (reviewed by Massague, J. et al. (1994) Trends Cell Biol. 4: 172 178; Miyazono, K. et al. (1994) Adv. Immunol. 55: 181-220). Activation of this heteromeric receptor complex occurs when TGF-beta binds to TbetaRII, which then recruits and phosphorylates TbetaRI. Activated TbetaRI then propagates the signal to downstream targets (Chen, F. and Weinberg, R. A. (1995) PNA892: 1565-1569; Wrana, J. L. et al. (1994) Nature 370: 341 347). | The effect of GDF-1 on signaling can be assayed by treating Primary BAECs transferred with a construct called p3TP-Lux, containing a TGF-beta responsive promoter fused to a reporter gene, and measuring luciferase gene expression (Wrana et al., 1994, Nature 370: 341-347). | Developmental disorders, Induction of Cartilage, Tissue and Bone Growth, and Diabetes |
| BMP-9 | GeneSeq Accession R86903 | WO9533830 | BMP-9 belongs to the transforming growth factor-beta (TGFB) superfamily. Bone morphogenic protein induces bone formation. | BMP-9 activity can be determined using the following assays known in the art: Nat Genet. 2001 January; 27(1): 84-8; Eur J Biochem 1996 Apr. 1; 237(1): 295-302; J Biol Chem, Vol. 274, Issue 16, 10897-10902, Apr. 16, 1999; and Hogan, B. L. M. (1996) Genes Dev. 10, 1580-1594. | Induction of Cartilage, Tissue and Bone Growth, and Diabetes |
| BMP-10 | GeneSeq Accession R66202 | WO9426893 | BMP-10 belongs to the transforming growth factor-beta (TGFB) superfamily. Bone morphogenic protein induces bone formation. | BMP-10 activity can be determined using the following assays known in the art: Nat Genet. 2001 January; 27(1): 84-8; Eur J Biochem 1996 Apr. 1; 237(1): 295-302; J Biol Chem, Vol. 274, Issue 16, 10897-10902, Apr. 16, | Induction of Cartilage, Tissue and Bone Growth, and Diabetes |

TABLE 1-continued

| Therapeutic Protein X | Exemplary Identifier | PCT/Patent Reference | Biological Activity | Exemplary Activity Assay | Preferred Indication Y |
|---|---|---|---|---|---|
| BMP-12 | GeneSeq Accession R78734 | WO9516035 | BMP-12 belongs to the transforming growth factor-beta (TGFB) superfamily. Bone morphogenic protein induces bone formation. | 1999; and Hogan, B. L. M. (1996) Genes Dev. 10, 1580-1594. BMP-12 activity can be determined using the following assays known in the art: Nat Genet. 2001 January; 27(1): 84-8; Eur J Biochem 1996 Apr. 1; 237(1): 295-302; J Biol Chem, Vol. 274, Issue 16, 10897-10902, Apr. 16, 1999; and Hogan, B. L. M. (1996) Genes Dev. 10, 1580-1594. | Induction of Cartilage, Tissue and Bone Growth, and Diabetes |
| BMP-15 | GeneSeq Accession W11261 | WO9636710 | BMP-15 belongs to the transforming growth factor-beta (TGFB) superfamily. Bone morphogenic protein induces bone formation. | BMP-15 activity can be determined using the following assays known in the art: Nat Genet. 2001 January; 27(1): 84-8; Eur J Biochem 1996 Apr. 1; 237(1): 295-302; J Biol Chem, Vol. 274, Issue 16, 10897-10902, Apr. 16, 1999; and Hogan, B. L. M. (1996) Genes Dev. 10, 1580-1594. | Induction of Cartilage, Tissue and Bone Growth, and Diabetes |
| BMP-17 | GeneSeq Accession Y17870 | WO9929718 | BMP-17 belongs to the transforming growth factor-beta (TGFB) superfamily. Bone morphogenic protein induces bone formation. | BMP-17 activity can be determined using the following assays known in the art: Nat Genet. 2001 January; 27(1): 84-8; Eur J Biochem 1996 Apr. 1; 237(1): 295-302; J Biol Chem, Vol. 274, Issue 16, 10897-10902, Apr. 16, 1999; and Hogan, B. L. M. (1996) Genes Dev. 10, 1580-1594. | Induction of Cartilage, Tissue and Bone Growth, and Diabetes |
| BMP-18 | GeneSeq Accession Y17871 | WO9929718 | BMP-18 belongs to the transforming growth factor-beta (TGFB) superfamily. Bone morphogenic protein induces bone formation. | BMP-18 activity can be determined using the following assays known in the art: Nat Genet. 2001 January; 27(1): 84-8; Eur J Biochem 1996 Apr. 1; 237(1): 295-302; J Biol Chem, Vol. 274, Issue 16, 10897-10902, Apr. 16, 1999; and Hogan, B. L. M. (1996) Genes Dev. 10, 1580-1594. | Induction of Cartilage, Tissue and Bone Growth, and Diabetes |
| Inhibin alpha | GeneSeq Accession B02806 | WO0020591 | The inhibin beta A subunit joins the alpha subunit to form a pituitary FSH secretion inhibitor. Inhibin has been shown to regulate gonadal stromal cell proliferation negatively and to have tumour-suppressor activity. In addition, serum levels of inhibin have been shown to reflect the size of granulosa-cell tumors and can therefore be used as a marker for primary as well as recurrent disease. | Tumor suppressor activity of inhibin can be determined using assays known in the art: Matzuk et al., Nature 1992 Nov. 26: 360 (6402); 313-9. | Tumor suppression. |
| Inhibin beta | GeneSeq Accession H02808 | WO0020591 | The inhibin beta A subunit joins the alpha subunit to form a pituitary FSH secretion inhibitor. Inhibin has been shown to regulate gonadal stromal cell proliferation negatively and to have | Tumor suppressor activity of inhibin can be determined using assays known in the art: Matzuk et al., Nature 1992 Nov. 26: 360 (6402); 313-9. | Tumor suppression. |

TABLE 1-continued

| Therapeutic Protein X | Exemplary Identifier | PCT/Patent Reference | Biological Activity | Exemplary Activity Assay | Preferred Indication Y |
|---|---|---|---|---|---|
| | | | tumour-suppressor activity. In addition, serum levels of inhibin have been shown to reflect the size of granulosa-cell tumors and can therefore be used as a marker for primary as well as recurrent disease. | | |
| Cerebus Protein | GeneSeq Accession W86032 | WO9849296 | Cerebus is believed to be involved in the inhibition of BMP activity | BMP activity, in the presence of the antagonist Cerebus, can be determined using the following assays known in the art: Nat Genet. 2001 January; 27(1): 84-8; Eur J Biochem 1996 Apr 1; 237(1): 295-302; J Biol Chem, Vol. 274, Issue 16, 10897-10902, Apr. 16, 1999; and Hogan, B. L. M. (1996) Genes Dev. 10, 1580-1594. | BMP Antagonist useful for Osteosarcoma, abnormal bone growth. |
| Soluble BMP Receptor Kinase Protein-3 | GeneSeq Accession R95227 | WO9614579 | Soluble BMP receptor kinase protein-3 is involved in the binding of BMPs. Soluble BMP receptor kinase protein-3 is useful as an antagonist for the inhibition of BMP activity. | BMP activity, in the presence of the soluble antagonist BMP receptor kinase protein-3, can be determined using the following assays known in the art: Nat Genet. 2001 January; 27(1): 84-8; 237(1): 295-302; J Biol Chem, Vol. 274, Issue 16, 10897-10902, Apr. 16, 1999; and Hogan, B. L. M. (1996) Genes Dev. 10, 1580-1594. | BMP Antagonist useful for Osteosarcoma, abnormal bone growth. |
| BMP Processing Enzyme Furin | GeneSeq Accession W36099 | WO9741250 | BMPs belong to the transforming growth factor-beta (TGFB) superfamily. Bone morphogenic protein induces bone formation. | BMP activity, in the presence of the Furin, can be determined using the following assays known in the art: Nat Genet. 2001 January; 27(1): 84-8; Eur J Biochem 1996 Apr 1; 237(1): 295-302; J Biol Chem, Vol. 274, Issue 16, 10897-10902, Apr. 16, 1999; and Hogan, B. L. M. (1996) Genes Dev. 10, 1580-1594. | Bone formation or Regeneration Abnormalities |
| TGF-beta 1 | GeneSeq Accession R29657 | WO9216228 | Members of the TGF-beta family of proteins initiate cell signaling by binding to heteromeric receptor complexes of type I (TbetaRI) and type II (TbetaRII) serine/threonine kinase receptors (reviewed by Massague, J. et al. (1994) Trends Cell Biol. 4: 172 178; Miyazono, K. et al. (1994) Adv. Immunol. 55: 181-220). Activation of this heteromeric receptor complex occurs when TGF-beta. binds to TbetaRII, which then recruits and phosphorylates TbetaRI. Activated TbetaRI then propagates the signal to downstream targets (Chen, F. and Weinberg, R. A. (1995) PNA892: 1565-1569; | The effect of TGF betas on signaling can be assayed by treating Primary BAECs transfected with a construct called p3TP-Lux, containing a TGF-beta responsive promoter fused to a reporter gene, and measuring luciferase gene expression (Wrana et al., 1994, Nature 370: 341-347). | Useful for treating cancer and to promote wound healing. |

TABLE 1-continued

| Therapeutic Protein X | Exemplary Identifier | PCT/Patent Reference | Biological Activity | Exemplary Activity Assay | Preferred Indication Y |
|---|---|---|---|---|---|
| TGF-beta 2 | GeneSeq Accession R39659 | EP542679 | Wrana, J. L. et al. (1994) Nature 370: 341. Members of the TGF-beta family of proteins initiate cell signaling by binding to heteromeric receptor complexes of type I (TbetaRI) and type II (TbetaRII) serine/threonine kinase receptors (reviewed by Massague, J. et al. (1994) Trends Cell Biol. 4: 172 178; Miyazono, K. et al. (1994) Adv. Immunol. 55: 181-220). Activation of this heteromeric receptor complex occurs when TGF-beta. binds to TbetaRII, which then recruits and phosphorylates TbetaRI. Activated TbetaRI then propagates the signal to downstream targets (Chen, F. and Weinberg. R. A. (1995) PNA892: 1565-1569; Wrana, J. L. et al. (1994) Nature 370: 341. | The effect of TGF betas on signaling can be assayed by treating Primary BAECs transfected with a construct called p3TP-Lux, containing a TGF-beta responsive promoter fused to a reporter gene, and measuring luciferase gene expression (Wrana et al., 1994, Nature 370: 341-347). | Useful for treating cancer and to promote wound healing. |
| ZTGF-beta 9 | GeneSeq Accession Y70654 | WO0015798 | Members of the TGF-beta family of proteins initiate cell signaling by binding to heteromeric receptor complexes of type I (TbetaRI) and type II (TbetaRII) serine/threonine kinase receptors (reviewed by Massague, J. et al. (1994) Trends Cell Biol. 4: 172 178; Miyazono, K. et al. (1994) Adv. Immunol. 55: 181-220). Activation of this heteromeric receptor complex occurs when TGF-beta. binds to TbetaRII, which then recruits and phosphorylates TbetaRI. Activated TbetaRI then propagates the signal to downstream targets (Chen, F. and Weinberg. R. A. (1995) PNA892: 1565-1569; Wrana, J. L. et al. (1994) Nature 370: 341. | The effect of TGF betas on signaling can be assayed by treating Primary BAECs transfected with a construct called p3TP-Lux, containing a TGF-beta responsive promoter fused to a reporter gene, and measuring luciferase gene expression (Wrana et al., 1994, Nature 370: 341-347). | Useful for treating cancer and to promote wound healing. |
| Anti-TGF beta family antibodies | | GB2305921 | Members of the TGF-beta family of proteins initiate cell signaling by binding to heteromeric receptor complexes of type I (TbetaRI) and type II (TbetaRII) serine/threonine kinase receptors (reviewed by Massague, J. et al. (1994) Trends Cell Biol. 4: 172 178; Miyazono, K. et al. (1994) Adv. Immunol. 55: 181-220). Activation of this heteromeric receptor complex occurs when TGF-beta. binds to TbetaRII, which then recruits and | The effect of TGF betas on signaling in the presence of an anti-TGF beta antibody, can be assayed by treating Primary BAECs transfected with a construct called p3TP-Lux, containing a TGF-beta responsive promoter fused to a reporter gene, and measuring luciferase gene expression (Wrana et al., 1994, Nature 370: 341-347). | Useful for control of fibrosis, immune, and inflammatory disease. |

TABLE 1-continued

| Therapeutic Protein X | Exemplary Identifier | PCT/Patent Reference | Biological Activity | Exemplary Activity Assay | Preferred Indication Y |
|---|---|---|---|---|---|
| | | | phosphorylates TbetaRI. Activated TbetaRI then propagates the signal to downstream targets (Chen, F. and Weinberg, R. A. (1995) PNA892: 1565-1569; Wrana, J. L. et al. (1994) Nature 370: 341. | | |
| Latent TGF beta binding protein II | GeneSeq Accession Y70552 | WO0012551 | Members of the TGF-beta family of proteins initiate cell signaling by binding to heteromeric receptor complexes of type I (TbetaRI) and type II (TbetaRII) serine/threonine kinase receptors (reviewed by Massague, J. et al. (1994) Trends Cell Biol. 4: 172 178; Miyazono, K. et al. (1994) Adv. Immunol. 55: 181-220). Activation of this heteromeric receptor complex occurs when TGF-beta. binds to TbetaRII, which then recruits and phosphorylates TbetaRI. Activated TbetaRI then propagates the signal to downstream targets (Chen, F. and Weinberg. R. A. (1995) PNA892: 1565-1569; Wrana, J. L. et al. (1994) Nature 370: 341. | The effect of TGF betas on signaling in the presence of a TGF beta binding protein, can be assayed by treating Primary BAECs transfected with a construct called p3TP-Lux, containing a TGF-beta responsive promoter fused to a reporter gene, and measuring luciferase gene expression (Wrana et al., 1994, Nature 370: 341-347). | Useful for inhibiting tissue or tumor growth. |
| MP52 | GeneSeq Accession W36100 | WO9741250 | Members of the TGF-beta family of proteins initiate cell signaling by binding to heteromeric receptor complexes of type I (TbetaRI) and type II (TbetaRII) serine/threonine kinase receptors (reviewed by Massague, J. et al. (1994) Trends Cell Biol. 4: 172 178; Miyazono, K. et al. (1994) Adv. Immunol. 55: 181-220). Activation of this heteromeric receptor complex occurs when TGF-beta. binds to TbetaRII, which then recruits and phosphorylates TbetaRI. Activated TbetaRI then propagates the signal to downstream targets (Chen, F. and Weinberg. R. A. (1995) PNA892: 1565-1569; Wrana, J. L. et al. (1994) Nature 370: 341. | The effect of TGF betas on signaling can be assayed by treating Primary BAECs transfected with a construct called p3TP-Lux, containing a TGF-beta responsive promoter fused to a reporter gene, and measuring luciferase gene expression (Wrana et al., 1994, Nature 370: 341-347). | Bone formation or Regeneration Abnormalities |
| b57 Protein | GeneSeq Accession W69293 | WO9837195 | BMPs are involved in the induction of bone formation. Specific antagonists are useful is preventing this activity from occurring. | BMP activity, in the presence of b57 protein, can be determined using the following assays known in the art: Nat Genet. 2001 January; 27(1): 84-8; Eur J Biochem 1996 Apr. 1; 237(1): 295-302; J Biol Chem, Vol. 274, Issue 16, 1089-10902., Apr. 16, 1999; and | BMP Antagonist useful for Osteosarcoma, abnormal bone growth. |

TABLE 1-continued

| Therapeutic Protein X | Exemplary Identifier | PCT/Patent Reference | Biological Activity | Exemplary Activity Assay | Preferred Indication Y |
|---|---|---|---|---|---|
| Resistin | GeneSeq Accession W69293 | WO0064920 | This gene belongs to the family defined by mouse FIZZl and FIZZ3 genes. The characteristic feature of this family is the C-terminal stretch of 10 cys residues with identical spacing. The mouse homolog of this protein is secreted by adipocytes, may be the hormone potantially linking obesity to type II diabetes. | Hogan, B. L. M. (1996) Genes Deve. 10, 1580-1594. Ability of resistin to influence type II diabetes can be determined using assays known in the art: Pontoglio et al., J Clin Invest 1998 May 15; 101(10): 2215-22. | Type II diabetes and Syndrome X. |
| Galectin-4 | GeneSeq Accession W11841 | WO9703190 | Galectins are a family of carbohydrate-binding proteins characterized by an affinity for beta-galactoside containing glycoconjugates. | Ability of Galectin-4 polypeptides to bind lactose can be determined using assays known in the art: Wada, et al., J Biol Chem 1997 Feb 28; 272(9): 6078-86. | Lactose intolerance. |
| APM-I; ACRP-30; Famoxin | GeneSeq Accession Y71035 | WO0026363 | ACRP30 gene is exclusively expressed in adipose tissue. ACRP30 is thought to increase fatty acid oxidation by muscle tissue. | Ability of ACRP30 polypeptides to influence obesity and fat oxidation can be determined using assays known in the art: Fruebis et al., Proc Nat'l Acad Sci USA 2001 Feb. 13; 98(4): 2005-10. | Obesity, Metabolic disorders, Lipid Metabolism; Hormone Secretion. |
| ACRP-30 Homologue; Complement Component C1q C | GeneSeq Accession B30234 | WO0063376 | ACPR30 gene is exclusively expressed in adipose tissue. ACRP30 is thought to increase fatty acid oxidation by muscle tissue. | Ability of ACRP30 homologue polypeptides to influence obesity and fat oxidation can be determined using assays known in the art: Fruebis et al., Proc Nat'l Acad Sci USA 2001 Feb. 13; 98(4): 2005-10. | Obesity, Metabolic disorders, Lipid Metabolism; Hormone Secretion. |
| Calpain-10a | GeneSeq Accession Y79567 | WO0023603 | Calpain is believed to play a role in insulin secretion and insulin activity, and therefore may be useful in the treatment of type II diabetes. | Ability of Calpain-10 to influence type II diabetes can be determined using assays known in the art: Pontoglio et al., J Clin Invest 1998 May 15; 101(10): 2215-22. | Diabetes mellitus; Regulation of Insulin secretory response; Insulin mediated glucose transport disorders. |
| Calpain-10b | GeneSeq Accession Y79568 | WO0023603 | Calpain is believed to play a role in insulin secretion and insulin activity, and therefore may be useful in the treatment of type II diabetes. | Ability of Calpain-10 to influence type II diabetes can be determined using assays known in the art: Pontoglio et al., J Clin Invest 1998 May 15; 101(10): 2215-22. | Diabetes mellitus; Regulation of Insulin secretory response; Insulin mediated glucose transport disorders. |
| Calpain-10c | GeneSeq Accession Y79569 | WO0023603 | Calpain is believed to play a role in insulin secretion and insulin activity, and therefore may be useful in the treatment of type II diabetes. | Ability of Calpain-10 to influence type II diabetes can be determined using assays known in the art: Pontoglio et al., J Clin Invest 1998 May 15; 101(10): 2215-22. | Diabetes mellitus; Regulation of Insulin secretory response; Insulin mediated glucose transport disorders |
| PDGF-D | GeneSeq Accession Y71130 | WO0027879 | Vascular Endothelial Growth Factor. | Proliferation assay using NR6R-3T3 cells (Rizzino 1988 Cancer Res. 48: 4266). | Wound Healing; Atherosclerosis. |

TABLE 1-continued

| Therapeutic Protein X | Exemplary Identifier | PCT/Patent Reference | Biological Activity | Exemplary Activity Assay | Preferred Indication Y |
|---|---|---|---|---|---|
| FasL | GeneSeq Accession Y28594 | WO9936079 | Activities associated with apoptosis and immune system functions. | Activity can be determined using Apoptosis assays known in the art: Walczak et al. (1996) EMBO J 16: 5386-5397. | Apoptosis-related disorders; Autoimmune disorders; Graft v-Host disorders. |
| Chondro modulin-like protein | GeneSeq Accession Y71262 | WO0029579 | Chondromodulin proteins are cartilage proteins thought to confer resistance to angiogeneis, and thus are useful as anti-angiogenic agents that may have utility in combating cancer. | Ability of Chondromodulin-like protein to inhibit vascularization can be determined using assays known in the art: Hirakie et al., J Biol Chem 1997 Dec. 19; 272(51): 32419-26. | Antianglogenic agent; Osteoblast proliferation stimulator; prevents vascularization of cartilage tissue; Useful to treat cancer. |
| Patched | GeneSeq Accession W72969 | U.S. Pat. No. 5837538 | Patched is a tumour-suppressor receptor for Sonic hedgehog (shh), which is a protein that controls developmental patterning and growth. | Ability of soluble Patched to bind to and inhibit the activities of shh can be determined using assays known in the art: Stone et al., Nature 1996 Nov. 14; 384(6605): 129-34. | Receptor for Hedgehog cellular proliferation signaling molecule. This receptor is useful as a means of preventing cellular proliferation via the shh signaling pathway, thus useful for cancers. |
| Patched-2 | GeneSeq Accession Y43261 | WO9953058 | Patched is a tumour-suppressor receptor for Sonic hedgehog (shh), which is a protein that controls developmental patterning and growth. | Ability of soluble Patched to bind to and inhibit the activities of shh can be determined using assays known in the art: Stone et al., Nature 1996 Nov. 14; 384(6605): 129-34. | Receptor for Hedgehog cellular proliferation signaling molecule. This receptor is useful as a means of preventing cellular proliferation via the shh signaling pathway, thus useful for cancers. |
| Maspin; Protease Inhibitor 5 | GeneSeq Accession R50938 | WO9405804 | Maspin is a member of the serpin family of serine protease inhibitors that is thought to suppress tumor metastasis. | The inhibitory effects of Maspin and other protease inhibitors can be assayed using methods known in the art such as a labeled protease substrate, for example, Universal Protease Substrate (casein, resorufin-labeled) Roche Molecular Biochemicals, Cat. No. 1080733. | Tumor suppressor which is down-regulated in breast cancers. The maspin protein has tumour suppressing and invasion suppressing activity. |
| Endostatin | GeneSeq Accession B28399 | WO0064946 | Endostatin is believed to inhibit effects of capillary endothelial cell proliferation. | The inhibitory effects of endostatin can be assayed using assays disclosed by Cao et al. (1996) J. Biol. Chem. 271 294461-29467. | Anti-angiogenic activity. Useful in the prevention and/or treatment of cancers. |
| aFGF; FGF-1 | GeneSeq Accession P94037 | EP298723 | Fibroblast Growth Factor | Proliferation assay using NR6R-3T3 cells (Rizzino 1988 Cancer Res. 48: 4266); Examples 23 and 39 disclosed herein. | Promotion of growth and proliferation of cells, such as epithelial cells and keratinocytes. Antagonists may be useful as anti-cancer agents. |
| bFGF; FGF-2 | GeneSeq Accession R06685 | FR2642086 | Fibroblast Growth Factor | Proliferation assay using NR6R-3T3 cells (Rizzino 1988 Cancer Res. 48: 4266); Examples 23 and 39 | Promotion of growth and proliferation of cells, such as epithelial cells |

TABLE 1-continued

| Therapeutic Protein X | Exemplary Identifier | PCT/Patent Reference | Biological Activity | Exemplary Activity Assay | Preferred Indication Y |
|---|---|---|---|---|---|
| | | | | disclosed herein. | and keratinocytes. Antagonists may be useful as anti-cancer agents. |
| FGF-3; INT-2 | GeneSeq Accession R07824 | WO9503831 | Fibroblast Growth Factor | Proliferation assay using NR6R-3T3 cells (Rizzino 1988 Cancer Res. 48: 4266); Examples 23 and 39 disclosed herein. | Promotion of growth and proliferation of cells, such as epithelial cells and keratinocytes. Antagonists may be useful as anti-cancer agents. |
| FGF-4; HST-1; HBGF-4 | GeneSeq Accession R07825 | WO9503831 | Fibroblast Growth Factor | Proliferation assay using NR6R-3T3 cells (Rizzino 1988 Cancer Res. 48: 4266); Examples 23 and 39 disclosed herein. | Promotion of growth and proliferation of cells, such as epithelial cells and keratinocytes. Antagonists may be useful as anti-cancer agents. |
| FGF-5 | GeneSeq Accession W22600 | WO9730155 | Fibroblast Growth Factor | Proliferation assay using NR6R-3T3 cells (Rizzino 1988 Cancer Res. 48: 4266); Examples 23 and 39 disclosed herein. | Promotion of growth and proliferation of cells, such as epithelial cells and keratinocytes. Antagonists may be useful as anti-cancer agents. |
| FGF-6; Heparin binding secreted transforming factor-2 | GeneSeq Accession R58555 | EP613946 | Fibroblast Growth Factor | Proliferation assay using NR6R-3T3 cells (Rizzino 1988 Cancer Res. 48: 4266); Examples 23 and 39 disclosed herein. | Promotion of growth and proliferation of cells, such as epithelial cells and keratinocytes. Antagonists may be useful as anti-cancer agents. |
| FGF-8 | GeneSeq Accession R80783 | WO9524928 | Fibroblast Growth Factor | Proliferation assay using NR6R-3T3 cells (Rizzino 1988 Cancer Res. 48: 4266); Examples 23 and 39 disclosed herein. | Promotion of growth and proliferation of cells, such as epithelial cells and keratinocytes. Antagonists may be useful as anti-cancer agents. |
| FGF-9; Gila activating factor | GeneSeq Accession R70822 | WO9503831 | Fibroblast Growth Factor | Proliferation assay using NR6R-3T3 cells (Rizzino 1988 Cancer Res. 48: 4266); Examples 23 and 39 disclosed herein. | Promotion of growth and proliferation of cells, such as epithelial cells and keratinocytes. Antagonists may be useful as anti-cancer agents. |
| FGF-12; Fibroblast growth factor homologous factor-1 | GeneSeq Accession W06309 | WO9635708 | Fibroblast Growth Factor | Proliferation assay using NR6R-3T3 cells (Rizzino 1988 Cancer Res. 48: 4266); Examples 23 and 39 disclosed herein. | Promotion of growth and proliferation of cells, such as epithelial cells and keratinocytes. |

TABLE 1-continued

| Therapeutic Protein X | Exemplary Identifier | PCT/Patent Reference | Biological Activity | Exemplary Activity Assay | Preferred Indication Y |
|---|---|---|---|---|---|
| FGF-15 | GeneSeq Accession Y08582 | WO9927100 | Fibroblast Growth Factor | Proliferation assay using NR6R-3T3 cells (Rizzino 1988 Cancer Res. 48: 4266); Examples 23 and 39 disclosed herein. | Antagonists may be useful as anti-cancer agents. Promotion of growth and proliferation of cells, such as epithelial cells and keratinocytes. Antagonists may be useful as anti-cancer agents. |
| FGF-16 | GeneSeq Accession Y05474 | WO9918128 | Fibroblast Growth Factor | Proliferation assay using NR6R-3T3 cells (Rizzino 1988 Cancer Res. 48: 4266); Examples 23 and 39 disclosed herein. | Promotion of growth and proliferation of cells, such as epithelial cells and keratinocytes. Antagonists may be useful as anti-cancer agents. |
| FGF-18 | GeneSeq Accession Y08590 | WO9927100 | Fibroblast Growth Factor | Proliferation assay using NR6R-3T3 cells (Rizzino 1988 Cancer Res. 48: 4266); Examples 23 and 39 disclosed herein. | Promotion of growth and proliferation of cells, such as epithelial cells and keratinocytes. Antagonists may be useful as anti-cancer agents. |
| flt-3 ligand | GeneSeq Accession R67541 | EP627487 | Stem Cell Progenitor | Chemokine activities can be determined using assays known in the art: Methods in Molecular Biology, 2000, vol. 138: Chemokine Protocols. Edited by: A. E. I. Proudfoot, T. N. C. Wells, and C. A. Power. © Humana Press Inc., Totowa, NJ | Promotion of immune cell growth and/or differentiation. |
| VEGF-110 | GeneSeq Accession Y69417 | WO0013702 | Promotes the growth and/or proliferation of endothelial cells. | VEGF activity can be determined using assays known in the art, such as those disclosed in International Publication No. WO0045835, for example. | Promotion of growth and proliferation of cells, such as vascular endothelial cells. Antagonists may be useful as anti-angiogenic agents, and may be applicable for cancer. |
| VEGB-121 | GeneSeq Accession B50432 | WO0071713 | Promotes the growth and/or proliferation of endothelial cells. | VEGF activity can be determined using assays known in the art, such as those disclosed in International Publication No. WO0045835, for example. | Promotion of growth and proliferation of cells, such as vascular endothelial cells. Antagonists may be useful as anti-angiogenic agents, and may be applicable for cancer. |
| VEGF-138 | GeneSeq Accession | WO9940197 | Promotes the growth and/or proliferation of endothelial cells. | VEGF activity can be determined using assays known in the art, such | Promotion of growth and proliferation of cells, |

TABLE 1-continued

| Therapeutic Protein X | Exemplary Identifier | PCT/Patent Reference | Biological Activity | Exemplary Activity Assay | Preferred Indication Y |
|---|---|---|---|---|---|
| | Y43483 | | | as those disclosed in International Publication No. WO0045835, for example. | such as vascular endothelial cells. Antagonists may be useful as anti-angiogenic agents, and may be applicable for cancer. |
| VEGF-145 | GeneSeq Accession Y69413 | WO0013702 | Promotes the growth and/or proliferation of endothelial cells. | VEGF activity can be determined using assays known in the art, such as those disclosed in International Publication No. WO0045835, for example. | Promotion of growth and proliferation of cells, such as vascular endothelial cells. Antagonists may be useful as anti-angiogenic agents, and may be applicable for cancer. |
| VEGF-162 | GeneSeq Accession Y43484 | WO9940197 | Promotes the growth and/or proliferation of endothelial cells. | VEGF activity can be determined using assays known in the art, such as those disclosed in International Publication No. WO0045835, for example. | Promotion of growth and proliferation of cells, such as vascular endothelial cells. Antagonists may be useful as anti-angiogenic agents, and may be applicable for cancer. |
| VEGF-165 | GeneSeq Accession Y69414 | WO0013702 | Promotes the growth and/or proliferation of endothelial cells. | VEGF activity can be determined using assays known in the art, such as those disclosed in International Publication No. WO0045835, for example. | Promotion of growth and proliferation of cells, such as vascular endothelial cells. Antagonists may be useful as anti-angiogenic agents, and may be applicable for cancer. |
| VEGF-182 | GeneSeq Accession Y43483 | WO9940197 | Promotes the growth and/or proliferation of endothelial cells. | VEGF activity can be determined using assays known in the art, such as those disclosed in International Publication No. WO0045835, for example. | Promotion of growth and proliferation of cells, such as vascular endothelial cells. Antagonists may be useful as anti-angiogenic agents, and may be applicable for cancer. |
| VEGF-189 | GeneSeq Accession Y69415 | WO0013702 | Promotes the growth and/or proliferation of endothelial cells. | VEGF activity can be determined using assays known in the art, such as those disclosed in International Publication No. WO0045835, for example. | Promotion of growth and proliferation of cells, such as vascular endothelial cells. Antagonists may be useful as anti-angiogenic agents, and may be applicable for cancer. |
| VEGF-206 | GeneSeq Accession Y69416 | WO0013702 | Promotes the growth and/or proliferation of endothelial cells. | VEGF activity can be determined using assays known in the art, such as those disclosed in International Publication No. WO0045835, for example. | Promotion of growth and proliferation of cells, such as vascular endothelial cells. |

TABLE 1-continued

| Therapeutic Protein X | Exemplary Identifier | PCT/Patent Reference | Biological Activity | Exemplary Activity Assay | Preferred Indication Y |
|---|---|---|---|---|---|
| | | | | example. | Antagonists may be useful as anti-angiogenic agents, and may be applicable for cancer. |
| VEGF-D | GeneSeq Accession W53240 | WO9807832 | Promotes the growth and/or proliferation of endothelial cells. | VEGF activity can be determined using assays known in the art, such as those disclosed in International Publication No. WO0045835, for example. | Promotion of growth and proliferation of cells, such as vascular endothelial cells. Antagonists may be useful as anti-angiogenic agents, and may be applicable for cancer. |
| VEGF-E; VEGF-X | GeneSeq Accession Y33679 | WO9947677 | Promotes the growth and/or proliferation of endothelial cells. | VEGF activity can be determined using assays known in the art, such as those disclosed in International Publication No. WO0045835, for example. | Promotion of growth and proliferation of cells, such as vascular endothelial cells. Antagonists may be useful as anti-angiogenic agents, and may be applicable for cancer. |
| VEGF Receptor; KDR; flk-1 | GeneSeq Accession W69679 | WO9831794 | Receptor for VEGF polypeptides | VEGF activity, in the presence of flk-1 polypeptides, can be determined using assays known in the art, such as those disclosed in International Publication No. WO0045835, for example. | VEGF Receptor. Fusion protein with the extracellular domain is useful as an anti-angiogenic agent. Antagonists may be useful in the promotion of angiogenesis. |
| Soluble VEGF Receptor | GeneSeq Accession W47037 | U.S. Pat. No. 5,712,380 | Receptor for VEGF polypeptides | VEGF activity, in the presence of VEGF Receptor polypeptides, can be determined using assays known in the art, such as those disclosed in International Publication No. WO0045835, for example. | VEGF Receptor. Fusion protein with the extracellular domain is useful as an anti-angiogenic agent. Antagonists may be useful in the promotion of angiogenesis. |
| flt-1 | GeneSeq Accession Y70751 | WO0021560 | Receptor for VEGF polypeptides | VEGF activity, in the presence of flt-1 polypeptides, can be determined using assays known in the art, such as those disclosed in International Publication No. WO0045835, for example. | VEGF Receptor. Fusion protein with the extracellular domain is useful as an anti-angiogenic agent. Antagonists may be useful in the promotion of angiogenesis. |
| VEGF R-3; flt-4 | GeneSeq Accession B29047 | WO0058511 | Receptor for VEGF polypeptides | VEGF activity, in the presence of flt-4 polypeptides, can be determined using assays known in the art, such as those disclosed in International Publication No. WO0045835, for example. | VEGF Receptor. Fusion protein with the extracellular domain is useful as an anti-angiogenic agent. Antagonists may be |

TABLE 1-continued

| Therapeutic Protein X | Exemplary Identifier | PCT/Patent Reference | Biological Activity | Exemplary Activity Assay | Preferred Indication Y |
|---|---|---|---|---|---|
| Neuropilin-1 | GeneSeq Accession Y06319 | WO9929858 | Vascular Endothelial Growth Factor | VEGF activity can be determined using assays known in the art, such as those disclosed in International Publication No. WO0045835, for example. | useful in the promotion of angiogenesis. Promotion of growth and proliferation of cells, such as vascular endothelial cells. Antagonists may be useful as anti-angiogenic agents, and may be applicable for cancer. |
| Neuropilin-2 | GeneSeq Accession Y03618 | WO9929858 | Vascular Endothelial Growth Factor | VEGF activity can be determined using assays known in the art, such as those disclosed in International Publication No. WO0045835, for example. | Promotion of growth and proliferation of cells, such as vascular endothelial cells. Antagonists may be useful as anti-angiogenic agents, and may be applicable for cancer. |
| Human fast twitch skeletal muscle troponin C | GeneSeq Accession W22597 | WO9730085 | Troponins are contractile proteins that are thought to inhibit angiogenesis. High levels may contribute to the difficulty encountered in revascularizing the ischemic myocardium after cardiovascular injury. | Ability of soluble Troponins to inhibit angiogenesis can be determined using assays known in the art.: Proc Natl Acad Sci USA 1999 Mar. 16; 96(6): 2645-50. | Anti-angiogenesis |
| Human fast twitch skeletal muscle troponin I | GeneSeq Accession W18054 | WO9730085 | Troponins are contractile proteins that are thought to inhibit angiogenesis. High levels may contribute to the difficulty encountered in revascularizing the ischemic myocardium after cardiovascular injury. | Ability of soluble Troponins to inhibit angiogenesis can be determined using assays known in the art.: Proc Natl Acad Sci USA 1999 Mar. 16; 96(6): 2645-50. | Anti-angiogenesis |
| Human fast twitch skeletal muscle troponin T | GeneSeq Accession W22599 | WO9730085 | Troponins are contractile proteins that are thought to inhibit angiogenesis. High levels may contribute to the difficulty encountered in revascularizing the ischemic myocardium after cardiovascular injury. | Ability of soluble Troponins to inhibit angiogenesis can be determined using assays known in the art.: Proc Natl Acad Sci USA 1999 Mar. 16; 96(6): 2645-50. | Anti-angiogenesis |
| fragment. myofibrillar protein troponin I | GeneSeq Accession W18053 | WO9719955 | Troponins are contractile proteins that are thought to inhibit angiogenesis. High levels may contribute to the difficulty encountered in revascularizing the ischemic myocardium after cardiovascular injury. | Ability of soluble Troponins to inhibit angiogenesis can be determined using assays known in the art.: Proc Natl Acad Sci USA 1999 Mar. 16; 96(6): 2645-50. | Anti-angiogenesis |
| myofibrillar protein troponin I | GeneSeq Accession W18054 | WO9719955 | Troponins are contractile proteins that are thought to inhibit angiogenesis. High levels may contribute to the difficulty encountered in revascularizing the ischemic myocardium after cardiovascular injury. | Ability of soluble Troponins to inhibit angiogenesis can be determined using assays known in the art.: Proc Natl Acad Sci USA 1999 Mar. 16; 96(6): 2645-50. | Anti-angiogenesis |
| Troponin peptides | GeneSeq Accessions | WO9933874 | Troponins are contractile proteins that are thought to inhibit angiogenesis. High | Ability of soluble Troponins to inhibit angiogenesis can be | Anti-angiogenesis |

TABLE 1-continued

| Therapeutic Protein X | Exemplary Identifier | PCT/Patent Reference | Biological Activity | Exemplary Activity Assay | Preferred Indication Y |
|---|---|---|---|---|---|
| | Y29581, Y29582, Y29583, Y29584, Y29585, and Y29586 | | levels may contribute to the difficulty encountered in revascularizing the ischemic myocardium after cardiovascular injury. | determined using assays known in the art.: Proc Natl Acad Sci USA 1999 Mar. 16; 96(6): 2645-50. | |
| Human fast twitch skeletal muscle Troponin subunit C | GeneSeq Accession B00134 | WO0054770 | Troponins are contractile proteins that are thought to inhibit angiogenesis. High levels may contribute to the difficulty encountered in revascularizing the ischemic myocardium after cardiovascular injury. | Ability of soluble Troponins to inhibit angiogenesis can be determined using assays known in the art.: Proc Natl Acad Sci USA 1999 Mar. 16; 96(6): 2645-50. | Anti-angiogenesis |
| Human fast twitch skeletal muscle Troponin subunit I Protein | GeneSeq Accession B00135 | WO0054770 | Troponins are contractile proteins that are thought to inhibit angiogenesis. High levels may contribute to the difficulty encountered in revascularizing the ischemic myocardium after cardiovascular injury. | Ability of soluble Troponins to inhibit angiogenesis can be determined using assays known in the art.: Proc Natl Acad Sci USA 1999 Mar. 16; 96(6): 2645-50. | Anti-angiogenesis |
| Human fast twitch skeletal muscle Troponin subunit T | GeneSeq Accession B00136 | WO0054770 | Troponins are contractile proteins that are thought to inhibit angiogenesis. High levels may contribute to the difficulty encountered in revascularizing the ischemic myocardium after cardiovascular injury. | Ability of soluble Troponins to inhibit angiogenesis can be determined using assays known in the art.: Proc Natl Acad Sci USA 1999 Mar. 16; 96(6): 2645-50. | Anti-angiogenesis |
| Activator Inhibitor-1; PAI-1 | GeneSeq Accession R08411 | WO9013648 | PAIs are believed to play a role in cancer, and cardiovascular disease and blood-clotting disorders. | Methods that measure plasminogen activator inhibitor (PAI) activity are known in the art, for example, assay the ability of PAI to inhibit tissue plasminogen activator (tPA) or urokinase (uPA): J Biochem Biophys Methods 2000 Sep. 11; 45(2): 127-40, Breast Cancer Res Treat 1996; 41(2): 141-6. Methods that measure anti-angiogenesis activity are known in the art, for example, Proc Natl Acad Sci USA 1999 Mar. 16; 96(6): 2645-50. | Anti-angiogenesis; blood-clotting disorders. |
| Plasminogen Activator Inhibitor-2; PAI-2 | GeneSeq Accession P94160 | DE3722673 | PAIs are believed to play a role in cancer, and cardiovascular disease and blood-clotting disorders. | Methods that measure plasminogen activator inhibitor (PAI) activity are known in the art, for example, assay the ability of PAI to inhibit tissue plasminogen activator (tPA) or urokinase (uPA): J Biochem Biophys Methods 2000 Sep. 11; 45(2): 127-40, Breast Cancer Res Treat 1996; 41(2): 141-6. Methods that measure anti-angiogenesis activity are known in the art, for example, Proc Natl Acad Sci USA 1999 Mar. 16; 96(6): 2645-50. | Anti-angiogenesis; blood-clotting disorders. |
| Activator Inhibitor-2; PAI-2 | GeneSeq Accession | WO9102057 | PAIs are believed to play a role in cancer, and cardiovascular disease and blood- | Methods that measure plasminogen activator inhibitor (PAI) activity are | Anti-angiogenesis; blood-clotting disorders. |

TABLE 1-continued

| Therapeutic Protein X | Exemplary Identifier | PCT/Patent Reference | Biological Activity | Exemplary Activity Assay | Preferred Indication Y |
|---|---|---|---|---|---|
| | R10921 | | clotting disorders. | known in the art, for example, assay the ability of PAI to inhibit tissue plasminogen activator (tPA) or urokinase (uPA): J Biochem Biophys Methods 2000 Sep. 11; 45(2): 127-40, Breast Cancer Res Treat 1996; 41(2): 141-6. Methods that measure anti-angiogenesis activity are known in the art, for example, Proc Natl Acad Sci USA 1999 Mar. 16; 96(6): 2645-50. | |
| Human PAI-1 mutants | GeneSeq Accessions R11755, R11756, R11757, R11758, R11759, R11760, R11761, R11762 and R11763 | WO9105048 | PAIs are believed to play a role in cancer, and cardiovascular disease and blood-clotting disorders. | Methods that measure plasminogen activator inhibitor (PAI) activity are known in the art, for example, assay the ability of PAI to inhibit tissue plasminogen activator (tPA) or urokinase (uPA): J Biochem Biophys Methods 2000 Sep. 11; 45(2): 127-40, Breast Cancer Res Treat 1996; 41(2): 141-6. Methods that measure anti-angiogenesis activity are known in the art, for example, Proc Natl Acad Sci USA 1999 Mar. 16; 96(6): 2645-50. | Anti-angiogenesis; blood-clotting disorders. |
| CXCR3; CXC | GeneSeq Accession Y79372 | WO0018431 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot, T. N. C. Wells, and C. A. Power. © Humana Press Inc., Totowa, NJ. | Soluble CXCR3 polypeptides may be useful for inhibiting chemokine activities and viral infection. |
| Modified Rantes | GeneSeq Accession W38129 | WO9737005 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. Over 40 human chemokines | Chemokine activities can be determined using assays known in the art: Methods in Molecular Biology, 2000, vol. 138: Chemokine Protocols. Edited by: A. E. I. Proudfoot, T. N. C. Wells, and C. A. Power. © Humana Press Inc., Totowa, NJ. | Immune disorders. |

TABLE 1-continued

| Therapeutic Protein X | Exemplary Identifier | PCT/Patent Reference | Biological Activity | Exemplary Activity Assay | Preferred Indication Y |
|---|---|---|---|---|---|
| RANTES | GeneSeq Accession Y05299 | EP905240 | have been described, which bind to ~17 receptors thus far identified. Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot, T. N. C. Wells, and C. A. Power. © Humana Press Inc., Totowa, NJ. | Immune disorders. |
| MCI-1a | GeneSeq Accession R73914 | WO9509232 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot, T. N. C. Wells, and C. A. Power. © Humana Press Inc., Totowa, NJ. | Immune disorders. |
| MCP-1b | GeneSeq Accession Y26176 | WO9929728 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot, T. N. C. Wells, and C. A. Power. © Humana Press Inc., Totowa, NJ. | Immune disorders. |
| MCP-1 receptor | GeneSeq Accession R79165 | WO9519436 | Chemokines are a family of related small, secreted proteins involved in biological processes ranging from hematopoiesis, angiogenesis, and leukocyte trafficking. Members of this family are involved in a similarly diverse range of pathologies | Chemokine activities can be determined using assays known in the art: Methods in Molecular Biology, 2000, vol. 138: Chemokine Protocols. Edited by: A. E. I. Proudfoot, T. N. C. Wells, and C. A. Power. | Soluble MCP-1 Receptor polypeptides may be useful for inhibiting chemokine activities and viral infection. |

TABLE 1-continued

| Therapeutic Protein X | Exemplary Identifier | PCT/Patent Reference | Biological Activity | Exemplary Activity Assay | Preferred Indication Y |
|---|---|---|---|---|---|
| | | | including inflammation, allergy, tissue rejection, viral infection, and tumor biology. The chemokines exert their effects by acting on a family of seven transmembrane G-protein coupled receptors. Over 40 human chemokines have been described, which bind to ~17 receptors thus far identified. | © Humana Press Inc., Totowa, NJ. | |
| MCP-3 | GeneSeq Accession R73915 | W09509232 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot, T. N. C. Wells, and C. A. Power. © Humana Press Inc, Totowa, NJ. | Immune disorders. |
| MCP-4 receptor | GeneSeq Accession W56689 | W09809171 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot, T. N. C. Wells, and C. A. Power. © Humana Press Inc, Totowa, NJ. | Soluble MCP-4 Receptor polypeptides may be useful for inhibiting chemokine activities and viral infection. |
| RANTES receptor | GeneSeq Accession W29588 | U.S. Pat. No. 5,652,133 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot, T. N. C. Wells, and C. A. Power. © Humana Press Inc, Totowa, NJ. | Soluble RANTES Receptor polypeptides may be useful for inhibiting chemokine activities and viral infection. |

TABLE 1-continued

| Therapeutic Protein X | Exemplary Identifier | PCT/Patent Reference | Biological Activity | Exemplary Activity Assay | Preferred Indication Y |
|---|---|---|---|---|---|
| CCR5 variant | GeneSeq Accession W88238 | WO9854317 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot, T. N. C. Wells, and C. A. Power. © Humana Press Inc, Totowa, NJ. | Soluble CCR5 polypeptides may be useful for inhibiting chemokine activities and viral infection. |
| CCR7 | GeneSeq Accession B50859 | U.S. Pat. No. 6,153,441 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot, T. N. C. Wells, and C. A. Power. © Humana Press Inc, Totowa, NJ. | Soluble CCR7 polypeptides may be useful for inhibiting chemokine activities and viral infection. |
| CXC3 | GeneSeq Accession W23345 | WO9727299 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot, T. N. C. Wells, and C. A. Power. © Humana Press Inc, Totowa, NJ. | Immune disorders. |
| Eotaxin | GeneSeq Accession W10099 | WO9700960 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor | Chemokine activities can be determined using assays known in the art: Methods in Molecular Biology, 2000, vol. 138: Chemokine Protocols. Edited by: A. E. I. Proudfoot, T. N. C. Wells, and C. A. Power. © Humana Press Inc, Totowa, NJ. | Immune disorders. |

TABLE 1-continued

| Therapeutic Protein X | Exemplary Identifier | PCT/Patent Reference | Biological Activity | Exemplary Activity Assay | Preferred Indication Y |
|---|---|---|---|---|---|
| | | | biology. The chemokines exert their effects by acting on a family of seven transmembrane G-protein coupled receptors. Over 40 human chemokines have been described, which bind to ~17 receptors thus far identified. | | |
| Neurotactin | GeneSeq Accessions Y77537, W34307, Y53259, and, Y77539 | U.S. Pat. No. 6,013,257 WO9742224 | Neurotactin may play a role in chemotactic leukocyte migration and brain inflammation processes. | Chemotactic leukocyte migration assays are known in the art, for example: J. Immunol. Methods 33, ((1980)); Nature 1997 Jun 5; 387(6633): 611-7. | Immune disorders. |
| Human CKbeta-9 | GeneSeq Accession B50860 | U.S. Pat. No. 6,153,441 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot, T. N. C. Wells, and C. A. Power. © Humana Press Inc., Totowa, NJ. | Immune disorders. |
| Lymphotactin | GeneSeq Accession B50052 | WO0073320 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G. | Chemokine activities can be determined using assays known in the art: Methods in Molecular Biology, 2000, vol. 138: Chemokine Protocols. Edited by: A. E. I. Proudfoot, T. N. C. Wells, and C. A. Power. © Humana Press Inc., Totowa, NJ. | Immune disorders. |
| MIP-3 alpha | GeneSeq Accession W44398 | WO9801557 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G. | Chemokine activities can be determined using assays known in the art: Methods in Molecular Biology, 2000, vol. 138: Chemokine Protocols. Edited by: A. E. I. Proudfoot, T. N. C. Wells, and C. A. Power. © Humana Press Inc., Totowa, NJ. | Immune disorders. |
| MIP-3 beta | GeneSeq Accession W44399 | WO9801557 | Chemokines are a family of related small, secreted proteins involved in biological processes ranging from hematopoiesis, | Chemokine activities can be determined using assays known in the art: Methods in Molecular | Immune disorders. |

TABLE 1-continued

| Therapeutic Protein X | Exemplary Identifier | PCT/Patent Reference | Biological Activity | Exemplary Activity Assay | Preferred Indication Y |
|---|---|---|---|---|---|
| | | | angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G. | Biology, 2000, vol. 138: Chemokine Protocols. Edited by: A. E. I. Proudfoot, T. N. C. Wells, and C. A. Power. © Humana Press Inc., Totowa, NJ. | |
| MIP-Gamma | GeneSeq Accession R70798 | WO9504158 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G. | Chemokine activities can be determined using assays known in the art: Methods in Molecular Biology, 2000, vol. 138: Chemokine Protocols. Edited by: A. E. I. Proudfoot, T. N. C. Wells, and C. A. Power. © Humana Press Inc., Totowa, NJ. | Immune disorders. |
| Stem Cell Inhibitory Factor | GeneSeq Accession R11553 | WO9104274 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G. | Chemokine activities can be determined using assays known in the art: Methods in Molecular Biology, 2000, vol. 138: Chemokine Protocols. Edited by: A. E. I. Proudfoot, T. N. C. Wells, and C. A. Power. © Humana Press Inc., Totowa, NJ. | Hematopoietic growth factors. |
| thrombopoietin | GeneSeq Accession R79905 | WO9521920 | Thrombopoietin is involved in the regulation of the growth and differentiation of megakaryocytes and preceptors thereof. | Thrombopoietin (TPO) can be assayed to determine regulation of growth and differentiation of megakaryocytes. Mol Cell Biol 2001 April; 21(8): 2659-70; Exp Hematol 2001 January; 29(1): 51-8 and within. | Hematopoietic growth factors. |
| c-kit ligand; SCF; Mast cell growth factor; MGF; Fibrosarcoma-derived stem cell factor | GeneSeq Accession Y53284, R83978 and R83977 | EP992579 and EP676470 | C-kit ligan is thought to stimulate the proliferation of mast cells, and is able to augment the proliferation of both myeloid and lymphoid hematopoietic progenitors in bone marrow culture. C-kit ligand is also thought to act synergistically with other cytokines. | Chemokine activities can be determined using assays known in the art: Methods in Molecular Biology, 2000, vol. 138: Chemokine Protocols. Edited by: A. E. I. Proudfoot, T. N. C. Wells, and C. A. Power. © Humana Press Inc., Totowa, NJ. | Hematopoietic growth factors. |
| Platelet derived growth factor | GeneSeq Accession B48653 | WO0066736 | Vascular Endothelial Growth Factor | VEGF activity can be determined using assays known in the art, such as those disclosed in International Publication No. WO0045835, for example. | Promotion of growth and proliferation of cells, such as vascular endothelial cells. Antagonists may be |

TABLE 1-continued

| Therapeutic Protein X | Exemplary Identifier | PCT/Patent Reference | Biological Activity | Exemplary Activity Assay | Preferred Indication Y |
|---|---|---|---|---|---|
| Melanoma inhibiting protein | GeneSeq Accession R69811 | WO9503328 | Melanoma inhibiting protein has melanoma-inhibiting activity and can be used to treat cancer (melanoma, glioblastoma, neuroblastoma, small cell lung cancer, neuroectodermal tumors) or as an immunosuppressant (it inhibits IL-2 or phytohaemagglutinin induced proliferation of peripheral blood lymphocytes. | Tumor suppressor activity of melanoma inhibiting protein can be determined using assays known in the art: Matzuk et al., Nature 1992 Nov 26; 360(6402): 313-9. | useful as anti-angiogenic agents, and may be applicable for cancer. Cancer; melanoma |
| Glioma-derived growth factor | GeneSeq Accession R08120 | EP399816 | Vascular Endothelial Growth Factor | VEGF activity can be determined using assays known in the art, such as those disclosed in International Publication No. WO0045835, for example. | Promotion of growth and proliferation of cells, such as vascular endothelial cells. Antagonists may be useful as anti-angiogenic agents, and may be applicable for cancer. |
| Platelet derived growth factor precursor A | GeneSeq Accession R84759 | EP682110 | Vascular Endothelial Growth Factor | VEGF activity can be determined using assays known in the art, such as those disclosed in International Publication No. WO0045835, for example. | Promotion of growth and proliferation of cells, such as vascular endothelial cells. Antagonists may be useful as anti-angiogenic agents, and may be applicable for cancer. |
| Platelet derived growth factor precursor B | GeneSeq Accession R84760 | EP682110 | Vascular Endothelial Growth Factor | VEGF activity can be determined using assays known in the art, such as those disclosed in International Publication No. WO0045835, for example. | Promotion of growth and proliferation of cells, such as vascular endothelial cells. Antagonists may be useful as anti-angiogenic agents, and may be applicable for cancer. |
| Platelet derived growth factor Bv-sis | GeneSeq Accession P80595 and P80596 | EP282317 | Vascular Endothelial Growth Factor | VEGF activity can be determined using assays known in the art, such as those disclosed in International Publication No. WO0045835, for example. | Promotion of growth and proliferation of cells, such as vascular endothelial cells. Antagonists may be useful as anti-angiogenic agents, and may be applicable for cancer. |
| Placental Growth Factor | GeneSeq Accessions R23059 and R23060 | WO9206194 | Vascular Endothelial Growth Factor | VEGF activity can be determined using assays known in the art, such as those disclosed in International Publication No. WO0045835, for example. | Promotion of growth and proliferation of cells, such as vascular endothelial cells. Antagonists may be useful as anti-angiogenic |

TABLE 1-continued

| Therapeutic Protein X | Exemplary Identifier | PCT/Patent Reference | Biological Activity | Exemplary Activity Assay | Preferred Indication Y |
|---|---|---|---|---|---|
| Placental Growth Factor-2 | GeneSeq Accession Y08289 | DE19748734 | Vascular Endothelial Growth Factor | VEGF activity can be determined using assays known in the art, such as those disclosed in International Publication No. WO0045835, for example. | agents, and may be applicable for cancer. Promotion of growth and proliferation of cells, such as vascular endothelial cells. Antagonists may be useful as anti-angiogenic agents, and may be applicable for cancer. |
| Thrombopoietin derivative1 | GeneSeq Accession Y77244 | WO0000612 | Thrombopoietin is involved in the regulation of the growth and differentiation of megakaryocytes and preceptors thereof. | Thrombopoietin (TPO) can be assayed to determine regulation of growth and differentiation of megakaryocytes. Mol Cell Biol 2001 April; 21(8); 2659-70; Exp Hematol 2001 January; 29(1): 51-8 and within. | Thrombocytopenia, cancer. |
| Thrombopoietin derivative2 | GeneSeq Accession Y77255 | WO0000612 | Thrombopoietin is involved in the regulation of the growth and differentiation of megakaryocytes and preceptors thereof. | Thrombopoietin (TPO) can be assayed to determine regulation of growth and differentiation of megakaryocytes. Mol Cell Biol 2001 April; 21(8); 2659-70; Exp Hematol 2001 January; 29(1): 51-8 and within. | Thrombocytopenia, cancer. |
| Thrombopoietin derivative3 | GeneSeq Accession Y77262 | WO0000612 | Thrombopoietin is involved in the regulation of the growth and differentiation of megakaryocytes and preceptors thereof. | Thrombopoietin (TPO) can be assayed to determine regulation of growth and differentiation of megakaryocytes. Mol Cell Biol 2001 April; 21(8); 2659-70; Exp Hematol 2001 January; 29(1): 51-8 and within. | Thrombocytopenia, cancer. |
| Thrombopoietin derivative4 | GeneSeq Accession Y77267 | WO0000612 | Thrombopoietin is involved in the regulation of the growth and differentiation of megakaryocytes and preceptors thereof. | Thrombopoietin (TPO) can be assayed to determine regulation of growth and differentiation of megakaryocytes. Mol Cell Biol 2001 April; 21(8); 2659-70; Exp Hematol 2001 January; 29(1): 51-8 and within. | Thrombocytopenia, cancer. |
| Thrombopoietin derivative5 | GeneSeq Accession Y77246 | WO0000612 | Thrombopoietin is involved in the regulation of the growth and differentiation of megakaryocytes and preceptors thereof. | Thrombopoietin (TPO) can be assayed to determine regulation of growth and differentiation of megakaryocytes. Mol Cell Biol 2001 April; 21(8); 2659-70; Exp Hematol 2001 January; 29(1): 51-8 and within. | Thrombocytopenia, cancer. |
| Thrombopoietin derivative6 | GeneSeq Accession Y77253 | WO0000612 | Thrombopoietin is involved in the regulation of the growth and differentiation of megakaryocytes and preceptors thereof. | Thrombopoietin (TPO) can be assayed to determine regulation of growth and differentiation of megakaryocytes. Mol Cell Biol 2001 April; 21(8); 2659-70; Exp Hematol 2001 January; 29(1): 51-8 and within. | Thrombocytopenia, cancer. |

TABLE 1-continued

| Therapeutic Protein X | Exemplary Identifier | PCT/Patent Reference | Biological Activity | Exemplary Activity Assay | Preferred Indication Y |
|---|---|---|---|---|---|
| Thrombopoietin derivative7 | GeneSeq Accession Y77256 | WO0000612 | Thrombopoietin is involved in the regulation of the growth and differentiation of megakaryocytes and preceptors thereof. | Hematol 2001 January; 29(1): 51-8 and within. Thrombopoietin (TPO) can be assayed to determine regulation of growth and differentiation of megakaryocytes. Mol Cell Biol 2001 April; 21(8): 2659-70; Exp Hematol 2001 January; 29(1): 51-8 and within. | Thrombocytopenia, cancer. |
| Fractalkine | GeneSeq Accession Y53255 | U.S. Pat. No. 6,043,086 | Fractalkine is believed to play a role in chemotactic leukocyte migration and neurological disorders. | Fractalkine activity can be determined using Chemotactic leukocyte migration assays known in the art, for example: J. Immunol. Methods 33, ((1980)): 611-7. Nature 1997 Jun 5; 387(6633): 611-7. | Immune disorders. |
| CXC3 | GeneSeq Accession W23345 | WO9757599 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot, T. N. C. Wells, and C. A. Power. © Humana Press Inc., Totowa, NJ. | Immune disorders. |
| CCR7 | GeneSeq Accession B50859 | U.S. Pat. No. 6,153,441 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot, T. N. C. Wells, and C. A. Power. © Humana Press Inc., Totowa, NJ. | Soluble CCR7 polypeptides may be useful for inhibiting chemokine activities and viral infection. |
| Nerve Growth Factor-beta | GeneSeq Accession R11474 | EP414151 | Nerve Growth Factor | Proliferation assay using NR6R-3T3 cells (Rizzino 1988 Cancer Res. 48: 4266) | Neurological disorders, cancer |
| Nerve Growth Factor-beta2 | GeneSeq Accession W69725 | EP859056 | Nerve Growth Factor | Proliferation assay using NR6R-3T3 cells (Rizzino 1988 Cancer Res. 48: 4266 | Neurological disorders, cancer |

TABLE 1-continued

| Therapeutic Protein X | Exemplary Identifier | PCT/Patent Reference | Biological Activity | Exemplary Activity Assay | Preferred Indication Y |
|---|---|---|---|---|---|
| Neurotrophin-3 | GeneSeq Accession W8889 | WO9821234 | Neurotrophins regulate neuronal cell survival and synaptic plasticity. | Trk tyrosine kinase activation assays known in the art can be used to assay for neurotrophin activity, for example, Proc Natl Acad Sci USA 2001 Mar 13; 98(6): 3555-3560. | Neurological disorders, cancer |
| Neurotrophin-3 | GeneSeq Accession R47100 | WO9325684 | Neurotrophins regulate neuronal cell survival and synaptic plasticity. | Trk tyrosine kinase activation assays known in the art can be used to assay for neurotrophin activity, for example, Proc Natl Acad Sci USA 2001 Mar 13; 98(6): 3555-3560. | Neurological disorders, cancer |
| Neurotrophin-4a | GeneSeq Accession R47101 | WO9325684 | Neurotrophins regulate neuronal cell survival and synaptic plasticity. | Trk tyrosine kinase activation assays known in the art can be used to assay for neurotrophin activity, for example, Proc Natl Acad Sci USA 2001 Mar 13; 98(6): 3555-3560 | Neurological disorders, cancer |
| Neurotrophin-4b | GeneSeq Accession R47102 | WO9325684 | Neurotrophins regulate neuronal cell survival and synaptic plasticity. tyrosine kinases. | Trk tyrosine kinase activation assays known in the art can be used to assay for neurotrophin activity, for example, Proc Natl Acad Sci USA 2001 Mar 13; 98(6): 3555-3560. | Neurological disorders, cancer |
| Neurotrophin-4c | GeneSeq Accession R47103 | WO9325684 | Neurotrophins regulate neuronal cell survival and synaptic plasticity. tyrosine kinases. | Trk tyrosine kinase activation assays known in the art can be used to assay for neurotrophin activity, for example, Proc Natl Acad Sci USA 2001 Mar 13; 98(6): 3555-3560. | Neurological disorders, cancer |
| Neurotrophin-4d | GeneSeq Accession R47102 | WO9325684 | Neurotrophins regulate neuronal cell survival and synaptic plasticity. tyrosine kinases. | Trk tyrosine kinase activation assays known in the art can be used to assay for neurotrophin activity, for example, Proc Natl Acad Sci USA 2001 Mar 13; 98(6): 3555-3560. | Neurological disorders, cancer |
| Platelet-Derived Growth Factor A chain | GeneSeq Accession R38918 | U.S. Pat. No. 5,219,739 | Vascular Endothelial Growth Factor | VEGF activity can be determined using assays known in the art, such as those disclosed in International Publication No. W00045835, for example. | Promotion of growth and proliferation of cells, such as vascular endothelial cells. Hematopoietic and immune disorders. Antagonists may be useful as anti-angiogenic agents, and may be applicable for cancer |
| Platelet-Derived Growth Factor B chain | GeneSeq Accession R38919 | U.S. Pat. No. 5,219,739 | Vascular Endothelial Growth Factor | VEGF activity can be determined using assays known in the art, such as those disclosed in International Publication No. W00045835, for example. | Promotion of growth and proliferation of cells, such as vascular endothelial cells. Hematopoietic and immune disorders. Antagonists may be useful as anti-angiogenic |

TABLE 1-continued

| Therapeutic Protein X | Exemplary Identifier | PCT/Patent Reference | Biological Activity | Exemplary Activity Assay | Preferred Indication Y |
|---|---|---|---|---|---|
| | | | | | agents, and may be applicable for cancer |
| Stromal Derived Factor-1 alpha | GeneSeq Accession Y39995 | WO9948528 | Stromal Growth Factor | Proliferation assay using NR6R-3T3 cells (Rizzino 1988 Cancer Res. 48: 4266) | Hematopoietic, immune disorders, cancer |
| Stromal Derived Factor-1 beta | GeneSeq Accession R75420 | CA2117953 | Stromal Growth Factor | Proliferation assay using NR6R-3T3 cells (Rizzino 1988 Cancer Res. 48: 4266) | Hematopoietic, immune disorders, cancer |
| Tarc | GeneSeq Accession W14917 | WO9711969 | Chemotactic for T lymphocytes. May play a role in T-cell development. Thought to bind CCR8 and CCR4 | Chemotactic leukocyte migration assays are known in the art, for example: J. Immunol. Methods 33 (1980)) | Antiinflammatory, Immune disorders, cancer |
| Prolactin | GeneSeq Accession R78691 | WO9521625 | Prolactin is involved in immune cell proliferation and apoptosis. | Immune coil proliferation and suppression of apoptosis by prolactin can be assayed by methods well-known in the art, for example, Buckley, AR and Buckley DJ, Ann N Y Acad Sci 2000; 917: 522-33, and within. | Reproductive system disorders, cancer. |
| Prolactin2 | GeneSeq Accession Y31764 | U.S. Pat. No. 5,955,346 | Prolactin is involved in immune cell proliferation and apoptosis. | Immune coil proliferation and suppression of apoptosis by prolactin can be assayed by methods well-known in the art, for example, Buckley, AR and Buckley DJ, Ann N Y Acad Sci 2000; 917: 522-33, and within. | Reproductive system disorders, cancer. |
| Follicle stimulating hormone Alpha subunit | GeneSeq Accession Y54160 | EP974359 | FSH stimulates secretion of interleukin-1 by cells isolated from women in the follicular phase | FSH activities can be determined using assays known in the art; J Gend Specif Med 1999 November-December; 2(6): 30-4; Mol Cell Endocrinol. 1997 Nov 15; 134(2): 109-18. | Reproductive system disorders, cancer. |
| Follicle stimulating hormone Beta subunit | GeneSeq Accession Y54161 | EP974359 | FSH stimulates secretion of interleukin-1 by cells isolated from women in the follicular phase | FSH activities can be determined using assays known in the art; J Gend Specif Med 1999 November-December; 2(6): 30-4; Mol Cell Endocrinol. 1997 Nov 15; 134(2): 109-18. | Reproductive system disorders, cancer. |
| Substance P (tachykinin) | GeneSeq Accession B23027 | WO0054053 | Substance P is associated with immunoregulation. | Immunoregulation and bone marrow, cell proliferation by substance P can be assayed by methods well-known in the art, for example, Lai et al. Proc Natl Acad Sci USA 2001 Mar 27; 98(7): 3970-5; Jallat-Daloz et al. Allergy Asthma Proc 2001 January-February; 22(1): 17-23; Kahler et al. Exp Lung Res 2001 January-February; 27(1): 25-46; and Adamus MA and Dabrowski ZI. J Cell Biochem 2001; 81(3)499-506. | diabetes mellitus, hypertension, cancer |
| Ocytocin (Neurophysin I) | GeneSeq Accession B24085 and | WO0053755 | Oxytocin is involved in the induction of prostaglandin (E2) release as well as an increased amount of calcium release by | Oxytocin and prostaglandin (Ca2+) release and Ocytocin (Ca2+) increase can be assayed by methods well- | inflammatory disorders, immunologic disorders, cancer |

TABLE 1-continued

| Therapeutic Protein X | Exemplary Identifier | PCT/Patent Reference | Biological Activity | Exemplary Activity Assay | Preferred Indication Y |
|---|---|---|---|---|---|
| | B24086 | | smooth muscle cells. | known in the art, for example, Pavan et al., AM J Obset Gynecol 2000 July; 183(1): 76-82 and Holda et al., Cell Calcium 1996 July; 20(1): 43 51. | |
| Vasopressin (Neurophysin II) | GeneSeq Accession B24085 and B24086 | WO0053755 | Vasopressinis believed to have a direct antidiuretic action on the kidney, and it is thought to cause vasoconstriction of the peripheral vessels. | Vasopressin activity can be determined using assays known in the art, for example, Endocr Regul 1996 March; 30(1): 13-17. | inflammatory disorders, immunologic disorders, cancer |
| IL-1 | GeneSeq Accession P60326 | EP165654 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferens: A Practical Approach, Clemens et al., eds, IRL Press, Washington, D.C. 1987, pp. 221-225; and Orencole & Dinarelio (1989) Cytokine 1, 14-20. | inflammatory disorders, immunologic disorders, cancer |
| IL-1 mature | GeneSeq Accession R14855 | EP456332 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferens: A Practical Approach, Clemens et al., eds, IRL Press, Washington, D.C. 1987, pp. 221-225; and Orencole & Dinarelio (1989) Cytokine 1, 14-20. | inflammatory disorders, immunologic disorders, cancer |
| IL-1 beta | GeneSeq Accession Y08322 | WO9922763 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferens: A Practical Approach, Clemens et al., eds, IRL Press, Washington, D.C. 1987, pp. 221-225; and Orencole & Dinarelio (1989) Cytokine 1, 14-20. | inflammatory disorders, immunologic disorders, cancer |
| IL-3 variants | GeneSeq Accession P80382, P80383, P80384, and P80381 | WO8806161 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferens: A Practical Approach, Clemens et al., eds, IRL Press, Washington, D.C. 1987, pp. 221-225; and Kitamura et al (1989) J Cell Physiol. 140 323-334. | inflammatory disorders, immunologic disorders, cancer |
| IL-4 | GeneSeq Accession P70615 | WO8702990 | Interleukins are a group of multifunctional cytokines synthesized by lymphocytes, monocytes, and macrophages. Known functions include stimulating proliferation of immune cells (e.g., T helper cells, B cells, eosinophils, | Interleukin activity can be determined using assays known in the art: Matthews et al., in Lymphokines and Interferens: A Practical Approach, Clemens et al., eds, IRL Press, Washington, D.C. 1987, pp. 221-225; | inflammatory disorders, immunologic disorders, cancer |

TABLE 1-continued

| Therapeutic Protein X | Exemplary Identifier | PCT/Patent Reference | Biological Activity | Exemplary Activity Assay | Preferred Indication Y |
|---|---|---|---|---|---|
| | | | and lymphocytes), chemotaxis of neutrophils and T lymphocytes, and/or inhibition of interferons. | and Siegel & Mostowski (1990) J Immunol Methods 132, 287-295. | |
| IL-4 muteins | GeneSeq Accession W52151 W52152 W52153 W52154 W52155 W52156 W52157 W52158 W52159 W52160 W52161 W52162 W52163 W52164 and W52165 | WO9747744 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferens: A Practical Approach, Clemens et al., eds, IRL Press, Washington, D.C. 1987, pp. 221-225; and Siegel & Mostowski (1990) J Immunol Methods 132, 287-295. | inflammatory disorders, immunologic disorders, cancer |
| IL-1 alpha | GeneSeq Accession P90108 | EP324447 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferens: A Practical Approach, Clemens et al.; eds, IRL Press, Washington, D.C. 1987, pp. 221-225; and Orencole & Dinarello (1989) Cytokine 1, 14-20. | inflammatory disorders, immunologic disorders, cancer |
| IL-3 variants | GeneSeq Accession R38561, R38562, R38563, R38564, R38565, R38566, R38567, R38568, R38569, R38570, R38571, and R38572 | WO9307171 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferens: A Practical Approach, Clemens et al., eds, IRL Press, Washington, D.C. 1987, pp. 221-225; and Aarden et al (1987) Eur. J. Immunol 17, 1411-16. | inflammatory disorders, immunologic disorders, cancer |
| IL-6 | GeneSeq Accession R45717 and R45718 | WO9402512 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferens: A Practical Approach, Clemens et al., eds, IRL Press, Washington, D.C. 1987, pp. 221-225; and Aarden et al (1987) Eur. J. Immunol 17, 1411-16. | inflammatory disorders, immunologic disorders, cancer |
| IL-13 | GeneSeq Accession R48624 | WO9404680 | Interleukins are a group of multifunctional cytokines synthesized by lymphocytes, monocytes, and | Interleukin activity can be determined using assays known in the art: Matthews et al., in Lymphokines and | inflammatory disorders, immunologic disorders, cancer |

TABLE 1-continued

| Therapeutic Protein X | Exemplary Identifier | PCT/Patent Reference | Biological Activity | Exemplary Activity Assay | Preferred Indication Y |
|---|---|---|---|---|---|
| | | | macrophages. Known functions include stimulating proliferation of immune cells (e.g., T helper cells, B cells, eosinophils, and lymphocytes), chemotaxis of neutrophils and T lymphocytes, and/or inhibition of interferons. | Interferens: A Practical Approach, Clemens et al., eds, IRL Press, Washington, D.C. 1987, pp. 221-225; and Bouteiler et al (1995) J. Immunol. Methods 181, 29. | |
| IL-4 mutein | GeneSeq Accession R47182 | DE4137333 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferens: A Practical Approach, Clemens et al., eds, IRL Press, Washington, D.C. 1987, pp. 221-225; and Siegel & Mostowski (1990) J Immunol Methods 132, 287-295. | inflammatory disorders, immunologic disorders, cancer |
| IL-4 mutein Y124X | GeneSeq Accession R47183 | DE4137333 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferens: A Practical Approach, Clemens et al., eds, IRL Press, Washington, D.C. 1987, pp. 221-225; and Siegel & Mostowski (1990) J Immunol Methods 132, 287-295. | inflammatory disorders, immunologic disorders, cancer |
| IL-4 mutein Y124G | GeneSeq Accession R47184 | DE4137333 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferens: A Practical Approach, Clemens et al., eds, IRL Press, Washington, D.C. 1987, pp. 221-225; and Siegel & Mostowski (1990) J Immunol Methods 132, 287-295. | inflammatory disorders, immunologic disorders, cancer |
| Human Interleukin-10 (precursor) | GeneSeq Accession R41664 | WO9317698 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferens: A Practical Approach, Clemens et al., eds, IRL Press, Washington, D.C. 1987, pp. 221-225; and Thompson-Snipes et al (1991) J. Exp. Med. 173, 507-510. | inflammatory disorders, immunologic disorders, cancer |
| Human Interleukin-10 | GeneSeq Accession R42642 | WO9318783-A | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of | Interleukin activity can be determined using assays known in the art: Matthews et al., in Lymphokines and Interferens: A Practical Approach, Clemens et al., eds, IRL Press, Washington, D.C. 1987, pp. 221-225; and Thompson-Snipes et al (1991) J. | inflammatory disorders, immunologic disorders, cancer |

TABLE 1-continued

| Therapeutic Protein X | Exemplary Identifier | PCT/Patent Reference | Biological Activity | Exemplary Activity Assay | Preferred Indication Y |
|---|---|---|---|---|---|
| Human interleukin-1 beta precursor. | GeneSeq Accession R42447 | EP569042 | neutrophils and T lymphocytes, and/or inhibition of interferons. Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Exp. Med. 173, 507-510. interleukin activity can be determined using assays known in the art: Matthews et al., in Lymphokines and Interferens: A Practical Approach, Clemens et al., eds, IRL Press, Washington, D.C. 1987, pp. 221-225; and Orencole & Dinarello (1989) Cytokine 1, 14-20. | inflammatory disorders, immunologic disorders, cancer |
| Interleukin-1alpha | GeneSeq Accession R45364 | EP578278 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferens: A Practical Approach, Clemens et al., eds, IRL Press, Washington, D.C. 1987, pp. 221-225. | inflammatory disorders, immunologic disorders, cancer |
| Human interleukin-3 variant | GeneSeq Accession R22814 | JP04063595 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferens: A Practical Approach, Clemens et al., eds, IRL Press, Washington, D.C. 1987, pp. 221-225; and Kitamura et al (1989) J Cell Physiol. 140 323-334. | inflammatory disorders, immunologic disorders, cancer |
| IL-1i fragments | GeneSeq Accession R35484 and R35485 | EP541920 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferens: A Practical Approach, Clemens et al., eds, IRL Press, Washington, D.C. 1987, pp. 221-225; and Orencole & Dinarello (1989) Cytokine 1, 14-20. | inflammatory disorders, immunologic disorders, cancer |
| IL-1 inhibitor (IL-1i) | GeneSeq Accession R35486 and R35484 | EP541920 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferens: A Practical Approach, Clemens et al., eds, IRL Press, Washington, D.C. 1987, pp. 221-225; and Orencole & Dinarello (1989) Cytokine 1, 14-20. | inflammatory disorders, immunologic disorders, cancer |
| ICE 22 kD subunit. | GeneSeq Accession R33780 | EP533350 | Interleukins are a group of multifunctional cytokines synthesized by lymphocytes, monocytes, and | Interleukin activity can be determined using assays known in the art: Matthews et al., in Lymphokines and | inflammatory disorders, immunologic disorders, cancer |

TABLE 1-continued

| Therapeutic Protein X | Exemplary Identifier | PCT/Patent Reference | Biological Activity | Exemplary Activity Assay | Preferred Indication Y |
|---|---|---|---|---|---|
| ICE 20 kD subunit | | | macrophages. Known functions include stimulating proliferation of immune cells (e.g., T helper cells, B cells, eosinophils, and lymphocytes), chemotaxis of neutrophils and T lymphocytes, and/or inhibition of interferons. | Interferens: A Practical Approach, Clemens et al., eds, IRL Press, Washington, D.C. 1987, pp. 221-225. | |
| ICE 10 kD subunit | GeneSeq Accession R33781 | EP533350 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferens: A Practical Approach, Clemens et al., eds, IRL Press, Washington, D.C. 1987, pp. 221-225. | inflammatory disorders, immunologic disorders, cancer |
| | GeneSeq Accession R33782 | EP533350 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferens: A Practical Approach, Clemens et al., eds, IRL Press, Washington, D.C. 1987, pp. 221-225. | inflammatory disorders, immunologic disorders, cancer |
| Human Interleukin-10 (precursor) | GeneSeq Accession R41664 | WO9317698 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferens: A Practical Approach, Clemens et al., eds, IRL Press, Washington, D.C. 1987, pp. 221-225; and Thompson-Snipes et al (1991) J. Exp. Med. 173, 507-510. | inflammatory disorders, immunologic disorders, cancer |
| Human Interleukin-10 | GeneSeq Accession R42642 | WO9318783 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferens: A Practical Approach, Clemens et al., eds, IRL Press, Washington, D.C. 1987, pp. 221-225; and Thompson-Snipes et al (1991) J. Exp. Med. 173, 507-510. | inflammatory disorders, immunologic disorders, cancer |
| Human Interleukin-1 beta precursor | GeneSeq Accession R42447 | EP569042 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of | Interleukin activity can be determined using assays known in the art: Matthews et al., in Lymphokines and Interferens: A Practical Approach, Clemens et al., eds, IRL Press, Washington, D.C. 1987, pp. 221-225; and Kitamura et al (1989) J Cell | inflammatory disorders, immunologic disorders, cancer |

TABLE 1-continued

| Therapeutic Protein X | Exemplary Identifier | PCT/Patent Reference | Biological Activity | Exemplary Activity Assay | Preferred Indication Y |
|---|---|---|---|---|---|
| Human interleukin-6 | GeneSeq Accession R49041 | WO9403492 | neutrophils and T lymphocytes, and/or inhibition of interferons. Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Physiol. 140 323-334. Interleukin activity can be determined using assays known in the art: Matthews et al., in Lymphokines and Interferens: A Practical Approach, Clemens et al., eds, IRL Press, Washington, D.C. 1987, pp. 221-225; and Aarden et al (1987) Eur. J. Immunol 17, 1411-16. | inflammatory disorders, immunologic disorders, cancer |
| Mutant Interleukin 6 S176R | GeneSeq Accession R54990 | WO9411402 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferens: A Practical Approach, Clemens et al., eds, IRL Press, Washington, D.C. 1987, pp. 221-225; and Aarden et al (1987) Eur. J. Immunol 17, 1411-16. | inflammatory disorders, immunologic disorders, cancer |
| Interleukin 6 | GeneSeq Accession R55256 | JP06145063 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferens: A Practical Approach, Clemens et al., eds, IRL Press, Washington, D.C. 1987, pp. 221-225; and Aarden et al (1987) Eur. J. Immunol 17, 1411-16. | inflammatory disorders, immunologic disorders, cancer |
| Interleukin 8 (IL-8) receptor | GeneSeq Accession R53932 | JP06100595 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferens: A Practical Approach, Clemens et al., eds, IRL Press, Washington, D.C. 1987, pp. 221-225; and Holmes et al (1991) Science 253, 1278-80. | Soluble IL-8 receptor polypeptides may be useful for inhibiting interleukin activities. |
| Human interleukin-7 | GeneSeq Accession R59919 | U.S. Pat. No. 5,328,988 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferens: A Practical Approach, Clemens et al., eds, IRL Press, Washington, D.C. 1987, pp. 221-225; and Park et al (1990) J. Exp. Med. 171, 1073-79. | inflammatory disorders, immunologic disorders, cancer |
| IL-3 containing fusion protein. | GeneSeq Accession R79342 and | WO9521254 | Interleukins are a group of multifunctional cytokines synthesized by lymphocytes, monocytes, and | Interleukin activity can be determined using assays known in the art: Matthews et al., in Lymphokines and | inflammatory disorders, immunologic disorders, cancer |

TABLE 1-continued

| Therapeutic Protein X | Exemplary Identifier | PCT/Patent Reference | Biological Activity | Exemplary Activity Assay | Preferred Indication Y |
|---|---|---|---|---|---|
| | R79344 | | macrophages. Known functions include stimulating proliferation of immune cells (e.g., T helper cells, B cells, eosinophils, and lymphocytes), chemotaxis of neutrophils and T lymphocytes, and/or inhibition of interferons. | Interferens: A Practical Approach, Clemens et al., eds, IRL Press, Washington, D.C. 1987, pp. 221-225; and Kitamura et al (1989) J Cell Physiol. 140 323-334. | inflammatory disorders, immunologic disorders, cancer |
| IL-3 mutant proteins | GeneSeq Accession R79254, R79255, R79256, R79257, R79258, R79259, R79260, R79261, R79262, R79263, R79264, R79265, R79266, R79267, R79268, R79269, R79270, R79271, R79272, R79273, R79274, R79275, R79276, R79277, R79278, R79279, R79280, R79281, R79282, 879283, R79284, and R79285 | ZA9402636 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferens: A Practical Approach, Clemens et al., eds, IRL Press, Washington, D.C. 1987, pp. 221-225; and Giri et al (1994) EMBO J. 13 2822-2830. | |
| IL-12 p40 subunit. | GeneSeq Accession R63018 | AU9466072 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferens: A Practical Approach, Clemens et al., eds, IRL Press, Washington, D.C. 1987, pp. 221-225. | inflammatory disorders, immunologic disorders, cancer |
| AGF | GeneSeq Accession R64240 | WO9429344 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferens: A Practical Approach, Clemens et al., eds, IRL Press, Washington, D.C. 1987, pp. 221-225. | inflammatory disorders, immunologic disorders, cancer |
| Human interleukin-12 40 kD subunit | GeneSeq Accession R79187 | WO9519786 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of | Interleukin activity can be determined using assays known in the art: Matthews et al., in Lymphokines and Interferens: A Practical Approach, Clemens et al., eds, IRL Press, Washington, D.C. 1987, pp. 221-225; and Hori et al (1987), Blood 70, | inflammatory disorders, immunologic disorders, cancer |

TABLE 1-continued

| Therapeutic Protein X | Exemplary Identifier | PCT/Patent Reference | Biological Activity | Exemplary Activity Assay | Preferred Indication Y |
|---|---|---|---|---|---|
| Human interleukin-15 receptor from clone P1 | GeneSeq Accession R90843 | WO9530695 | neutrophils and T lymphocytes, and/or inhibition of interferons. | 1069-1078. | Soluble IL-8 receptor polypeptides may be useful for inhibiting interleukin activities. |
| Human interleukin-7 | GeneSeq Accession R92796 | WO9604306 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferens: A Practical Approach, Clemens et al., eds, IRL Press, Washington, D.C. 1987, pp. 221-225; and Giri et al (1994) EMBO J. 13 2822-2830. | inflammatory disorders, immunologic disorders, cancer |
| interleukin-9 | GeneSeq Accesion R92797 | WO9604306 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferens: A Practical Approach, Clemens et al., eds, IRL Press, Washington, D.C. 1987, pp. 221-225; and Park et al (1990) J. Exp. Med. 171, 1073-79. | inflammatory disorders, immunologic disorders, cancer |
| interleukin-3 | GeneSeq Accession R92801 | WO9604306 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferens: A Practical Approach, Clemens et al., eds, IRL Press, Washington, D.C. 1987, pp. 221-225; and Yang et al (1989) Blood 74, 1880-84. | inflammatory disorders, immunologic disorders, cancer |
| Human interleukin-5 | GeneSeq Accession R92802 | WO9604306 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferens: A Practical Approach, Clemens et al., eds, IRL Press, Washington, D.C. 1987, pp. 221-225; and Kitamura et al (1989) J Cell Physiol. 140 323-334. | inflammatory disorders, immunologic disorders, cancer |
| Recombinant interleukin-16 | GeneSeq Accession W33373 | DE19617202 | Interleukins are a group of multifunctional cytokines synthesized by lymphocytes, monocytes, and | Interleukin activity can be determined using assays known in the art: Matthews et al., in Lymphokines and | inflammatory disorders, immunologic disorders, cancer |

TABLE 1-continued

| Therapeutic Protein X | Exemplary Identifier | PCT/Patent Reference | Biological Activity | Exemplary Activity Assay | Preferred Indication Y |
|---|---|---|---|---|---|
| | | | macrophages. Known functions include stimulating proliferation of immune cells (e.g., T helper cells, B cells, eosinophils, and lymphocytes), chemotaxis of neutrophils and T lymphocytes, and/or inhibition of interferons. | Interferens: A Practical Approach, Clemens et al., eds, IRL Press, Washington, D.C. 1987, pp. 221-225; and Lim et al (1996) J. Immunol. 156, 2566-70. | |
| Human IL-16 protein | GeneSeq Accession W33234 | DE19617202 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferens: A Practical Approach, Clemens et al., eds, IRL Press, Washington, D.C. 1987, pp. 221-225; and Lim et al (1996) J. Immunol. 156, 2566-70. | inflammatory disorders, immunologic disorders, cancer |
| Thr17 human interleukin 9 | GeneSeq Accession W27521 | WO9708321 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferens: A Practical Approach, Clemens et al., eds, IRL Press, Washington, D.C. 1987, pp. 221-225. | inflammatory disorders, immunologic disorders, cancer |
| Met17 human interleukin 9 | GeneSeq Accession W27522 | WO9708321 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferens: A Practical Approach, Clemens et al., eds, IRL Press, Washington, D.C. 1987, pp. 221-225; and Yang et al (1989) Blood 74, 1880-84. | inflammatory disorders, immunologic disorders, cancer |
| Human intracellular IL-1 receptor antagonist. | GeneSeq Accession W77158 | EP86-4585 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferens: A Practical Approach, Clemens et al., eds, IRL Press, Washington, D.C. 1987, pp. 221-225; and Orencole & Dinarello (1989) Cytokine 1, 14-20. | inflammatory disorders, immunologic disorders, cancer |
| Human interleukin-18 protein (IL-18) | GeneSeq Accession W77158 | EP864585 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of | Interleukin activity can be determined using assays known in the art: Matthews et al., in Lymphokines and Interferens: A Practical Approach, Clemens et al., eds, IRL Press, Washington, D.C. 1987, pp. 221-225; and USHIO et al (1996) J. Immunol. | inflammatory disorders, immunologic disorders, cancer |

TABLE 1-continued

| Therapeutic Protein X | Exemplary Identifier | PCT/Patent Reference | Biological Activity | Exemplary Activity Assay | Preferred Indication Y |
|---|---|---|---|---|---|
| Human interleukin-18 | GeneSeq Accession W77077 | EP861663 | neutrophils and T lymphocytes, and/or inhibition of interferons. | 156, 4274-79. | |
| Human interleukin 18 derivatives | GeneSeq Accessions W77083, W77084, W77085, W77086, W77087, W77088, and W77089 | EP861663 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225; and USHIO et al (1996) J. Immunol. 156, 4274-79. | inflammatory disorders, immunologic disorders, cancer |
| Interleukin-9 (IL-9) mature protein (Thr117 version). | GeneSeq Accession W68158 | WO9827997 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225; and USHIO et al (1996) J. Immunol. 156, 4274-79. | inflammatory disorders, immunologic disorders, cancer |
| | | | | Interleukin activity can be determined using assays known in the art: Matthews et al., in Lymphokines and Interferons: A Practical Approach, Clemens et al., eds, IRL Press, Washington, D.C. 1987, pp. 221-225; and Yang et al (1989) Blood 74, 1880-84. | inflammatory disorders, immunologic disorders, cancer |
| IL-9 mature protein variant (Met117 version) | GeneSeq Accession W68157 | WO9827997 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225; and Yang et al (1989) Blood 74, 1880-84. | inflammatory disorders, immunologic disorders, cancer |
| Human IL-9 receptor protein variant #3. | GeneSeq Accession W64058 | WO9824904 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225; and Yang et al (1989) Blood 74, 1880-84. | inflammatory disorders, immunologic disorders, cancer |
| Human IL-9 receptor protein variant fragment | GeneSeq Accession W64060 | WO9824904 | Interleukins are a group of multifunctional cytokines synthesized by lymphocytes, monocytes, and | Interleukin activity can be determined using assays known in the art: Matthews et al., in Lymphokines and | Soluble IL-9 receptor polypeptides may be useful for inhibiting |

TABLE 1-continued

| Therapeutic Protein X | Exemplary Identifier | PCT/Patent Reference | Biological Activity | Exemplary Activity Assay | Preferred Indication Y |
|---|---|---|---|---|---|
| | | | macrophages. Known functions include stimulating proliferation of immune cells (e.g., T helper cells, B cells, eosinophils, and lymphocytes), chemotaxis of neutrophils and T lymphocytes, and/or inhibition of interferons. | Interferons: A Practical Approach, Clemens et al., eds, IRL Press, Washington, D.C. 1987, pp. 221-225; and Yang et al (1989) Blood 74, 1880-84. | interleukin activities. |
| Human IL-9 receptor protein variant #3. | GeneSeq Accession W64061 | WO9824904 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225; and Yang et al (1989) Blood 74, 1880-84. | Soluble IL-9 receptor polypeptides may be useful for inhibiting interleukin activities. |
| Human Interleukin-12 p40 protein | GeneSeq Accession W51311 | WO9817689 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225; and Hori et al (1987), Blood 70, 1069-1078. | inflammatory disorders, immunologic disorders, cancer |
| Human Interleukin-12 p35 protein | GeneSeq Accession W51312 | WO9817689 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225; and Hori et al (1987), Blood 70, 1069-1078. | inflammatory disorders, immunologic disorders, cancer |
| Human protein with IL-16 activity | GeneSeq Accession W63753 | DE19649233 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225; and Lim et al (1996) J. Immunol. 156, 2566-70. | inflammatory disorders, immunologic disorders, cancer |
| Human protein with IL-16 activity | GeneSeq Accession W59425 | DE19649233- | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of | Interleukin activity can be determined using assays known in the art: Matthews et al., in Lymphokines and Interferons: A Practical Approach, Clemens et al., eds, IRL Press, Washington, D.C. 1987, pp. 221-225; and Lim et al (1996) J. Immunol. 156, | inflammatory disorders, immunologic disorders, cancer |

TABLE 1-continued

| Therapeutic Protein X | Exemplary Identifier | PCT/Patent Reference | Biological Activity | Exemplary Activity Assay | Preferred Indication Y |
|---|---|---|---|---|---|
| Human interleukin-15 | GeneSeq Accession W53878 | U.S. Pat. No. 5,747,024 | neutrophils and T lymphocytes, and/or inhibition of interferons. | 2566-70. | inflammatory disorders, immunologic disorders, cancer |
| Human wild-type interleukin-4 (hIL-4) protein | GeneSeq Accession W52149 | WO9747744 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225; and Giri et al (1994) EMBO J. 13 2822-2830. | inflammatory disorders, immunologic disorders, cancer |
| interleukin-4 muteins | GeneSeq Accessions W52150, W52151, W52153, W52154, W52155, W52156, W52157, W52158, W52159, W52160, W52161, W52162, W52163, W52164, W52165, W52166, and W52167 | WO9747744 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225; and Siegel & Mostowski (1990) J Immunol Methods 132, 287-295. | inflammatory disorders, immunologic disorders, cancer |
| | | | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225; and Siegel & Mostowski (1990) J Immunol Methods 132, 287-295. | |
| Human interleukin 1 delta | GeneSeq Accession Y28408 | WO9935268 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225; and Orencole & Dinarello (1989) Cytokine 1, 14-20. | inflammatory disorders, immunologic disorders, cancer |
| Human interleukin-1 | GeneSeq Accession | WO9935268 | Interleukins are a group of multifunctional cytokines synthesized by | Interleukin activity can be determined using assays known in the art: | inflammatory disorders, immunologic disorders, |

TABLE 1-continued

| Therapeutic Protein X | Exemplary Identifier | PCT/Patent Reference | Biological Activity | Exemplary Activity Assay | Preferred Indication Y |
|---|---|---|---|---|---|
| receptor antagonist beta | Y24395 | | lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Matthews et al., in Lymphokines and Interferons: A Practical Approach, Clemens et al., eds, IRL, Press, Washington, D.C. 1987, pp. 221-225; and Orencole & Dinarello (1989) Cytokine 1, 14-20. | cancer |
| Human EDIRF II protein sequence | GeneSeq Accession Y22199 | WO9932632 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225. | inflammatory disorders, immunologic disorders, cancer |
| Human EDIRF I protein sequence | GeneSeq Accession Y22197 | WO9932632 | Interleukins are a group of multifunctional cytokines synthesized by lymphocytes, monocytes, and macrophages. Known functions include stimulating proliferation of immune cells (e.g., T helper cell, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225. | inflammatory disorders, immunologic disorders, cancer |
| Human IL-1RD10 protein sequence | GeneSeq Accession Y14131 | WO9919480 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225; and Orencole & Dinarello (1989) Cytokine 1, 14-20. | Soluble IL-1RD10 receptor polypeptides may be useful for inhibiting interleukin activites. |
| Human IL-1RD9 | GeneSeq Accession Y14122 | WO9919480 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225; and Orencole & Dinarello (1989) Cytokine 1, 14-20. | Soluble IL-1RD10 receptor polypeptides may be useful for inhibiting interleukin activites. |
| Human DNAX interleukin-40 | GeneSeq Accession Y09196 | WO9919491 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of | Interleukin activity can be determined using assays known in the art: Matthews et al., in Lymphokines and Interferons: A Practical Approach, Clemens et al., eds, IRL Press, Washington, D.C. 1987, pp. 221-225. | inflammatory disorders, immunologic disorders, cancer |

TABLE 1-continued

| Therapeutic Protein X | Exemplary Identifier | PCT/Patent Reference | Biological Activity | Exemplary Activity Assay | Preferred Indication Y |
|---|---|---|---|---|---|
| (DIL-40) alternative sequence | GeneSeq Accession Y09197 | WO9919491 | neutrophils and T lymphocytes, and/or inhibition of interferons. Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225. | inflammatory disorders, immunologic disorders, cancer |
| IL-11 | GeneSeq Accession R50176 | WO9405318 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225; and Lu et al (1994) J immunol. Methods 173, 19. | inflammatory disorders, immunologic disorders, cancer |
| Human adipogenesis inhibitory factor | GeneSeq Accession R43260 | EP566410 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225. | inflammatory disorders, immunologic disorders, cancer |
| IL-11 | GeneSeq Accession W02202 | JP08127539 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225; and Lu et al (1994) J immunol. Methods 173, 19. | inflammatory disorders, immunologic disorders, cancer |
| IL-14 | GeneSeq Accession R55800 | WO9416074 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225; and Ambrus et al (1993) PNAS 90, 63330-34. | inflammatory disorders, immunologic disorders, cancer |
| IL-17 receptor | GeneSeq Accession B03807 | U.S. Pat. No. 6,072,033 | Interleukins are a group of multifunctional cytokines synthesized by lymphocytes, monocytes, and | Interleukin activity can be determined using assays known in the art: Matthews et al., in Lymphokines and | Soluble IL-17 receptor polypeptides may be useful for inhibiting |

TABLE 1-continued

| Therapeutic Protein X | Exemplary Identifier | PCT/Patent Reference | Biological Activity | Exemplary Activity Assay | Preferred Indication Y |
|---|---|---|---|---|---|
| | | | macrophages. Known functions include stimulating proliferation of immune cells (e.g., T helper cells, B cells, eosinophils, and lymphocytes), chemotaxis of neutrophils and T lymphocytes, and/or inhibition of interferons. | Interferons: A Practical Approach, Clemens et al., eds, IRL Press, Washington, D.C. 1987, pp. 221-225; and Yao et al (1995) J. Immunol. 155, 5483-86. | interleukin activities. |
| IL-17 | GeneSeq Accession R76573 | WO9518826 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225; and Yao et al (1995) J. Immunol. 155, 5483-86. | inflammatory disorders, immunologic disorders, cancer |
| CTLA-8 | GeneSeq Accession W13651 | WO9704097 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225. | inflammatory disorders, immunologic disorders, cancer |
| IL-19 | GeneSeq Accession W37935 | WO9808870 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225; and Gallagher et al (2000) Genes Immun. 1, 442-50. | inflammatory disorders, immunologic disorders, cancer |
| IL-21 (TIF) | GeneSeq Accession Y92879 | WO0024758 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225; and Parrish-Novak et al (2000) Nature 408, 57-63. | inflammatory disorders, immunologic disorders, cancer |
| IL-8 receptor | GeneSeq Accession R33420 | WO9306229 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of | Interleukin activity can be determined using assays known in the art: Matthews et al., in Lymphokines and Interferons: A Practical Approach, Clemens et al., eds, IRL Press, Washington, D.C. 1987, pp. 221-225; and Holmes et al (1991) Science 253, | Soluble IL-8 receptor polypeptides may be useful for inhibiting interleukin activities. |

TABLE 1-continued

| Therapeutic Protein X | Exemplary Identifier | PCT/Patent Reference | Biological Activity | Exemplary Activity Assay | Preferred Indication Y |
|---|---|---|---|---|---|
| Human type II interleukin-1 receptor | GeneSeq Accession R85480 | U.S. Pat. No. 5,464,937 | neutrophils and T lymphocytes, and/or inhibition of interferons. Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | 1278-80.. Interleukin activity can be determined using assays known in the art: Matthews et al., in Lymphokines and Interferons: A Practical Approach, Clemens et al., eds. IRL Press, Washington, D.C. 1987, pp. 221-225; and Orencole & Dinarello (1989) Cytokine 1, 14-20. | Soluble type II interleukin-1 receptor polypeptides may be useful for inhibiting interleukin activities. |
| Human interleukin-12 receptor | GeneSeq Accession R69632 | EP638644 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds. IRL Press, Washington, D.C. 1987, pp. 221-225; and Hori et al (1987), Blood 70, 1069-1078. | Soluble IL-12 receptor polypeptides may be useful for inhibiting interleukin activities. |
| Interleukin 8 receptor B | GeneSeq Accession R80758 | U.S. Pat. No. 5,440,021 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds. IRL Press, Washington, D.C. 1987, pp. 221-225; and Holmes et al (1991) Science 253, 1278-80. | Soluble IL-8 receptor B polypeptides may be useful for inhibiting interleukin activities. |
| Human IL-8 receptor protein hIL8RA | GeneSeq Accession B09989 | JP08103276 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds. IRL Press, Washington, D.C. 1987, pp. 221-225; and Holmes et al (1991) Science 253, 1278-80. | Soluble IL-8 receptor A polypeptides may be useful for inhibiting interleukin activities. |
| Human IL-8 receptor protein hIL8R | GeneSeq Accession B09990 | JP08103276 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds. IRL Press, Washington, D.C. 1987, pp. 221-225; and Holmes et al (1991) Science 253, 1278-80. | Soluble IL-8 receptor polypeptides may be useful for inhibiting interleukin activities. |
| Interleukin-2 receptor associated | GeneSeq Accession | WO9621732 | Interleukins are a group of multifunctional cytokines synthesized | Interleukin activity can be determined using assays known in | Soluble IL-2 receptor polypeptides may be |

TABLE 1-continued

| Therapeutic Protein X | Exemplary Identifier | PCT/Patent Reference | Biological Activity | Exemplary Activity Assay | Preferred Indication Y |
|---|---|---|---|---|---|
| protein p43 | R97569 | | by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | the art: Matthews et al., in Lymphokines and Interferons: A Practical Approach, Clemens et al., eds, IRL Press, Washington, D.C. 1987, pp. 221-225; and Gillis et al (1978) J. Immunol. 120, 2027. | useful for inhibiting interleukin activities. |
| Human interleukin-17 receptor | GeneSeq Accession W04185 | WO9629408 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225; and Yao et al (1995) J. Immunol. 155, 5483-86. | Soluble IL-17 receptor polypeptides may be useful for inhibiting interleukin activities. |
| Human interleukin-11 receptor | GeneSeq Accession R99090 | WO9619574 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225; and Lu et al (1994) J immunol. Methods 173, 19. | Soluble IL-11 receptor polypeptides may be useful for inhibiting interleukin activities. |
| Human interleukin-1 receptor accessory protein | GeneSeq Accession W01911 | WO9623067 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225; and Orencole & Dinarello (1989) Cytokine 1, 14-20. | Inflammatory disorders, immunologic disorders, cancer |
| AGF Protein | GeneSeq Accession R92749 | U.S. Pat. No. 5,488,032 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225. | Inflammatory disorders, immunologic disorders, cancer |
| Human interleukin-1 type- | GeneSeq Accession | WO9607739 | Interleukins are a group of multifunctional cytokines synthesized | Interleukin activity can be determined using assays in | Soluble IL-type-3 receptor polypeptides |

TABLE 1-continued

| Therapeutic Protein X | Exemplary Identifier | PCT/Patent Reference | Biological Activity | Exemplary Activity Assay | Preferred Indication Y |
|---|---|---|---|---|---|
| 3 receptor | R91064 | | by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | the art: Matthews et al., in Lymphokines and Interferons: A Practical Approach, Clemens et al., eds, IRL Press, Washington, D.C. 1987, pp. 221-225; and Orencole & Dinarello (1989) Cytokine 1, 14-20. | may be useful for inhibiting interleukin activities |
| Human interleukin-13 beta receptor | GeneSeq Accession W24972 | WO9720926 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225; and Boutelier et al (1995) J. Immunol. Methods 181, 29. | Soluble IL-13 beta receptor polypeptides may be useful for inhibiting interleukin activities. |
| Human interleukin-13 alpha receptor | GeneSeq Accession W24973 | WO9720926 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225; and Boutelier et al (1995) J. Immunol. Methods 181, 29. | Soluble IL-13 alpha receptor polypeptides may be useful for inhibiting interleukin activities. |
| Human interleukin-4 receptor | GeneSeq Accession W13499 | U.S. Pat. No. 5,599,905 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225; and Siegel & Mostowski (1990) J Immunol Methods 132, 287-295. | Soluble IL-4 receptor polypeptides may be useful for inhibiting interleukin activities. |
| Human interleukin-12 beta-2 receptor | GeneSeq Accession W12771 | EP759466 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225; and Hori et al (1987), Blood 70, 1069-1078. | Soluble IL-12 beta-2 receptor polypeptides may be useful for inhibiting interleukin activities. |
| Human interleukin-12 | GeneSeq Accession | EP759466 | Interleukins are a group of multifunctional cytokines synthesized | Interleukin activity can be determined using assays known in | Soluble IL-12 beta-1 receptor polypeptides |

TABLE 1-continued

| Therapeutic Protein X | Exemplary Identifier | PCT/Patent Reference | Biological Activity | Exemplary Activity Assay | Preferred Indication Y |
|---|---|---|---|---|---|
| beta-1 receptor. | W12772 | | by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | the art: Matthews et al., in Lymphokines and Interferons: A Practical Approach, Clemens et al., eds, IRL Press, Washington, D.C. 1987, pp. 221-225; and Hori et at (1987), Blood 70, 1069-1078. | may be useful for inhibiting interleukin activities. |
| Human IL-9 receptor protein | GeneSeq Accessions W64055, W64056, and W64057 | WO9824904 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225; and Yang et al (1989), Blood 74, 1880-84. | Soluble IL-9 receptor polypeptides may be useful for inhibiting interleukin activities. |
| IL-10 receptor | GeneSeq Accession W41804 | U.S. Pat. No. 5,716,804 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225; and Thompson-Snipes et al (1991) J. Exp. Med. 173, 507-510. | Soluble IL-10 receptor polypeptides may be useful for inhibiting interleukin activities. |
| Human IL-6 receptor | GeneSeq Accession Y30938 | JP11196867 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225; and Aarden et al (1987) Eur. J. Immunol 17, 1411-16. | Soluble IL-6 receptor polypeptides may be useful for inhibiting interleukin activities. |
| Il-17 receptor | GeneSeq Accession Y97181 | U.S. Pat. No. 6,096,305 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225; and Yao et al (1995) J. Immunol. 155, 5483-86. | Soluble IL-17 receptor polypeptides may be useful for inhibiting interleukin activities. |
| Il-17 receptor | GeneSeq Accession | U.S. Pat. No. 6,100,235 | Interleukins are a group of multifunctional cytokines synthesized | Interleukin activity can be determined using assays known in | Soluble IL-17 receptor polypeptides may be |

TABLE 1-continued

| Therapeutic Protein X | Exemplary Identifier | PCT/Patent Reference | Biological Activity | Exemplary Activity Assay | Preferred Indication Y |
|---|---|---|---|---|---|
| | Y97131 | | by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | the art: Matthews et al., in Lymphokines and Interferons: A Practical Approach, Clemens et al., eds, IRL Press, Washington, D.C. 1987, pp. 221-225; and Yao et al (1995) J. Immunol. 155, 5483-86. | useful for inhibiting interleukin activities. |
| Human interleukin-3 receptor | GeneSeq Accession R25300 | EP509826 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225; and Kitamura et al (1989) J Cell Physiol. 140 323-334. | Soluble IL-3 receptor polypeptides may be useful for inhibiting interleukin activities. |
| Human GM-CSF receptor | GeneSeq Accession R10919 | WO9102063 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225. | Soluble GM-CSF receptor polypeptides may be useful for inhibiting interleukin activities. |
| Human IL-5 receptor alpha chain | GeneSeq Accession R25064 | EP492214 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225; and Kitamura et al (1989) J Cell Physiol. 140, 323-334. | Soluble IL-5 receptor alpha polypeptides may be useful for inhibiting interleukin activities. |
| IL-5 receptor | GeneSeq Accession W82842 | WO9847923 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225; and Kitamura et al (1989) J Cell Physiol. 140, 323-334. | Soluble IL-5 receptor polypeptides may be useful for inhibiting interleukin activities. |
| Il-6 receptor | GeneSeq Accession | JP05091892 | Interleukins are a group of multifunctional cytokines synthesized | Interleukin activity can be determined using assays known in | Soluble IL-6 receptor polypeptides may be |

TABLE 1-continued

| Therapeutic Protein X | Exemplary Identifier | PCT/Patent Reference | Biological Activity | Exemplary Activity Assay | Preferred Indication Y |
|---|---|---|---|---|---|
| | R37215 | | by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | the art: Matthews et al., in Lymphokines and Interferons: A Practical Approach, Clemens et al., eds, IRL Press, Washington, D.C. 1987, pp. 221-225; and Aarden et al (1987) Eur. J. Immunol 17, 1411-16. | useful for inhibiting interleukin activities. |
| Human B cell stimulating factor-2 receptor | GeneSeq Accession P90525 | AU8928720 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225. | Soluble B cell stimulating factor-2 receptor polypeptides may be useful for inhibiting interleukin activities. |
| IL-7 receptor clone | GeneSeq Accession R08330 | EP403114 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225; and Park et al (1990) J. Exp. Med. 171, 1073-79. | Soluble IL-7 receptor polypeptides may be useful for inhibiting interleukin activities. |
| EPO receptor; EPOR | GeneSeq Accession R06512 | WO9008822 | EPO Receptor is involved in the proliferation and differentiation of erythroblasts. | EPO Receptor activity can be determined using assays known in the art, such as, J Biol Chem 2001 Mar 23; 276(12: 8995-9002; JAK2 protein tyrosine kinase activity: Blood 1994 Sep 1; 84(5): 1501-7 and Mol Cell Biol. 1994 Oct; 14(10: 6506-14. | inflammatory disorders, immunologic disorders, cancer, erythroblast proliferation and differentiation |
| IL-15 receptor | GeneSeq Accession R90843 | WO9530695 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225; and Giri et al (1994) EMBO J. 13 2822-2830. | Soluble IL-15 receptor polypeptides may be useful for inhibiting interleukin activities. |
| CD137; 4-1BB Receptor Protein | GeneSeq Accession R70977 | WO9507984 | Activities associated with apoptosis, NF-kB activation, and co-stimulation of immune cells such as T and B cells. | Apoptosis activity, NF-kB activation, and B and T cell co-stimulation can be determined using assays known in the art: Moore et | Soluble 4-1BB receptor polypeptides may be useful for inhibiting apoptosis, NF-kB |

TABLE 1-continued

| Therapeutic Protein X | Exemplary Identifier | PCT/Patent Reference | Biological Activity | Exemplary Activity Assay | Preferred Indication Y |
|---|---|---|---|---|---|
| BCMA | GeneSeq Accession Y71979 | WO0068378 | Activities associated with apoptosis, NF-kB activation, and co-stimulation of immune cells such as T and B cells. | al., 1999, Science, 285(5425): 260-3; Song HY et al., 1997 Proc Natl Acad Sci USA 94(18): 9792-6; Epsevik and Nissen-Meyer, 1986, J. Immunol. Methods. Apoptosis activity, NF-kB activation, and B and T cell co-stimulation can be determined using assays known in the art: Moore et al., 1999, Science, 285(5425): 260-3; Song HY et al., 1997 Proc Natl Acad Sci USA 94(18): 9792-6; Epsevik and Nissen-Meyer, 1986, J. Immunol. Methods. | activation, and/or co-stimulation of immune cells such as B and T cells. Soluble BCMA receptor polypeptides may be useful for inhibiting apoptosis, NF-kB activation, and/or co-stimulation of immune cells such as B and T cells. |
| CD27 | GeneSeq Accession R20814 | WO9201049 | Activities associated with apoptosis, NF-kB activation, and co-stimulation of immune cells such as T and B cells. | Apoptosis activity, NF-kB activation, and B and T cell co-stimulation can be determined using assays known in the art: Moore et al., 1999, Science, 285(5425): 260-3; Song HY et al., 1997 Proc Natl Acad Sci USA 94(18): 9792-6; Epsevik and Nissen-Meyer, 1986, J. Immunol. Methods. | Soluble CD27 polypeptides may be useful for inhibiting apoptosis, NF-kB activation, and/or co-stimulation of immune cells such as B and T cells. |
| CD30 | GeneSeq Accession R35478 | DE4200043 | Activities associated with apoptosis, NF-kB activation, and co-stimulation of immune cells such as T and B cells. | Apoptosis activity, NF-kB activation, and B and T cell co-stimulation can be determined using assays known in the art: Moore et al., 1999, Science, 285(5425): 260-3; Song HY et al., 1997 Proc Natl Acad Sci USA 94(18): 9792-6; Epsevik and Nissen-Meyer, 1986, J. Immunol. Methods. | Soluble CD30 polypeptides may be useful for inhibiting apoptosis, NF-kB activation, and/or co-stimulation of immune cells such as B and T cells. |
| CD40 | GeneSeq Accession Y33499 | WO9945944 | Activities associated with apoptosis, NF-kB activation, and co-stimulation of immune cells such as T and B cells. | Apoptosis activity, NF-kB activation, and B and T cell co-stimulation can be determined using assays known in the art: Moore et al., 1999, Science, 285(5425): 260-3; Song HY et al., 1997 Proc Natl Acad Sci USA 94(18): 9792-6; Epsevik and Nissen-Meyer, 1986, J. Immunol. Methods. | Soluble CD40 polypeptides may be useful for inhibiting apoptosis, NF-kB activation, and/or co-stimulation of immune cells such as B and T cells. |
| EDAR | Genbank Accession AAD50077 | | Activities associated with apoptosis, NF-kB activation, and co-stimulation of immune cells such as T and B cells. | Apoptosis activity, NF-kB activation, and B and T cell co-stimulation can be determined using assays known in the art: Moore et al., 1999, Science, 285(5425): 260-3; Song HY et al., 1997 Proc Natl Acad Sci USA 94(18): 9792-6; Epsevik and Nissen-Meyer, 1986, J. Immunol. Methods. | Immune Disorders, Lymphomas, X-linked hypohidrotic ectodermal dysplasia |

TABLE 1-continued

| Therapeutic Protein X | Exemplary Identifier | PCT/Patent Reference | Biological Activity | Exemplary Activity Assay | Preferred Indication Y |
|---|---|---|---|---|---|
| OX40; ACT-4 | GeneSeq Accession R74737 | WO9512673 | Activities associated with apoptosis, NF-kB activation, and co-stimulation of immune cells such as T and B cells. | Apoptosis activity, NF-kB activation, and B and T cell co-stimulation can be determined using assays known in the art: Moore et al., 1999, Science, 285(5425): 260-3; Song HY et al., 1999, Science, 285(5425): 260-3; Epsevik and Nissen-Meyer, 1986, J. Immunol. Methods. 94(18): 9792-6; Epsevik and Nissen-Meyer, 1986, J. Immunol. Methods. | Immune Disorders, Lymphomas, T cell disorders |
| TACI | GeneSeq Accession W75783 | WO9833961 | Activities associated with apoptosis, NF-kB activation, and co-stimulation of immune cells such as T and B cells. | Apoptosis activity, NF-kB activation, and B and T cell co-stimulation can be determined using assays known in the art: Moore et al., 1999, Science, 285(5425): 260-3; Song HY et al., 1999, Science, 285(5425): 260-3; Epsevik and Nissen-Meyer, 1986, J. Immunol. Methods. 94(18): 9792-6; Epsevik and Nissen-Meyer, 1986, J. Immunol. Methods. | Soluble TACI receptor polypeptides may be useful for inhibiting apoptosis, NF-kB activation, and/or co-stimulation of immune cells such as B and T cells. |
| TNF-R | GeneSeq Accession R10986 | AU9058976 | Activities associates with apoptosis, NF-kB activation, and co-stimulation of immune cells such as T and B cells. | Apoptosis activity, NF-kB activation, and B and T cell co-stimulation can be determined using assays known in the art: Moore et al., 1999, Science, 285(5425): 260-3; Song HY et al., 1997 Proc Natl Acad Sci USA 94(18): 9792-6; Epsevik and Nissen-Meyer, 1986, J. Immunol. Methods. | Soluble TNF-R receptor polypeptides may be useful for inhibiting apoptosis, NF-kB activation, and/or co-stimulation of immune cells such as B and T cells. |
| TNF-RII; TNF p75 receptor; Death Receptor | GeneSeq Accession R11141 | EP418014 | Activities associated with apoptosis, NF-kB activation, and co-stimulation of immune cells such as T and B cells. | Apoptosis activity, NF-kB activation, and B and T cell co-stimulation can be determined using assays known in the art: Moore et al., 1999, Science, 285(5425): 260-3; Song HY et al., 1997 Proc Natl Acad Sci USA 94(18)9792-6; Epsevik and Nissen-Meyer, 1986, J. Immunol. Methods. | Soluble TNFR-II receptor polypeptides may be useful for inhibiting apoptosis, NF-kB activation, and/or co-stimulation of immune cells such as B and T cells. |
| hAPO-4; TROY | GeneSeq Accession W93581 | WO9911791 | Activities associated with apoptosis, NF-kB activation, and co-stimulation of immune cells such as T and B cells. | Apoptosis activity, NF-kB activation, and B and T cell co-stimulation can be determined using assays known in the art: Moore et al., 1999, Science, 285(5425): 260-3; Song HY et al., 1997 Proc Natl Acad Sci USA 94(18): 9792-6; Epsevik and Nissen-Meyer, 1986, J. Immunol. Methods. | Immune Disorders, Cancers |
| TNF-alpha precursor | GeneSeq Accession P60074 | EP205038 | Activities associated with apoptosis, NF-kB activation, and co-stimulation of immune cells such as T and B cells. | Apoptosis activity, NF-kB activation, and B and T cell co-stimulation can be determined using assays known in the art: Moore et al., 1999, Science, 285(5425): 260-3; Song HY et al., 1997 Proc Natl Acad Sci USA 94(18): 9792-6; Epsevik and Nissen-Meyer, 1986, J. Immunol. Methods. | Inflammatory disorders, immunologic disorders, cancer |
| Human TNF- | GeneSeq | EP619372 | Activities associated with apoptosis, | Apoptosis activity, NF-kB activation, | Inflammatory disorders, |

TABLE 1-continued

| Therapeutic Protein X | Exemplary Identifier | PCT/Patent Reference | Biological Activity | Exemplary Activity Assay | Preferred Indication Y |
|---|---|---|---|---|---|
| alpha | Accession R62463 | | NF-kB activation, and co-stimulation of immune cells such as T and B cells | and B and T cell co-stimulation can be determined using assays known in the art: Moore et al., 1999, Science, 285(5425): 260-3; Song HY et al., 1997 Proc Natl Acad Sci USA 94(18): 9792-6; Epsevik and Nissen-Meyer, 1986, J. Immunol. Methods. | immunologic disorders, cancer |
| Human TNF-alpha | GeneSeq Accession R42679 | EP563714 | Activities associated with apoptosis, NF-kB activation, and co-stimulation of immune cells such as T and B cells. | Apoptosis activity, NF-kB activation, and B and T cell co-stimulation can be determined using assays known in the art: Moore et al., 1999, Science, 285(5425): 260-3; Song HY et al., 1997 Proc Natl Acad Sci USA 94(18): 9792-6; Epsevik and Nissen-Meyer, 1986, J. Immunol. Methods. | Inflammatory disorders, immunologic disorders, cancer |
| Human TNF-beta (LT-alpha) | GeneSeq Accession B37799 | WO0064479 | Activities associated with apoptosis, NF-kB activation, and co-stimulation of immune cells such as T and B cells. | Apoptosis activity, NF-kB activation, and B and T cell co-stimulation can be determined using assays known in the art: Moore et al., 1999, Science, 285(5425): 260-3; Song HY et al., 1997 Proc Natl Acad Sci USA 94(18): 9792-6; Epsevik and Nissen-Meyer, 1986, J. Immunol. Methods. | Inflammatory disorders, immunologic disorders, cancer |
| LT-alpha | GeneSeq Accession P70107 | EP250000 | Activities associated with apoptosis, NF-kB activation, and co-stimulation of immune cells such as T and B cells. | Apoptosis activity, NF-kB activation, and B and T cell co-stimulation can be determined using assays known in the art: Moore et al., 1999, Science, 285(5425): 260-3; Song HY et al., 1997 Proc Natl Acad Sci USA 94(18): 9792-6; Epsevik and Nissen-Meyer, 1986, J. Immunol. Methods. | Inflammatory disorders, immunologic disorders, cancer |
| LT-beta | GeneSeq Accession R56869 | WO9413808 | Activities associated with apoptosis, NF-kB activation, and co-stimulation of immune cells such as T and B cells. | Apoptosis activity, NF-kB activation, and B and T cell co-stimulation can be determined using assays known in the art: Moore et al., 1999, Science, 285(5425): 260-3; Song HY et al., 1997 Proc Natl Acad Sci USA 94(18): 9792-6; Epsevik and Nissen-Meyer, 1986, J. Immunol. Methods. | Inflammatory disorders, immunologic disorders, cancer |
| OPGL | GeneSeq Accession W83195 | WO9846751 | Activities associated with apoptosis, NF-kB activation, and co-stimulation of immune cells such as T and B cells. | Apoptosis activity, NF-kB activation, and B and T cell co-stimulation can be determined using assays known in the art: Moore et al., 1999, Science, 285(5425): 260-3; Song HY et al., 1997 Proc Natl Acad Sci USA 94(18): 9792-6; Epsevik and Nissen-Meyer, 1986, J. Immunol. Methods. | Inflammatory disorders, immunologic disorders, cancer, loss of bone mass |
| FasL | GeneSeq Accession W98071 | WO9903999 | Activities associated with apoptosis, NF-kB activation, and co-stimulation of immune cells such as T and B cells. | Apoptosis activity, NF-kB activation, and B and T cell co-stimulation can be determined using assays known in | Inflammatory disorders, immunologic disorders, cancer |

TABLE 1-continued

| Therapeutic Protein X | Exemplary Identifier | PCT/Patent Reference | Biological Activity | Exemplary Activity Assay | Preferred Indication Y |
|---|---|---|---|---|---|
| | | | | the art: Moore, et al., 1999, Science, 285(5425): 260-3; Song HY et al., 1997 Proc Natl Acad Sci USA 94(18)9792-6; Epsevik and Nissen-Meyer, 1986, J. Immunol. Methods. | |
| FasL | GeneSeq Accession W95041 | WO9903998 | Activities associated with apoptosis, NF-kB activation, and co-stimulation of immune cells such as T and B cells. | Apoptosis activity, NF-kB activation, and B and T cell co-stimulation can be determined using assays known in the art: Moore et al., 1999, Science, 285(5425): 260-3; Song HY et al., 1997 Proc Natl Acad Sci USA 94(18): 9792-6; Epsevik and Nissen-Meyer, 1986, J. Immunol. Methods. | Inflammatory disorders, immunologic disorders, cancer |
| CD27L | GeneSeq Accession R50121 | WO9405691 | Activities associated with apoptosis, NF-kB activation, and co-stimulation of immune cells such as T and B cells. | Apoptosis activity, NF-kB activation, and B and T cell co-stimulation can be determined using assays known in the art: Moore et al., 1999, Science, 285(5425): 260-3; Song HY et al., 1997 Proc Natl Acad Sci USA 94(18): 9792-6; Epsevik and Nissen-Meyer, 1986, J. Immunol. Methods. | Inflammatory disorders, immunologic disorders, cancer |
| CD30 ligand | GeneSeq Accession R45007 | WO9324135 | Activities associated with apoptosis, NF-kB activation, and co-stimulation of immune cells such as T and B cells. | Apoptosis activity, NF-kB activation, and B and T cell co-stimulation can be determined using assays known in the art: Moore et al., 1999, Science, 285(5425): 260-3; Song HY et al., 1997 Proc Natl Acad Sci USA 94(18): 9792-6; Epsevik and Nissen-Meyer, 1986, J. Immunol. Methods. | Inflammatory disorders, immunologic disorders, cancer |
| CD40L | GeneSeq Accession R85486 | WO9529935 | Activities associated with apoptosis, NF-kB activation, and co-stimulation of immune cells such as T and B cells. | Apoptosis activity, NF-kB activation, and B and T cell co-stimulation can be determined using assays known in the art: Moore et al., 1999, Science, 285(5425): 260-3; Song HY et al., 1997 Proc Natl Acad Sci USA 94(18): 9792-6; Epsevik and Nissen-Meyer, 1986, J. Immunol. Methods. | Inflammatory disorders, immunologic disorders, cancer |
| 4-1BB ligand | GeneSeq Accession W26657 | U.S. Pat. No. 5,674,704 | Activities associated with apoptosis, NF-kB activation, and co-stimulation of immune cells such as T and B cells. | Apoptosis activity, NF-kB activation, and B and T cell co-stimulation can be determined using assays known in the art: Moore et al., 1999, Science, 285(5425): 260-3; Song HY et al., 1997 Proc Natl Acad Sci USA 94(18): 9792-6; Epsevik and Nissen-Meyer, 1986, J. Immunol. Methods. | Inflammatory disorders, immunologic disorders, cancer |
| FAS Ligand Inhibitory Protein (DcR3) | GeneSeq Accession B19335 | WO0058465 | Activities associated with apoptosis, NF-kB activation, and co-stimulation of immune cells such as T and B cells. | Apoptosis activity, NF-kB activation, and B and T cell co-stimulation can be determined using assays known in the art: Moore et al., 1999, Science, 285(5425): 260-3; Song HY et al., | Soluble DcR3 polypeptides may be useful for inhibiting apoptosis, NF-kB activation, and/or co- |

TABLE 1-continued

| Therapeutic Protein X | Exemplary Identifier | PCT/Patent Reference | Biological Activity | Exemplary Activity Assay | Preferred Indication Y |
|---|---|---|---|---|---|
| OX40L | GeneSeq Accession R79903 | WO9521915 | Activities associated with apoptosis, NF-kB activation, and co-stimulation of immune cells such as T and B cells. | 1997 Proc Natl Acad Sci USA 94(18): 9792-6; Epsevik and Nissen-Meyer, 1986, J. Immunol. Methods Apoptosis activity, NF-kB activation, and B and T cell co-stimulation can be determined using assays known in the art: Moore et al., 1999, Science, 285(5425): 260-3; Song HY et al., 1997 Proc Natl Acad Sci USA 94(18): 9792-6; Epsevik and Nissen-Meyer, 1986, J. Immunol. Methods. | stimulation of immune cells such as B and T cells. Inflammatory disorders, immunologic disorders, cancer |
| Protease inhibitor peptides | GeneSeq Accessions R12435, R12436, R12437, R12438, R12439, R12440, and R1244 | WO9106561 | Peptides that inhibit the function/binding of HIV | HIV protease activities are known in the art: HIV protease assays: EP0387231. One can modify the assay to look for inhibition using any of the disclosed protease inhibitor polypeptides. | HIV, inflammatory disorders, immunologic disorders, cancer, viral infections |
| Retroviral protease inhibitors | GeneSeq Accessions R06660, R06661, R06662, R06663, R06664, R06665, R06666, R06667, R06668, R06669, R06670, R06671, R06672, R06673, R06674, R06675, and R06676 | EP387231 | Peptides that inhibit the function/binding of HIV | HIV protease activities are known in the art: HIV protease assays: EP0387231. One can modify the assay to look for inhibition using any of the disclosed protease inhibitor polypeptides. | HIV, inflammatory disorders, immunologic disorders, cancer, viral infections |
| HIV protease inhibiting peptides | GeneSeq Accessions R59293, R59294, R59295, R59296, R59297, R59298, R59299, R592300, R59301, R59302, R59303, R59304, R59305, R59306, R59307, R59308, R59309, R59310, R59311, R59312, R59313, R59314, R59315, R59316, R59317, R59318, R59319, R59320, R59321, R59322, R59323, R59324, R59325, R59326, R59327, R59328, R59329, | WO9301828 | Peptides that inhibit the function/binding of HIV | HIV protease activities are known in the art: HIV protease assays: EP0387231. One can modify the assay to look for inhibition using any of the disclosed protease inhibitor polypeptides. | HIV, inflammatory disorders, immunologic disorders, cancer, viral infections |

TABLE 1-continued

| Therapeutic Protein X | Exemplary Identifier | PCT/Patent Reference | Biological Activity | Exemplary Activity Assay | Preferred Indication Y |
|---|---|---|---|---|---|
| HIV-1 protease hinibitors | R59330, R59331, R59332, R59333, R59334, R59335, R59336, R59337, R59338, R59339, R59340, R59341, R59342, R59343, R59344, R59345, R59346, R59347, R59348, R59349, and R59350 | DE4412174 | Peptides that inhibit the function/binding of HIV | HIV protease activities are known in the art: HIV protease assays: EP0387231. One can modify the assay to look for inhibition using any of the disclosed protease inhibitor polypeptides. | HIV, inflammatory disorders, immunologic disorders, cancer, viral infections |
| | GeneSeq Accessions R86326, R86327, R86328, R86329, R86330, R86331, R86332, R86333, R86334, R86335, R86336, R86337, R86338, R86339, R86340, R86341, R86342, R86343, R86344, R86345, R86346, R86347, R86348, R86349, R86350, R86351, R86352, R86353, R86354, R86355, R86356, R86357, R86358, R86359, R86360, R86361, R86362, R86363, R86364, R86365, R86366, R86367, R86368, R86369, R86370, and R86371 | | | | |
| HIV Inhibitor Peptide | GeneSeq Accession Y89687 | WO9959615 | Peptides that inhibit the function/binding of HIV | HIV protease activities are known in the art: HIV protease assays: EP0387231. One can modify the assay to look for inhibition using any of the disclosed protease inhibitor polypeptides. | HIV, inflammatory disorders, immunologic disorders, cancer, viral infections |
| HIV Inhibitor Peptide | GenSeq Accession Y31955 | WO9948513 | Peptides that inhibit the function/binding of HIV | HIV Protease activities are known in the art; HIV protease assays: EP0387231. One can modify the assay to look for inhibition using any of the disclosed protease inhibitor polypeptides. | HIV, inflammatory disorders, immunologic disorders, cancer, viral infections |
| HIV Inhibitor Peptide | www.sciencexpress.org; Published | | Peptides that inhibit the function/binding of HIV | HIV protease activities are known in the art: HIV protease assays: | HIV, inflammatory disorders, immunologic |

TABLE 1-continued

| Therapeutic Protein X | Exemplary Identifier | PCT/Patent Reference | Biological Activity | Exemplary Activity Assay | Preferred Indication Y |
|---|---|---|---|---|---|
| | online 12 Jan. 2001; 10.1126/science.1057453 | | | EP0387231: One can modify the assay to look for inhibition using any of the disclosed protease inhibitor polypeptides. | disorders, cancer, viral infections |
| Human monocyte chemoattractant factor hMCP-3 | GeneSeq Accession R73915 | WO9509232 | Chemokines are a family of small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot, T. N. C. Wells, and C. A. Power. © Humana Press Inc., Totowa, NJ | Immune disorders, particularly useful for treating bacterial and/or viral menigitis |
| Human monocyte chemoattractant factor hMCP-1 | GeneSeq Accession R73914 | WO9509232 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot, T. N. C. Wells, and C. A. Power. © Humana Press Inc., Totowa, NJ | Immune disorders, particularly useful for treating bacterial and/or viral menigitis |
| Human gro-beta chemokine | GeneSeq Accessions R66699 and W17671 | WO9429341 | Chemokines are a family of small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot, T. N. C. Wells, and C. A. Power. © Humana Press Inc., Totowa, NJ | immune disorders, inflammatory disorders, blood-related disorders, stem cell transplantation, cancer |
| Human gro-gamma chemokine | GeneSeq Accessions R66700 and | WO9429341 | Chemokines are a family of related small, secreted proteins involved in | Chemokine activities can be determined using assays known in the art: Methods in Molecular | Immune disorders, inflammatory disorders, blood-related disorders, |

TABLE 1-continued

| Therapeutic Protein X | Exemplary Identifier | PCT/Patent Reference | Biological Activity | Exemplary Activity Assay | Preferred Indication Y |
|---|---|---|---|---|---|
| | W17672 | | hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, which bind to ~17 receptors thus far identified | Biology, 2000, vol. 138: Chemokine Protocols. Edited by: A. E. I. Proudfoot, T. N. C. Wells, and C. A. Power. © Humana Press Inc., Totowa, NJ | stem cell transplantation, cancer |
| Human gro-alpha chemokine | GeneSeq Accessions R66698 and W18024 | WO9429341 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, which bind to ~17 receptors thus far identified | Chemokine activities can be determined using assays known in the art: Methods in Molecular Biology, 2000, vol. 138: Chemokine Protocols. Edited by: A. E. I. Proudfoot, T. N. C. Wells, and C. A. Power. © Humana Press Inc., Totowa, NJ | Immune disorders, inflammatory disorders, blood-related disorders, stem cell transplantation, cancer |
| Human eosinophil-expressed chemokine (EEC) | GeneSeq Accession W05186 | WO9632481 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, which bind to ~17 receptors thus far identified | Chemokine activities can be determined using assays known in the art: Methods in Molecular Biology, 2000, vol. 138: Chemokine Protocols. Edited by: A. E. I. Proudfoot, T. N. C. Wells, and C. A. Power. © Humana Press Inc., Totowa, NJ | Immune disorders, particularly treatment of eosinophilia, inflammation, allergies, asthma, leukaemia and lymphoma |
| Chemokine-like protein PF4-414 Full-Length and Mature | GeneSeq Accessions R92318 and R99809 | WO9613587 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, | Chemokine activities can be determined using assays known in the art: Methods in Molecular Biology, 2000, vol. 138: Chemokine Protocols. Edited by: A. E. I. Proudfoot, T. N. C. Wells, and C. A. Power. © Humana Press Inc., Totowa, NJ | Cancer and blood-related disorders, particularly myelosuppression |

TABLE 1-continued

| Therapeutic Protein X | Exemplary Identifier | PCT/Patent Reference | Biological Activity | Exemplary Activity Assay | Preferred Indication Y |
|---|---|---|---|---|---|
| Chemokine-like protein IL-8M3 | GeneSeq Accession R99812 | WO9613587 | viral infection, and tumor biology. The chemokines exert their effects by acting on a family of seven transmembrane G-protein-coupled receptors. Over 40 human chemokines have been described, which bind to ~17 receptors thus far identified<br>Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, which bind to ~17 receptors thus far identified | Chemokine activities can be determined using assays known in the art: Methods in Molecular Biology, 2000, vol. 138: Chemokine Protocols. Edited by: A. E. I. Proudfoot, T. N. C. Wells, and C. A. Power. © Humana Press Inc., Totowa, NJ; and Holmes et al (1991) Science 253, 1278-80. | Cancer and blood-related disorders, particularly myelosuppression |
| Human interleukin-8 (IL-8) | GeneSeq Accession R99814 | WO9613587 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, which bind to ~17 receptors thus far identified | Chemokine activities can be determined using assays known in the art: Methods in Molecular Biology, 2000, vol. 138: Chemokine Protocols. Edited by: A. E. I. Proudfoot, T. N. C. Wells, and C. A. Power. © Humana Press Inc., Totowa, NJ; and Holmes et al (1991) Science 253, 1278-80. | Cancer and blood-related disorders, particularly myelosuppression |
| Chemokine-like protein IL-8M1 Full-Length and Mature | GeneSeq Accessions R99815 and R99803 | WO9613587 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, | Chemokine activities can be determined using assays known in the art: Methods in Molecular Biology, 2000, vol. 138: Chemokine Protocols. Edited by: A. E. I. Proudfoot, T. N. C. Wells, and C. A. Power. © Humana Press Inc., Totowa, NJ; and Holmes et al (1991) Science 253, 1278-80. | Cancer and blood-related disorders, particularly myelosuppression |

TABLE 1-continued

| Therapeutic Protein X | Exemplary Identifier | PCT/Patent Reference | Biological Activity | Exemplary Activity Assay | Preferred Indication Y |
|---|---|---|---|---|---|
| Chemokine-like protein IL-8M8 Full-Length and Mature | GeneSeq Accessions R99816 and R99805 | WO9613587 | which bind to ~17 receptors thus far identified Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot; T. N. C. Wells, and C. A. Power. © Humana Press Inc., Totowa, NJ; and Holmes et al (1991) Science 253, 1278-80. | Cancer and blood-related disorders, particularly myelosuppression. |
| Chemokine-like protein IL-8M8 Full-Length and Mature | GeneSeq Accessions R99817 and R99806 | WO9613587 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot; T. N. C. Wells, and C. A. Power. © Humana Press Inc., Totowa, NJ; and Holmes et al (1991) Science 253, 1278-80. | Cancer and blood-related disorders, particularly myelosuppression. |
| Chemokine-like protein IL-8M8 Full-Length and Mature | GeneSeq Accessions R99818 and R99804 | WO9613587 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot; T. N. C. Wells, and C. A. Power. © Humana Press Inc., Totowa, NJ; and Holmes et al (1991) Science 253, 1278-80. | Cancer and blood-related disorders, particularly myelosuppression. |
| Chemokine-like protein IL-8M8 Full-Length and | GeneSeq Accessions R99819 and | WO9613587 | Chemokines are a family of related small, secreted proteins involved in biological processes ranging from | Chemokine activities can be determined using assays known in the art: Methods in Molecular | Cancer and blood-related disorders, particularly |

| Therapeutic Protein X | Exemplary Identifier | PCT/Patent Reference | Biological Activity | Exemplary Activity Assay | Preferred Indication Y |
|---|---|---|---|---|---|
| Mature | R99807 | | hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, which bind to ~17 receptors thus far identified. | Biology, 2000, vol. 138: Chemokine Protocols. Edited by: A. E. I. Proudfoot; T. N. C. Wells, and C. A. Power. © Humana Press Inc., Totowa, NJ | myelosuppression. |
| Chemokine-like protein IL-8M8 Full-Length and Mature | GeneSeq Accessions R99822 and R99807 | WO9613587 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, which bind to ~17 receptors thus far identified. | Chemokine activities can be determined using assasys known in the art: Methods in Molecular Biology, 2000, vol. 138: Chemokine Protocols. Edited by: A. E. I. Proudfoot; T. N. C. Wells, and C. A. Power. © Humana Press Inc., Totowa, NJ | Cancer and blood-related disorders, particularly myelosuppression. |
| Human foetal spleen expressed chemokine, FSEC | GeneSeq Accession R98499 | WO9622374 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, which bind to ~17 receptors thus far identified. | Chemokine activities can be determined using assasys known in the art: Methods in Molecular Biology, 2000, vol. 138: Chemokine Protocols. Edited by: A. E. I. Proudfoot; T. N. C. Wells, and C. A. Power. © Humana Press Inc., Totowa, NJ | Immune disorders |
| Liver expressed chemokine-1(LVEC-1) | GeneSeq Accession R95689 | WO9616979 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, | Chemokine activities can be determined using assasys known in the art: Methods in Molecular Biology, 2000, vol. 138: Chemokine Protocols. Edited by: A. E. I. Proudfoot; T. N. C. Wells, and C. A. Power. © Humana Press Inc., Totowa, NJ | Inflammation of the liver |

TABLE 1-continued

| Therapeutic Protein X | Exemplary Identifier | PCT/Patent Reference | Biological Activity | Exemplary Activity Assay | Preferred Indication Y |
|---|---|---|---|---|---|
| | | | viral infection, and tumor biology. The chemokines exert their effects by acting on a family of seven transmembrane G-protein-coupled receptors. Over 40 human chemokines have been described, which bind to ~17 receptors thus far identified. | | |
| Liver expressed chemokine-2(LVEC-2) | GeneSeq Accession R95690 | WO9616979 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot; T. N. C. Wells, and C. A. Power. © Humana Press Inc, Totowa, NJ | Inflammation of the liver |
| Pituitary expressed chemokine (PGEC) | GeneSeq Accession R95691 | WO9616979 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot; T. N. C. Wells, and C. A. Power. © Humana Press Inc, Totowa, NJ | Inflammation, particularly of the liver |
| Adenoid-expressed chemokine (ADEC) | GeneSeq Accession R97664 | WO9617868 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, | Chemokine activities can be determined using assays known in the art: Methods in Molecular Biology, 2000, vol. 138: Chemokine Protocols. Edited by: A. E. I. Proudfoot; T. N. C. Wells, and C. A. Power. © Humana Press Inc, Totowa, NJ | Inflammation, angiogenesis, tumorigenesis, musculoskeletal disorders |

| Therapeutic Protein X | Exemplary Identifier | PCT/Patent Reference | Biological Activity | Exemplary Activity Assay | Preferred Indication Y |
|---|---|---|---|---|---|
| Human chemokine CC-2 | GeneSeq Accession W38170 | | which bind to ~17 receptors thus far identified. Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, which bind to ~17 receptors thus far identified. | Chemokine activities can be determined using assays known in the art: Methods in Molecular Biology, 2000, vol. 138; Chemokine protocols. Edited by: A. E. I. Proudfoot, T. N. C. Wells, and C. A. Power. © Humana Press Inc. Totowa, NJ | Immune disorders, cell migration, proliferation, and differentiation, disorders |
| Human chemokine HCC-1 | GeneSeq Accession W38171 | WO9741230 | Chemokines are a family of related small, secreted proteins involved in biological processes ranging from hematopoiesis, angiogenesis and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, which bind to ~17 receptors thus far identified. | Chemokine activities can be determined using assays known in the art: Methods in molecular Biology 2000, vol. 138: Chemokine Protocols. Edited by A. E. I. Proudfoot, T. N. C. Wells, and C. A. Power © Humana Press Inc, Totowa, NJ | Immune disorders, cell migration, proliferation, and differentiation disorders |
| Human chemokine CC-3 | GeneSeq Accession W38172 | WO9741230 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, which bind to ~17 receptors thus far identified. | Chemokine activities can be determined using assays known in the art: Methods in molecular Biology, 2000, vol. 138: Chemokine Protocols. Edited by A. E. I. Proudfoot, T. N. C. Wells, and C. A. Power © Humana Press Inc, Totowa, NJ | Immune disorders, cell migration, proliferation and differentiation disorders |
| Novel betachemokine designated PTEC | GeneSeq Accession W27271 | WO9739126 | Chemokines are a family of related small, secreted proteins involved in biological processes ranging from | Chemokine activities can be determined using assays known in the art: Methods in molecular Biology, | Immune disorders, vascular disorders, cancer |

TABLE 1-continued

| Therapeutic Protein X | Exemplary Identifier | PCT/Patent Reference | Biological Activity | Exemplary Activity Assay | Preferred Indication Y |
|---|---|---|---|---|---|
| | | | hemotopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, which bind to ~17 receptors thus far identified. | 2000, vol. 138: Chemokine Protocols, Edited by A. E. I. Proudfoot, T. N. C. Wells, and C. A. Power © Humana Press Inc., Totowa, NJ | |
| Human CX3C 111 amino acid chemokine | GeneSeq Accession W23344 | WO9727299 | Chemokines are a family of related small, secreted proteins involved in biological processes ranging from hemotopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, which bind to ~17 receptors thus far identified. | Chemokine activities can be determined using assays known in the art: Methods in molecular Biology, 2000, vol. 138: Chemokine Protocols, Edited by A. E. I. Proudfoot, T. N. C. Wells, and C. A. Power © Humana Press Inc., Totowa, NJ | Immune disorders, inflammatory diseases, abnormal proliferation, regeneration, degeneration, and atrophy |
| Human CCF18 chemokine | GeneSeq Accession W25942 | WO9721812 | Chemokines are a family of related small, secreted proteins involved in biological processes ranging from hemotopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, which bind to ~17 receptors thus far identified. | Chemokine activities can be determined using assays known in the art: Methods in molecular Biology, 2000, vol. 138: Chemokine Protocols, Edited by A. E. I. Proudfoot, T. N. C. Wells, and C. A. Power © Humana Press Inc., Totowa, NJ | Abnormal physiology and development disorders, can also be used as an anti-viral agent |
| Human beta-chemokine H1305 (MCP-2) | GeneSeq Accession W26655 | WO9725427 | Chemokines are a family of related small, secreted proteins involved in biological processes ranging from hemotopoiesis, angiogenesis, and leukocyte trafficking. Members of this family are involved in a similarly diverse range of pathologies including inflammation, allergy, tissue rejection, | Chemokine activities can be determined using assays known in the art: Methods in molecular Biology, 2000, vol. 138: Chemokine Protocols, Edited by A. E. I. Proudfoot, T. N. C. Wells, and C. A. Power © Humana Press Inc., Totowa, NJ | Chemotaxis, blood-related disorders, viral infection, HIV, wound healing, cancer |

TABLE 1-continued

| Therapeutic Protein X | Exemplary Identifier | PCT/Patent Reference | Biological Activity | Exemplary Activity Assay | Preferred Indication Y |
|---|---|---|---|---|---|
| Human eosinocyte CC type chemokine eotaxin | GeneSeq Accession W14990 | WO9712914 | viral infection, and tumor biology. The chemokines exert their effects by acting on a family of seven transmembrane G-protein-coupled receptors. Over 40 human chemokines have been described, which bind to ~17 receptors thus far identified. Chemokines are a family of related small, secreted proteins involved in biological processes ranging from hemotopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, which bind to ~17 receptors thus far identified. | Chemokine activities can be determined using assays known in the art: Methods in molecular Biology, Protocols, Edited by A. E. I. Proudfoot, T. N. C. Wells, and C. A. Power 2000, vol. 138: Chemokine © Humana Press Inc, Totowa, NJ | Inflammatory and immune disorders |
| Human thymus and activation regulated cytokine (TARC) | GeneSeq Accession W14018 | WO9711969 | Chemokines are a family of related small, secreted proteins involved in biological processes ranging from hemotopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, which bind to ~17 receptors thus far identified. | Chemokine activities can be determined using assays known in the art: Methods in molecular Biology, Protocols, Edited by A. E. I. Proudfoot, T. N. C. Wells, and C. A. Power 2000, vol. 138: Chemokine © Humana Press Inc, Totowa, NJ | Inflammatory and immune disorders |
| Human chemokine beta-8 short forms | GeneSeq Accession W16315 | WO9712041 | Chemokines are a family of related small, secreted proteins involved in biological processes ranging from hemotopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, | Chemokine activities can be determined using assays known in the art: Methods in molecular Biology, Protocols, Edited by A. E. I. Proudfoot, T. N. C. Wells, and C. A. Power 2000, vol. 138: Chemokine © Humana Press Inc, Totowa, NJ | Cancer, would healing, immune disorders |

TABLE 1-continued

| Therapeutic Protein X | Exemplary Identifier | PCT/Patent Reference | Biological Activity | Exemplary Activity Assay | Preferred Indication Y |
|---|---|---|---|---|---|
| Macrophage derived chemokine, MDC | GeneSeq Accession W20058 | WO9640923 | which bind to ~17 receptors thus far identified. Chemokines are a family of related small, secreted proteins involved in biological processes ranging from hemaatopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot, T. N. C. Wells, and C. A. Power. © Humana Press Inc., Totowa, NJ | Inflammatory diseases, wound healin, angiogenesis |
| Human chemokine ZSIG-35 | GeneSeq Accession W30565 | WO9844117 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot, T. N. C. Wells, and C. A. Power. © Humana Press Inc., Totowa, NJ | Inflammatory and immune diseases |
| Primate CC chemokine "ILINCK" | GeneSeq Accesssion W69990 | WO9832858 | Chemokines are a family of related small, secreted proteins involved in biological processes ranging from hematopoiesis, angiogenesis, and leukocyte trafficking. | Chemokine activities can be determined using assays known in the art: Methods in Molecular Biology, 2000, vol. 138: Chemokine Protocols. Edited by: A. E. I. Prodfoot, T. N. C. Wells, and C. A. Power. © Humana Press Inc., Totowa, NJ | Immune and inflammatory disorders, abnormal proliferation, regeneration, generation and atrophy disorders |
| Primate CXC chemokine "IBICK" | GeneSeq Accession W69989 | WO9832858 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting | Chemokine activities can be determined using assays known in the art: Methods in Molecular Biology, 2000, vol. 138: Chemokine Protocols. Editd by: A. E. I. Proudfoot, T. N. C. Wells, and C. A. Power. © Humana Press Inc., Totowa, NJ | Immune and inflammatory disorders, abnormal proliferation, regeneration, generation and atrophy disorders |

TABLE 1-continued

| Therapeutic Protein X | Exemplary Identifier | PCT/Patent Reference | Biological Activity | Exemplary Activity Assay | Preferred Indication Y |
|---|---|---|---|---|---|
| Human CC-type chemokine protein designated SLC (secondary lymphoid chemokine) | GeneSeq Accession W69163 | WO9831809 | on a family of seven transmembrane G-protein-coupled receptors. Over 40 human chemokines have been described, which bind to ~17 receptors thus far identified. Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot, T. N. C. Wells, and C. A. Power. © Humana Press Inc., Totowa, NJ | Immune, inflammatory, and infectious disorders, cancer |
| Human CC chemokine ELC protein | GeneSeq Accession W62542 | WO9826071 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot, T. N. C. Wells, and C. A. Power. © Humana Press Inc., Totowa, NJ | Cancer and infectious diseases, particularly herpes virus |
| Human DVic-1 C-C chemokine | GeneSeq Accession W60649 | WO9823750 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot, T. N. C. Wells, and C. A. Power. © Humana Press Inc., Totowa, NJ | Abnormal proliferation, regeneration, degeneration, and atrophy disorders, including cancer |

TABLE 1-continued

| Therapeutic Protein X | Exemplary Identifier | PCT/Patent Reference | Biological Activity | Exemplary Activity Assay | Preferred Indication Y |
|---|---|---|---|---|---|
| Human C-C chemokine DGWCC | GeneSeq Accession W60650 | WO9823750 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot, T. N. C. Wells, and C. A. Power. © Humana Press Inc., Totowa, NJ | Immune disorders, cell proliferation disorders, cancer |
| Human STCP-1 | GeneSeq Accession W62783 | WO9824907 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot, T. N. C. Wells, and C. A. Power. © Humana Press Inc., Totowa, NJ | Immune disorders, particularly T cell related disorders, viral infection, and inflammation, especially joint |
| Exodua protein | GeneSeq Accession W61279 | WO9821330 | Chamokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot, T. N. C. Wells, and C. A. Power. © Humana Press Inc., Totowa, NJ | Immune and inflammatory disorders, angiogenesis, cancer, and proliferation disorders, particularly myeloproliferative diseases |
| Human Chr19Kine protein | GeneSeq Acession W50887 | WO9814581 | Chemokines are a family of related small, secreted proteins involved in biological processes ranging from hematopoiesis, angiogenesis, and leukocyte trafficking. Members of this | Chemokine activities can be determined using assays known in the art: Methods in Molecular Biology, 2000, vol. 138: Chemokine Protocols. Edited by: | Cancer and degenerative disorders |

TABLE 1-continued

| Therapeutic Protein X | Exemplary Identifier | PCT/Patent Reference | Biological Activity | Exemplary Activity Assay | Preferred Indication Y |
|---|---|---|---|---|---|
| | | | family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, which bind to ~17 receptors thus far identified. | A. E. I. Proudfoot, T. N. C. Wells, and C. A. Power. © Humana Press Inc., Totowa, NJ | |
| Human T cell mixed lymphocyte reaction expressed chemokine (TMEC) | GeneSeq Accession W58703 | U.S. Pat. No. 5,780,268 | Chemokines area family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, which bind to ~17 receptors thus far identified. | Chemokine activities can be determined using assays known in the art: Mehtods of Molecular Biology, 2000, vol. 138: Chemokine Protocols. Edited by: A. E. I. Proudfoot, T. N. C. Wells, and C. A. Power © Humana Press Inc. Totowa, NJ | Immune, inflammatory, and infectious disorders, cancer |
| Human 6CKine protein | GeneSeq Accession W50885 | WO9814581 | Chemokines area family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, which bind to ~17 receptors thus far identified. | Chemokine activities can be determined using assays known in the art: Mehtods of Molecular Biology, 2000, vol. 138: Chemokine Protocols. Edited by: A. E. I. Proudfoot, T. N. C. Wells, and C. A. Power © Humana Press Inc. Totowa, NJ | Cancer and degenerative disorders |
| human liver and activation regulated chemokine (LARC) | GeneSeq Accession W57475 | WO9817800 | Chemokines area family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting | Chemokine activities can be determined using assays known in the art: Mehtods of Molecular Biology, 2000, vol. 138: Chemokine Protocols. Edited by: A. E. I. Proudfoot, T. N. C. Wells, and C. A. Power © Humana Press Inc. Totowa, NJ | Immune, inflammatory, and infectious disorders, cancer |

TABLE 1-continued

| Therapeutic Protein X | Exemplary Identifier | PCT/Patent Reference | Biological Activity | Exemplary Activity Assay | Preferred Indication Y |
|---|---|---|---|---|---|
| RANTES peptide | GeneSeq Accession W29538 | WO9744462 | on a family of seven transmembrane G-protein-coupled receptors. Over 40 human chemokines have been described, which bind to ~17 receptors thus far identified. Chemokines area family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, which bind to ~17 receptors thus far identified. | Chemokine activities can be determined using assays known in the art: Mehtods of Molecular Biology, 2000, vol. 138: Chemokine Protocols. Edited by: A. E. I. Proudfoot, T. N. C. Wells, and C. A. Power © Humana Press Inc., Totowa, NJ | Infectious diseases, particularly HIV |
| RANTES 8-68 | GeneSeq Accession W29529 | WO9744462 | Chemokines area family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, which bind to ~17 receptors thus far identified. | Chemokine activities can be determined using assays known in the art: Mehtods of Molecular Biology, 2000, vol. 138: Chemokine Protocols. Edited by: A. E. I. Proudfoot, T. N. C. Wells, and C. A. Power © Humana Press Inc., Totowa, NJ | Infectious diseases, particularly HIV |
| RANTES 9-68 | GeneSeq Accession W29528 | WO9744462 | Chemokines area family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, which bind to ~17 receptors thus far identified. | Chemokine activities can be determined using assays known in the art: Mehtods of Molecular Biology, 2000, vol. 138: Chemokine Protocols. Edited by: A. E. I. Proudfoot, T. N. C. Wells, and C. A. Power © Humana Press Inc., Totowa, NJ | Infectious diseases, particularly HIV |

TABLE 1-continued

| Therapeutic Protein X | Exemplary Identifier | PCT/Patent Reference | Biological Activity | Exemplary Activity Assay | Preferred Indication Y |
|---|---|---|---|---|---|
| Human chemokine protein 331D5 | GeneSeq Accession W59433 | WO9811226 | Chemokines area family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, which bind to ~17 receptors thus far identified. | Chemokine activities can be determined using assays known in the art: Mehtods of Molecular Biology, 2000, vol. 138: Chemokine Protocols. Edited by: A. E. I. Proudfoot, T. N. C. Wells, and C. A. Power © Humana Press Inc, Totowa, NJ | Abnormal proliferation, regeneration, degeneration or atrophy, including cancer |
| Human chemokine protein 61164 | GeneSeq Accession W59430 | WO9811226 | Chemokines area family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, which bind to ~17 receptors thus far identified. | Chemokine activities can be determined using assays known in the art: Mehtods of Molecular Biology, 2000, vol. 138: Chemokine Protocols. Edited by: A. E. I. Proudfoot, T. N. C. Wells, and C. A. Power © Humana Press Inc, Totowa, NJ | Abnormal proliferation, regeneration, degeneration or atrophy, including cancer |
| Chemokine MCP-4 | GeneSeq Accession W56690 | WO9809171 | Chemokines area family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, which bind to ~17 receptors thus far identified. | Chemokine activities can be determined using assays known in the art: Mehtods of Molecular Biology, 2000, vol. 138: Chemokine Protocols. Edited by: A. E. I. Proudfoot, T. N. C. Wells, and C. A. Power © Humana Press Inc, Totowa, NJ | Immune, Inflammatory, and infectious diseases |
| Human stromal cell-derived chemokine, SDF-1 | GeneSeq Accession W50766 | FR2751658 | Chemokines are a family of related small, secreted proteins involved in biological processes ranging from hematopoiesis, angiogenesis, and leukocyte trafficking. Members of this | Chemokine activities can be determined using assays known in the art: Methods in Molecular Biology, 2000, vol. 138: Chemokine Protocols. Edited by: A. E. I. Proudfoot, | HIV infections |

TABLE 1-continued

| Therapeutic Protein X | Exemplary Identifier | PCT/Patent Reference | Biological Activity | Exemplary Activity Assay | Preferred Indication Y |
|---|---|---|---|---|---|
| | | | family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, which bind to ~17 receptors thus far identified. | T. N. C. Wells, and C. A. Power. © Humana Press Inc., Totowa, NJ | |
| Thymus expressed chemokine (TECK) | GeneSeq Accession W44397 | WO9801557 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot, T. N. C. Wells, and C. A. Power. © Humana Press Inc, Totowa, NJ | Immune and inflammatory disorders |
| Human chemokine MIP-3alpha | GeneSeq Accession W44398 | WO9801557 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot, T. N. C. Wells, and C. A. Power. © Humana Press Inc, Totowa, NJ | Immune and inflammatory disorders |
| Human chemokine MIP-3beta | GeneSeq Accession W44399 | WO9801557 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting | Chemokine activities can be determined using assays known in the art: Methods in Molecular Biology, 2000, vol. 138: Chemokine Protocols. Edited by: A. E. I. Proudfoot, T. N. C. Wells, and C. A. Power. © Humana Press Inc., Totowa, NJ | Immune and inflammatory disorders |

TABLE 1-continued

| Therapeutic Protein X | Exemplary Identifier | PCT/Patent Reference | Biological Activity | Exemplary Activity Assay | Preferred Indication Y |
|---|---|---|---|---|---|
| | | | on a family of seven transmembrane G-protein-coupled receptors. Over 40 human chemokines have been described, which bind to ~17 receptors thus far identified. | | |
| Human monocyte chemotactic proprotein (MCPP) sequence | GeneSeq Accession W42072 | WO9802459 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot, T. N. C. Wells, and C. A. Power. © Humana Press Inc., Totowa, NJ | Immune disorders, respiratory disorders, cancer |
| Macrophage-derived chemokine (MDC) | GeneSeq Accessions W40811 and Y24414 | U.S. Pat. No. 5,688,927/ U.S. Pat. No. 5,932,703 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot, T. N. C. Wells, and C. A. Power. © Humana Press Inc., Totowa, NJ | Immune, and inflammatory disorders, cancer |
| Macrophage derived chemokine analogue MDC-eyfy | GeneSeq Accession Y24416 | U.S. Pat. No. 5,932,703 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot, T. N. C. Wells, and C. A. Power. © Humana Press Inc., Totowa, NJ | Immune and inflammatory disorders |

TABLE 1-continued

| Therapeutic Protein X | Exemplary Identifier | PCT/Patent Reference | Biological Activity | Exemplary Activity Assay | Preferred Indication Y |
|---|---|---|---|---|---|
| Macrophage derived chemokine analogue MDC (n + 1) | GeneSeq Accession Y24413 | U.S. Pat. No. 5,932,703 | Chemokines are a

TABLE 1-continued

| Therapeutic Protein X | Exemplary Identifier | PCT/Patent Reference | Biological Activity | Exemplary Activity Assay | Preferred Indication Y |
|---|---|---|---|---|---|
| | | | family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, which bind to ~17 receptors thus far identified. | T. N. C. Wells, and C. A. Power. © Humana Press Inc., Totowa, NJ | |
| Human IP-10 and human Muc-1 core epitope (VNT) fusion protein | GeneSeq Accession Y29894 | WO9946392 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot, T. N. C. Wells, and C. A. Power. © Humana Press Inc, Totowa, NJ | Cancer and immune disorders, particularly HIV infection |
| Human IP-10 and HIV-1 gp 120 hypervariable region fusion protein | GeneSeq Accession Y TABLE 1-continued

| Therapeutic Protein X | Exemplary Identifier | PCT/Patent Reference | Biological Activity | Exemplary Activity Assay | Preferred Indication Y |
|---|---|---|---|---|---|
| | | | on a family of seven transmembrane G-protein-coupled receptors. Over 40 human chemokines have been described, which bind to ~17 receptors thus far identified. | | |
| Tim-1 protein | GeneSeq Accession Y28290 | WO9933990 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot, T. N. C. Wells, and C. A. Power. © Humana Press Inc., Totowa, NJ | Inflammation due to stimuli such as heart attacks and stroke, infection, physical trauma, UV or ionizing radiation, burns, frostbite or corrosive chemicals |
| Human Lkn-1 Full-Length and Mature protein | GeneSeq Accessions Y17280, Y17274, Y17281, and Y17275 | WO9928473 and WO9928472 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot, T. N. C. Wells, and C. A. Power. © Humana Press Inc., Totowa, NJ | HIV infection and cancer, particularly leukemia |
| N-terminal modified chemokine met-hSDF-1 alpha | GeneSeq Accession Y05818 | WO9920759 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot, T. N. C. Wells, and C. A. Power. © Humana Press Inc., Totowa, NJ | Inhibit or stimulate angiogenesis, inhibit the binding of HIV |

TABLE 1-continued

| Therapeutic Protein X | Exemplary Identifier | PCT/Patent Reference | Biological Activity | Exemplary Activity Assay | Preferred Indication Y |
|---|---|---|---|---|---|
| N-terminal modified chemokine met-hSDF-1 beta | GeneSeq Accession Y05819 | WO9920759 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot, T. N. C. Wells, and C. A. Power. © Humana Press Inc, Totowa, NJ | Inhibit or stimulate angiogenesis, inhibit the binding of HIV, antiinflammatory; immunosuppressant |
| N-terminal modified chemokine GroHEK/hSDF-1alpha | GeneSeq Accession Y05820 | WO9920759 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot, T. N. C. Wells, and C. A. Power. © Humana Press Inc, Totowa, NJ | Inhibit or stimulate angiogenesis, inhibit the binding of HIV, antiinflammatory; immunosuppressant |
| N-terminal modified chemokine GroHEK/hSDF-1beta | GeneSeq Accession Y05821 | WO9920759 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot, T. N. C. Wells, and C. A. Power. © Humana Press Inc, Totowa, NJ | Inhibit or stimulate angiogenesis, inhibit the binding of HIV, antiinflammatory; immunosuppressant |
| Chemokine Eotaxin | GeneSeq Accession Y14230 | WO9912968 | Chemokines are a family of related small, secreted proteins involved in biological processes ranging from hematopoiesis, angiogenesis, and leukocyte trafficking. Members of this | Chemokine activities can be determined using assays known in the art: Methods in Molecular Biology, 2000, vol. 138: Chemokine Protocols. Edited by: A. E. I. Proudfoot, | Increase or enhance an inflammatory response, an immune response orhaematopoietic cell-associated activity; treat |

TABLE 1-continued

| Therapeutic Protein X | Exemplary Identifier | PCT/Patent Reference | Biological Activity | Exemplary Activity Assay | Preferred Indication Y |
|---|---|---|---|---|---|
| | | | family are involved in a similarly diverse range of pathologies including inflammation, allergy, tissue rejection, viralk infection, and tumor biology. The chemokines exert their effects by acting on a family of seven transmembrane G-protein-coupled receptors. Over 40 human chemokines have been described, which bind to ~17 receptors thus far identified. | T. N. C. Wells, and C. A. Power. © Humana Press Inc., Totowa, NJ | a vascular indication; Cancer; enhance wound healing, to prevent or treat asthma, organ transplant rejection, rheumatoid arthritis or allergy |
| Chemokine hMCP1a | GeneSeq Accession Y14225 | WO9912968 | Chemokines are a family of related small, secreted proteins involved in biological processes ranging from hematopoiesis, agiogenesis, and leukocye trafficking. Members of this family are involved in a similarly diverse range of pathologies including inflammation, allergy, tissue rejection, viralk infection, and tumor biology. The chemokines exert their effects by acting on a family of seven transmembrane G-protein-coupled receptors. Over 40 human chemokines have been described, which bind to ~17 receptors thus far identified. | Chemokine activities can be determined using assays known in the art: Methods in Molecular Bilogy, 2000, vol. 138: Chemokine Protocols. Edited by: A. E. I. Proudfoot, T. N. C. Wells, and C. A. Power. © Humana Press Inc., Totowa, NJ | Immune disorders, Vascular disorders, Wound healing, cancer, prevent organ transplant rejection, Increase or enhance an inflammatory response, |
| Chemokine hMCP1b | GeneSeq Accession Y14226 | WO9912968 | Chemokines are a family of related small, secreted proteins involved in biological processes ranging from hematopoiesis, agiogenesis, and leukocye trafficking. Members of this family are involved in a similarly diverse range of pathologies including inflammation, allergy, tissue rejection, viralk infection, and tumor biology. The chemokines exert their effects by acting on a family of seven transmembrane G-protein-coupled receptors. Over 40 human chemokines have been described, which bind to ~17 receptors thus far identified. | Chemokine activities can be determined using assays known in the art: Methods in Molecular Bilogy, 2000, vol. 138: Chemokine Protocols. Edited by: A. E. I. Proudfoot, T. N. C. Wells, and C. A. Power. © Humana Press Inc., Totowa, NJ | Immune disorders, Vascular disorders, Wound healing, cancer, prevent organ transplant rejection, Increase or enhance an inflammatory response, |
| Chemokine hSDF1b | GeneSeq Accession Y14228 | WO9912968 | Chemokines are a family of related small, secreted proteins involved in biological processes ranging from hematopoiesis, agiogenesis, and leukocye trafficking. Members of this family are involved in a similarly diverse range of pathologies including inflammation, allergy, tissue rejection, viralk infection, and tumor biology. The chemokines exert their effects by acting | Chemokine activities can be determined using assays known in the art: Methods in Molecular Bilogy, 2000, vol. 138: Chemokine Protocols. Edited by: A. E. I. Proudfoot, T. N. C. Wells, and C. A. Power. © Humana Press Inc., Totowa, NJ | Immune disorders, Vascular disorders, Wound healing, cancer, prevent organ transplant rejection, Increase or enhance an inflammatory response, |

TABLE 1-continued

| Therapeutic Protein X | Exemplary Identifier | PCT/Patent Reference | Biological Activity | Exemplary Activity Assay | Preferred Indication Y |
|---|---|---|---|---|---|
| | | | on a family of seven transmembrane G-protein-coupled receptors. Over 40 human chemokines have been described, which bind to ~17 receptors thus far identified. | | |
| Chemokine hIL-8 | GeneSeq Accession Y14229 | WO9912968 | Chemokines are a family of related small, secreted proteins involved in biological processes ranging from hematopoiesis, angiogenesis, and leukocye trafficking. Members of this family are involved in a similarly diverse range of pathologies including inflammation, allergy, tissue rejection, viralk infection, and tumor biology. The chemokines exert their effects by acting on a family of seven transmembrane G-protein-coupled receptors. Over 40 human chemokines have been described, which bind to ~17 receptors thus far identified. | Chemokine activities can be determined using assays known in the art: Methods in Molecular Bilogy, 2000, vol. 138: Chemokine Protocols. Edited by: A. E. I. Proudfoot, T. N. C. Wells, and C. A. Power. © Humana Press Inc., Totowa, NJ; and Holmes et al (1991) Science 253, 1278-80. | Immune disorders, Vascular disorders, Wound healing, cancer, prevent organ transplant rejection, Increase or enhance an inflammatory response, |
| Chemokine hMCP1 | GeneSeq Accession Y14222 | WO9912968 | Chemokines are a family of related small, secreted proteins involved in biological processes ranging from hematopoiesis, angiogenesis, and leukocye trafficking. Members of this family are involved in a similarly diverse range of pathologies including inflammation, allergy, tissue rejection, viralk infection, and tumor biology. The chemokines exert their effects by acting on a family of seven transmembrane G-protein-coupled receptors. Over 40 human chemokines have been described, which bind to ~17 receptors thus far identified. | Chemokine activities can be determined using assays known in the art: Methods in Molecular Bilogy, 2000, vol. 138: Chemokine Protocols. Edited by: A. E. I. Proudfoot, T. N. C. Wells, and C. A. Power. © Humana Press Inc., Totowa, NJ | Immune disorders, Vascular disorders, Wound healing, cancer, prevent organ transplant rejection, Increase or enhance an inflammatory response, |
| Chemokine hMCP2 | GeneSeq Accession Y14223 | WO9912968 | Chemokines are a family of related small, secreted proteins involved in biological processes ranging from hematopoiesis, angiogenesis, and leukocye trafficking. Members of this family are involved in a similarly diverse range of pathologies including inflammation, allergy, tissue rejection, viralk infection, and tumor biology. The chemokines exert their effects by acting on a family of seven transmembrane G-protein-coupled receptors. Over 40 human chemokines have been described, which bind to ~17 receptors thus far identified. | Chemokine activities can be determined using assays known in the art: Methods in Molecular Bilogy, 2000, vol. 138: Chemokine Protocols. Edited by: A. E. I. Proudfoot, T. N. C. Wells, and C. A. Power. © Humana Press Inc., Totowa, NJ | Immune disorders, Vascular disorders, Wound healing, cancer, prevent organ transplant rejection, Increase or enhance an inflammatory response, |

TABLE 1-continued

| Therapeutic Protein X | Exemplary Identifier | PCT/Patent Reference | Biological Activity | Exemplary Activity Assay | Preferred Indication Y |
|---|---|---|---|---|---|
| Chemokine hMCP3 | GeneSeq Accession Y14224 | WO9912968 | Chemokines are a family of related small, secreted proteins involved in biological processes ranging from hematopoiesis, agiogenesis, and leukocye trafficking. Members of this family are involved in a similarly diverse range of pathologies including inflammation, allergy, tissue rejection, viralk infection, and tumor biology. The chemokines exert their effects by acting on a family of seven transmembrane G-protein-coupled receptors. Over 40 human chemokines have been described, which bind to ~17 receptors thus far identified. | Chemokine activities can be determined using assays known in the art: Methods in Molecular Bilogy, 2000, vol. 138: Chemokine Protocols. Edited by: A. E. I. Proudfoot, T. N. C. Wells, and C. A. Power. © Humana Press Inc., Totowa, NJ | Immune disorders, Vascular disorders, Wound healing, cancer, prevent organ transplant rejection, Increase or enhance an inflammatory response, |
| C-C chemokine, MCP2 | GeneSeq Accession Y05300 | EP905240 | Chemokines are a family of related small, secreted proteins involved in biological processes ranging from hematopoiesis, agiogenesis, and leukocye trafficking. Members of this family are involved in a similarly diverse range of pathologies including inflammation, allergy, tissue rejection, viralk infection, and tumor biology. The chemokines exert their effects by acting on a family of seven transmembrane G-protein-coupled receptors. Over 40 human chemokines have been described, which bind to ~17 receptors thus far identified. | Chemokine activities can be determined using assays known in the art: Methods in Molecular Bilogy, 2000, vol. 138: Chemokine Protocols. Edited by: A. E. I. Proudfoot, T. N. C. Wells, and C. A. Power. © Humana Press Inc., Totowa, NJ | Inflammatory, Immune and infectious diseases; pulmonary diseases and skin disorders; tumours, and angiogenesis-and haematopoiesis-related diseases |
| Wild type monocyte chemotactic protein 2 | GeneSeq Accession Y07233 | EP906954 | Chemokines are a family of related small, secreted proteins involved in biological processes ranging from hematopoiesis, agiogenesis, and leukocye trafficking. Members of this family are involved in a similarly diverse range of pathologies including inflammation, allergy, tissue rejection, viralk infection, and tumor biology. The chemokines exert their effects by acting on a family of seven transmembrane G-protein-coupled receptors. Over 40 human chemokines have been described, which bind to ~17 receptors thus far identified. | Chemokine activities can be determined using assays known in the art: Methods in Molecular Bilogy, 2000, vol. 138: Chemokine Protocols. Edited by: A. E. I. Proudfoot, T. N. C. Wells, and C. A. Power. © Humana Press Inc., Totowa, NJ | Inflammatory, Immune and infectious diseases; pulmonary diseases and skin disorders; tumours, and angiogenesis-and haematopoiesis-related diseases |
| Truncated monocyte chemotactic protein 2 (6-76) | GeneSeq Accession Y07234 | EP906954 | Chemokines area family of related small, secreted proteins involved in biological processes ranging from hematopoiesis, angiogenesis, and leukocyte trafficking. Members of this family are involved in a | Chemokines activities can be determined using assays known in the art: Methods in Molecular Biology, 2000, vol. 138: Chemokine Protocols. Edited by: A. E. I. Proudfoot, | Inflammatory, immune and infectious diseases; pulmonry diseases and skin disorders; tumours, and angiogenesis-and |

TABLE 1-continued

| Therapeutic Protein X | Exemplary Identifier | PCT/Patent Reference | Biological Activity | Exemplary Activity Assay | Preferred Indication Y |
|---|---|---|---|---|---|
| | | | similarly diverse range of pathologies including inflammation, allergy, tissue rejection, viral infection, and tumor biology. The chemokines exert their effects by acting on a finaily of seven transmembrane G-protein-coupled receptors. Over 40 human chemokines have been described, which bind to ~17 receptors thus far identified. | T. N. C. Wells, and C. A. Power, Humana Press Inc., Totowa, NJ | haematopoiesis-related diseases |
| Truncated RANTES protein (3-68) | GeneSeq Accessions Y07236 and Y07232 | EP905241; EP906954 | Chemokines area family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a finaily of seven transmembrane G-protein-coupled receptors. Over 40 human chemokines have been described, which bind to ~17 receptors thus far identified. | Chemokines activities can be determined using assays known in the art: Methods in Molecular Biology, 2000, vol. 138: Chemokine Protocols. Edited by: A. E. I. Proudfoot, T. N. C. Wells, and C. A. Power, Humana Press Inc, Totowa, NJ | Inflammatory, immune and infectious diseases; pulmonry diseases and skin disorders; tumours, and angiogenesis-and haematopoiesis-related diseases |
| Wild type monocyte chemotactic protein 2 | GeneSeq Accession Y07237 | EP905241 | Chemokines area family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a finaily of seven transmembrane G-protein-coupled receptors. Over 40 human chemokines have been described, which bind to ~17 receptors thus far identified. | Chemokines activities can be determined using assays known in the art: Methods in Molecular Biology, 2000, vol. 138: Chemokine Protocols. Edited by: A. E. I. Proudfoot, T. N. C. Wells, and C. A. Power, Humana Press Inc, Totowa, NJ | Inflammatory, immune and infectious diseases; pulmonry diseases and skin disorders; tumours, and angiogenesis-and haematopoiesis-related diseases |
| Truncated monocyte chemotactic protein 2 (6-76) | GeneSeq Accession Y07238 | EP905241 | Chemokines area family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a finaily of seven transmembrane G-protein-coupled receptors. Over 40 human chemokines | Chemokines activities can be determined using assays known in the art: Methods in Molecular Biology, 2000, vol. 138: Chemokine Protocols. Edited by: A. E. I. Proudfoot, T. N. C. Wells, and C. A. Power, Humana Press Inc, Totowa, NJ | Inflammatory, immune and infectious diseases; pulmonry diseases and skin disorders; tumours, and angiogenesis-and haematopoiesis-related diseases |

TABLE 1-continued

| Therapeutic Protein X | Exemplary Identifier | PCT/Patent Reference | Biological Activity | Exemplary Activity Assay | Preferred Indication Y |
|---|---|---|---|---|---|
| A partial CXCR4B protein | GeneSeq Accession W97363 | EP897980 | have been described, which bind to ~17 receptors thus far identified. Chem TABLE 1-continued

| Therapeutic Protein X | Exemplary Identifier | PCT/Patent Reference | Biological Activity | Exemplary Activity Assay | Preferred Indication Y |
|---|---|---|---|---|---|
| | | | including inflammation, allergy, tissue rejection, viral infection, and tumor biology. The chemokines exert their effects by acting on a family of seven transmembrane G-protein-coupled receptors. Over 40 human chemokines have been described, which bind to ~17 receptors thus far identified. | Humana Press Inc., Totowa, NJ; and Holmes et al (1991) Science 253, 1278-80. | |
| Epithelial neutrophil activating protein-78 (ENA-78) | GeneSeq Accession W96712 | U.S. Pat. No. 5,871,723 | Chemokines area family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, which bind to ~17 receptors thus far identified. | Chemokines activities can be determined using assays known in the art: Methods in Molecular Biology, 2000, vol. 138: Chemokine Protocols. Edited by: A. E. I. Proudfoot, T. N. C. Wells, and C. A. Power, Humana Press Inc, Totowa, NJ | Angiogenesis, Cancer, Inflammatory and Immune disorders, Cardio-Vascular disorders, Musco-skeletal disorders |
| Growth related oncogene-alpha (GRO-alpha). | GeneSeq Accession W96713 | U.S. Pat. No. 5,871,723 | Chemokines area family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, which bind to ~17 receptors thus far identified. | Chemokines activities can be determined using assays known in the art: Methods in Molecular Biology, 2000, vol. 138: Chemokine Protocols. Edited by: A. E. I. Proudfoot, T. N. C. Wells, and C. A. Power, Humana Press Inc, Totowa, NJ | Angiogenesis, Cancer, Inflammatory and Immune disorders, Cardio-Vascular disorders, Musco-skeletal disorders |
| Growth related oncogene-beta (GRO-beta). | GeneSeq Accession W96714 | U.S. Pat. No. 5,871,723 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection and tumor biology. The chemokines exert their effects by acting on a family of seven transmembrane G-protein-coupled receptors. Over 40 human chemokines have been described, | Chemokines activities can be determined using assays known in the art: Methods in Molecular Biology, 2000, vol. 138: Chemokine Protocols. Edited by: A. E. I. Proudfoot, T. N. C. Wells, and C. A. Power, © Humana Press Inc., Totowa, NJ | Angiogenesis, Cancer, Inflammatory and Immune disorders, Cardio-Vascular disorders, Musco-skeletal disorders |

TABLE 1-continued

| Therapeutic Protein X | Exemplary Identifier | PCT/Patent Reference | Biological Activity | Exemplary Activity Assay | Preferred Indication Y |
|---|---|---|---|---|---|
| Growth related oncogene-gamma (GRO-gamma) | GeneSeq Accession W96715 | U.S. Pat. No. 5,871,723 | which bind to ~17 receptors thus far identified Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot, T. N. C. Wells, and C. A. Power, © Humana Press Inc., Totowa, NJ | Angiogenesis, Cancer, Inflammatory and Immune disorders, Cardio-Vascular disorders, Musco-skeletal disorders |
| A platelet basic protein (PBP) | GeneSeq Accession W96716 | U.S. Pat. No. 5,871,723 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot, T. N. C. Wells, and C. A. Power, © Humana Press Inc., Totowa, NJ | Angiogenesis, Cancer, Inflammatory and Immune disorders, Cardio-Vascular disorders, Musco-skeletal disorders |
| Connective tissue activating protein-III (CTAP-III) | GeneSeqAccession S96717 | U.S. Pat. No. 5,871,723 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot, T. N. C. Wells, and C. A. Power, © Humana Press Inc., Totowa, NJ | Angiogenesis, Cancer, Inflammatory and Immune disorders, Cardio-Vascular disorders, Musco-skeletal disorders |
| Beta-thromboglobulin protein (beta-TG) | GeneSeq Accession W96718 | U.S. Pat. No. 5,871,723 | Chemokines are a family of related small, secreted proteins involved in biological processes ranging from | Chemokine activities can be determined using assays known in the art: Methods in Molecular | Angiogenesis, Cancer, Inflammatory and Immune disorders, |

TABLE 1-continued

| Therapeutic Protein X | Exemplary Identifier | PCT/Patent Reference | Biological Activity | Exemplary Activity Assay | Preferred Indication Y |
|---|---|---|---|---|---|
| | | | hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, which bind to ~17 receptors thus far identified. | Biology, 2000, vol. 138: Chemokine Protocols. Edited by: A. E. I. Proudfoot, T. N. C. Wells, and C. A. Power, © Humana Press Inc., Totowa, NJ | Cardio-Vascular disorders, Musco-skeletal disorders |
| Neutrophil activating peptide-2 (NAP-2) | GeneSeq Accession W96719 | U.S. Pat. No. 5,871,723 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot, T. N. C. Wells, and C. A. Power, © Humana Press Inc., Totowa, NJ | Angiogenesis, Cancer, Inflammatory and Immune disorders, Cardio-Vascular disorders, Musco-skeletal disorders |
| Granulocyte chemotactic protein-2 (GCP-2) | GeneSeq Accession W96720 | U.S. Pat. No. 5,871,723 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot, T. N. C. Wells, and C. A. Power, © Humana Press Inc., Totowa, NJ | Angiogenesis, Cancer, Inflammatory and Immune disorders, Cardio-Vascular disorders, Musco-skeletal disorders |
| Human chemokine MIG-beta protein | GeneSeq Accession W90124 | EP887409 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, | Chemokine activities can be determined using assays known in the art: Methods in Molecular Biology, 2000, vol. 138: Chemokine Protocols. Edited by: A. E. I. Proudfoot, T. N. C. Wells, and C. A. Power, © Humana Press Inc., Totowa, NJ | Immune disorders, viral, parasitic, fungal or bacterial infections, Cancer; autoimmune diseases or transplant rejection |

TABLE 1-continued

| Therapeutic Protein X | Exemplary Identifier | PCT/Patent Reference | Biological Activity | Exemplary Activity Assay | Preferred Indication Y |
|---|---|---|---|---|---|
| | | | viral infection, and tumor biology. The chemokines exert their effects by acting on a family of seven transmembrane G-protein-coupled receptors. Over 40 human chemokines have been described, which bind to ~17 receptors thus far identified. | | |
| Human ZCHEMO-8 | GeneSeq Accession W82716 | WO9854326 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot, T. N. C. Wells, and C. A. Power, © Humana Press Inc., Totowa, NJ | Immune disorders, cancer, myelopoietic disorders, autoimmune disorders and immunodeficiencies, Inflammatory and infectious diseases, Vascular disorders, wound healing |
| Human ZCHEMO-8 | GeneSeq Accession W82716 | WO9854326 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot, T. N. C. Wells, and C. A. Power, © Humana Press Inc., Totowa, NJ | Immune disorders, cancer, myelopoietic disorders, autoimmune disorders and immunodeficiencies, Inflammatory and infectious diseases, Vascular disorders, wound healing |
| Human Act-2 protein | GeneSeq Accession W82717 | WO9854326 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, | Chemokine activities can be determined using assays known in the art: Methods in Molecular Biology, 2000, vol. 138: Chemokine Protocols. Edited by: A. E. I. Proudfoot, T. N. C. Wells, and C. A. Power, © Humana Press Inc., Totowa, NJ | Immune disorders, cancer, myelopoietic disorders, autoimmune disorders and immunodeficiencies, Inflammatory and infectious diseases, Vascular disorders, wound healing |

TABLE 1-continued

| Therapeutic Protein X | Exemplary Identifier | PCT/Patent Reference | Biological Activity | Exemplary Activity Assay | Preferred Indication Y |
|---|---|---|---|---|---|
| Human SISD protein | GeneSeq Acession W82720 | WO9854326 | which bind to ~17 receptors thus far identified. Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot, T. N. C. Wells, and C. A. Power. © Humana Press Inc., Totowa, NJ | Immune disorders, cancer, myelopoietic disorders, autoimmune disorders and immunodeficiencies, Inflammatory and infectious diseases, Vascular disorders, wound healing |
| Human M110 protein | GeneSeq Accession W82721 | WO9854326 | Chemokines area family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, which bind to ~17 receptors thus far identified. | Chemokine activities can be determined using assays known in the art: Mehtods of Molecular Biology, 2000, vol. 138: Chemokine Protocols. Edited by: A. E. I. Proudfoot, T. N. C. Wells, and C. A. Power © Humana Press Inc, Totowa, NJ | Immune disorders, cancer, myelopoietic disorders, autoimmune disorders and immunodeficiencies, Inflammatory and infectious diseases, Vascular disorders, wound healing |
| Human M11A protein | GeneSeq Accession W82722 | WO9854326 | Chemokines area family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, which bind to ~17 receptors thus far identified. | Chemokine activities can be determined using assays known in the art: Mehtods of Molecular Biology, 2000, vol. 138: Chemokine Protocols. Edited by: A. E. I. Proudfoot, T. N. C. Wells, and C. A. Power © Humana Press Inc, Totowa, NJ | Immune disorders, cancer, myelopoietic disorders, autoimmune disorders and immunodeficiencies, Inflammatory and infectious diseases, Vascular disorders, wound healing |
| Human CCC3 protein | GeneSeq Accession W82723 | WO9854326 | Chemokines area family of related small, secreted proteins involved in biological processes ranging from | Chemokine activities can be determined using assays known in the art: Mehtods of Molecular Biology, | Immune disorders, cancer, myelopoietic disorders, autoimmune |

TABLE 1-continued

| Therapeutic Protein X | Exemplary Identifier | PCT/Patent Reference | Biological Activity | Exemplary Activity Assay | Preferred Indication Y |
|---|---|---|---|---|---|
| | | | hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, which bind to ~17 receptors thus far identified. | 2000, vol. 138: Chemokine Protocols. Edited by: A. E. I. Proudfoot, T. N. C. Wells, and C. A. Power © Humana Press Inc., Totowa, NJ | disorders and immunodeficiencies, Inflammatory and infectious diseases, Vascular disorders, wound healing |
| A human L105 chemokine designated huL105_3. | GeneSeq Accession W87588 | WO9856818 | Chemokines area family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, which bind to ~17 receptors thus far identified. | Chemokine activities can be determined using assays known in the art: Mehtods of Molecular Biology, 2000, vol. 138: Chemokine Protocols. Edited by: A. E. I. Proudfoot, T. N. C. Wells, and C. A. Power © Humana Press Inc., Totowa, NJ | Cancer, wound healing |
| A human L105 chemokine designated huL105_7. | GeneSeq Accession W87589 | WO9856818 | Chemokines area family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, which bind to ~17 receptors thus far identified. | Chemokine activities can be determined using assays known in the art: Mehtods of Molecular Biology, 2000, vol. 138: Chemokine Protocols. Edited by: A. E. I. Proudfoot, T. N. C. Wells, and C. A. Power © Humana Press Inc., Totowa, NJ | Cancer, wound healing |
| Human mature gro-alpha polypeptide used to treat sepsis | GeneSeq Accession W81498 | WO9848828 | Chemokines area family of related small, secreted proteins involved in biological processes ranging from hematopoiesis, angiogenesis, and leukocyte trafficking. Members of this family are involved in a similarly diverse range of pathologies including inflammation, allergy, tissue rejection, | Chemokine activities can be determined using assays known in the art: Mehtods of Molecular Biology, 2000, vol. 138: Chemokine Protocols. Edited by: A. E. I. Proudfoot, T. N. C. Wells, and C. A. Power © Humana Press Inc., Totowa, NJ | Infectious diseases, sepsis |

TABLE 1-continued

| Therapeutic Protein X | Exemplary Identifier | PCT/Patent Reference | Biological Activity | Exemplary Activity Assay | Preferred Indication Y |
|---|---|---|---|---|---|
| | | | viral infection, and tumor biology. The chemokines exert their effects by acting on a family of seven transmembrane G-protein-coupled receptors. Over 40 human chemokines have been described, which bind to ~17 receptors thus far identified. | | |
| Human mature gro-gamma polypeptide used to treat sepsis | GeneSeq Accession W81500 | WO9848828 | Chemokines area family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, which bind to ~17 receptors thus far identified. | Chemokine activities can be determined using assays known in the art: Mehtods of Molecular Biology, 2000, vol. 138: Chemokine Protocols. Edited by: A. E. I. Proudfoot, T. N. C. Wells, and C. A. Power © Humana Press Inc, Totowa, NJ | Infectious diseases, sepsis |
| Human thymus expressed chemokine TECK and TECK variant | GeneSeq Accessions B19607 and B19608 | WO0053635 | Chemokines area family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, which bind to ~17 receptors thus far identified. | Chemokine activities can be determined using assays known in the art: Mehtods of Molecular Biology, 2000, vol. 138: Chemokine Protocols. Edited by: A. E. I. Proudfoot, T. N. C. Wells, and C. A. Power © Humana Press Inc, Totowa, NJ | Inflammatory disorders, cancer, Immune and vascular disorders |
| Human chemokine SDF1alpha | GeneSeq Accession B15791 | WO0042071 | Chemokines area family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, | Chemokine activities can be determined using assays known in the art: Mehtods of Molecular Biology, 2000, vol. 138: Chemokine Protocols. Edited by: A. E. I. Proudfoot, T. N. C. Wells, and C. A. Power © Humana Press Inc, Totowa, NJ | Autoimmune disorders, Immune, Vascular and Inflammatory disorders |

TABLE 1-continued

| Therapeutic Protein X | Exemplary Identifier | PCT/Patent Reference | Biological Activity | Exemplary Activity Assay | Preferred Indication Y |
|---|---|---|---|---|---|
| Human chemokine GROalpha | GeneSeq Accession B15793 | WO0042071 | which bind to ~17 receptors thus far identified. Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot; T. N. C. Wells, and C. A. Power. © Humana Press Inc., Totowa, NJ | Autoimmune disorders, Immune, Vascular and Inflammatory disorders |
| Human chemokine eotaxin | GeneSeq Accession B15794 | WO0042071 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot; T. N. C. Wells, and C. A. Power. © Humana Press Inc., Totowa, NJ | Autoimmune disorders, Immune, Vascular and Inflammatory disorders |
| Human chemokine MIG | GeneSeq Accession B15803 | WO0042071 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot; T. N. C. Wells, and C. A. Power. © Humana Press Inc., Totowa, NJ | Autoimmune disorders, Immune, Vascular and Inflammatory disorders |
| Human chemokine PF4 | GeneSeq Accession B15804 | WO0042071 | Chemokines are a family of related small, secreted proteins involved in biological processes ranging from | Chemokine activities can be determined using assays known in the art: Methods in Molecular | Autoimmune disorders, Immune, Vascular and Inflammatory disorders |

TABLE 1-continued

| Therapeutic Protein X | Exemplary Identifier | PCT/Patent Reference | Biological Activity | Exemplary Activity Assay | Preferred Indication Y |
|---|---|---|---|---|---|
| | | | hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, which bind to ~17 receptors thus far identified. | Biology, 2000, vol. 138: Chemokine Protocols. Edited by: A. E. I. Proudfoot; T. N. C. Wells, and C. A. Power. © Humana Press Inc., Totowa, NJ | |
| Human chemokine I-309 | GeneSeq Accession B15805 | WO0042071 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot; T. N. C. Wells, and C. A. Power. © Humana Press Inc., Totowa, NJ | Autoimmune disorders, Immune, Vascular and Inflammatory disorders |
| Human chemokine HCC-1 | GeneSeq Accession B15806 | WO0042071 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot; T. N. C. Wells, and C. A. Power. © Humana Press Inc., Totowa, NJ | Autoimmune disorders, Immune, Vascular and Inflammatory disorders |
| Human chemokine C10 | GeneSeq Accession B15807 | WO0042071 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, | Chemokine activities can be determined using assays known in the art: Methods in Molecular Biology, 2000, vol. 138: Chemokine Protocols. Edited by: A. E. I. Proudfoot; T. N. C. Wells, and C. A. Power. © Humana Press Inc., Totowa, NJ | Autoimmune disorders, Immune, Vascular and Inflammatory disorders |

TABLE 1-continued

| Therapeutic Protein X | Exemplary Identifier | PCT/Patent Reference | Biological Activity | Exemplary Activity Assay | Preferred Indication Y |
|---|---|---|---|---|---|
| | | | viral infection, and tumor biology. The chemokines exert their effects by acting on a family of seven transmembrane G-protein-coupled receptors. Over 40 human chemokines have been described, which bind to ~17 receptors thus far identified. | | |
| Human chemokine CCR-2 | GeneSeq Accession B15808 | WO0042071 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, which bind to ~17 receptors thus far identified. | Chemokine activities can be determined using assasys known in the art: Methods in Molecular Biology, 2000, vol. 138: Chemokine Protocols. Edited by: A. E. I. Proudfoot; T. N. C. Wells, and C. A. Power. © Humana Press Inc., Totowa, NJ | Autoimmune disorders, Immune, Vascular and Inflammatory disorders |
| Human chemokine ENA-78 | GeneSeq Accession B15809 | WO0042071 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, which bind to ~17 receptors thus far identified. | Chemokine activities can be determined using assasys known in the art: Methods in Molecular Biology, 2000, vol. 138: Chemokine Protocols. Edited by: A. E. I. Proudfoot; T. N. C. Wells, and C. A. Power. © Humana Press Inc., Totowa, NJ | Autoimmune disorders, Immune, Vascular and Inflammatory disorders |
| Human chemokine GRObeta | GeneSeq Accession B15810 | WO0042071 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, | Chemokine activities can be determined using assasys known in the art: Methods in Molecular Biology, 2000, vol. 138: Chemokine Protocols. Edited by: A. E. I. Proudfoot; T. N. C. Wells, and C. A. Power. © Humana Press Inc., Totowa, NJ | Autoimmune disorders, Immune, Vascular and Inflammatory disorders |

TABLE 1-continued

| Therapeutic Protein X | Exemplary Identifier | PCT/Patent Reference | Biological Activity | Exemplary Activity Assay | Preferred Indication Y |
|---|---|---|---|---|---|
| Human chemokine IP-10 | GeneSeq Accession B15811 | WO0042071 | which bind to ~17 receptors thus far identified. Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot, T. N. C. Wells, and C. A. Power. © Humana Press Inc., Totowa, NJ | Autoimmune disorders, Immune, Vascular and Inflammatory disorders |
| Human chemokine SDF1beta | GeneSeq Accession B15812 | WO0042071 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot, T. N. C. Wells, and C. A. Power. © Humana Press Inc., Totowa, NJ | Autoimmune disorders, Immune, Vascular and Inflammatory disorders |
| Human chemokine GRO alpha | GeneSeq Accession B15813 | WO0042071 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot, T. N. C. Wells, and C. A. Power. © Humana Press Inc., Totowa, NJ | Autoimmune disorders, Immune, Vascular and Inflammatory disorders |
| Human chemokine MIP1beta | GeneSeq Accession B15831 | WO0042071 | Chemokines are a family of related small, secreted proteins involved in biological processes ranging from | Chemokine activities can be determined using assays known in the art: Methods in Molecular | Autoimmune disorders, Immune, Vascular and Inflammatory disorders |

TABLE 1-continued

| Therapeutic Protein X | Exemplary Identifier | PCT/Patent Reference | Biological Activity | Exemplary Activity Assay | Preferred Indication Y |
|---|---|---|---|---|---|
| A human C-C chemokine designated exodus | GeneSeq Accession B07939 | U.S. Pat. No. 6,096,300 | hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, which bind to ~17 receptors thus far identified. | Biology, 2000, vol. 138: Chemokine Protocols. Edited by: A. E. I. Proudfoot, T. N. C. Wells, and C. A. Power. © Humana Press Inc., Totowa, NJ | |
| | | | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot, T. N. C. Wells, and C. A. Power. © Humana Press Inc., Totowa, NJ | Cancer |
| Human chemokine L105_7 | GeneSeq Accession Y96922 | U.S. Pat. No. 6,084,071 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot, T. N. C. Wells, and C. A. Power. © Humana Press Inc., Totowa, NJ | Chemotaxis, Gene Therapy, Wound healing |
| Human chemokine L105_3 | GeneSeq Accession Y96923 | U.S. Pat. No. 6,084,071 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, | Chemokine activities can be determined using assays known in the art: Methods in Molecular Biology, 2000, vol. 138: Chemokine Protocols. Edited by: A. E. I. Proudfoot, T. N. C. Wells, and C. A. Power. © Humana Press Inc., Totowa, NJ | Chemotaxis, Gene Therapy, Wound healing |

TABLE 1-continued

| Therapeutic Protein X | Exemplary Identifier | PCT/Patent Reference | Biological Activity | Exemplary Activity Assay | Preferred Indication Y |
|---|---|---|---|---|---|
| | | | viral infection, and tumor biology. The chemokines exert their effects by acting on a family of seven transmembrane G-protein-coupled receptors. Over 40 human chemokines have been described, which bind to ~17 receptors thus far identified. | | |
| Human secondary lymphoid chemokine (SLC) | GeneSeq Accession B01434 | WO0038706 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot, T. N. C. Wells, and C. A. Power. © Humana Press Inc, Totowa, NJ | Cancer, Vascular and Immune disorders |
| Human non-ELR CXC chemokine H174 | GeneSeq Accession Y96310 | WO0029439 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot, T. N. C. Wells, and C. A. Power. © Humana Press Inc, Totowa, NJ | Immune and Inflammatory disorders, Cancer, Haemostatic and thrombolytic activity |
| Human non-ELR CXC chemokine IP10 | GeneSeq Accession Y96311 | WO0029439 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, | Chemokine activities can be determined using assays known in the art: Methods in Molecular Biology, 2000, vol. 138: Chemokine Protocols. Edited by: A. E. I. Proudfoot, T. N. C. Wells, and C. A. Power. © Humana Press Inc, Totowa, NJ | Immune and Inflammatory disorders, Cancer, haemostatic and thrombolytic activity |

TABLE 1-continued

| Therapeutic Protein X | Exemplary Identifier | PCT/Patent Reference | Biological Activity | Exemplary Activity Assay | Preferred Indication Y |
|---|---|---|---|---|---|
| Human non-ELR CXC chemokine Mig | GeneSeq Accession Y96313 | WO0029439 | which bind to ~17 receptors thus far identified. Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot, T. N. C. Wells, and C. A. Power. © Humana Press Inc., Totowa, NJ | Immune and Inflammatory disorders, Cancer, haemostatic and thrombolytic activity |
| Human chemokine Ckbeta-7 | GeneSeq Accession Y96280 | WO0028035 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot, T. N. C. Wells, and C. A. Power. © Humana Press Inc., Totowa, NJ | Cancer, wound healing, inflammatory and immunoregulatory disorders |
| Human chemokine MIP-1alpha | GeneSeq Accession Y96281 | WO0028035 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot, T. N. C. Wells, and C. A. Power. © Humana Press Inc., Totowa, NJ | Cancer, wound healing, inflammatory and immunoregulatory disorders |
| Human mature chemokine Ckbeta-7 | GenSeq Accession Y96282 | WO0028035 | Chemokines are a family of related small, secreted proteins involved in biological processes ranging from | Chemokine activities can be determined using assays known in the art: Methods in Molecular | Cancer, wound healing, inflammatory and immunoregulatory |

TABLE 1-continued

| Therapeutic Protein X | Exemplary Identifier | PCT/Patent Reference | Biological Activity | Exemplary Activity Assay | Preferred Indication Y |
|---|---|---|---|---|---|
| (optionally truncated) | | | hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, which bind to ~17 receptors thus far identified. | Biology, 2000, vol. 138: Chemokine Protocols. Edited by: A. E. I. Proudfoot, T. N. C. Wells, and C. A. Power. © Humana Press Inc., Totowa, NJ | disorders |
| Human chemokine receptor CXCR3 | GeneSeq Accession Y79372 | WO0018431 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot, T. N. C. Wells, and C. A. Power. © Humana Press Inc., Totowa, NJ | Soluble CXCR3 polypeptides may be useful for inhibiting chemokine activities and viral infection. |
| Human neurotactin chemokine like domain | GeneSeq Accession Y53259 | U.S. Pat. No. 6,043,086 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot, T. N. C. Wells, and C. A. Power. © Humana Press Inc., Totowa, NJ | Neurological disorders, Immune and respiratory disorders |
| Human CC type chemokine interleukin C | GeneSeq Accession Y57771 | JP11302298 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, | Chemokine activities can be determined using assays known in the art: Methods in Molecular Biology, 2000, vol. 138: Chemokine Protocols. Edited by: A. E. I. Proudfoot, T. N. C. Wells, and C. A. Power. © Humana Press Inc., Totowa, NJ | Cancer and infectious diseases |

TABLE 1-continued

| Therapeutic Protein X | Exemplary Identifier | PCT/Patent Reference | Biological Activity | Exemplary Activity Assay | Preferred Indication Y |
|---|---|---|---|---|---|
| | | | viral infection, and tumor biology. The chemokines exert their effects by acting on a family of seven transmembrane G-protein-coupled receptors. Over 40 human chemokines have been described, which bind to ~17 receptors thus far identified | | |
| Human CKbeta-9 | GeneSeq Accession B50860 | U.S. Pat. No. 6,153,441 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein-coupled receptors. Over 40 human chemokines have been described, which bind to ~17 receptors thus far identified | Chemokine activities can be determined using assays known in the art: Methods in Molecular Biology, 2000, vol. 138: Chemokine Protocols. Edited by: A. E. I. Proudfoot, T. N. C. Wells, and C. A. Power. © Humana Press Inc., Totowa, NJ | Cancer, Auto-immune and inflammatory disorders, Cardiovascular disorders |
| Preproapolipoprotein "paris" variant | GeneSeq Accession W08602 | WO9637608 | Apoa-1 participates in the reverse transport of cholesterol from tissues to the liver for excretion by promoting cholesterol efflux from tissues and by acting as a cofactor for the lecithin cholesterol acyltransferase (lcat). | Lipid binding activity can be determined using assays known in the art, such as, for example, the Cholesterol Efflux Assays of Takahaski et al., P.N.A.S., Vol. 96, Issue 20, 11358-11363, Sep. 28, 1999. | Useful for cardiovascular disorders, cholesterol disorders, and Hyperlipidaemia |
| Preproapolipoprotein "milano" variant | | 5,721,114 | Apoa-1 participates in the reverse transport of cholesterol from tissues to the liver for excretion by promoting cholesterol efflux from tissues and by acting as a cofactor for the lecithin cholesterol acyltransferase (lcat). | Lipid binding activity can be determined using assays known in the art, such as, for example, the Cholesterol Efflux Assays of Takahaski et al., P.N.A.S., Vol. 96, Issue 20, 11358-11363, Sep. 28, 1999. | Useful for cardiovascular disorders, cholesterol disorders, and Hyperlipidaemia |
| Glycodelin-A; Progesterone-associated endometrial protein | GeneSeq Accession W00289 | WO9628169 | Naturally produced female contraceptive that is removed rapidly from the body following 2-3 days production. Uses include contraception | Glycodelin-A activity can be determined using the hemizona assay as described in Oehninger, S., Coddington, C. C., Hodgen, G. D., and Seppala, M (1995) Fertil. Steril. 63, 377-383. | Naturally derived contraceptive useful for the prevention of pregnancy. |
| NOGO-A | Genbank Accession CAB99248 | | NOGO polypeptides are potent inhibitors of neurite growth. | Inhibition of Neurite outgrowth. Antagonists to NOGO polypeptides may promote the outgrowth of neurites, thus inducing regeneration of neurons. | NOGO-A polypeptide antagonists are useful for the promotion of neural growth, which could be useful in the treatment of neural disorders and dysfunction due to |

TABLE 1-continued

| Therapeutic Protein X | Exemplary Identifier | PCT/Patent Reference | Biological Activity | Exemplary Activity Assay | Preferred Indication Y |
|---|---|---|---|---|---|
| | | | | | degenerative diseases or trauma; useful in the treatment of neoplastic diseases of the CNS; induce regeneration of neurons or to promote the structural plasticity of the CNS. |
| NOGO-B | Genbank Accession CAB99249 | | NOGO polypeptides are potent inhibitors of neurite growth. | Inhibition of Neurite outgrowth. Antagonists to NOGO polypeptides may promote the outgrowth of neurites, thus inducing regeneration of neurons. | NOGO-B polypeptide antagonists are useful for the promotion of neural growth, which could be useful in the treatment of neural disorders and dysfunction due to degenerative diseases or trauma; useful in the treatment of neoplastic diseases of the CNS; induce regeneration of neurons or to promote the structural plasticity of the CNS. |
| NOGO-C | Genbank Accession CAB99250 | | NOGO polypeptides are potent inhibitors of neurite growth. | Inhibition of Neurite outgrowth. Antagonists to NOGO polypeptides may promote the outgrowth of neurites, thus inducing regeneration of neurons. | NOGO-C polypeptide antagonists are useful for the promotion of neural growth, which could be useful in the treatment of neural disorders and dysfunction due to degenerative diseases or trauma; useful in the treatment of neoplastic diseases of the CNS; induce regeneration of neurons or to promote the structural plasticity of the CNS. |
| NOGO-66 Receptor | Genbank Accession AAG53612 | | NOGO polypeptides are potent inhibitors of neurite growth, and are thought to mediate their effects through the NOGO-66 Receptor. | Inhibition of Neurite outgrowth by mediating the biological effects of NOGO polypeptides. Soluble NOGO-66 receptor polypeptides may promote the outgrowth of neurites, thus inducing regeneration of neurons. | NOGO-66 receptor polypeptides are useful for the promotion of neural growth, which could be useful in the treatment of neural disorders and dysfunction due to degenerative diseases or trauma; useful in the |

TABLE 1-continued

| Therapeutic Protein X | Exemplary Identifier | PCT/Patent Reference | Biological Activity | Exemplary Activity Assay | Preferred Indication Y |
|---|---|---|---|---|---|
| | | | | | treatment of neoplastic diseases of the CNS; induce regeneration of neurons or to promote the structural plasticity of the CNS. |
| Antibodies specific for collapsin | | U.S. Pat. No. 5,416,197 | These antibodies are useful for the promotion of neurite outgrowth | Collapsin activity, which is thought to inhibit the outgrowth of neurites, can be assayed in the presence of antibodies specific for collapsing using assays known in the art, such as, for example, the collapse assay disclosed by Luo et al., Cell 1993 Oct 22; 75(2): 217-27 | Useful for the promotion of neural growth, which could be useful in the treatment of neural disorders and dysfunction due to degenerative diseases or trauma. |
| Humanized Anti-VEGF Antibodies, and fragments thereof | | WO9845331 | These agents have anti-inflammatory and anti-cancer applications | VEGF activity can be determined using assays known in the art, such as those disclosed in International Publication No. WO0045835, for example. | Promotion of growth and proliferation of cells, such as vascular endothelial cells. Antagonists may be useful as anti-angiogenic agents, and may be applicable for cancer |
| Humanized Anti-VEGF Antibodies, and fragments thereof | | WO0029584 | These agents have anti-inflammatory and anti-cancer applications | VEGF activity can be determined using assays known in the art, such as those disclosed in International Publication No. WO0045835, for example. | Promotion of growth and proliferation of cells, such as vascular endothelial cells. Antagonists may be useful as anti-angiogenic agents, and may be applicable for cancer |
| Membrane bound proteins | GeneSeq. Accession Y66631-Y66765 | WO9963088 | Cancer, Immune Disorders | These proteins can be used for linking bioactive molecules to cells and for modulating biological activities of cells, using the polypeptides for specific targeting. The polypeptide targeting can be used to kill the target cells, e.g. for the treatment of cancers. These proteins are useful for the treatment of immune system disorders. | Activities can be determined using assay known in the art, suchas, for example, the assays disclosed in International Publication No. WO0121658. |
| Secreted and Transmembrane polypeptides | GenSeq Accession B44241-B44334 | WO0053756 | Cancer, Immune Disorders | These proteins can be used for linking bioactive molecules to cells and for modulating biological activities of cells, using the polypeptides for specific targeting. The polypeptide targeting can be used to kill the target cells, e.g. for the treatment of cancers. These | Activities can be determined using assay known in the art, suchas, for example, the assays disclosed in International Publication No. WO0121658 |

TABLE 1-continued

| Therapeutic Protein X | Exemplary Identifier | PCT/Patent Reference | Biological Activity | Exemplary Activity Assay | Preferred Indication Y |
|---|---|---|---|---|---|
| Secreted and Transmembrane polypeptides | GeneSeq Accession Y41685-Y41774 | WO9946281 | Cancer, Immune Disorders | proteins are useful for the treatment of immune system disorders. These proteins can be used for linking bioactive molecules to cells and for modulating biological activities of cells, using the polypeptides for specific targeting. The polypeptide targeting can be used to kill the target cells, e.g. for the treatment of cancers. These proteins are useful for the treatment of immune system disorders. | Activities can be determined using assay known in the art, suchas, for example, the assays disclosed in International Publication No. WO0121658 |

β-Interferon

Most cytokines, including β-IFN, have relatively short circulation half-lives since they are produced in vivo to act locally and transiently. To use β-IFN as an effective systemic therapeutic, one needs relatively large doses and frequent administrations. Such frequent parenteral administrations are inconvenient and painful. Further, toxic side effects are associated with β-IFN administration which are so severe that some multiple sclerosis patients cannot tolerate the treatment. These side effects are probably associated with administration of a high dosage.

The present invention provides β-IFN/transferrin fusion proteins with increased half-lives and pharmaceutical compositions comprising such fusion proteins with increased stability. Such fusion proteins can be administered to patients at lower doses, thus reducing the toxic side effects associated with β-IFN. The present invention contemplates the use of the β-IFN/transferrin fusion proteins to treat various diseases and conditions associated with β-IFN, such as but not limited to multiple sclerosis, cancer including brain tumors and skin cancer, and viral infections such as hepatitis B and C. Preferably, the β-IFN/transferrin fusion proteins are used to treat subjects suffering from multiple sclerosis. As discussed below, formulations for oral administration may also be produced.

β-interferon (β-IFN) is a glycoprotein with an apparent molecular weight (MW) of 23 kilodaltons. The gene encoding β-IFN is located on chromosome 9. Its amino acid sequence containing 166 residues was determined by K. Hosoi et al. (J. Interferon Res., 8, pp 375-384 (1988)), and its glucoside sequence was reported by Y. Kagawa et al. (J. Biol. Chem., 263, pp 17508-17515 (1988)).

β-IFN is secreted by fibroblasts in response to a viral or bacterial infection, or exposure to foreign cells, macromolecules, or RNA. In particular, β-IFN inhibits the proliferation of infected cells and stimulates the immune system. The specific antiviral activity of homogeneous Hu-β-IFN is considered to be between $3 \times 10^8$ and $1 \times 10^9$ iu/mg (international units per milligram of total protein) inclusive (see U.S. Pat. No. 4,289,689 and EP-A-94 672).

"Interferon-beta" (IFN-β) or "beta-interferon" (β-IFN) includes native and recombinant Type I interferons exhibiting the same or similar pharmaceutical characteristics as the Type I interferons commonly known as IFN-β-1a and IFN-β-1b.

Any β-IFN sequence may be used to prepare Tf fusion proteins of the present invention. For instance, U.S. Pat. No. 4,738,931 discloses the human β-IFN gene derived from human chromosomal DNA. A 1.8 kb EcoRI fragment, containing the nucleic acid encoding the human β-IFN, introduced into *Escherichia coli* has been deposited with the American Type Culture Collection in U.S.A. as *Escherichia coli* CI4 under accession number ATCC 31905. The GenBank accession number for the amino acid sequence of Human β-IFN amino acid sequence is AAA72588. The β-IFN could also be a mutein as described in U.S. Pat. No. 4,588,585, in which the cysteine (Cys) normally occurring at position 17 of the wild-type or native molecule has been replaced by a neutral amino acid, such as serine or alanine. Mark et al. (Proc. Natl. Acad. Sci. USA 81: 5662-5666 (1984)) showed that when Cys 17 was changed for serine, the IFN exhibited the same spectrum of biological activities as β-IFN, such as anticellular and antiproliferative activity, activation of NK cells and neutralization of anti-human IFN antibodies. The mutein also exhibited greater stability than natural human (Hu) β-IFN when incubated at 70° C.

Because of its activity, β-IFN is regarded as an active principle not only in the treatment and prophylaxis of viral diseases such as herpes, influenza etc, but also in the treatment of tumoral conditions such as encephaloma and leukemia. β-IFN is used to treat multiple sclerosis, brain tumor, skin cancer and hepatitis B and C. β-IFN fusion proteins of the present invention may be used to treat any of these diseases.

Human β-IFN is also effective in treating coronary restenosis in humans by selectively inhibiting the proliferation of coronary smooth muscle cell at the site of vascular injury following a surgical procedure while having no inhibitory effect on the normal proliferation of coronary endothelial cells following the procedure. U.S. Pat. No. 5,681,558 discloses a method of treating restenosis comprising administering β-IFN to the patient. Accordingly, β-IFN fusion proteins of the present invention may be used to treat restenosis.

β-IFN has an erythropoietic effect on the growth of progenitor cells from individuals suffering from several diseases with a very low production of red blood cells. Additionally, β-IFN increases burst formation as well as promotes a more rapid maturation toward normoblasts and even late reticulocytes. U.S. Pat. No. 5,104,653 discloses a method for the stimulation of erythropoiesis in a patient suffering from a disorder characterized by lack of maturation of progenitor blood cells to red blood cells comprising administering to said patient an erythropoietic effective amount of human β-IFN. Therefore, β-IFN fusion proteins of the present invention may be used to stimulate erythropoiesis.

β-IFN, acting via STAT1 and STAT2, is known to upregulate and downregulate a wide variety of genes, most of which are involved in the antiviral immune response. Although most IFN responses are induced by the presence of dsRNA, both DNA and RNA viruses are sensitive to the effects of β-IFN (Biron, Seminars in Immunology, 10: 383-390 (1998)).

β-IFN is generally produced in response to a viral infection. Interferon β-IFN exerts its biological effects by binding to specific receptors on the surface of human cells. This binding initiates a complex cascade of intracellular events that leads to the expression of numerous interferon-induced gene products and markers, for example, 2',5'-oligoadenylate synthetase, $b_2$-microglobulin, and neopterin.

(2'-5')-Oligoadenylate synthetase and dsRNA dependent protein kinase are the two best-known IFN-β-induced proteins (Biron, 1998, supra). (2'-5')-oligoadenylate synthetase polymerizes ATP in a unique 2'-5' fashion (Janeway et al., Immunobiology: The Immune System in Health and Disease, 4th Edition, New York, Elsevier Science/Garland Publishing pp 385-386 (1999)); the resultant oligomers activate RNase L, which cleaves mRNA (Biron, 1998, supra). dsRNA dependent protein kinase phosphorylates and inactivates eIF2, a transcriptional initiator. Both (2'-5')-oligoadenylate synthetase and dsRNA dependent protein kinase act only in the presence of dsRNA, i.e. in virally infected cells. The net result of the action of these two proteins is to inhibit protein translation, which will retard viral replication (Biron, 1998, supra).

β-IFN dependent upregulation of TAP (transporter associated with antigen processing), Lmp2, Lmp7 serves to increase presentation of viral peptides by MHC class I molecules in order to facilitate CD8 T cell recognition and destruction of infected cells. TAP is the molecule responsible for loading peptide fragments onto MHC class I molecules in the ER; the Lmp proteins are components of the proteasome which cleave proteins specifically for MHC class I presentation (Janeway et al., 1999, supra).

β-IFN is known to both activate and induce some proliferation in natural killer (NK) cells (Janeway et al., 1999, supra). However, interferons themselves are not mitogens.

The proliferation of NK cells is probably caused by an intermediary cytokine which is induced by IFN-β (Biron, 1998, supra). NK cells can kill cells which exhibit atypical patterns of MHC class I expression; such cells are generally virally infected (Janeway et al., 1999, supra).

Although at the end of a successfully defeated infection, T cells die by apoptosis as the immune system returns to a homeostatic balance, some T cells must avoid apoptosis and enter a $G_0/G_1$ memory state to preserve immunological memory. These memory T cells are rescued from apoptosis by interacting with stromal cells, which secrete β-IFN and some IFN-α (Pilling et al., European Journal of Immunology 29:1041-1050 (1999)). T cell apoptosis may be induced by either cytokine deprivation or ligation of Fas on the cell surface, but β-IFN is able to block both apoptotic pathways. The former apoptotic pathway is blocked by β-IFN dependent upregulation of Bcl-x, an apoptotic inhibitor. Fas ligation-induced apoptosis occurs much too quickly to be blocked by upregulation of a gene, so β-IFN must block that apoptotic pathway by different means (Scheel-Toellner et al., European Journal of Immunology 29:2603-2612 (1999)). The existence of a second blocking mechanism is supported by the results of Marrack et al. (Journal of Experimental Medicine 189:521-529 (1999)), who found that β-IFN prevented T cell apoptosis without increased production of Bcl-x.

Der et al. (Proc. Nat. Acad. Sci. USA 95: 15623-15628 (1998)) found that β-IFN increased transcription of well over 100 proteins in human fibrosarcoma cells. Induced proteins ranged in function from cytochromes and cell scaffolding proteins to immunologically active proteins such as Complement components and dsRNA adenosine deaminase. These results indicate that β-IFN has truly pleiotropic effects, Many of which are not fully understood.

Much clinical research on β-IFN is currently focused on its use as a treatment for multiple sclerosis (MS). MS is an autoimmune disease in which T cells mount an immune response against self myelin antigens in the glial cells of the central nervous system (Goodkin, 1999. Multiple sclerosis: Treatment options for patients with relapsing-remitting and secondary progressive multiple sclerosis. <http://www.m-snews.org/goodkin1_99.htm>). In 1993, the FDA approved subcutaneous injections of IFN-β1b for treatment of MS (Revelle M., 1993, FDA licenses interferon beta-1b. <http://www.fda.gov/bbs/topics/NEWS/NEW00424.html>). β-IFN 1b is a non-glycosylated form of IFN-β produced in *E. coli* (Arduini et al., Protein Science 8: 1867-1877 (1999)). Adverse experiences associated with β-IFN 1b therapy include: injection site reactions (inflammation, pain, hypersensitivity and necrosis), and a flu-like symptom complex (fever, chills, anxiety and confusion). These adverse side effects may be, in fact, reduced or alleviated by fusing β-IFN 1b to transferrin as described above.

Currently, β-IFN 1a (an eukaryotic, glycosylated form) is also available (Goodkin, 1999, supra). β-IFN 1a is produced by recombinant DNA technology. Interferon beta-1a is a 166 amino acid glycoprotein with a predicted molecular weight of approximately 22,500 daltons. It is produced by mammalian cells (Chinese Hamster Ovary cells) into which the human IFN-β gene has been introduced. The amino acid sequence of β-IFN 1a is identical to that of natural human β-IFN and may be used to make Tf fusion proteins of the present invention.

β-IFN/transferrin fusion proteins treatment may also ameliorate autoimmune attacks by restoring suppressor T cell function; cotreatment with all-trans-retinoic acid seems to increase this restorative action for unknown reasons (Qu et al., 1998. All-trans retinoic acid potentiates the ability of interferon beta-1b. <http://members.tripod.com/~ThJuland/ra-beta1b.html>). β-IFN may also inhibit the induction of inducible nitric oxide synthase (INOS) expression by IL-1 and IFN-γ. Production of nitric oxide by INOS in astrocytes has been implicated as a factor in the parthenogenesis of MS (Hua et al. 1998. Beta inteferon prevents nitric oxide/peroxynitrate from damaging the central nervous system. <http://members.tripod.com/~ThJuland/nitric-oxide_beta.html>).

In one aspect, the present invention includes the use of β-IFN analogs that are therapeutically effective for treating various diseases associated with β-IFN for generating β-IFN/transferrin fusion proteins.

In another aspect, the present invention includes the use of the β-IFN/transferrin fusion protein in the methods described above to inhibit or stimulate various cellular processes and for the treatment and prevention of the various disease and conditions described above. In particular, the β-IFN/transferrin fusion protein may be used to treat multiple sclerosis, herpes, influenza, brain tumor, and skin cancer.

The β-IFN/transferrin fusion protein of the present invention can be formulated into pharmaceutical compositions by well known methods. See, e.g., Remington's Pharmaceutical Sciences by E. W. Martin, hereby incorporated by reference, describes suitable formulations. The pharmaceutical composition of the β-IFN/transferrin fusion protein of the present invention may be formulated in a variety of forms, including liquid, gel, lyophilized, or any other suitable form. The preferred form will depend upon the particular indication being treated and will be apparent to one of skill in the art The β-IFN/transferrin fusion protein can be administered in pure form or in an appropriate pharmaceutical composition. Administration can be carried out via any of the accepted modes. Thus, administration can be, for example, orally, nasally, parenterally, topically, transdermally, or rectally, in the form of solid, semi-solid, lyophilized powder, or liquid dosage forms, such as for example, tablets, suppositories, pills, soft elastic and hard gelatin capsules, powders, solutions, suspensions, or aerosols, or the like, preferably in unit dosage forms suitable for simple administration of precise dosages. The compositions will include a conventional pharmaceutical carrier or excipient and the β-IFN/transferrin fusion protein as the active agent, and, in addition, may include other medicinal agents, pharmaceutical agents, carriers, adjuvants, etc.

Generally, depending on the intended mode of administration, the pharmaceutically acceptable compositions will contain about 1% to about 99% by weight of the β-IFN/transferrin fusion protein, and 99% to 1% by weight of a suitable pharmaceutical excipient. The composition could be about 5% to 75% by weight of the β-IFN/transferrin fusion protein with the rest being suitable pharmaceutical excipients.

The route of administration could be parenterally, using a convenient daily dosage regimen which can be adjusted according to the degree of severity of the disease, preferably multiple sclerosis, to be treated. For such parenteral administration, a pharmaceutically acceptable composition containing the β-IFN/transferrin fusion protein may be formed by the methods disclosed in U.S. Pat. Nos. 4,462,940, 4,588, 585 and 4,992,271.

Alternatively, the β-IFN/transferrin fusion protein pharmaceutical compositions may be administered orally, intravenously, intramuscularly, intraperitoneally, intradermally or subcutaneously or in any other acceptable manner. The preferred mode of administration will depend upon the particular indication being treated and will be apparent to one of skill in the art.

U.S. Pat. No. 6,333,032 describes effective methods of using β-IFN to treat diseases in warm-blooded vertebrates, such as multiple sclerosis. Treatment of multiple sclerosis comprises administering β-IFN at a dosage of 0.01 to about 5 IU/lb per day in a dosage form adapted to promote contact of said dosage of interferon with the oral and pharyngeal mucosa of said animal. The dosage of interferon could be from 0.1 to about 4.0 IU/lb per day, or from 0.5 to about 1.5 IU/lb of body weight per day.

The present invention contemplates administering the β-IFN in a dosage form adapted to assure maximum contact of the interferon in said dosage form with the oral and pharyngeal mucosa of the human or animal undergoing treatment. Contact of interferon with the mucosa can be enhanced by maximizing residence time of the treatment solution in the oral or pharyngeal cavity. Thus, best results seem to be achieved in human patients when the patient is requested to hold said solution of interferon in the mouth for a period of time. Contact of interferon with the oral and pharyngeal mucosa and thereafter with the lymphatic system of the treated human or animal is unquestionably the most efficient method administering immunotherapeutic amounts of interferon.

Further, the present invention contemplates the use of the β-IFN/transferrin protein for the manufacture of a medicament which is useful for the treatment of diseases associated with β-IFN. The diseases contemplated by the present invention include but are not limited to those described above.

Glucagon-Like Peptide-1 (GLP-1)

Glucagon-Like Peptide-1 (GLP-1) is a gastrointestinal hormone that regulates insulin secretion belonging to the so-called enteroinsular axis. The enteroinsular axis designates a group of hormones, released from the gastrointestinal mucosa in response to the presence and absorption of nutrients in the gut, which promote an early and potentiated release of insulin. The incretin effect which is the enhancing effect on insulin secretion is probably essential for a normal glucose tolerance. GLP-1 is a physiologically important insulinotropic hormone because it is responsible for the incretin effect.

GLP-1 is a product of proglucagon (Bell, et al., Nature, 1983, 304: 368-371). It is synthesized in intestinal endocrine cells in two principal major molecular forms, as GLP-1(7-36) amide and GLP-1(7-37). The peptide was first identified following the cloning of cDNAs and genes for proglucagon in the early 1980s.

Initial studies done on the full length peptides GLP-1(1-37) and GLP-1(1-36$^{amide}$) concluded that the larger GLP-1 molecules are devoid of biological activity. In 1987, three independent research groups demonstrated that removal of the first six amino acids resulted in a GLP-1 molecule with enhanced biological activity.

The amino acid sequence of GLP-1 is disclosed by Schmidt et al. (1985 Diabetologia 28 704-707). Human GLP-1 is a 37 amino acid residue peptide originating from preproglucagon which is synthesized in the L-cells in the distal ileum, in the pancreas, and in the brain. Processing of preproglucagon to GLP-1(7-36$^{amide}$), GLP-1(7-37) and GLP-2 occurs mainly in the L-cells. The amino acid sequence of GLP-1(7-36$^{amide}$) and GLP-1(7-37) is (SEQ ID NO: 6):

```
His-Ala-Glu-Gly-Thr-Phe-Thr-Ser-Asp-Val-

Ser-Ser-Tyr-Leu-Glu-Gly-Gln-Ala-Ala-Lys-

Glu-Phe-Ile-Ala-Trp-Leu-Val-Lys-Gly-Arg-X
``` wherein X is NH$_2$ for GLP-1(7-36$^{amide}$) and X is Gly for GLP-1(7-37).

GLP-1 like molecules possesses anti-diabetic activity in human subjects suffering from Type II (non-insulin-dependent diabetes mellitus (NIDDM)) and, in some cases, even Type I diabetes. Treatment with GLP-1 elicits activity, such as increased insulin secretion and biosynthesis, reduced glucagon secretion, delayed gastric emptying, only at elevated glucose levels, and thus provides a potentially much safer therapy than insulin or sulfonylureas. Post-prandial and glucose levels in patients can be moved toward normal levels with proper GLP-1 therapy. There are also reports suggesting GLP-1-like molecules possess the ability to preserve and even restore pancreatic beta cell function in Type-II patients.

Any GLP-1 sequence may be used to make Tf fusion proteins of the present invention, including GLP-1(7-35), GLP-1(7-36), and GLP-1(7-37). GLP-1 also has powerful actions on the gastrointestinal tract. Infused in physiological amounts, GLP-1 potently inhibits pentagastrin-induced as well as meal-induced gastric acid secretion (Schjoldager et al., Dig. Dis. Sci. 1989, 35:703-708; Wettergren et al., Dig Dis Sci 1993; 38:665-673). It also inhibits gastric emptying rate and pancreatic enzyme secretion (Wettergren et al., Dig Dis Sci 1993; 38:665-673). Similar inhibitory effects on gastric and pancreatic secretion and motility may be elicited in humans upon perfusion of the ileum with carbohydrate- or lipid-containing solutions (Layer et al., Dig Dis Sci 1995, 40:1074-1082; Layer et al., Digestion 1993, 54: 385-38). Concomitantly, GLP-1 secretion is greatly stimulated, and it has been speculated that GLP-1 may be at least partly responsible for this so-called "ileal-brake" effect (Layer et al., Digestion 1993; 54: 385-38). In fact, recent studies suggest that, physiologically, the ileal-brake effects of GLP-1 may be more important than its effects on the pancreatic islets. Thus, in dose response studies GLP-1 influences gastric emptying rate at infusion rates at least as low as those required to influence islet secretion (Nauck et al., Gut 1995; 37 (suppl. 2): A124).

GLP-1 seems to have an effect on food intake. Intraventricular administration of GLP-1 profoundly inhibits food intake in rats (Schick et al. in Ditschuneit et al. (eds.), Obesity in Europe, John Libbey & Company ltd, 1994; pp. 363-367; Turton et al., Nature 1996, 379: 69-72). This effect seems to be highly specific. Thus, N-terminally extended GLP-1(PG 72-107) amide is inactive and appropriate doses of the GLP-1 antagonist, exendin 9-39, abolish the effects of GLP-1(Tang-Christensen et al., Am. J. Physiol., 1996, 271(4 Pt 2):R848-56). Acute, peripheral administration of GLP-1 does not inhibit food intake acutely in rats (Tang-Christensen et al., Am. J. Physiol., 1996, 271(4 Pt 2):R848-56; Turton et al., Nature 1996, 379: 69-72). However, it remains possible that GLP-1 secreted from the intestinal L-cells may also act as a satiety signal.

In diabetic patients, GLP's insulinotropic effects and the effects of GLP-1 on the gastrointestinal tract are preserved (Willms et al, Diabetologia 1994; 37, suppl.1: A118), which may help curtail meal-induced glucose excursions, but, more importantly, may also influence food intake. Administered intravenously, continuously for one week, GLP-1 at 4 ng/kg/min has been demonstrated to dramatically improve glycaemic control in NIDDM patients without significant side effects (Larsen et al., Diabetes 1996; 45, suppl. 2: 233A.).

GLP-1/transferrin fusion proteins comprising at least one analog of GLP-1 and fragments thereof are useful in the treatment of Type 1 and Type 2 diabetes and obesity and may be formulated for oral administration as described below.

As used herein, the term "GLP-1 molecule" means GLP-1, a GLP-1 analog, or GLP-1 derivative.

As used herein, the term "GLP-1 analog" is defined as a molecule having one or more amino acid substitutions, deletions, inversions, or additions compared with GLP-1. Many GLP-1 analogs are known in the art and include, for example, GLP-1(7-34), GLP-1(7-35), GLP-1(7-36), Val$^8$-GLP-1(7-37), Gly$^8$-GLP-1(7-37), Ser$^8$-GLP-1(7-37), Gln$^9$-GLP1(7-37), D-Gln$^9$-GLP-1(7-37), Thr$^{16}$-Lys$^{18}$-GLP-1(7-37), and Lys$^{18}$-GLP-1(7-37). Other analogs include dipeptidyl-peptidase resistant versions of GLP-1, wherein the N-terminal end of the peptide is protected. Such analogs include, but are not limited to GLP-1 with additional amino acids, such as histidine residue added to the N-terminal end or substituted into the N-terminal amino acids (amino acid 7 or 8 in GLP-1(7-36) or GLP-1(7-37). In these analogs, the N-terminal end may comprise the residues His-His-Ala, Gly-His-Ala, His-Gly-Glu, His-Ser-Glu, His-Ala-Glu, His-Gly-Glu, His-Ser-Glu, His-His-Ala-Glu, His-His-Gly-Glu, His-His-Ser-Glu, Gly-His-Ala-Glu, Gly-His-Gly-Glu, Gly-His-Ser-Glu, His-X-Ala-Glu, His-X-Gly-Glu, His-X-Ser-Glu, wherein X is any amino acid. U.S. Pat. No. 5,118,666 discloses examples of GLP-1 analogs such as GLP-1(7-34) and GLP-1(7-35).

The term "GLP-1 derivative" is defined as a molecule having the amino acid sequence of GLP-1 or a GLP-1 analog, but additionally having chemical modification of one or more of its amino acid side groups, α-carbon atoms, terminal amino group, or terminal carboxylic acid group. A chemical modification includes, but is not limited to, adding chemical moieties, creating new bonds, and removing chemical moieties.

As used herein, the term "GLP-1 related compound" refers to any compound falling within the GLP-1, GLP-1 analog, or GLP-1 derivative definition.

WO 91/11457 discloses analogs of the active GLP-1 peptides 7-34, 7-35, 7-36, and 7-37 which can also be useful as GLP-1 moieties.

EP 0708179-A2 (Eli Lilly & Co.) discloses GLP-1 analogs and derivatives that include an N-terminal imidazole group and optionally an unbranched $C_6$-$C_{10}$ acyl group in attached to the lysine residue in position 34.

EP 0699686-A2 (Eli Lilly & Co.) discloses certain N-terminal truncated fragments of GLP-1 that are reported to be biologically active.

U.S. Pat. No. 5,545,618 discloses GLP-1 molecules consisting essentially of GLP-1(7-34), GLP1(7-35), GLP-1(7-36), or GLP-1(7-37), or the amide forms thereof, and pharmaceutically-acceptable salts thereof, having at least one modification selected from the group consisting of: (a) substitution of glycine, serine, cysteine, threonine, asparagine, glutamine, tyrosine, alanine, valine, isoleucine, leucine, methionine, phenylalanine, arginine, or D-lysine for lysine at position 26 and/or position 34; or substitution of glycine, serine, cysteine, threonine, asparagine, glutamine, tyrosine, alanine, valine, isoleucine, leucine, methionine, phenylalanine, lysine, or a D-arginine for arginine at position 36; (b) substitution of an oxidation-resistant amino acid for tryptophan at position 31; (c) substitution of at least one of: tyrosine for valine at position 16; lysine for serine at position 18; aspartic acid for glutamic acid at position 21; serine for glycine at position 22; arginine for glutamine at position 23; arginine for alanine at position 24; and glutamine for lysine at position 26; and (d) substitution of at least one of: glycine, serine, or cysteine for alanine at position 8; aspartic acid, glycine, serine, cysteine, threonine, asparagine, glutamine, tyrosine, alanine, valine, isoleucine, leucine, methionine, or phenylalanine for glutamic acid at position 9; serine, cysteine, threonine, asparagine, glutamine, tyrosine, alanine, valine, isoleucine, leucine, methionine, or phenylalanine for glycine at position 10; and glutamic acid for aspartic acid at position 15; and (e) substitution of glycine, serine, cysteine, threonine, asparagine, glutamine, tyrosine, alanine, valine, isoleucine, leucine, methionine, or phenylalanine, or the D- or N-acylated or alkylated form of histidine for histidine at position 7; wherein, in the substitutions is (a), (b), (d), and (e), the substituted amino acids can optionally be in the D-form and the amino acids substituted at position 7 can optionally be in the N-acylated or N-alkylated form.

U.S. Pat. No. 5,118,666 discloses a GLP-1 molecule having insulinotropic activity. Such molecule is selected from the group consisting of a peptide having the amino acid sequence His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys (SEQ ID NO: 7) or His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly (SEQ ID NO: 8); and a derivative of said peptide and wherein said peptide is selected from the group consisting of: a pharmaceutically-acceptable acid addition salt of said peptide; a pharmaceutically-acceptable carboxylate salt of said peptide; a pharmaceutically-acceptable lower alkylester of said peptide; and a pharmaceutically-acceptable amide of said peptide selected from the group consisting of amide, lower alkyl amide, and lower dialkyl amide.

U.S. Pat. No. 6,277,819 teaches a method of reducing mortality and morbidity after myocardial infarction comprising administering GLP-1, GLP-1 analogs, and GLP-1 derivatives to the patient. The GLP-1 analog being represented by the following structural formula (SEQ ID NO: 9): $R_1$-$X_1$-Glu-Gly-Thr-Phe-Thr-Ser-Asp-Val-Ser-Ser-Tyr-Leu-$X_2$-Gly-Gln-Ala-Ala-Lys-$X_3$-Phe-Ile-Ala-Trp-Leu-Val-Lys-Gly-Arg-$R_2$ and pharmaceutically-acceptable salts thereof, wherein: $R_1$ is selected from the group consisting of L-histidine, D-histidine, desamino-histidine, 2-amino-histidine, .beta.-hydroxy-histidine, homohistidine, alpha-fluoromethyl-histidine, and alpha-methyl-histidine; $X_1$ is selected from the group consisting of Ala, Gly, Val, Thr, Ile, and alpha-methyl-Ala; $X_2$ is selected from the group consisting of Glu, Gln, Ala, Thr, Ser, and Gly; $X_3$ is selected from the group consisting of Glu, Gln, Ala, Thr, Ser, and Gly; $R_2$ is selected from the group consisting of $NH_2$, and Gly-OH; provided that the GLP-1 analog has an isoelectric point in the range from about 6.0 to about 9.0 and further providing that when $R_1$ is His, $X_1$ is Ala, $X_2$ is Glu, and $X_3$ is Glu, must be $NH_2$.

Ritzel et al. (Journal of Endocrinology, 1998, 159: 93-102) disclose a GLP-1 analog, [Ser$^8$]GLP-1, in which the N-terminal second amino acid, alanine, is replaced with serine. The modification did not impair the insulinotropic action of the peptide but produced an analog with increased plasma stability as compared to GLP-1.

U.S. Pat. No. 6,429,197 teaches that GLP-1 treatment after acute stroke or hemorrhage, preferably intravenous administration, can be an ideal treatment because it provides a means for optimizing insulin secretion, increasing brain anabolism, enhancing insulin effectiveness by suppressing glucagon, and maintaining euglycemia or mild hypoglycemia with no risk of severe hypoglycemia or other adverse side effects. The present invention provides a method of treating the ischemic or reperfused brain with GLP-1 or its biologically active analogues after acute stroke or hemorrhage to optimize insulin secretion, to enhance insulin effectiveness by suppressing glucagon antagonism, and to maintain euglycemia or mild hypoglycemia with no risk of severe hypoglycemia.

U.S. Pat. No. 6,277,819 provides a method of reducing mortality and morbidity after myocardial infarction, comprising administering to a patient in need thereof, a compound selected from the group consisting of GLP-1, GLP-1 analogs, GLP-1 derivatives and pharmaceutically-acceptable salts thereof, at a dose effective to normalize blood glucose.

U.S. Pat. No. 6,191,102 discloses a method of reducing body weight in a subject in need of body weight reduction by administering to the subject a composition comprising a glucagon-like peptide-1 (GLP-1), a glucagon-like peptide analog (GLP-1 analog), a glucagon-like peptide derivative (GLP-1 derivative) or a pharmaceutically acceptable salt thereof in a dose sufficient to cause reduction in body weight for a period of time effective to produce weight loss, said time being at least 4 weeks.

GLP-1 is fully active after subcutaneous administration (Ritzel et al., Diabetologia 1995; 38: 720-725), but is rapidly degraded mainly due to degradation by dipeptidyl peptidase IV-like enzymes (Deacon et al., J Clin Endocrinol Metab 1995, 80: 952-957; Deacon et al., 1995, Diabetes 44: 1126-1131). Thus, unfortunately, GLP-1 and many of its analogues have a short plasma half-life in humans (Orskov et al., Diabetes 1993; 42:658-661). Accordingly, it is an objective of the present invention to provide transferrin fusion proteins comprising GLP-1 or analogues thereof which have a protracted profile of action relative to GLP-1(7-37). It is a further object of the invention to provide derivatives of GLP-1 and analogues thereof which have a lower clearance than GLP-1(7-37). Moreover, it is an object of the invention to provide pharmaceutical compositions comprising GLP-1/transferrin fusion proteins or GLP-1 analog/transferrin fusion proteins with improved stability. Additionally, the present invention includes the use of GLP-1/transferrin fusion proteins or GLP-1 analog/transferrin fusion proteins to treat diseases associated with GLP-1 such as but not limited to those described above.

In one aspect of the present invention, the pharmaceutical compositions comprising the GLP-1 peptide/transferrin fusion proteins and GLP-1 analog/transferrin fusion proteins may be formulated by any of the established methods of formulating pharmaceutical compositions, e.g. as described in Remington's Pharmaceutical Sciences, 1985. The composition may be in a form suited for systemic injection or infusion and may, as such, be formulated with a suitable liquid vehicle such as sterile water or an isotonic saline or glucose solution. The compositions may be sterilized by conventional sterilization techniques which are well known in the art. The resulting aqueous solutions may be packaged for use or filtered under aseptic conditions and lyophilized, the lyophilized preparation being combined with the sterile aqueous solution prior to administration. The composition may contain pharmaceutically acceptable auxiliary substances as required to approximate physiological conditions, such as buffering agents, tonicity adjusting agents and the like, for instance sodium acetate, sodium lactate, sodium chloride, potassium chloride, calcium chloride, etc.

The GLP-1/transferrin fusion proteins and GLP-1 analog/transferrin fusion proteins of the present invention may also be adapted for oral, nasal, transdermal, pulmonal or rectal administration. The pharmaceutically acceptable carrier or diluent employed in the composition may be any conventional solid carrier. Examples of solid carriers are lactose, terra alba, sucrose, talc, gelatin, agar, pectin, acacia, magnesium stearate and stearic acid. Similarly, the carrier or diluent may include any sustained release material known in the art, such as glyceryl monostearate or glyceryl distearate, alone or mixed with a wax.

It may be of particular advantage to provide the composition of the invention in the form of a sustained release formulation. As such, the composition may be formulated as microcapsules or microparticles containing the GLP-1/transferrin fusion protein or GLP-1 analog/transferrin fusion protein encapsulated by or dispersed in a suitable pharmaceutically acceptable biodegradable polymer such as polylactic acid, polyglycolic acid or a lactic acid/glycolic acid copolymer.

For nasal administration, the preparation may contain GLP-1/transferrin fusion proteins or GLP-1 analog/transferrin fusion proteins dissolved or suspended in a liquid carrier, in particular an aqueous carrier, for aerosol application. The carrier may contain additives such as solubilizing agents, e.g. propylene glycol, surfactants, absorption enhancers such as lecithin (phosphatidylcholine) or cyclodextrin, or preservatives such as parabenes.

Generally, the compounds of the present invention are dispensed in unit dosage form comprising 0.5-500 mg of the fusion protein together with a pharmaceutically acceptable carrier per unit dosage.

Moreover, the present invention contemplates the use of the GLP-1/transferrin and GLP-1 analog/transferrin fusion proteins for the manufacture of a medicinal product which can be used in the treatment of diseases associated with elevated glucose level, such as but not limited to those described above. Specifically, the present invention contemplates the use of GLP-1/transferrin fusion protein for the treatment of diabetes including type II diabetes, obesity, severe burns, and heart failure, including congestive heart failure and acute coronary syndrome.

The N-terminus of GLP-1 is normally amidated. In yeast, amidation does not occur. In one aspect of the invention, in order to compensate for amidation on the N-terminus which does not occur in yeast, an extra amino acid is added on the N-terminus of GLP-1. The addition of an amino acid to the N-terminus of GLP-1 may prevent dipeptidyl peptidase from cleaving at the second amino acid of GLP-1 due to steric hindrance. Therefore, GLP-1 will remain functionally active. Any one of the 20 amino acids may be added to the N-terminus of GLP-1. In some instances, an uncharged or positively charged amino acid may be used and preferably, a smaller amino acid such as Glycine is added. The GLP-1 with the extra amino acid is then fused to transferrin. Accordingly, the GLP-1 with the added amino acid will be fused at the N-terminus of the GLP-1/transferrin fusion protein.

In one embodiment of making the GLP-1(7-36) or GLP-1 (7-37) peptide more resistant to dipeptidyl peptidase, a His residue is added at the N-terminus of GLP-1 or is inserted after the His residue at the N-terminus of GLP-1, so that the N-terminus of GLP-1 begins with His-His.

In another embodiment of the invention, the second residue from the N-terminus in the GLP-1(7-36) or GLP-1(7-37) peptide (SEQ ID NO: 6) is substituted with another amino acid. For example, the Ala residue at the second residue from the N-terminus in the GLP-1(7-36) or GLP-1(7-37) peptide may be substituted with Ser, Gly, Val, or another amino acid.

GLP-mTf Fusion Protein for Treating Type 2 Diabetes

As discussed above, GLP-1 activates and regulates important endocrine hormone systems in the body and plays a critical management role in the metabolism of glucose. Unlike all other diabetic treatments on the market GLP-1 has the potential to be restorative by acting as a growth factor for B-cells thus improving the ability of the pancreas to secrete insulin and also, to make the existing insulin levels act more efficiently by improving sensitivity and better stabilizing glucose levels. This reduces the burden on daily monitoring of glucose levels and potentially offers a delay in the serious long term side effects caused by fluctuations in blood glucose due to diabetes. Furthermore, GLP-1 can reduce appetite and reduce weight. Obesity is an inherent consequence of poor control of glucose metabolism and this only serves to aggravate the diabetic condition.

Clinical application of natural GLP-1 is limited because it is rapidly degraded in the circulation (half-life is several minutes). To maintain therapeutic levels in the circulation requires constant administration of high doses using pumps or patch devices which adds to the cost of treatment. This is inconvenient for long term chronic use especially in conjunction with all the other medications for treating diabetes and monitoring of glucose levels. The GLP-1 fusion proteins retain the activity of GLP-1 but have the long half-life (14-17 days), solubility, and biodistribution properties of transferrin (mTf) and they can be administered orally. These properties could provide for a low cost, small volume, monthly s.c. (subcutaneous) injection and this type of product is absolutely needed for long term chronic use.

Insulin

Human insulin contains two peptide chains, known as the A and B chains, which are 21 and 30 amino acids in length, respectively, and which are connected by two cystine disulphide bridges. This peptide has a molecular weight of approximately 6 kDa. The immediate precursor of insulin is proinsulin, a single chain peptide composed of the B and A chains linked to a connecting peptide of approximately 31 amino acids, known as the C-peptide, by adjacent pairs of basic residues. The arrangement of these three peptides in the proinsulin molecule, beginning with the amino-terminal end, is as follows: B chain-Arg-Arg-C-peptide-Lys-Arg-A chain. When translated into mRNA, however, preproinsulin is produced, which contains proinsulin joined at its amino-terminal end to a largely hydrophobic signal peptide 24 amino acids in length.

Preproinsulin is synthesized in pancreatic beta cells located within the islets of Langerhans, which are dispersed throughout the pancreas. Removal of the signal peptide occurs in the rough endoplasmic reticulum, and the resulting proinsulin is then transported to the Golgi apparatus for packaging into secretion granules. The folded proinsulin is stabilized by disulfide bonds. During processing of the secretion granules, the folded proinsulin molecule is cleaved by specific proteases at the paired basic residues to liberate insulin and the C-peptide.

Diabetes mellitus is a disease that affects approximately 17 million people in the United States, or 6.2% of the population. About one million people over the age of 20 are diagnosed with diabetes annually, and diabetes is the sixth leading cause of death in the United States (http://www.niddk.nih.gov/health/diabetes/pubs/dmstats/dmstats.htm#7). Approximately 90-95% of diabetes cases are Type 2, formerly called adult-onset diabetes, which begins as insulin resistance (failure of the body's cells to use insulin properly) as progresses to an inability of the pancreas to produce insulin. Type 1 diabetes, formerly called juvenile diabetes or insulin-dependent diabetes, accounts for the remaining 5-10% of diabetes cases. In type 1 diabetes, the body's immune system destroys the beta cells in the pancreas, which manufacture insulin.

Because human insulin contains only 51 amino acid residues, it is readily made by recombinant techniques, and a large number of insulin analogues and variants have been prepared. Any of these analogues or variants can be used to make mTf fusion proteins of the invention.

Diabetics typically require insulin replacement therapy, which involves one or more doses of the drug per day by subcutaneous injection. Treatment by injection, however, is both psychologically and physically painful, as well as demanding of technical expertise, and many diabetics require assistance in administering injections. Oral formulations of insulin have not been successful, however, because the peptide is rapidly degraded in the acidic environment of the GI tract, particularly in the stomach. Nevertheless, alternatives to injection, such as oral, nasal and topical formulations have been attempted. U.S. Pat. No. 5,824,638, Burnside et al., describes oral emulsion preparations in which insulin is dissolved in a hydrophilic phase, such as water, saline or a water-miscible alcohol, and dispersed with a surfactant in a hydrophobic phase, such as a long chain fatty acid or fatty acid ester. Although an emulsion keeps insulin dispersed, it cannot protect the peptide from the harsh conditions of the stomach. Nasal preparations, which deliver insulin in an aerosol to the lungs, are disclosed in U.S. Pat. No. 6,427,681, Gonda et al., while topical preparations are disclosed in U.S. Pat. No. 6,399,566, Dardai et al.

Modified insulins for injection, containing amino acid substitutions or glycosylated residues, to enhance activity, inhibit degradation or inhibit peptide aggregation have also been developed (see U.S. Pat. No. 4,478,746, Kim et al., glycosylated insulin derivatives; U.S. Pat. No. 4,992,418, Katsoyanis et al., $Asp_{10}$-containing insulin (B chain) for increased activity; U.S. Pat. No. 5,716,927, Balschmidt et al., Lys or Arg at position 28 in the B chain, or A18, A21 or B3 modified from Asn, or other modifications at the C-terminal end of the B chain, to prevent aggregation and reduced activity) Additional amino acid substitutions that confer a longer active phase, because they can be acylated, are disclosed in U.S. Pat. No. 5,750,497, Havelund et al. A21 B3 and B30 can be replaced by any amino acid except Lys, Arg or Cys. B1 may be deleted, and B30 may be replaced by a lipophilic chain of 10-24 carbon atoms. Fusion proteins for improved recombinant production of insulin (higher yields, soluble, allowing correct folding) are described in U.S. Pat. No. 6,534,288, Habermann et al. These peptides contain a fusion portion at the amino terminal end of the B chain, followed by amino acids $RDVP-Y_n$-A chain, where Y is a peptide 2-50 amino acids in length, terminating with a basic amino acid.

The present invention includes fusion proteins comprising transferrin and an insulin protein or peptide. In one embodiment, the fusion proteins are formulated for oral delivery. The present invention, therefore, also includes methods of orally administering insulin fusion proteins of the invention to a patient in need thereof, in particular, a diabetic patient.

In one embodiment, the present invention includes transferrin fusion protein comprising single chain insulin analog (Lee et al., 2000, Nature, 408: 483). In another embodiment, the insulin in the transferrin fusion protein may contain a protease cleavage site specific to the gastrointestinal (GI) tract, or a specific part of the gastrointestinal tract, such that the site would be recognized by one or more enzymes in the GI tract. The proinsulin could be activated in this manner. The cleavage site could reside in the peptide linking the A and B chain.

EPO Mimetic Peptide (EMP)

Erythropoietin (EPO) is a glycoprotein hormone that is synthesized in the kidneys of mammals for stimulating mitotic cell division and differentiation of erythrocyte precursor cells. Accordingly, EPO acts to stimulate and regulate the production of erythrocytes. Because of its role in red blood cell formation, EPO is useful in both the diagnosis and the treatment of blood disorders characterized by low or defective red blood cell production.

Studies have shown the efficacy of EPO therapy in a variety of disease states, disorders, and states of hematologic irregularity, for example, beta-thalassemia (Vedovato et al. (1984) Acta. Haematol. 71:211-213); cystic fibrosis (Vichinsky et al.

(1984) J. Pediatric 105:15-21); pregnancy and menstrual disorders (Cotes et al. (1983) Brit. J. Ostet. Gyneacol. 90:304-311); early anemia of prematurity (Haga et al. (1983) Acta Pediatr. Scand. 72:827-831); spinal cord injury (Claus-Walker et al. (1984) Arch. Phys. Med. Rehabil. 65:370-374); space flight (Dunn et al. (1984) Eur. J. Appl. Physiol. 52:178-182); acute blood loss (Miller et al. (1982) Brit. J. Haematol. 52:545-590); aging (Udupa et al. (1984) J. Lab. Clin. Med. 103:574-588); various neoplastic disease states accompanied by abnormal erythropoiesis (Dainiak et al. (1983) Cancer 5:1101-1106); and renal insufficiency (Eschbach et al. (1987) N. Eng. J. Med. 316:73-78). During the last fifteen years, EPO has been used for the treatment of the anemia of renal failure, anemia of chronic disease associated with rheumatoid arthritis, inflammatory bowel disease, AIDS, and cancer, as well as for the treatment of anemia in hematopoietic malignancies, post-bone marrow transplantation, and autologous blood donation.

The activity of EPO is mediated by its receptor. The EPO-receptor (EPO-R) belongs to the class of growth-factor-type receptors which are activated by a ligand-induced protein dimerization. Other hormones and cytokines such as human growth hormone (hGH), granulocyte colony stimulating factor (G-CSF), epidermal growth factor (EGF) and insulin can cross-link two receptors resulting in juxtaposition of two cytoplasmic tails. Many of these dimerization-activated receptors have protein kinase domains within the cytoplasmic tails that phosphorylate the neighboring tail upon dimerization. While some cytoplasmic tails lack intrinsic kinase activity, these function by association with protein kinases. The EPO receptor is of the latter type. In each case, phosphorylation results in the activation of a signaling pathway.

There has been an increasing interest in molecular mimicry with EPO potency. For example, dimerization of the erythropoietin receptor (EPOR) in the presence of either natural EPO or synthetic EPO mimetic peptides (EMPs) is the extracellular event that leads to activation of the receptor and downstream signal transduction events. In general, there is an interest in obtaining mimetics with equivalent potency to EPO.

Wrighton et al (1996, Science, 273:458-463) employed phage display where random peptides are to be exposed on coat proteins of filamentous phage. A library of random peptide-phage was allowed to bind to and subsequently eluted from the extracellular domain of EPO receptor in the screening system. They used weak-binding system to first fish out EPO domain-weak-binding (Kd 10 mM) CRIGPITWVC (SEQ ID NO: 10) as the consensus sequence. Consequently, a 20-amino acid peptide, EMP1, (GGTYSCHFG-PLTWVCKPQGG, SEQ ID NO: 11) with an affinity (Kd) of 200 nM, compared to 200 pM for EPO was isolated, the sequence of which does not actually exist in the native EPO. The crystal structure at 2.8 Å resolution of a complex of this mimetic agonist peptide with the extracellular domain of EPO receptor revealed that a peptide dimer induces an almost perfect twofold dimerization of the receptor (Livnah et al., 1996 Science, 273 (274): 464-471). This 20-amino acid peptide has a b-sheet structure and is stabilized by the C—C disulfide bond.

The biological activity of EMP1 indicates that EMP1 can act as an EPO mimetic. For example, EMP1 competes with EPO in receptor binding assays to cause cellular proliferation of cell lines engineered to be responsive to EPO (Wrighton et al., 1996, Science, 273:458-463). Both EPO and EMP1 induce a similar cascade of phosphorylation events and cell cycle progression in EPO responsive cells (Wrighton et al., 1996, Science, 273:458-463). Further, EMP1 demonstrates significant erythropoietic effects in mice as monitored by two different in vivo assays of nascent red blood cell production (Wrighton et al., 1996, Science, 273:458-463).

Johnson et al. (1998, Biochemistry, 37:3699-3710) identified the minimal peptide that retained activity in the assays for EPO mimetic action. Using N- and C-terminal deletions, they found that the minimal active peptide is EMP20 having the sequence, YSCHFGPLTWVCK (SEQ ID NO: 12), namely amino acids 4 through 16 of EMP1. They also found Tyr4 and Trp 13 of EMP1 are critical for mimetic action.

The present invention provides EMP1/transferrin fusion proteins with increased half-life and pharmaceutical compositions comprising such fusion proteins. Any EMP sequence may be used to make EMP1/transferrin fusion proteins, including EMP1 sequences wherein one or more C residues is deleted or replaced. These sequences can then be inserted into a mTf loop to provide three dimensional structure to the EMP1 region of the fusion protein. The present invention contemplates the use of the fusion protein to treat various diseases and conditions associated with EPO such as but not limited to those described above.

In one embodiment of the present invention, the pharmaceutical compositions comprising the EMP1/transferrin fusion protein and may be formulated by any of the established methods of formulating pharmaceutical compositions, e.g. as described in Remington's Pharmaceutical Sciences, 1985. The composition may be in a form suited for systemic injection or infusion and may, as such, be formulated with a suitable liquid vehicle such as sterile water or an isotonic saline or glucose solution. These pharmaceutical compositions may contain buffers, salts and other excipients to stabilize the composition or assist in the delivery of the transferrin fusion proteins.

In a preferred embodiment, the present invention provides a method for treating disorders associated with EPO. The method is accomplished by administering a EMP1/transferrin fusion protein provided herein for a time and under conditions sufficient to alleviate the symptoms of the disorder, i.e. sufficient to effect dimerization or biological activation of EPO receptors. In the case of EPO such methodology is useful in the treatment of end-stage renal failure/dialysis; anemia, especially associated with AIDS or chronic inflammatory diseases such as rheumatoid arthritis and chronic bowel inflammation; auto-immune disease; and for boosting the red blood cell count of patient when necessary, e.g. prior to surgery or as pretreatment to transfusion. The EMP1/transferrin fusion protein of the present invention which behave as EPO agonists can be used to activate megakaryocytes.

Since EPO has been shown to have a mitogenic and chemotactic effect on vascular endothelial cells as well as an effect on central cholinergic neurons (Amagnostou et al. (1990) Proc. Natl. Acad. Sci. USA 87:597805982; Konishi et al. (1993) Brain Res. 609:29-35), the compounds of this invention can also be used to treat a variety of vascular disorders, such as promoting wound healing, growth of collateral coronary blood vessels (such as those that may occur after myocardial infarction), trauma, and post vascular graft treatment, and a variety of neurological disorders, generally characterized by low absolute levels of acetyl choline or low relative levels of acetyl choline as compared to other neuroactive substances e.g., neurotransmitters.

Accordingly, the present invention includes pharmaceutical compositions comprising, as an active ingredient, the EMP1/transferrin fusion protein of the present invention in association with a pharmaceutical carrier or diluent. The EMP1/transferrin fusion protein of this invention can be administered by oral, parenteral (intramuscular, intraperitoneal, intravenous (IV) or subcutaneous injection), transdermal (either passively or using iontophoresis or electroporation) or transmucosal (nasal, vaginal, rectal, or sublingual) routes of administration in dosage forms appropriate for each route of administration.

Solid dosage forms for oral administration include capsules, tablets, pill, powders, and granules. In such solid dosage forms, the active compound is admixed with at least one inert pharmaceutically acceptable carrier such as sucrose, lactose, or starch. Such dosage forms can also comprise, as it normal practice, additional substances other than inert diluents, e.g., lubricating, agents such as magnesium stearate. In the case of capsules, tablets and pills, the dosage forms may also comprise buffering, agents. Tablets and pills can additionally be prepared with enteric coatings.

Liquid dosage forms for oral administration include pharmaceutically acceptable emulsions, solutions, suspensions, syrups, with the elixirs containing inert diluents commonly used in the art, such as water. Besides such inert diluents, compositions can also include adjuvants, such as wetting agents, emulsifying and suspending agents, and sweetening, flavoring and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria retaining filter, by incorporating sterilizing agents into the compositions, by irradiating the compositions, or by heating the compositions. They can also be manufactured using sterile water, or some other sterile injectable medium, immediately before use.

Compositions for rectal or vaginal administration are preferably suppositories which may contain, in addition to the active substance, excipients such as cocoa butter or a suppository wax. Compositions for nasal or sublingual administration are also prepared with standard excipients well known in the art.

The dosage of active ingredient in the compositions of this invention may be varied; however, it is necessary that the amount of the active ingredient shall be such that a suitable dosage form is obtained. The selected dosage depends upon the desired therapeutic effect, on the route of administration, and on the duration of the treatment desired. Generally dosage levels of between 0.001 to 10 mg/kg of body weight daily are administered to mammals.

Moreover, the present invention also contemplates the use of the transferrin fusion protein comprising EMP1 or analogs thereof for the manufacture of a medicinal product which can be used in the treatment of diseases associated with low or defective red blood cell production. Examples of such diseases are not limited to those described above.

T-20 and T-1249

HIV infection is pandemic and HIV associated diseases represent a major world health problem. Although considerable effort is being put into the successful design of effective therapeutics, currently no curative anti-retroviral drugs against AIDS exist. In attempts to develop such drugs, several stages of the HIV life cycle have been considered as targets for therapeutic intervention (Mitsuya, H. et al., 1991, FASEB J. 5:2369-2381). For example, virally encoded reverse transcriptase has been one focus of drug development. A number of reverse-transcriptase-targeted drugs, including 2',3'-dideoxynucleoside analogs such as AZT, ddI, ddc, and d4T have been developed which have been shown to been active against HIV (Mitsuya, H. et al., 1991, Science 249:1533-1544). While beneficial, these nucleoside analogs are not curative, probably due to the rapid appearance of drug resistant HIV mutants (Lander, B. et al., 1989, Science 243:1731-1734). In addition, the drugs often exhibit toxic side effects, such as bone marrow suppression, vomiting, and liver function abnormalities.

Entry inhibitors are distinct from the existing classes of drugs that fight HIV. Other drugs work inside the infected cell. Nucleoside reverse transcriptase inhibitors such as AZT and abacavir and non-nucleoside reverse transcriptase inhibitors like nevirapine and efavirenz all act by shutting down the reverse transcriptase enzyme that HIV uses to replicate itself once it is inside the cell. Protease inhibitors shut down the viral protease enzyme HIV uses to package itself up for export. By contrast, entry inhibitors are drugs that interfere with the processes involved in the virus' initial assault on the cell's outer membrane.

T-20 is the most studied of all the entry inhibitors and is the first member of the fusion inhibitor class. Unlike existing AIDS drugs that work inside the cell and target viral enzymes involved in the replication of the virus, T-20 inhibits fusion of HIV with host cells before the virus enters the cell and begins its replication process. T-20 binds to one of the two helical domains of gp41. Gp41 is a spring-loaded HIV-1 protein that is activated when CD4 binds to HIV gp-120. The fusion action of gp41 is inhibited if its two helical domains cannot fold together. T-20 binds to gp41, effectively keeping the protein from functioning. It has been shown in early, single-arm clinical studies to be about as potent as a protease inhibitor by itself-giving greater than 10 fold reductions in viral load and to be safe in combination with other antiretrovirals.

U.S. Pat. No. 5,464,933 discloses T-20 (pentafuside, DP-178) as a 36 amino acid synthetic peptide. Since this drug is a peptide, it cannot be given orally because it is readily broken down by the digestive system. When administered by subcutaneous injection, T-20 achieves sufficient levels in the blood to have anti-HIV activity. It is administered by subcutaneous injection twice daily. However, patients develop skin reactions at the injection site. The most frequently reported treatment related adverse events were mild to moderate local injection site reactions. These consist of mild pain, temporary swelling and redness at the site of injection.

U.S. Pat. No. 6,479,055 discloses peptide analogs of the DP-178 (peptides corresponding to amino acid residues 638 to 673 of transmembrane protein gp41 of HIV-1$_{LAI}$, which exhibit anti-membrane fusion capability, antiviral activity, such as the ability to inhibit HIV transmission to uninfected CD-4$^+$ cells, or an ability to modulate intracellular processes involving coiled-coil peptide structures. Further, the patent relates to the use of DP-178 and DP-178 portions and/or analogs as antifusogenic or antiviral compounds or as inhibitors of intracellular events involving coiled-coil peptide structures. Further, the patent teaches the use of the peptides as diagnostic agents. For example, a DP178 peptide may be used as an HIV subtype-specific diagnostic.

T-1249 is a sister compound of T-20. Like T-20, T-1249 targets the HIV glycoprotein known as gp41 which HIV uses to bind onto CD4 cells. T-1249 has shown potent anti-HIV effects in animal and laboratory studies. Preliminary safety, dosing and efficacy studies in humans have provided support for ongoing research.

T-1249 is currently administered by subcutaneous (under the skin) injection once or twice daily. The first safety study of T-1249 conducted in humans found two serious adverse events: hypersensitivity reaction (oral ulcers, maculopapular rash, fever) and severe neutropenia. Forty percent of recipients developed injection site reactions but these were deemed to be mild. Dizziness, diarrhea, headache and fever have also been reported by recipients. No dose-limiting toxicity was identified and experiments with higher doses are likely.

T-1249 has completed phase I/II safety and dosing studies. Initial results indicated that higher doses produced an average viral load drop of 1.3 log.

Dose-dependent decreases in HIV RNA have been reported. In the study of T-1249, the average reduction from baseline ranged from 0.29 to 1.96 log copies/ml (Gulick 2002).

The present invention provides transferrin fusion proteins comprising T-20, T-1249, or analogs thereof with increased half-life and pharmaceutical compositions comprising such fusion proteins. The present invention also provides pharmaceutical compositions comprising these transferrin fusion proteins for therapeutic purposes. The present invention contemplates the use of such fusion proteins as inhibitors of human and non-human retroviral, especially HIV, transmission to uninfected cells. The human retroviruses whose transmission may be inhibited by the peptides of the invention include, but are not limited to all strains of HIV-1 and HIV-2 and the human T-lymphocyte viruses (HTLV-I, II, III). The non-human retroviruses whose transmission may be inhibited by the peptides of the invention include, but are not limited to bovine leukosis virus, feline sarcoma and leukemia viruses, simian sarcoma and leukemia viruses, and sheep progress pneumonia viruses.

With respect to HIV, the transferrin fusion protein of the present invention comprising T-20, T-1249 or analogs thereof may be used as a therapeutic in the treatment of AIDS. These transferrin fusion proteins may be administered using techniques well known to those in the art. Preferably, the pharmaceutical compositions comprising these transferrin fusion proteins are formulated and administered systemically. Techniques for formulation and administration may be found in "Remington's Pharmaceutical Sciences" 18th ed., 1990 Mack Publishing Co., Easton, Pa. Suitable routes may include oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections, just to name a few. Most preferably, administration is intravenous. For injection, the transferrin fusion proteins comprising T-20, T1249, or analogs thereof may be formulated in aqueous solutions, preferably in physiologically compatible buffers such as Hanks' solution, Ringer's solution, or physiological saline buffer. For such transmucosal administration, penetrants appropriate to the barrier to be permeated are used in the formulation. Such penetrants are generally known in the art.

In addition, the transferrin fusion protein comprising T-20, T1249, or analogs thereof may be used as a prophylactic measure in previously uninfected individuals after acute exposure to an HIV virus. Examples of such prophylactic use of the peptides may include, but are not limited to, prevention of virus transmission from mother to infant and other settings where the likelihood of HIV transmission exists, such as, for example, accidents in health care settings wherein workers are exposed to HIV-containing blood products. The transferrin fusion proteins of the present invention comprising T-20, T-1249, or analogs thereof in such cases may serve the role of a prophylactic vaccine, wherein the host raises antibodies against the fusion proteins of the invention, which then serve to neutralize HIV viruses by, for example, inhibiting further HIV infection. Administration of the transferrin fusion proteins of the invention as a prophylactic vaccine, therefore, would comprise administering to a host a concentration of transferrin fusion protein effective in raising an immune response which is sufficient to neutralize HIV, by, for example, inhibiting HIV ability to infect cells. The exact concentration will depend upon the specific peptide in the transferrin fusion protein to be administered, but may be determined by using standard techniques for assaying the development of an immune response which are well known to those of ordinary skill in the art. The transferrin fusion proteins to be used as vaccines are usually administered intramuscularly.

Effective dosages of the transferrin fusion proteins comprising T-20, T-1249, or analogs thereof to be administered may be determined through procedures well known to those in the art which address such parameters as biological half-life, bioavailability, and toxicity. Given the data presented below in Section 6, DP-178, for example, may prove efficacious in vivo at doses required achieve circulating levels of 10 ng per ml of peptide.

Furthermore, the present invention contemplates the use of the transferrin fusion proteins comprising T-20, T-1249, or analogs thereof for the manufacture of a medicinal product for the treatment of diseases associated with the transmission of a virus.

Delivery of a Drug or Therapeutic Protein to the Inside of a Cell and/or Across the Blood Brain Barrier (BBB)

Within the scope of the invention, the modified transferrin fusion proteins may be used as a carrier to deliver a molecule or small molecule therapeutic complexed to the ferric ion of transferrin to the inside of a cell or across the blood brain barrier or other barriers including across the cell membrane of any cell type that naturally or engineered to express a Tf receptor. In these embodiments, the Tf fusion protein will typically be engineered or modified to inhibit, prevent or remove glycosylation to extend the serum half-life of the fusion protein and/or therapeutic protein portion. The addition of a targeting peptide is specifically contemplated to further target the Tf fusion protein to a particular cell type, e.g., a cancer cell.

In one embodiment, the iron-containing, anti-anemic drug, ferric-sorbitol-citrate complex is loaded onto a modified Tf fusion protein of the invention. Ferric-sorbitol-citrate (FSC) has been shown to inhibit proliferation of various murine cancer cells in vitro and cause tumor regression in vivo, while not having any effect on proliferation of non-malignant cells (Poljak-Blazi et al. (June 2000) *Cancer Biotherapy and Radiopharmaceuticals* (United States), 15/3:285-293).

In another embodiment, the antineoplastic drug Adriamycin® (doxorubicin) and/or the chemotherapeutic drug bleomycin, both of which are known to form complexes with ferric ion, is loaded onto a Tf fusion protein of the invention. In other embodiments, a salt of a drug, for instance, a citrate or carbonate salt, may be prepared and complexed with the ferric iron that is then bound to Tf. As tumor cells often display a higher turnover rate for iron; transferrin modified to carry at least one anti-tumor agent, may provide a means of increasing gent exposure or load to the tumor cells. (Demant, E. J., (1983) *Eur. J. Biochem.* 137/(1-2):113-118; Padbury et al. (1985) *J. Biol. Chem.* 260/13:7820-7823).

Pharmaceutical Formulations and Treatment Methods

The modified fusion proteins of the invention may be administered to a patient in need thereof using standard administration protocols. For instance, the modified Tf fusion proteins of the present invention can be provided alone, or in combination, or in sequential combination with other agents that modulate a particular pathological process. As used herein, two agents are said to be administered in combination when the two agents are administered simultaneously or are administered independently in a fashion such that the agents will act at the same or near the same time.

The agents of the present invention can be administered via parenteral, subcutaneous, intravenous, intramuscular, intraperitoneal, transdermal and buccal routes. For example, an agent may be administered locally to a site of injury via microinfusion. Alternatively, or concurrently, administration may be noninvasive by either the oral, inhalation, nasal, or pulmonary route. The dosage administered will be dependent upon the age, health, and weight of the recipient, kind of concurrent treatment, if any, frequency of treatment, and the nature of the effect desired.

While any method of administration may be used to deliver the mTF fusion proteins of the invention, administration or delivery orally may be a preferred embodiment for certain classes of fusion proteins or to treat certain conditions.

The present invention further provides compositions containing one or more fusion proteins of the invention. While individual needs vary, determination of optimal ranges of effective amounts of each component is within the skill of the art. Typical dosages comprise about 1 pg/kg to about 100 mg/kg body weight. The preferred dosages for systemic administration comprise about 100 ng/kg to about 100 mg/kg body weight. The preferred dosages for direct administration to a site via microinfusion comprise about 1 ng/kg to about 1 mg/kg body weight. When administered via direct injection or microinfusion, modified fusion proteins of the invention may be engineered to exhibit reduced or no binding of iron to prevent, in part, localized iron toxicity.

In addition to the pharmacologically active fusion protein, the compositions of the present invention may contain suitable pharmaceutically acceptable carriers comprising excipients and auxiliaries that facilitate processing of the active compounds into preparations which can be used pharmaceutically for delivery to the site of action. Suitable formulations for parenteral administration include aqueous solutions of the active compounds in water-soluble form, for example, water-soluble salts. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension including, for example, sodium carboxymethyl cellulose, sorbitol and dextran. Optionally, the suspension may also contain stabilizers. Liposomes can also be used to encapsulate the agent for delivery into the cell.

The pharmaceutical formulation for systemic administration according to the invention may be formulated for enteral, parenteral or topical administration. Indeed, all three types of formulations may be used simultaneously to achieve systemic administration of the active ingredient. Suitable formulations for oral administration include hard or soft gelatin capsules, pills, tablets, including coated tablets, elixirs, suspensions, syrups or inhalations and controlled release forms thereof.

In practicing the methods of this invention, the agents of this invention may be used alone or in combination, or in combination with other therapeutic or diagnostic agents. In certain preferred embodiments, the compounds of this invention may be co-administered along with other compounds typically prescribed for these conditions according to generally accepted medical practice. The compounds of this invention can be utilized in vivo, ordinarily in mammals, such as humans, sheep, horses, cattle, pigs, dogs, cats, rats and mice, ex vivo or in vitro.

Modified fusion proteins of the present invention may be used in the diagnosis, prognosis, prevention and/or treatment of diseases and/or disorders relating to diseases and disorders of the endocrine system, the nervous system, the immune system, respiratory system, cardiovascular system, reproductive system, digestive system, diseases and/or disorders relating to cell proliferation, and/or diseases or disorders relating to the blood.

In yet other embodiments of the invention, modified Tf fusion proteins may be used in the diagnosis, prognosis, prevention and/or treatment of diseases and/or disorders relating to diseases and disorders known to be associated with or treatable by therapeutic protein moieties as known in the art and exemplified by PCT Patent Publication Nos. WO 01/79258, WO 01/77137, WO 01/79442, WO 01/79443, WO 01/79444 and WO 01/79480, all of which are herein incorporated by reference in their entirety. Accordingly, the present invention encompasses a method of treating a disease or disorder listed in the "Preferred Indication Y" column of Table 1 comprising administering to a patient in which such treatment, prevention or amelioration is desired a modified transferrin fusion protein of the invention that comprises a therapeutic protein portion corresponding to a therapeutic protein disclosed in the "Therapeutic Protein X" column of Table 1 in an amount effective to treat, prevent or ameliorate the disease or disorder.

In certain embodiments, a transferrin fusion protein of the present invention may be used to diagnose and/or prognose diseases and/or disorders.

Modified transferrin fusion proteins of the invention and polynucleotides encoding transferrin fusion proteins of the invention may be useful in treating, preventing, diagnosing and/or prognosing diseases, disorders, and/or conditions of the immune system. Moreover, fusion proteins of the invention and/or polynucleotides encoding transferrin fusion proteins of the invention can be used as a marker or detector of a particular immune system disease or disorder.

In a preferred embodiment fusion proteins of the invention and/or polynucleotides encoding modified transferrin fusion proteins of the invention could be used as an agent to boost immunoresponsiveness among immunodeficient individuals. In specific embodiments, fusion proteins of the invention and/or polynucleotides encoding transferrin fusion proteins of the invention could be used as an agent to boost immunoresponsiveness among B cell and/or T cell immunodeficient individuals.

The modified transferrin fusion proteins of the invention and/or polynucleotides encoding transferrin fusion proteins of the invention may be useful in treating, preventing, diagnosing, and/or prognosing autoimmune disorders. Many autoimmune disorders result from inappropriate recognition of self as foreign material by immune cells. This inappropriate recognition results in an immune response leading to the destruction of the host tissue. Therefore, the administration of fusion proteins of the invention and/or polynucleotides encoding transferrin fusion proteins of the invention, that can inhibit an immune response, particularly the proliferation, differentiation, or chemotaxis of T-cells, may be an effective therapy in preventing autoimmune disorders.

Modified transferrin fusion proteins of the invention and/or polynucleotides encoding transferrin fusion proteins of the invention may be useful in treating, preventing, prognosing, and/or diagnosing diseases, disorders, and/or conditions of hematopoietic cells. Transferrin fusion proteins of the invention and/or polynucleotides encoding transferrin fusion proteins of the invention could be used to increase differentiation and proliferation of hematopoietic cells, including the pluripotent stem cells, in an effort to treat or prevent those diseases, disorders, and/or conditions associated with a decrease in certain (or many) types hematopoietic cells, including but not limited to, leukopenia, neutropenia, anemia, and thrombocytopenia.

Alternatively, modified fusion proteins of the invention and/or polynucleotides encoding transferrin fusion proteins of the invention could be used to increase differentiation and proliferation of hematopoietic cells, including the pluripotent stem cells, in an effort to treat or prevent those diseases, disorders, and/or conditions associated with an increase in certain (or many) types of hematopoietic cells, including but not limited to, histiocytosis.

Allergic reactions and conditions, such as asthma (particularly allergic asthma) or other respiratory problems, may also be treated, prevented, diagnosed and/or prognosing and using modified fusion proteins of the invention and/or polynucleotides encoding transferrin fusion proteins of the invention. Moreover, these molecules can be used to treat, prevent, prognose, and/or diagnose anaphylaxis, hypersensitivity to an antigenic molecule, or blood group incompatibility.

Additionally, modified fusion proteins of the invention and/or polynucleotides encoding transferrin fusion proteins of the invention, may be used to treat, prevent, diagnose and/or prognose IgE-mediated allergic reactions. Such allergic reactions include, but are not limited to, asthma, rhinitis, and eczema. In specific embodiments, fusion proteins of the invention and/or polynucleotides encoding transferrin fusion proteins of the invention may be used to modulate IgE concentrations in vitro or in vivo.

Moreover, modified fusion proteins of the invention and/or polynucleotides encoding transferrin fusion proteins of the invention have uses in the diagnosis, prognosis, prevention, and/or treatment of inflammatory conditions. For example, since fusion proteins of the invention and/or polynucleotides encoding transferrin fusion proteins of the invention may inhibit the activation, proliferation, and/or differentiation of cells involved in an inflammatory response, these molecules can be used to prevent and/or treat chronic and acute inflammatory conditions. Such inflammatory conditions include, but are not limited to, for example, inflammation associated with infection (e.g., septic shock, sepsis, or systemic inflammatory response syndrome), ischemia-reperfusion injury, endotoxin lethality, complement-mediated hyperacute rejection, nephritis, cytokine or chemokine induced lung injury, inflammatory bowel disease, Crohn's disease, over production of cytokines (e.g., TNF or IL-1.), respiratory disorders (e.g., asthma and allergy); gastrointestinal disorders (e.g., inflammatory bowel disease); cancers (e.g., gastric, ovarian, lung, bladder, liver, and breast); CNS disorders (e.g., multiple sclerosis; ischemic brain injury and/or stroke, traumatic brain injury), neurodegenerative disorders (e.g., Parkinson's disease and Alzheizmer's disease); AIDS-related dementia; and prion disease); cardiovascular disorders (e.g., atherosclerosis, myocarditis, cardiovascular disease, and cardiopulmonary bypass complications); as well as many additional diseases, conditions, and disorders that are characterized by inflammation (e.g., hepatitis, rheumatoid arthritis, gout, trauma, pancreatitis, sarcoidosis, dermatitis, renal ischemia-reperfusion injury, Grave's disease, systemic lupus erythematosus, diabetes mellitus, and allogenic transplant rejection).

Because inflammation is a fundamental defense mechanism, inflammatory disorders can affect virtually any tissue of the body. Accordingly, modified fusion proteins of the invention and/or polynucleotides encoding transferrin fusion proteins of the invention, have uses in the treatment of tissue-specific inflammatory disorders, including, but not limited to, adrenalitis, alveolitis, angiocholecystitis, appendicitis, balanitis, blepharitis, bronchitis, bursitis, carditis, cellulitis, cervicitis, cholecystitis, chorditis, cochiftis, colitis, conjunctivitis, cystitis, dermatitis, diverticulitis, encephalitis, endocarditis, esophagitis, eustachitis, fibrositis, folliculitis, gastritis, gastroenteritis, gingivitis, glossitis, hepatosplenitis, keratitis, labyrinthitis, laryngitis, lymphangitis, mastitis, media otitis, meningitis, metritis, mucitis, myocarditis, myositis, myringitis, nephritis, neuritis, orchitis, osteochondritis, otitis, pericarditis, peritendonitis, peritonitis, pharyngitis, phlebitis, poliomyelitis, prostatititis, Pulpitis, retinitis, rhinitis, salpingitis, scleritis, sclerochoroiditis, scrotitis, sinusitis, spondylitis, steatitis, stomatitis, synovitis, syringitis, tendonitis, tonsillitis, urethritis, and vaginitis.

In specific embodiments, modified fusion proteins of the invention and/or polynucleotides encoding transferrin fusion proteins of the invention, are useful to diagnose, prognose, prevent, and/or treat organ transplant rejections and graft-versus-host disease (GVHD). Organ rejection occurs by host immune cell destruction of the transplanted tissue through an immune response. Similarly, an immune response is also involved in GVHD, but, in this case, the foreign transplanted immune cells destroy the host tissues. Polypeptides, antibodies, or polynucleotides of the invention, and/or agonists or antagonists thereof, that inhibit an immune response, particularly the activation, proliferation, differentiation, or chemotaxis of T-cells, may be an effective therapy in preventing organ rejection or GVHD.

In another specific embodiment, modified transferrin fusion proteins of the invention and/or polynucleotides encoding transferrin fusion proteins of the invention are used as an adjuvant to enhance anti-viral immune responses. Anti-viral immune responses that may be enhanced using the compositions of the invention as an adjuvant include virus and virus associated diseases or symptoms described herein or otherwise known in the art. In specific embodiments, the compositions of the invention are used as an adjuvant to enhance an immune response to a virus, disease, or symptom selected from the group consisting of AIDS, meningitis, Dengue, EBV, and hepatitis (e.g., hepatitis B). In another specific embodiment, the compositions of the invention are used as an adjuvant to enhance an immune response to a virus, disease, or symptom selected from the group consisting of: HIV/AIDS, respiratory syncytial virus, Dengue, rotavirus, Japanese B encephalitis, influenza A and B, parainfluenza, measles, cytomegalovirus, rabies, Junin, Chikungunya, Rift Valley Fever, herpes simplex, and yellow fever.

In another specific embodiment, modified transferrin fusion proteins of the invention and/or polynucleotides encoding transferrin fusion proteins of the invention are used as an adjuvant to enhance anti-bacterial or anti-fungal immune responses. Anti-bacterial or anti-fungal immune responses that may be enhanced using the compositions of the invention as an adjuvant include bacteria or fungus and bacteria or fungus associated diseases or symptoms described herein or otherwise known in the art. In specific embodiments, the compositions of the invention are used as an adjuvant to enhance an immune response to a bacterium or fungus disease, or symptom selected from the group consisting of tetanus, Diphtheria, botulism, meningitis type B, and candidiasis.

In another specific embodiment, the compositions of the invention are used as an adjuvant to enhance an immune response to a bacterium or fungus, disease, or symptom selected from the group consisting of *Vibrio cholerae, Mycobacterium leprae, Salmonella typhi, Salmonella paratyphi, Neisseria meningitidis, Streptococcus pneumoniae*, Group B *streptococcus, Shigella* spp., Enterotoxigenic *Escherichia coli, Enterohemorrhagic E. coli, Borrelia burgdorferi*, and *Candida*.

In another specific embodiment, modified transferrin fusion proteins of the invention and/or polynucleotides encoding transferrin fusion proteins of the invention are used as an adjuvant to enhance anti-parasitic immune responses. Anti-parasitic immune responses that may be enhanced using the compositions of the invention as an adjuvant include parasite and parasite associated diseases or symptoms described herein or otherwise known in the art. In specific embodiments, the compositions of the invention are used as an adjuvant to enhance an immune response to a parasite. In another specific embodiment, the compositions of the invention are used as an, adjuvant to enhance an immune response to *Plasmodium* (malaria) or *Leishmania*.

In another specific embodiment, modified transferrin fusion proteins of the invention and/or polynucleotides encoding transferrin fusion proteins of the invention may also be employed to treat infectious diseases including silicosis, sarcoidosis, and idiopathic pulmonary fibrosis; for example, by preventing the recruitment and activation of mononuclear phagocytes.

In another specific embodiment, modified transferrin fusion proteins of the invention and/or polynucleotides encoding transferrin fusion proteins of the invention are used as an antigen for the generation of antibodies to inhibit or enhance immune mediated responses against polypeptides of the invention.

In one embodiment, modified transferrin fusion proteins of the invention and/or polynucleotides encoding transferrin fusion proteins of the invention are administered to an animal (e.g., mouse, rat, rabbit, hamster, guinea pig, pigs, micro-pig, chicken, camel, goat, horse, cow, sheep, dog, cat non-human primate, and human, most preferably human) to boost the immune system to produce increased quantities, of one or more antibodies (e.g., IgG, IgA, IgM, and IgE), to induce higher affinity antibody production and immunoglobulin class switching (e.g., IgG, IgA, IgM, and IgE), and/or to increase an immune response.

In another embodiment, modified transferrin fusion proteins of the invention and/or polynucleotides encoding transferrin fusion proteins of the invention are used in one or more of the applications described herein, as they may apply to veterinary medicine.

In another specific embodiment, modified transferrin fusion proteins of the invention, and/or polynucleotides encoding transferrin fusion proteins of the invention are used as a means of blocking various aspects of immune responses to foreign agents or self. Examples of diseases or conditions in which blocking of certain aspects of immune responses may be desired include autoimmune disorders such as lupus, and arthritis, as well as immunoresponsiveness to skin allergies, inflammation-, bowel disease, injury, and diseases/disorders associated with pathogens.

In another specific embodiment, modified transferrin fusion proteins of the invention and/or polynucleotides encoding transferrin fusion proteins of the invention are used as a therapy for preventing the B cell proliferation and Ig secretion associated with autoimmune diseases such as idiopathic thrombocytopenic purpura, systemic lupus erythematosus and multiple sclerosis.

In another specific embodiment, modified transferrin fusion proteins or polynucleotides encoding transferrin fusion proteins of the invention are used as an inhibitor of B and/or T cell migration in endothelial cells. This activity disrupts tissue architecture or cognate responses and is useful, for example in disrupting immune responses, and blocking sepsis.

In another specific embodiment, modified transferrin fusion proteins of the invention, and/or polynucleotides encoding transferrin fusion proteins of the invention are used as a therapy for chronic hypergammaglobulinen evident in such diseases as monoclonal gammopathy of undetermined significance (MGUS), Waldenstrom's disease, related idiopathic monoclonal gammopathies, and plasmacytomas.

Another specific embodiment, modified transferrin fusion proteins of the invention and/or polynucleotides encoding transferrin fusion proteins of the invention may be employed for instance to inhibit polypeptide chemotaxis and activation of macrophages and their precursors, and of neutrophils, basophils, B lymphocytes and some T-cell subsets, e.g., activated and CD8 cytotoxic T cells and natural killer cells, in certain autoimmune and chronic inflammatory and infective diseases. Examples of autoimmune diseases are described herein and include multiple sclerosis, and insulin-dependent diabetes.

In another specific embodiment, modified transferrin fusion proteins of the invention and/or polynucleotides encoding transferrin fusion protein of the invention may also be employed for treating atherosclerosis, for example, by preventing monocyte infiltration in the artery wall.

In another specific embodiment, modified transferrin fusion proteins of the invention and/or -polynucleotides encoding transferrin fusion proteins of the invention may be employed to treat adult respiratory distress syndrome (ARDS).

In another specific embodiment, modified transferrin fusion proteins of the invention and/or polynucleotides encoding transferrin fusion proteins of the invention may be useful for stimulating wound and tissue repair, stimulating angiogenesis, and/or stimulating the repair of vascular or lymphatic diseases or disorders. Additionally, fusion proteins of the invention and/or polynucleotides encoding transferrin fusion proteins of the invention may be used to stimulate the regeneration of mucosal surfaces.

In a specific embodiment, modified transferrin fusion proteins of the invention and/or polynucleotides encoding transferrin fusion proteins of the invention are used to diagnose, prognose, treat, and/or prevent a disorder characterized by primary or acquired immunodeficiency, deficient serum immunoglobulin production, recurrent infections, and/or immune system dysfunction. Moreover, modified fusion proteins of the invention and/or polynucleotides encoding transferrin fusion proteins of the invention may be used to treat or prevent infections of the joints, bones, skin, and/or parotid glands, blood-borne infections (e.g., sepsis, meningitis, septic arthritis, and/or osteomyelitis), autoimmune diseases (e.g., those disclosed herein), inflammatory disorders, and malignancies, and/or any disease or disorder or condition associated with these infections, diseases, disorders and/or malignancies) including, but not limited to, Common Variable Immunodeficiency (CVID), other primary immune deficiencies, HIV disease, Chronic Lymphocytic Leukemia (CLL), recurrent bronchitis, sinusitis, otitis media, conjunctivitis, pneumonia, hepatitis, meningitis, herpes zoster (e.g., severe herpes zoster), and/or *pneumocystis carnii*. Other diseases and disorders that may be prevented, diagnosed, prognosed, and/or treated with fusion proteins of the invention and/or polynucleotides encoding transferrin fusion proteins of the invention include, but are not limited to, HIV infection, HTLV-BLV infection, lymphopenia, phagocyte bactericidal dysfunction anemia, thrombocytopenia, and hemoglobinuria.

In a specific embodiment, modified transferrin fusion proteins of the invention and/or polynucleotides encoding transferrin fusion proteins of the invention may be used to diagnose, prognose, prevent, and/or treat cancers or neoplasms including immune cell or immune tissue-related cancers or neoplasms. Examples of cancers or neoplasms that may be prevented, diagnosed, or treated by fusion proteins of the invention and/or polynucleotides encoding transferrin fusion proteins of the invention include, but are not limited to, acute myelogenous leukemia, chronic myelogenous leukemia, Hodgkin's disease, non-Hodgkin's lymphoma, acute lymphocytic leukemia (ALL), chronic lymphocyte leukemia, plasmacytomas, multiple myeloma, Burkitt's lymphoma, EBV transformed diseases, and/or diseases and disorders described in the section entitled "Hyperproliferative Disorders" elsewhere herein.

In another specific embodiment, modified transferrin fusion proteins of the invention and/or polynucleotides encoding transferrin fusion proteins of the invention are used as a therapy for decreasing cellular proliferation of Large B-cell Lymphomas.

In specific embodiments, the compositions of the invention are used as an agent to boost immunoresponsiveness among B cell immunodeficient individuals, such as, for example, an individual who has undergone a partial or complete splenectomy.

The modified transferrin fusion proteins of the invention and/or polynucleotides encoding transferrin fusion proteins of the invention may be used to modulate hemostatic (the stopping of bleeding) or thrombolytic (clot dissolving) activity. For example, by increasing hemostatic or thrombolytic activity, fusion proteins of the invention and/or polynucleotides encoding transferrin fusion proteins of the invention could be used to treat or prevent blood coagulation diseases, disorders, and/or conditions (e.g., afibrinogenemia, factor deficiencies, hemophilia), blood platelet diseases, disorders, and/or conditions (e.g. thrombocytopenia), or wounds resulting from trauma, surgery, or other causes. Alternatively, fusion proteins of the invention and/or polynucleotides encoding transferrin fusion proteins of the invention that can decrease hemostatic or thrombolytic activity could be used to inhibit or dissolve clotting. These molecules could be important in the treatment or prevention of heart attacks (infarction), strokes, or scarring.

In specific embodiments, the modified transferrin fusion proteins of the invention and/or polynucleotides encoding transferrin fusion proteins of the invention may be used to prevent diagnose, prognose, and/or treat thrombosis, arterial thrombosis, venous thrombosis, thromboembolism, pulmonary embolism, atherosclerosis, myocardial infarction, transient ischemic attack, unstable angina. In specific embodiments, the transferrin fusion proteins of the invention and/or polynucleotides encoding transferrin fusion proteins of the invention maybe used for the prevention of occulsion of saphenous grafts, for reducing the risk of periprocedural thrombosis as might accompany angioplasty procedures, for reducing the risk of stroke in patients with atrial fibrillation including nonrheumatic atria fibrillation, for reducing the risk of embolism associated with mechanical heart valves and/or mitral valves disease. Other uses for the modified transferrin fusion proteins of the invention and/or polynucleotides encoding transferrin fusion proteins of the invention, include, but are not limited to, the prevention of occlusions in extracorporeal devices (e.g., intravascular canals, vascular access shunts in hemodialysis patients, hemodialysis machines, and cardiopulmonary bypass machines).

In another embodiment, modified transferrin fusion proteins of the invention and/or polynucleotides encoding transferrin fusion proteins of the invention, may be used to prevent, diagnose, prognose, and/or treat diseases and disorders of the blood and/or blood forming organs associated with the tissue(s) in which the polypeptide of the invention is expressed.

The modified fusion proteins of the invention and/or polynucleotides encoding transferrin fusion proteins of the invention may be used to modulate hematopoietic activity (the formation of blood cells). For example, the transferrin fusion proteins of the invention and/or polynucleotides encoding transferrin fusion proteins of the invention may be used to increase the quantity of all or subsets of blood cells, such as, for example, erythrocytes, lymphocytes (B or T cells), myeloid cells (e.g., basophils, eosinophils, neutrophils, mast cells, macrophages) and platelets. The ability to decrease the quantity of blood cells or subsets of blood cells may be useful in the prevention, detection, diagnosis, and/or treatment of anemias and leukopenias described below. Alternatively, the modified transferrin fusion proteins of the invention and/or polynucleotides encoding transferrin fusion proteins of the invention maybe used to decrease the quantity of all or subsets of blood cells, such as, for example, erythrocytes, lymphocytes (B or T cells), myeloid cells (e.g., basophils, eosinophils, neutrophils, mast cells, macrophages) and platelets. The ability to decrease the quantity of blood cells or subsets of blood cells may be useful in the prevention, detection, diagnosis, and/or treatment of leukocytoses, such as, for example eosinophilia. The modified fusion proteins of the invention and/or polynucleotides encoding transferrin fusion proteins of the invention may be used to prevent, treat, or diagnose blood dyscrasia.

Anemias are conditions in which the number of red blood cells or amount of hemoglobin (the protein that carries oxygen) in them is below normal. Anemia may be caused by excessive bleeding, decreased red blood cell production, or increased red blood cell destruction (hemolysis). The modified transferrin fusion proteins of the invention and/or polynucleotides encoding transferrin fusion proteins of the invention may be useful in treating, preventing, and/or diagnosing anemias. Anemias that may be treated prevented or diagnosed by the transferrin fusion proteins of the invention and/or polynucleotides encoding transferrin fusion proteins of the invention include iron deficiency anemia, hypochromic anemia, microcytic anemia, chlorosis, hereditary sideroblastic anemia, idiopathic acquired sideroblastic anemia, red cell aplasia, megaloblastic anemia (e.g., pernicious anemia, (vitamin B12 deficiency) and folic acid deficiency anemia), aplastic anemia, hemolytic anemias (e.g., autoimmunune hemolytic anemia, microangiopathic hemolytic anemia, and paroxysmal nocturnal hemoglobinuria). The modified transferrin fusion proteins of the invention and/or polynucleotides encoding transferrin fusion proteins of the invention may be useful in treating, preventing, and/or diagnosing anemias associated with diseases including but not limited to, anemias associated with systemic lupus erythematosus, cancers, lymphomas, chronic renal disease, and enlarged spleen. The transferrin fusion proteins of the invention and/or polynucleotides encoding transferrin fusion proteins of the invention may be useful in treating, preventing, and/or diagnosing anemia arising from drug treatments such as anemias associated with methyldopa, dapsone, and/or sulfa drugs. Additionally, modified fusion proteins of the invention and/or polynucleotides encoding transferrin fusion proteins of the invention maybe useful in treating, preventing, and/or diagnosing anemias associated with abnormal red blood cell architecture including but not limited to, hereditary spherocytosis, hereditary elliptocytosis, glucose-6-phosphate dehydrogenase deficiency, and sickle cell anemia.

The modified transferrin fusion proteins of the invention and/or polynucleotides encoding transferrin fusion proteins of the invention may be useful in treating, preventing, and/or diagnosing hemoglobin abnormalities, (e.g., those associated with sickle cell anemia, hemoglobin C disease, hemoglobin S-C disease, and hemoglobin E disease). Additionally, the transferrin fusion proteins of the invention and/or polynucleotides encoding transferrin fusion proteins of the invention may be useful in diagnosing, preventing, and/or prognosing in treating thalassemias, including, but not limited to, major and minor forms of alpha-thalassemia and beta-thalassemia.

In another embodiment, the modified transferrin fusion proteins of the invention and/or polynucleotides encoding transferrin fusion proteins of the invention may be useful in diagnosing, prognosing, preventing, and/or treating bleeding disorders including, but not limited to, thrombocytopenia (e.g., idiopathic thrombocytopenic purpura, and thrombotic thrombocytopenic purpura), Von Willebrand's disease, hereditary platelet disorders (e.g., storage pool disease such as Chediak-Higashi and Hermansky-Pudlak syndromes, thromboxane A2 dysfunction, thromboasthenia, and Bernard-Soulier syndrome), hemolyticuremic syndrome, hemophilias such as hemophilia A or Factor V11 deficiency and Christmas disease or Factor IX deficiency, Hereditary Hemorhhagic Telangiectsia, also known as Rendu-Osler-Webe syndrome, allergic purpura (Henoch Schonlein purpura) and disseminated intravascular coagulation.

In other embodiments, the modified transferrin fusion proteins of the invention and/or polynucleotides encoding transferrin fusion proteins of the invention may be useful as an agent to increase cytokine production.

In certain embodiments, fusion proteins of the invention, and/or polynucleotides encoding transferrin fusion proteins of the invention can be used to treat or detect hyperproliferative disorders, including neoplasms. Transferrin fusion proteins of the invention and/or polynucleotides encoding transferrin fusion proteins of the invention may inhibit the proliferation of the disorder through direct or indirect interactions. Alternatively, fusion proteins of the invention and/or polynucleotides encoding transferrin fusion proteins of the invention may cause proliferation of other cells which can inhibit the hyperproliferative disorder.

For example, by increasing an immune response, particularly increasing antigenic qualities of the hyperproliferative disorder or by proliferating, differentiating, or mobilizing T-cells, hyperproliferative disorders can be treated. This immune response may be increased by either enhancing an existing immune response, or by initiating a new immune response. Alternatively, decreasing an immune response may also be a method of treating hyperproliferative disorders, such as a chemotherapeutic agent.

Examples of hyperproliferative disorders that can be treated or detected by modified fusion proteins of the invention and/or polynucleotides encoding transferrin fusion proteins of the invention include, but are not limited to neoplasms located in the colon, abdomen, bone, breast, digestive system, liver, pancreas, peritoneum, endocrine glands (adrenal, parathyroid, pituitary, testicles, ovary, thymus, thyroid), eye, head and neck, nervous (central and peripheral), lymphatic system, pelvis, skin, soft tissue, spleen, thorax, and urogenital tract.

Similarly, other hyperproliferative disorders can also be treated or detected by modified fusion proteins of the invention and/or polynucleotides encoding transferrin fusion proteins of the invention. Examples of such hyperproliferative disorders include, but are not limited to Acute Childhood Lymphoblastic Leukemia; Acute Lymphoblastic Leukemia, Acute Lymphocytic Leukemia, Acute Myeloid Leukemia, Adrenocortical Carcinoma, Adult (Primary) Hepatocellular Cancer, Adult (Primary) Liver Cancer, Adult Acute Lymphocytic Leukemia, Adult Acute Myeloid Leukemia, Adult Hodgkin's Disease, Adult Hodgkin's Lymphoma, Adult Lymphocytic Leukemia, Adult Non-Hodgkin's Lymphoma, Adult Primary Liver Cancer, Adult Soft Tissue Sarcoma, AIDS-Related Lymphoma, AIDS-Related Malignancies, Anal Cancer, Astrocytoma, Bile Duct Cancer, Bladder Cancer, Bone Cancer, Brain Stem Glioma, Brain Tumors, Breast Cancer, Cancer of the Renal Pelvis and Ureter, Central Nervous System (Primary) Lymphoma, Central Nervous System Lymphoma, Cerebellar Astrocytoma, Cerebral Astrocytoma, Cervical Cancer, Childhood (Primary) Hepatocellular Cancer, Childhood (Primary) Liver Cancer, Childhood Acute Lymphoblastic Leukemia, Childhood Acute Myeloid Leukemia, Childhood Brain Stem Glioma, Childhood Cerebellar Astrocytoma, Childhood Cerebral Astrocytoma, Childhood Extracranial Germ Cell Tumors, Childhood Hodgkin's Disease, Childhood Hodgkin's Lymphoma, Childhood Hypothalamic and Visual Pathway Glioma, Childhood Lymphoblastic Leukemia, Childhood Medulloblastoma, Childhood Non-Hodgkin's Lymphoma, Childhood Pineal and Supratentorial Primitive Neuroectodermal Tumors, Childhood Primary Liver Cancer, Childhood Rhabdomyosarcoma, Childhood Soft Tissue Sarcoma, Childhood Visual Pathway and Hypothalamic Glioma, Chronic Lymphocytic Leukemia, Chronic Myelogenous Leukemia, Colon Cancer, Cutaneous T-Cell Lymphoma, Endocrine Pancreas Islet Cell Carcinoma. Endometrial Cancer, Ependymoma, Epithelial Cancer, Esophageal Cancer, Ewing's Sarcoma and Related Tumors, Exocrine Pancreatic Cancer, Extracranial Germ Cell Tumor, Extragonadal Germ Cell Tumor, Extrahepatic Bile Duct Cancer, Eye Cancer, Female Breast Cancer, Gaucher's Disease, Gallbladder Cancer, Gastric Cancer, Gastrointestinal Carcinoid Tumor, Gastrointestinal Tumors, Germ Cell Tumors, Gestational Trophoblastic Tumor, Hairy Cell Leukemia, Head and Neck Cancer, Hepatocellular Cancer, Hodgkin's Disease, Hodgkin's Lymphoma, Hypergammaglobulinemia, Hypopharyngeal Cancer, Intestinal Cancers, Intraocular Melanoma, Islet Cell Carcinoma, Islet Cell Pancreatic Cancer, Kaposi's Sarcoma, Kidney Cancer, Laryngeal Cancer, Lip and Oral Cavity Cancer, Liver Cancer, Lung Cancer, Lympho proliferative Disorders, Macroglobulinemia, Male Breast Cancer, Malignant Mesothelioma, Malignant Thymoma, Medulloblastomia, Melanoma, Mesothelioma, Metastatic Occult Primary Squamous Neck Cancer, Metastatic Primary Squamous Neck Cancer, Metastatic Squamous Neck Cancer, Multiple Myeloma, Multiple Myeloma/Plasma Cell Neoplasm, Myelodysplastic Syndrome, Myelogenous Leukemia, Myeloid Leukemia, Myeloproliferative Disorders, Nasal Cavity and Paranasal Sinus Cancer, Nasopharyngeal Cancer, Neuroblastoma, Non-Hodgkin's Lymphoma During Pregnancy, Nonmelanoma Skin Cancer, Non-Small Cell Lung Cancer, Occult Primary Metastatic Squamous Neck Cancer, Oropharyngeal Cancer, Osteo/Malignant Fibrous Sarcoma, Osteosarcoma/Malignant Fibrous Histiocytoma, Osteosarcoma/Malignant Fibrous Histiocytoma of Bone, Ovarian Epithelial Cancer, Ovarian Germ Cell Tumor, Ovarian Low Malignant Potential Tumor, Pancreatic Cancer, Paraproteinemias, Purpura, Parathyroid, Cancer, Penile Cancer, Pheochromocytoma, Pituitary Tumor, Plasma Cell Neoplasm/Multiple Myeloma, Primary Central Nervous System Lymphoma, Primary Liver Cancer, Prostate Cancer, Rectal Cancer, Renal Cell Cancer, Renal Pelvis and Ureter Cancer, Retinoblastoma, Rhabdomyosarcoma, Salivary Gland Cancer, Sarcoidosis Sarcomas, Sezary Syndrome, Skin Cancer, Small Cell Lung Cancer, Small Intestine Cancer, Soft Tissue Sarcoma, Squamous Neck Cancer, Stomach Cancer, Supratentorial Primitive Neuroectodermal and Pineal Tumors, T-Cell Lymphoma, Testicular Cancer, Thymoma, Thyroid Cancer, Transitional Cell Cancer of the Renal Pelvis and Ureter, Transitional Renal Pelvis and Ureter Cancer, Trophoblastic Tumors, Ureter and Renal Pelvis Cell Cancer, Urethral Cancer, Uterine Cancer, Uterine Sarcoma, Vaginal Cancer, Visual Pathway and Hypothalamic Glioma, Vulvar Cancer, Waldenstrom's Macroglobulinemia, Wilm's Tumor, and any other hyperproliferative disease, besides neoplasia, located in an organ system listed above.

In another preferred embodiment, modified transferrin fusion proteins of the invention and/or polynucleotides encoding transferrin fusion proteins of the invention are used to diagnose, prognose, prevent, and/or treat premalignant conditions and to prevent progression to a neoplastic or malignant state, including but not limited to those disorders described above. Such uses are indicated in conditions known or suspected of preceding progression to neoplasia or cancer, in particular, where non-neoplastic cell growth is consisting of hyperplasia, metaplasia, or most particularly, dysplasia has occurred (for review of such abnormal growth conditions, see Robbins. and Angell, 1976, Basic Pathology, 2d Ed. W.B. Saunders Co., Philadelphia, pp. 68-79).

Hyperplasia is a form of controlled cell proliferation, involving an increase in cell number in a tissue or organ, without significant alteration in structure or function. Hyperplastic disorders which can be diagnosed, prognosed, prevented, and/or treated with fusion proteins of the invention and/or polynucleotides encoding transferrin fusion proteins of the invention include, but are not limited to, angiofollicular mediastinal lymph node hyperplasia, angiolymphoid hyperplasia with eosinophilia, atypical melanocytic hyperplasia, basal cell hyperplasia, benign giant lymph node hyperplasia, cementum hyperplasia, congenital adrenal hyperplasia, congenital sebaceous hyperplasia, cystic hyperplasia, cystic hyperplasia of the breast, denture hyperplasia, ductal hyperplasia, endometrial hyperplasia, fibromuscular hyperplasia, foca epithelial hyperplasia, gingival hyperplasia, inflammatory fibrous hyperplasia, inflammatory papillary hyperplasia, intravascular papillary endothelial hyperplasia, nodular hyperplasia of prostate, nodular regenerative hyperplasia, pseudoepitheliomatous hyperplasia, senile sebaceous hyperplasia, and verrucous hyperplasia.

In another embodiment, modified transferrin fusion proteins of the invention and/or polynucleotides encoding transferrin fusion proteins of the invention conjugated to a toxin or a radio-active isotope, as described herein, may be used to treat cancers and neoplasms, including, but not limited to, those described herein. In a further preferred embodiment, transferrin fusion proteins of the invention and/or polynucleotides encoding transferrin fusion proteins of the invention conjugated to a toxin or a radioactive isotope, as described herein, may be used to treat acute myelogenous leukemia.

Additionally, modified fusion proteins of the invention and/or polynucleotides encoding transferrin fusion proteins of the invention may affect apoptosis, and therefore, would be useful in treating a number of diseases associated with increased cell survival or the inhibition of apoptosis. For example, diseases associated with increased cell survival or the inhibition of apoptosis that could be diagnosed, prognosed, prevented, and/or treated by polynucleotides, polypeptides, and/or agonists or antagonists of the invention, include cancers (such as follicular-lymphomas, carcinomas with p53 mutations, and hormone-dependent tumors, including, but not limited to, colon cancer, cardiac tumors, pancreatic cancer, melanoma, retinoblastoma, glioblastoma, lung cancer, intestinal cancer, testicular cancer, stomach cancer, neuroblastoma, myxoma, myoma, lymphoma, endothelioma, osteoblastoma, osteoclastoma, osteosarcoma, chondrosarcoma, adenoma, breast cancer, prostrate cancer, Kaposi's sarcoma and ovarian cancer); autoimmune disorders such as, multiple sclerosis, Sjogren's syndrome, Hashimoto's thyroiditis, biliary cirrhosis, Behcet's disease, Crohn's disease, polymyositis, systemic lupus erythematosus and immune-related glomerulonephritis and rheumatoid arthritis) and viral infections (such as herpes viruses, pox viruses and adenoviruses), inflammation, graft v. host disease, acute graft rejection, and chronic graft rejection.

In preferred embodiments, modified fusion proteins of the invention and/or polynucleotides encoding transferrin fusion proteins of the invention are used to inhibit growth, progression, and/or metastasis of cancers, in particular those listed above.

Additional diseases or conditions associated with increased cell survival that could be diagnosed, prognosed, prevented, and/or treated by modified fusion proteins of the invention and/or polynucleotides encoding transferrin fusion proteins of the invention, include but are not limited to, progression and/or metastases of malignancies and related disorders such as leukemia (including acute leukemia (e.g., acute lymphocytic leukemia, acute myelocytic leukemia (including myeloblastic, promyelocytic, mylomonocytic, monocytic, and erythroleukemia)) and chronic leukemia (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, fiposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, emangioblastoma, acoustic neuroma, oligodendrogliomia, menangioma, melanoma, neuroblastoma, and retinoblastoma.

Diseases associated with increased apoptosis that could be diagnosed, prognosed, prevented, and/or treated by modified fusion proteins of the invention and/or polynucleotides encoding transferrin fusion proteins of the invention, include AIDS; neurodegenerative disorders (such as Alzheimer's disease, Parkinson's disease, amyotrophic lateral sclerosis, retinitis pigmentosa, cerebral degeneration and brain tumor or prion associated disease); autoimmune disorders (such as, multiple sclerosis, Sjogren's syndrome, Hashimoto's thyroiditis, biliary cirrhosis, Behcet's disease, Crohn's disease, polymyositis, systemic lupus erythematosus and immune-related glomerulonephritis and rheumatoid arthritis) myelodysplastic syndromes (such as aplastic anemia), graft Y host disease, ischemic injury (such as that caused by myocardial infarction, stroke and repercussion injury), liver injury (e.g., hepatitis related liver injury, ischemia/reperfusion injury, cholestosis (bile duct injury) and liver cancer); toxin-induced liver disease (such as that caused by alcohol), septic shock, cachexia and anorexia.

Another preferred embodiment utilizes polynucleotides encoding modified transferrin fusion proteins of the invention to inhibit aberrant cellular division, by gene therapy using the present invention, and/or protein fusions or fragments thereof.

Thus, the present invention provides a method for treating cell proliferative disorders by inserting into an abnormally proliferating cell a polynucleotide encoding modified transferrin fusion protein of the present invention, wherein said polynucleotide represses said expression.

Another embodiment of the present invention provides a method of treating cell proliferative disorders in individuals comprising administration of one or more active gene copies of the present invention to an abnormally proliferating cell or cells.

The polynucleotides of the present invention may be delivered directly to cell proliferative disorderly disease sites in internal organs, body cavities, and the like by use of imaging devices used to guide an injecting needle directly to the disease site. The polynucleotides of the present invention may also be administered to disease sites at the time of surgical intervention.

By cell proliferative disease is meant any human or animal disease or disorder, affecting any one or any combination of organs, cavities, or body parts, which is characterized by single or multiple local abnormal proliferations of cells, groups of cells, or tissues, whether benign or malignant.

Any amount of the polynucleotides of the present invention may be administered as long as it has a biologically inhibiting effect on the proliferation of the treated cells.

Moreover, it is possible to administer more than one of the polynucleotides of the present invention simultaneously to the same site. By "biologically inhibiting" is meant partial or total growth inhibition as well as decreases in the rate of proliferation or growth of the cells.

Modified transferrin fusion proteins of the invention and/or polynucleotides encoding transferrin fusion proteins of the invention are useful in inhibiting the metastasis of proliferative cells or tissues. Inhibition may occur as a direct result of administering these transferrin fusion proteins and/or polynucleotides, or indirectly, such as activating the expression of proteins known to inhibit metastasis, for example alpha, integrins, (See, e.g., Curr. Top. Mirobiol. Immunol. 1998; 231:1 41, which is hereby incorporated by reference). Such therapeutic affects of the present invention may be achieved either alone, or in combination with small molecule drugs or adjuvants.

In another embodiment, the invention provides a method of delivering compositions containing the transferrin fusion proteins of the invention and/or polynucleotides encoding transferrin fusion proteins of the invention to targeted cells expressing a polypeptide bound by, that binds to, or associates with a modified transferrin fusion protein of the invention. Transferrin fusion proteins of the invention may be associated with heterologous polypeptides, heterologous nucleic acids, toxins, or prodrugs via hydrophobic, hydrophilic, ionic and/or covalent interactions.

Kidney diseases which can be diagnosed, prognosed, prevented, and/or treated with compositions of the invention include, but are not limited to, acute kidney failure, chronic kidney failure, atheroembolic renal failure, end-stage renal disease, inflammatory diseases of the kidney (e.g., acute glomerulonephritis, post infectious glomerulonephritis, rapidly progressive glomerulonephritis, nephritic syndrome, membranous glomerulonephritis, familial nephritic syndrome, membrane proliferative glomerulonephritis and mesangial proliferative glomerulonephritis, chronic glomerulonephritis, acute tubulo-interstitial nephritis, chronic tubulointerstitial nephritis, acute post-streptococcal glomerulonephritis (PSGN), pyelonephritis, lupus nephritis, chronic nephritis, interstitial nephritis, and post streptococcal glomerulonephritis), blood vessel disorders of the kidneys (e.g., kidney infarction, atheroembolic kidney disease, cortical necrosis, malignant nephrosclerosis, renal vein thrombosis, renal under perfusion, renal retinopathy, renal ischemia-reperfusion, renal artery embolism and renal artery stenosis), and kidney disorders resulting form urinary tract disease (e.g., pyelonephritis, hydronephrosis, urolithiasis (renal lithiasis, nephrolithiasis), reflux nephropathy, urinary tract infections, urinary retention, and acute or chronic unilateral obstructive uropathy). In addition, compositions of the invention can be used to diagnose, prognose, prevent, and/or treat metabolic and congenital disorders of the kidney (e.g., uremia, renal amyloidosis, renal osteodystrophy, renal tubular acidosis, renal glycosuria, nephrogenic diabetes insipidus, cystinuria, Fanconi's syndrome, renal fibrocystic osteosis (renal rickets), Hartnup disease, Bartter's syndrome, Liddle's syndrome, polycystic kidney disease, medullary cystic disease, medullary sponge kidney, Alport's syndrome, nail-patella syndrome, congenital nephritic syndrome, CRUSH syndrome, horseshoe kidney, diabetic nephropathy, nephrogenic diabetes insipidus, analgesic nephropathy, kidney stones, and membranous nephropathy), and autoimmune disorders of the kidney (e.g., systemic lupus erythematosus (SLE), Good pasture syndrome, IgA nephropathy, and ICFM mesangial proliferative glomerulonephritis).

Compositions of the invention can also be used to diagnose, prognose, prevent, and/or treat sclerotic or lecrotic disorders of the kidney (e.g., glomerulosclerosis, diabetic nephropathy, focal Fsegmental glomerulo sclerosis (FSGS), narcotizing glomerulonephritis, and renal papillary necrosis), cancers of the kidney (e.g., nephroma, hypernephroma, nephroblastoma, renal cell cancer, transitional cell cancer, renal adenocarcinoma, squamous cell cancer, and Wilm's tumor), and electrolyte imbalances (e.g., nephrocalcinosis, pyuria, edema, hydronephritis, proteinuria, hyponatremia, hypernatremia, hypokalemia, hyperkalemia, hypocalcemia, hypercalcemia, hypophosphatemia, and hyperphosphatemia).

Compositions of the invention may be administered using any method known in the art, including, but not limited to, direct needle injection at the delivery site, intravenous injection, topical administration, catheter infusion, biolistic injectors, particle accelerators, gel foam sponge depots, other commercially available depot materials, osmotic pumps, oral or suppositorial solid pharmaceutical formulations, decanting or topical applications during surgery, aerosol delivery. Such methods are known in the art. Compositions of the invention may be administered as part of a Therapeutic, described in more detail below.

Modified transferrin fusion proteins of the invention and/or polynucleotides encoding transferrin fusion proteins of the invention, may be used to treat, prevent, diagnose, and/or prognose cardiovascular disorders, including, but not limited to, peripheral artery disease, such as limb ischemia.

Cardiovascular disorders, includes, but is not limited to, cardiovascular abnormalities, such as arterio arterial fistula, arteriovenous fistula, cerebral arteriovenous malformations, congenital heart defects, pulmonary atresia, and Scimitar Syndrome.

Congenital heart defects include, but are not limited to, aortic coarctation, cortriatriatum, coronary vessel anomalies, crisscross heart, dextrocardia, patent ductus arteriosus, Ebstein's anomaly, Eisenmenger complex, hypoplastic left heart syndrome, levocardia, tetralogy of fallot, transposition of great vessels, double outlet right ventricle, tricuspidatresia, persistent truncus arteriosus, and heart septal defects, such as aortopulmonary septald defect, endocardial cushion defects, Lutembacher's Syndrome, trilogy of Fallot, ventricular heart septal defects.

Cardiovascular disorders also include, but are not limited to, heart disease, such arrhythmias, carcinoid heart disease, high cardiac output, low cardiac output, cardiactamponade, endocarditis (including bacteria), heart aneurysm, cardiac arrest, congestive heart failure, congestive cardiomyopathy, paroxysmal dyspnea, cardiac edema, heart hypertrophy, congestive cardiomyopathy left ventricular hypertrophy, right ventricularhypertrophy, post-infarction heart rupture, ventricular septal rupture, heart valve diseases myocardial diseases, myocardial ischemia, pericardial effusion, pericarditis (including constrictive and tuberculous), pricumopericardium, post pericardiotomy syndrome, pulmonary heart disease, rheumatic heart disease, ventricular dysfunction, hyperemia, cardiovascular pregnancy complications, Scimitar Syndrome, cardiovascular syphilis, and cardiovascular tuberculosis.

Arrhythmias include, but are not limited to, sinus arrhythmia, atrial fibrillation, atrial flutter, bradycardia, extrasystole, Adams-Stokes Syndrome, bundle-branch block, sinoatrial block, long QT syndrome, parasystole, Lown-Ganong-Levine Syndrome, Mahaim-type pre-excitation syndrome, Wolff-Parkinson-White syndrome, sick sinus syndrome, itachycardias, and ventricular fibrillation. Tachycardias include paroxysmal tachycardia, suprayentriculai tachycardia, accelerated idioventricular rhythm, atrioventricular nodal reentry tachyeardia, ectopic atrial tachycardia, ectopic junctional tachycardia, sinoattial nodalreentry tachycardia, sinus tachycardia, Torsades de Pointes, and ventricular tachycardia.

Heart valve diseases include, but are not limited to, aortic valve insufficiency aortic valve stenosis, heart murmurs, aortic valve prolapse, neutral valve prolapse, tricuspid valve prolapse, mitral valve insufficiency, mitral valve stenosis, pulmonary atresia, pulmonary valve insufficiency, pulmonary valve stenosis, tricuspid atresia, tricuspid valve insufficiency, and tricuspid valve stenosis.

Myocardial diseases include, but are not limited to, alcoholic cardiomyopathy, congestive cardiomyopathy, hypertrophic cardiomyopathy, aortic subvalvular stenosis, pulmonary subvalvular stenosis, restrictive cardiomyopathy, Chagas cardiomyopathy, endocardial fibroelastosis, endomyocardial fibrosis, Kearns Syndrome, myocardial reperfusion injury, and myocarditis.

Myocardial ischemias include, but are not limited to, coronary disease, such as angina pectoris, coronary aneurysm, coronary arteriosclerosis, coronary thrombosis, coronary vasospasm, myocardial infarction, and myocardial stunning.

Cardiovascular diseases also include vascular diseases such as aneurysms, angiodysplasia, angiomatosis, bacillary angiomiatosis, Hippel-Lindau Disease, Klippel Trenaunay Weber Syndrofne, Sturge Weber Syndrome, angioneurotic edema, aortic diseases, Takayasu's Arthritis, aortitis, Leriche's Syndrome, arterial occlusive diseases, arthritis, enarteritis, polyarteritis nodosa, cerebrovascular disorders, diabetic angiopathies, diabetic retinopathy, embolisms, thrombosis, erythromelalgia, hemorrhoids, hepatic veno-occlusive disease, hypertension, hypotension, ischemia, peripheral vascular diseases, phlebitis, pulmonary veno-occlusive disease, Raynaud's disease, CREST syndrome, retinal vein occlusion, Scimitar syndrome, superior vena cava syndrome, telangiectasia, ataxia telangiectasia, hereditary hemorrhagic telangiectasia, varicocele, varicose veins, varicoseulcer, vasculitis, and venous insufficiency.

Cerebrovascular disorders include, but are not limited to, cardio artery diseases but includes respiratory disorders. Transferrin fusion proteins of the invention and/or polynucleotides encoding transferrin fusion proteins of the invention may be used to treat, prevent, diagnose, and/or prognose diseases and/or disorders of the respiratory system.

Diseases and disorders of the respiratory system include, but are not limited to, nasalvestibulitis, nonallergic rhinitis (e.g., acute rhinitis, chronic rhinitis, atrophic rhinitis, vasomotor rhinitis), nasal polyps, and sinusitis, juvenile angiofibromas, cancer of the nose and juvenile papillomas, vocal cord polyps, nodules (singer's nodules), contact ulcers, vocal cord paralysis, laryngoceles, pharyngitis (e.g., viral and bacterial), tonsillitis, tonsillar cellulitis, parapharyngeal abscess, laryngitis, laryngoceles, and throat cancers (e.g., cancer of the nasopharynx, tonsil cancer, larynx cancer), lung cancer (e.g., squamous cell carcinoma, small cell (oat cell) carcinoma, large cell carcinoma, and adenocarcinoma), allergic disorders (eosinophilic pneumonia, hypersensitivity pneumonitis (e.g., extrinsicallergic alveolitis, allergic interstitial pneumonitis, organic dust pneumoconiosis, allergic bronchopulmoniary aspergillosis, asthma, Wegener's granulomatosis (granulomatous vasculitis), Goodpasture's syndrome), pneumonia (e.g., bacterial pneumonia (e.g., *Streptococcus pneumoniae* (pneumonccoccal pneumonia), *Staphylococcus aureus* (staphylococeal pneumonia), Gram negative bacteria pneumonia (caused by, e.g., *Klebsiella* and *Pseudomonas* spp.), *Mycoplasma pneumoniae* pneumonia, *Hemophilus influenza* pneumonia, *Legionella pneumophila* (Legionnaires' disease), and *Chlamydia psittaci* (Psittacosis)), and viral pneumonia (e.g., influenza, chickenpox (varicella).

Additional diseases and disorders of the respiratory system include, but are not limited to bronchiolitis, polio (poliomyelitis), croup, respiratory syncytial viral infection, mumps, erythema infectiosum (fifth disease), roseola infantum, progressive rubellapanencephalitis, German measles, and subacute sclerosing panencephalitis), fungal pneumonia (e.g., Histoplasmosis, Coccidioidomycosis, Blastomycosis, fungal infections in people with severely suppressed immune systems (e.g., cryptococcosis, caused by *Cryptococcus neoformans*; aspergillosis, caused by *Aspergillus* spp.) candidiasis, caused by *Candida*; and mucormycosis)), *Pneumocystis carinii* (pneumocystis pneumonia), atypicalpneumonias (e.g., *Mycoplasma* and *Chlamydia* spp.), opportunistic infection pneumonia, nosocomial pneumonia, chemical pneumonitis, and aspiration pneumonia, pleural disorders (e.g., pleurisy, pleural effusion, and pneumothorax (e.g., simple spontaneous pneumothorax, complicated spontaneous pneumothorax, tension pneumothorax)), obstructive airway diseases (e.g., asthma, chronic obstructive pulmonary disease (COPID), emphysema, chronic or acute bronchitis), occupational lung diseases (e.g., silicosis, blacklung (coal workers' pneumoconiosis, asbestosis, berylliosis, occupational asthma, and byssinosis), Infiltrative Lung Disease (e.g., pulmonary-fibrosis (e.g., usual interstitial pneumonia), idiopathic pulmonary fibrosis, desquamative interstitial pneumonia, lymphoid interstitial pneumonia, histiocytosis (e.g., Letterer-Siwe disease, Hand-Schüller-Christian disease, eosinophilic granuloma), idiopathic pulmonary hemosiderosis, sarcoidosis and pulmonary, alveolar proteinosis), Acute respiratory distress syndrome (also called, e.g., adult respiratory distress syndrome), edema, pulmonary embolism, bronchitis (e.g., viral, bacterial), bronchiectasis, atelectasis, lung abscess (caused by, e.g., *Staphylococcus aureus* or *Legionella pneumophila*), and cystic fibrosis.

Cancers which may be treated with modified fusion proteins of the invention and/or polynucleotides encoding transferrin fusion proteins of the invention include, but are not limited to solid tumors, including prostate, lung, breast, ovarian, stomach, pancreas, larynx, esophagus, liver, parotid, biliary tract, colon, rectum, cervix, uterus, endometrium, kidney, bladder, thyroid cancer; primary tumors and metastases; melanomas; glioblastoma; Kaposi's sarcoma; leiomyosarcoma; non-small cell lung cancer; colorectal cancer; advanced malignancies; and blood born tumors such as leukemia. For example, fusion proteins of the invention and/or polynucleotides encoding transferrin fusion proteins of the invention may be delivered topically, in order to treat cancers such as skin cancer, head and neck tumors, breast tumors, and Kaposi's sarcoma.

Modified transferrin fusion proteins of the invention and/or polynucleotides encoding transferrin fusion proteins of the invention may be useful, in treating other disorders, besides cancers, which involve angiogenesis. These disorders include, but are not limited to: benign tumors, for example hemangiomas, acoustic neuromas, neurofibromas, trachomas, and pyogenicgranulomas; artheroscleric plaques; ocular angiogenic diseases, for example, diabetic retinopathy, retinopathy of prematurity, macular degeneration, corneal graft rejection, neovascular glaucoma, retrolental fibroplasia, rubeosis, retinoblastoma, uvietis and Pterygiaab normal blood vessel growth) of the eye; rheumatoid arthritis; psoriasis; delayed wound healing; endometriosis; vasculogenesis; granulations; hypertrophic scars (keloids); nonunion fractures; scleroderma; trachoma; vascular adhesions; myocardial angiogenesis; coronary collaterals; cerebral collaterals; arteriovenous malformations; ischemic limb angiogenesis; Osler-Webber Syndrome; plaque neovascularization; telangiectasia; hemophiliac joints; angiofibroima; fibromuscular dysplasia; wound granulation; Crohn's disease; and atherosclerosis.

Thus, within one aspect of the present invention methods are provided for treating neovascular diseases of the eye.

Additionally, disorders which can be treated with modified fusion proteins of the invention and/or polynucleotides encoding transferrin fusion proteins of the invention include, but are not limited to, hemangioma, arthritis, psoriasis, angiofibroma, atherosclerotic plaques, delayed wound healing, granulations, hemophilic joints hypertrophic scars, nonunion fractures, Osler-Weber syndrome, pyogenic granuloma, scleroderma, trachoma; and vascular adhesions.

Moreover, disorders and/or states, which can be treated, prevented, diagnosed, and/or prognosed with the modified transferrin fusion proteins of the invention and/or polynucleotides encoding transferrin fusion proteins of the invention include, but are not limited to, solid tumors, blood born tumors such as leukemia, tumor metastasis, Kaposi's sarcoma, benign tumors, for example hemangiomas, acoustic neuromas, neurofibromas, trachomas, and pyogenic granulomas, rheumatoid arthritis, psoriasis, ocularangiogenic diseases, for example, diabetic retinopathy, retinopathy of prematurity, macular degeneration, corneal graft rejection, neovascular glaucoma, retrolental fibroplasia, rubeosis, refi- noblastoma, and uvietis, delayed wound healing, endometriosis, vasculogenesis, granulations, hypertrophic scars (keloids, nonunion fractures, sclerodemm, trachoma, vascular adhesions, myocardial angiogenesis, coronary collaterals, cerebral collaterals, arteriovenous malformations, ischemic limb angiogenesis, Osler-Webber Syndrome, plaque neovascularization, telangiectasia, hemophiliac joints, angiofibroma fibromuscular dysplasia, wound granulation, Crohn's disease, atherosclerosis, birth control agent by preventing vascularization required for embryo, implantation controlling menstruation, diseases that have angiogenesis as a pathologic consequence such as cat scratch disease (Rochele nunalia quintosa), ulcers (*Helicobacter pylori*), Bartonellosis and baculary angiomatosis.

In one aspect of the birth control method, an amount of the compound sufficient to block embryo implantation is administered before or after intercourse and fertilization have occurred, thus providing an effective method of birth control, possibly a "morning after" method. Modified transferrin fusion proteins of the invention and/or polynucleotides encoding transferrin fusion proteins of the invention may also be used in controlling menstruation or administered as either a peritoneal lavage fluid or for peritoneal implantation in the treatment of endometriosis.

Modified transferrin fusion proteins of the invention and/or polynucleotides encoding transferrin fusion proteins of the invention may be utilized in a wide variety of surgical procedures.

Diseases associated with increased cell survival or the inhibition of apoptosis that could be treated, prevented, diagnosed, and/or prognosed using modified fusion proteins of the invention and/or polynucleotides encoding transferrin fusion proteins of the invention, include cancers (such as follicular lymphomas, carcinomas with mutations, and hormone-dependent tumors, including, but not limited to colon cancer, cardiac tumors, pancreatic cancer, melanoma, retinoblastoma, glioblastoma, lung cancer, intestinal cancer, testicular cancer, stomach cancer, neuroblastoma, myxoma, myoma, lymphoma, endothelioma, osteoblastoma, osteoclastoma, osteosarcoma, chondrosarcoma, adenoma, breast cancer, prostate cancer, Kaposi's sarcoma and ovarian cancer); autoimmune disorders (such as, multiple sclerosis, Sjogren's syndrome, Hashimoto's thyroiditis, biliary cirrhosis, Behcet's disease, Crohn's disease, polymyositis, systemic lupus thematosus and immune-related ryglomerulonephritis and rheumatoid arthritis) and viral infections (such as herpes viruses, pox viruses and adenoviruses), inflammation, graft v. host disease, acute graft rejection, and chronic graft rejection.

In preferred embodiments, modified fusion proteins of the invention and/or polynucleotides encoding transferrin fusion proteins of the invention are used to inhibit growth, progression, and/or metasis of cancers, in particular those listed above.

Additional diseases or conditions associated with increased cell survival that could be treated or detected by modified fusion proteins of the invention and/or polynucleotides encoding, transferrin fusion proteins of the invention include, but are not limited to, progression, and/or metastases of malignances and related disorders such as leukemia (including acute leukemia (e.g., acute lymphocytic leukemia, acute myelocytic leukemia (including myeloblastic, promyelocytic, myelomonocytic, monocytic, and erythroleukemia)) and chronic leukemia (e.g., chronic myelocytic (granulocytic) leukemia and chroniclymphocytic leukemia)), polycytemia vera, lymphomas (e.g., Hodgkin's disease and non-Hodgkin's disease), multiple myeloma, Waldenstrom's macroglobulinemia, heavy chain disease, and solid tumors including, but not limited to, Sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basa cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct Carcinoma, choriocarcinoma, seminoma, embryonal carcinoma, Wilm's tumor, cervical cancer, testicular tumor, Jung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma neuroblastoma, and retinoblastoma.

Diseases associated with increased apoptosis that could be treated, prevented, diagnosed, and/or prognosed using modified fusion proteins of the invention and/or polynucleotides encoding transferrin fusion proteins of the invention, include, but are not limited to, AIDS; neurodegenerative disorders (such as Alzheimer's disease, Parkinson's disease, Amyotrophic lateral sclerosis, Retinitis pigmentosa, Cerebellar degeneration and brain tumor or prion associated disease); autoimmune disorders (such as, multiple sclerosis, Sjogren's syndrome, Hashimoto's thyroiditis, biliary cirrhosis, Behcet's disease, Crohn's' disease, polymyositis, systemic lupus erythematosus and immune-related glomerulonephritis and rheumatoid arthritis) Myelodysplastic syndromes (such as aplastic anemia), graft v. host disease, ischemic injury (such as that caused, by myocardial infarction, stroke and reperfusion injury), liver injury (e.g., hepatitis related liver injury, ischemia/reperfusion injury, cholestosis (bile duct injury) and liver cancer); toxin-induced liver disease (such as that caused by alcohol), septic shock, cachexia and anorexia.

In addition, modified fusion proteins of the invention and/or polynucleotides encoding transferrin fusion proteins of the invention could be, used to treat or prevent the onset of diabetes mellitus. In patients with newly diagnosed Types I and II diabetes, where some islet cell function remains, fusion proteins of the invention and/or polynucleotides encoding transferrin fusion proteins of the invention, could be used to maintain the islet function so as to alleviate, delay or prevent permanent manifestation of the disease. Also, fusion proteins of the invention and/or polynucleotides encoding transferrin fusion proteins of the invention could be used as an auxiliary in islet cell transplantation to improve or promote islet cell function.

The modified transferrin fusion proteins of the invention and/or polynucleotides encoding transferrin fusion proteins of the invention may be used for the diagnosis and/or treatment of diseases, disorders, damage or injury of the brain and/or nervous system. Nervous system disorders that can be treated with the compositions of the invention (e.g., fusion proteins of the invention and/or polynucleotides encoding transferrin fusion proteins of the invention), limited to nervous systems include, but are not limited injuries, and diseases or disorders which result in either a disconnection of axons, a diminution or degeneration of neurons, or demyelination. Nervous system lesions which may be treated in a patient (including human and non-human mammalian patients) according to the methods of the invention, include but are not limited to, the following lesions of either the central (including spinal cord, brain) or peripheral nervous systems: (1) ischemic lesions, in which a lack of oxygen in a portion of the nervous system results in neuronal injury or death, including cerebral infarction or ischemia, or spinal cord infarction or ischemia; (2) traumatic lesions, including lesions caused by physical injury or associated with surgery, for example, lesions which sever a portion of the nervous system, or compression injuries; (3) malignant lesions, in which a portion of the nervous system is destroyed or injured by malignant tissue which is either a nervous system associated malignancy or a malignancy derived from nervous system tissue; (4) infectious lesions in which a portion of the nervous system is destroyed or injured as a result of infection, for example, by an abscess or associated with infection by human immunodeficiency virus, herpes zoster, or herpes simplex virus or with, Lyme disease, tuberculosis, or syphilis; (5) degenerative lesions, in which a portion of the nervous system is destroyed or injured as a result of a degenerative process including but not limited to, degeneration associated with Parkinson's disease, Alzheimer's disease, Huntington's chorea, or amyotrophic lateral sclerosis (ALS); (6) lesions associated with nutritional diseases or disorders, in which a portion of the nervous system is destroyed or injured by a nutritional disorder or disorder of metabolism including, but not limited to vitamin B12 deficiency, folic acid deficiency, Wernicke disease, tobacco-alcohol amblyopic, Marchiafava-Blanami disease (primary degeneration of the corpus callosum), and alcoholic cerebral degeneration; (7) neurological lesions associated with systemic diseases including, but not limited to diabetes (diabetic neuropathy, Bell's palsy), systemic lupus erythematosus, carcinoma, or sarcoidoisis; (8) lesions caused by toxic substances including alcohol, lead, or particular, neurotoxins; and (9) demyelinated lesions in which a portion of the nervous system is destroyed or injured by a demyelinating disease including, but not limited to, multiple sclerosis, human immunodeficiency virus-associated myelopathy, transverse myelopathy or various etiologies, progressive multifocal leukoencephalopathy, and central pontine myelinolysis.

In one embodiment, the modified transferrin fusion proteins of the invention and/or polynucleotides encoding transferrin fusion proteins of the invention are used to protect neural cells from the damaging effects of hypoxia. In a further preferred embodiment, the modified transferrin fusion proteins of the invention and/or polynucleotides encoding transferrin fusion proteins of the invention are used to protect neural cells from the damaging effects of cerebral hypoxia.

In specific embodiments, motor neuron disorders that may be treated according to the invention include, but are not limited to, disorders such as infarction, infection, exposure to toxin, trauma, surgical damage, degenerative disease or malignancy that may affect motor neurons as well as other components of the nervous system, as well as disorders that selectively affect neurons such as amyotrophic lateral sclerosis, and including, but not limited to, progressive spinal muscular atrophy, progressive bulbar palsy, primary lateral sclerosis, infantile and juvenile muscular atrophy, progressive bulbar paralysis of childhood (Fazio-Londe syndrome), poliomyelitis and the post polio syndrome, and Hereditary Motor sensory Neuropathy (Charcot-Marie-Tooth Disease).

Further, modified fusion proteins of the invention and/or polynucleotides encoding transferrin fusion proteins of the invention may play a role in neuronal survival; synapse formation; conductance; neural differentiation, etc. Thus, compositions of the invention (including fusion proteins of the invention and/or polynucleotides encoding transferrin fusion proteins of the invention) may be used to diagnose and/or treat or prevent diseases or disorders associated with these roles, including, but not limited to, learning and/or cognition disorders. The compositions of the invention may also be useful in the treatment or prevention of neurodegenerative disease states and/or behavioral disorders. Such neurodegenerative disease states and/or behavioral disorders include, but are not limited to, Alzheimer's Disease, Parkinson's Disease, Huntington's Disease, Tourette Syndrome, schizophrenia, mania, dementia, paranoia, obsessive compulsive disorder, panic disorder, learning disabilities, ALS, psychoses, autism, and altered behaviors, including disorders in feeding, sleep patterns, balance, and perception.

Examples of neurologic diseases which can be treated or detected with modified fusion proteins of the invention and/or polynucleotides encoding transferrin fusion proteins of the invention include, brain diseases, such as metabolic brain diseases which includes phenylketonuria such as maternal phenylketonuria, pyruvate carboxylase deficiency, pyruvate dehydrogenase complex deficiency, Wernicke's Encephalopathy, brain edema, brain neoplasms such as cerebellar neoplasms which include infratentorial neoplasms, cerebral ventricle neoplasms such as choroid plexus neoplasms, hypothalamic neoplasms, supratentorial neoplasms, canavan disease, cerebellar diseases such as cerebellar ataxia which include spinocerebellar degeneration such as ataxia telangiectasia, cerebellar dyssynergia, Friederich's Ataxia, Machado-Joseph Disease, olivopontocerebellar atrophy, cerebellar neoplasms such as infratentorial neoplasms, diffuse cerebral sclerosis such as encephalitis periaxialis, globoid cell leukodystrophy, metachromatic leukodystrophy and subacute sclerosing panencephalitis.

Additional neurologic diseases which can be treated or detected with modified fusion proteins of the invention and/or polynucleotides encoding transferrin fusion proteins of the invention include cerebrovascular disorders (such as carotid artery diseases which include carotid artery thrombosis, carotid stenosis and Moyamoya Disease), cerebral amyloid angiopathy, cerebral aneurysm, cerebral anoxia, cerebral arteriosclerosis, cerebral arteriovenous malformations, cerebral artery diseases, cerebral embolism and thrombosis such as carotid artery thrombosis, sinus thrombosis and Wallenberg's Syndrome, cerebral hemorrhage such as epidermal hematoma, subdural hematoma and subarachnoid hemorrhage, cerebral infarction, cerebral ischemia such as transient cerebral ischemia, Subclavian Steal Syndrome and vertebrobasilar insufficiency, vascular dementia such as multi-infarct dementia, periventricular leukomalacia, vascular headache such as cluster headache and migraine.

Additional neurologic diseases which can be treated or detected with modified fusion proteins of the invention and/or polynucleotides encoding transferrin fusion proteins of the invention include dementia such as AIDS Dementia Complex, presenile dementia such as Alzheimer's Disease and Creutzfeldt-Jakob Syndrome, senile dementia such as Alzheimer's Disease and progressive supranuclear palsy, vascular dementia such as multi-infarct dementia, encephalitis which include encephalitis periaxialis, viral encephalitis such as epidemicencephalitis, Japanese Encephalitis, St. Louis Encephalitis, tick-borne encephalitis and West Nile Fever, acute disseminated encephalomyelitis, meningoencephalitis such as uveomeningoencephalitic syndrome, Postencephalitic Parkinson Disease and subacute sclerosing panencephalitis, encephalomalacia such as periventricular leukomalacia, epilepsy such as generalized epilepsy, which includes infantile spasms, absence epilepsy, myoclonic epilepsy which includes MERRF Syndrome, tonic-clonic epilepsy, partial epilepsy such as complex partial epilepsy, frontal lobe epilepsy and temporal lobe epilepsy, post-traumatic epilepsy, status epilepticus such as Epilepsia Partialis Continua, and Hallervorden-Spatz Syndrome.

Additional neurologic diseases which can be treated or detected with modified fusion proteins of the invention and/or polynucleotides encoding transferrin fusion proteins of the invention include hydrocephalus such as Dandy-Walker Syndrome and normal pressure hydrocephalus, hypothalamic diseases such as hypothalamic neoplasms, cerebral malaria, narcolepsy which includes cataplexy, bulbar poliomyelitis, cerebripseudo tumor, Rett Syndrome, Reye's Syndrome, thalamic diseases, cerebral toxoplasmosis, intracranialtuberculoma and Zellweger Syndrome, central nervous system infections such as AIDS, Dementia Complex, Brain Abscess, subdural empyema, encephalomyelitis such as Equine Encephalomyelitis, Venezuelan Equine Encephalomyelitis, Necrotizing Hemorrhabaic Encephalomyelitis, Visna, and cerebral malaria.

Additional neurologic diseases which can be treated or detected with modified fusion proteins of the invention and/or polynucleotides encoding transferrin fusion proteins of the invention include meningitis such as arachnoiditis, aseptic meningitis such as viral meningitis which includes lymphocytic chronic meningitis, Bacterial meningitis which includes *Haemophilus* Meningitis, *Listeria* Meningitis, Meningococcal Meningitis such as Waterhouse-Fridericlisen Syndrome, Pneumococcal Meningitis and meningeal tuberculosis, fungal meningitis such as Cryptococcal Meningitis, subdural effusion, meningencephalitis, myelitis such as transverse myelitis, neurosyphilis such as tabes dorsalis, poliomyelitis which includes bulbar poliomyelitis and post poliomyelitis syndrome, prion diseases (such as Creutzfeldt-Jakob Syndrome, Bovine Spongiform Encephalopathy, Gerstmann-Straussler Syndrome, Kuru, Scrapie), and cerebral toxoplasmosis.

Additional neurologic diseases which can be treated or detected with modified fusion proteins of the invention and/or polynucleotides encoding transferrin fusion proteins of the invention include central nervous system neoplasms such as brain neoplasms that include cerebellarneoplasms such as infratentorial neoplasms, cerebral ventricle neoplasms such as choroids plexus neoplasms, hypothalamic neoplasms and supratentorial neoplasms, meningealneoplasms, spinal cord neoplasms which include epidural neoplasms, demyelinating diseases such as Canavan Diseases, diffuse cerebral sculleries which include sadrenoleukodystrophy, encephalitis periaxialis, globoid cell leukodystrophy, diffuse cerebral sclerosis such as metachromatic leukodystrophy, allergic encephalomyelitis, necrotizing hemorrhagic encephalomyelitis, progressive multifocal leukoencephalopathy, in multiple sclerosis, central pontine myelinolysis, transverse myelitis, neuromyelitis optica, Scrapie, Swayback, Chronic Fatigue Syndrome, Visna, High Pressure Nervous Syndrome, Meningism, spinal cord diseases such as amyotonia congenita, amyotrophic lateral-sclerosis, spinal muscular atrophy such as Werdnig-Hoffmann Disease, spinal cord compression, spinal cord neoplasms such as epidural neoplasms, syringomyelia., Tabes Dorsalis, Stiff-Man Syndrome, mental retardation such as Angelman Syndrome, Cri-du-Chat Syndrome, De Lange's Syndrome, Down Syndrome, Gangliosidoses such as gangliosidoses G(MI), Sandhoff Disease, Tay-Sachs Disease, Hartnup Disease, homocystinuria, Laurence-Moon-Bied Syndrome, Lesch-Nylian Syndrome, Maple Syrup Urine Disease, mucolipidosis such as fucosidosis, neuronal ceroid-lipofuscinosis, oculocerebrorenal syndrome, phenylketonuria such as maternal phenylketonuria, Prader-Willi Syndrome, Rett Syndrome, Rubinstein-Taybi Syndrome, Tuberous Sclerosis, WAGR Syndrome, nervous system abnormalities such as holoprosencephaly, neural tube defects such as anencephaly which includes hydrangencephaly, Arnold-Chairi Deformity, encephalocele, meningocele, meningomyelocele, spinal dysraphism such as Spina bifida cystica and spina bifida occulta.

Endocrine system and/or hormone imbalance and/or diseases encompass disorders of uterine motility including, but not limited to complications with pregnancy and labor (e.g., pre-term labor, post-term pregnancy, spontaneous abortion, and slow or stopped labor); and disorders and/or diseases of the menstrual cycle, (e.g., dysmenorrhea and endometriosis).

Endocrine system and/or hormone imbalance disorders and/or diseases include disorders and/or diseases of the pancreas, such as, for example, diabetes mellitus, diabetes insipidus, congenital pancreatic agenesis, pheochromocytoma islet cell tumor syndrome; disorders and/or diseases of the adrenal glands such as, for example, Addison's Disease, corticosteroid deficiency, virilizing disease, hirsutism, Cushing's Syndrome, hyperaldosterlonism, pheochromocytoma; disorders and/or diseases of the pituitary gland, such as, for example, hyperpituitarism, hypopituitarism, pituitary dwarfism, pituitary adenoma, panhypopituitarism, acromegaly, gigantism; disorders and/or diseases of the thyroid, including but not limited to, hyperthyroidism, hypothyroidism, Plummer's disease, Graves' disease (toxic diffuse goiter), toxic nodular goiter, thyroiditis (Hashimoto's thyroiditis, subacute granulomatous thyroiditis, and silent lymphocytic thyroiditis), Pendred's syndrome, myxedema, cretinism, thyrotoxicosis, thyroid hormone coupling defect, thymic aplasia, Hurthle cell tumors of the thyroid, thyroid cancer, thyroid carcinoma, Medullary thyroid carcinoma; disorders and/or diseases of the parathyroid, such as, for example, hyperparathyroidism, hypoparathyroidism; disorders and/or diseases of the hypothalamus.

In addition, endocrine system and/or hormone imbalance disorders and/or diseases may also include disorders and/or diseases of the testes or ovaries, including cancer. Other disorders and/or diseases of the testes or ovaries further include, for example, ovarian cancer, polycystic ovary syndrome, Klinefelter's syndrome, vanishing testes syndrome (bilateral anorchia), congenital absence of Leydig's cells, cryptorchidism, Noonan's syndrome, myotonic dystrophy, capillary haemangioma of the testis (benign), neoplasias of the testis and neotestis.

Moreover, endocrine system and/or hormone imbalance disorders and/or diseases may also include disorders and/or diseases such as, for example, polyglandular deficiency syndromes, pheochromocytoma, neuroblastoma, multiple Endocrine neoplasia, and disorders and/or cancers of endocrine tissues.

The modified transferrin fusion proteins of the invention and/or polynucleotides encoding transferrin fusion proteins of the invention may be used for the diagnosis, treatment, or prevention of diseases and/or disorders of the reproductive system. Reproductive system disorders that can be treated by the compositions of the invention, include, but are not limited to, reproductive system injuries, infections, neoplastic disorders, congenital defects, and diseases or disorders will result in infertility, complications with pregnancy, labor, or parturition, and postpartum difficulties.

Reproductive system disorders and/or diseases include diseases and/or disorders, of the testes, including testicular atrophy, testicular feminization, cryptorchism (unilateral and bilateral), anorchia, ectopic testis, epididymitis and orchitis (typically resulting from infections such as, for example, gonorrhea, mumps, tuberculosis, and syphilis), testiculartorsiori, vasitis nodosa, germ cell tumors (e.g., seminomas, embryonal cell carcinomas, teratocarcinomas, choriocarcinomas, yolk sac tumors, and teratomas), stromal tumors (e.g., Leydig cell tumors), hydrocele, hematocele, varicocele, spermatocele, inguinal hernia, and disorders of sperm production (e.g. immotile cilia syndrome, spermia, asthenozoospermia, azoospermia, oligospermia, and teratozoospermia).

Reproductive system disorders also include disorders of the prostate gland, such as acute non-bacterial prostatitis, chronic non-bacterial prostatitis, acute bacterial prostatitis, chronic bacterial prostatitis, postatodystonia, prostatosis, granulomatotis prostatitis, malacoplakia, benign prostatic hypertrophy or hyperplasia, and prostate neoplastic disorders, including adenocarcinomas, transitional cell carcinomas, ductal carcinomas, and squamous cell carcinomas.

Additionally, the compositions of the invention may be useful in the diagnosis, treatment, and/or prevention of disorders or diseases of the penis and urethra, including inflammatory disorders, such as balanopbsthitis, balanitis xerotica obliterans, phimosis, paraphimosis, syphilis, herpes simplex virus, gonorrhea, non-gonococcal urethritis, chlamydia, mycoplasma, trichomonas, HIV, AIDS; Reiter's syndrome, condyloma acuminatum, condyloma latum, and pearly penile papules, urethral abnormalities, such as hypospadias, epispadias, and phimosis, premalignant lesions, including Erythroplasia of Queyrat, Bowen's disease, Bowenoid paplosis, criant condyloma of Buscke-Lowenstein, and varrucous carcinoma; penile cancers, including squamous cell carcinomas, carcinoma in situ, verrucous carcinoma, and disseminated penile carcinoma; urethral neoplastic disorders, including penile urethial carcinoma, bulbomembranotis urethial carcinoma, and prostaticurethral carcinoma; and erectile disorders, such as priapism, Peyronie's disease, erectile dysfunction, and impotence.

Moreover, diseases and/or disorders of the vas deferens include vasculititis and CBAVD (congenital bilateral absence of the vas deferens); additionally, the transferrin fusion proteins of the invention and/or polynucleotides encoding transferrin fusion proteins of the invention may be used in the diagnosis, treatment, and/or prevention of diseases and/or disorders of the seminal vesicles, including hydatid disease, congenital chloride diarrhea, and polycystic kidney disease.

Other disorders and/or diseases of the male reproductive system include, for example, Klinefelters syndrome, Young's syndrome, premature ejaculation, diabetes mellitus, cystic fibrosis, Kartagener's syndrome, high fever, multiple sclerosis, and gynecomastia.

Further, the polynucleotides, modified fusion proteins of the invention and/or polynucleotides encoding transferrin fusion proteins of the invention may be used in the diagnosis treatment and/or prevention of diseases and/or disorders of the vagina and vulva, including bacterial vaginosis, candida vaginitis, herpes simplex virus, chancroid, granuloma inguinale, lymphogranuloma venereum, scabies, human papillomavirus, vaginal trauma, vulvartrauma, adenosis, chlamydia vaginitis, gonorrhea, trichomonas vaginitis, condylomaacuminatum, syphilis, molluscum contagiosum, atrophic vaginitis, Paaet's disease, lichensclerosus, lichen planus, vulvodynia, toxic shock syndrome, vaginismus, vulvovaginitis, vulvar vestibulitis, and neoplastic disorders, such as squamous cell hyperplasia, clear cell carcinoma, basal cell carcinoma, melanomas, cancer of Bartholin's gland, and vulvarintraepaelial neoplasia.

Disorders and/or diseases of the uterus include dysmenorrhea, retroverted uterus, endometriosis, fibroids, adenomyosis, anovulatory bleeding, amenorrhea, Cushiner's syndrome, hydatidiform moles, Asherman's syndrome, premature menopause, precocious puberty, uterine polyps, dysfunctional uterine bleeding (e.g., due to aberrant hormonal signals), and neoplastic disorders, such as adenocarcinomas, keiomyosarcomas, and sarcomas. Additionally, the transferrin fusion proteins of the invention and/or polynucleotides encoding transferrin fusion proteins of the invention may be useful as a marker or detector of, as well as, in the diagnosis, treatment, and/or prevention of congenital uterine abnormalities, such as bicornuate uterus, septate uterus, simple unicornuate uterus, unicornuate uterus with a noncavitary rudimentary horn, unicorriuate uterus with a non-communicating cavitary rudimentary horn, unicornuate uterus with a communicating cavitary horn, arcuate uterus, uterine didelfus, and T-shaped uterus.

Ovarian diseases and/or disorders include an ovulation, polycystic ovary syndrome (Stein-Leventhal syndrome), ovarian cysts, ovarian hypofunction, ovarian insensitivity to gonadotropins, ovarian over production of androgens, right ovarian vein syndrome, in amenorrhea, hirutism, and ovarian cancer (including, but not limited to, primary and secondary cancerous growth, Sertoli-Leydig tumors, endometriod carcinoma of the ovary, ovarian papillary serous adenocarcinoma, ovarian mucinous adenocarcinoma, and Ovarian Krukenberg tumors).

Cervical diseases and/or disorders include cervicitis, chronic cervicitis, mucopurulent cervicitis, and cervical dysplasia, cervical polyps, Nabothian cysts, cervical erosion, cervical incompetence, and cervical neoplasms (including, for example, cervical carcinoma, squamous metaplasia, squamous cell carcinoma, adenosquamous cell neoplasia, and columnar cell neoplasia).

Modified transferrin fusion proteins of the invention and/or polynucleotides encoding transferrin fusion proteins of the invention can be used to treat or detect infectious agents. For example, by increasing the immune response, particularly increasing the proliferation and differentiation of B and/or T cells, infectious diseases may be treated. The immune response may be increased by either enhancing an existing immune response, or by fusion proteins of the invention and/or initiating a new immune response. Alternatively, polynucleotides encoding transferrin fusion proteins of the invention may also directly inhibit infectious agent, without necessarily eliciting an immune response.

Viruses are one example of an infectious agent that can cause disease or symptoms that can be treated or detected by transferrin fusion proteins of the invention and/or polynucleotides encoding transferrin fusion proteins of the invention. Examples of viruses, include, but are not limited to the following DNA and RNA viruses and viral families: Arbovirus, Adenoviridae, Arenaviridae, Arterivirus, Bimaviridae, Bunyaviridae, Caliciviridae, Circoviridae, Coronaviridae, Dengue, EBV, HIV, Flaviviridae, Hepadnaviridae Hepatitis, Herpesviridae (such as, Cytomegalovirus, Herpes Simplex, Herpes Zoster), Mononegavirus (e.g., Paramyxoviridae, Morbillivirus, Rhabdoviridae), Orthomyxoviridae (e.g., Influenza A, Influenza B, and parainfluenza), Papilloma virus, Papovaviridae, Parvoviridaes, Picornaviridae, Poxviridae (such as Smallpox or Vaccinia), Reoviridae (e.g., Rotavirus), Retroviridae (HTLV-I, HTLV-11, -Lentivirus), and Togaviridae (e.g., Rubivirus).

Similarly, bacterial and fungal agents that can cause disease or symptoms that can be treated or detected by transferrin fusion proteins of the invention and/or polynucleotides encoding transferrin fusion proteins of the invention include, but not limited to, the following Gram-negative and Gram-positive bacteria, bacterial families, and fungi: *Actinomyces* (e.g., *Norcardia*), *Acinetobacter, Cryptococcus neoformans, Aspergillus*, Bacillaceae (e.g., *Bacillus anthrasis*), *Bacteroides* (e.g., *Bacteroides fragilis*), Blastomycosis, *Bordetella, Borrelia* (e.g., *Borrelia burgdorferi*) *Brucella, Candidia, Campylobacter, Chlamydia, Clostridiuffi* (e.g., *Clostridium botulinum, Clostridium difficile, Clostridium perfringens, Clostridiumtetani*), *Coccidioides, Corynebacterium* (e.g., *Corynebacterium-diptheriae*), *Cryptococcus, Dermatocycoses, E. coli* (e.g., Enterotoxigenic *E. coli* and Enterohemorrhagic *E. coli*), *Enterobacter* (e.g. *Enterobacter aerogenes*), Enterobacteriaceae (*Klebsiella, Salmonella* (e.g., *Salmonella typhi, Salmonella enteritidis, Salmonella typhi*), *Serratia, Yersinia, Shigella*), *Erysipelothrix, Haemophilus* (e.g., *Haemophilus influenza* type B), *Helicobacter, Legionella* (e.g., *Legionella pneumophila*), *Leptospira, Listeria* (e.g., *Listeria monocytogenes*), *Mycoplasma, Mycobacterium* (e.g., *Mycobacterium leprae* and *Mycobacterium tuberculosis*), *Vibrio* (e.g., *Vibrio cholerae*), Neisseriaceae (*Neisseriagonorrhea, Neisseria meningitidis*), Pasteurellaceae, *Proteus, Pseudomonas* (e.g., *Pseudomionas aeruginosa*), Rickettsiaceae, Spirochetes (e.g., *Treponenza.* spp., *Leptospiraspp., Borrielia* spp), *Shigella* spp., *Staphylococcus* (e.g., *Staphylococcus aureus*), *Meningiococcus, Pneumococcus* and *Streptococcus* (e.g., *Streptococcus pneumoniae* and Groups A, B, and C Streptococci), and Ureaplasmas.

Moreover, parasitic agents causing disease or that can be treated, prevented, and/or diagnosed by fusion proteins of the invention and/or polynucleotides encoding transferrin fusion proteins of the invention include, but not limited to, the following families or class: Amebiasis, Babesiosis, Coccidiosis, Cryptosporidiosis, Dientamoebiasis, Dourine, Ectoparasitic, Giardias, Helminthiasis, Leishmaniasis, Schistisoma, Theileriasis, Toxoplasmosis, Trypanosomiasis, and Trichomonas and Sporozoans (e.g., *Plasmodium vivax, Plasmodium falciparium, Plasmodium malariae* and *Plasmodium ovale*).

Modified transferrin fusion proteins of the invention and/or polynucleotides encoding transferrin fusion proteins of the invention can be used to differentiate, proliferate, and attract cells, pleading to the regeneration of tissues. (See, Science 276:59-87 (1997)). The regeneration of tissues could be used to repair, replace, or protect tissue damaged by congenital defects, trauma (wounds, burns, incisions, or ulcers), age, disease (e.g. osteoporosis, osteocarthritis, periodontal disease, liver failure), surgery, including cosmetic plastic surgery, fibrosis, reperfusion injury, or systemic cytokine damage.

Tissues that could be regenerated using the present invention include organs (e.g., pancreas, liver, intestine, kidney, skin, endothelium), muscle (smooth, skeletal or cardiac), vasculature (including vascular and lymphatics), nervous, hematopoietic, and skeletal (bone, cartilage, tendon, and ligament) tissue. Preferably, regeneration occurs without or decreased scarring. Regeneration also may include angiogenesis.

Modified transferrin fusion proteins of the invention and/or polynucleotides encoding transferrin fusion proteins of the invention, may be used to treat, prevent, diagnose, and/or prognose gastrointestinal disorders, including inflammatory diseases and/or conditions, infections, cancers (e.g., intestinal neoplasms (carcinoid tumor of the small intestine, non-Hodgkin's lymphoma of the small intestine, small bowel lymphoma), and ulcers, such as peptic ulcers.

Gastrointestinal disorders include dysphagia, odynophagia, inflammation of the esophagus, peptic esophagitis, gastric reflux, submucosal fibrosis and structuring, Mallory-Weiss lesions, lipomas, epidennal cancers, adeoncarcinomas, gastric retention disorders, gastroenteritis, gastric atrophy, gastric/stomach cancers, polyps of the stomach, autoimmune disorders such as pernicious anemia, pyloric stenosis, gastritis (bacterial, viral, eosinophilic, stress-induced, chronic erosive, atrophic, plasma cell, and Menetrier's), and peritoneal diseases (e.g., chylo perioneum, hemoperitoneum, mesenteric cyst, mesentericlymphadenitis, mesenteric vascular occlusion, panniculiti, neoplasms, peritonitis, pneumoperitoneum, bubphrenic abscess.

Gastrointestinal disorders also include disorders associated with the small intestine, such as malabsorption syndrome's, distension, irritable bowel syndrome, sugar intolerance, celiac disease, duodenal ulcers, duodenitis, tropical sprue, Whipple's disease, intestinal lymphangiectasia, Crohn's disease, appendicitis, obstructions of the ileum, Meckel's diverticulum, multiple diverticula, failure of complete rotation of the small and large intestine, lymphoma, and bacterial and parasitic diseases (such as Traveler's diarrhea, typhoid and paratyphoid, cholera, infection by Roundworms (*Ascariasis lumbricoides*), Hookworms (*Ancylostoma duodenale*), Threadworms (*Enterobius vermicularis*), Tapeworms *Taenia saginata, Echinococcus granulosus, Diphyllobothrium* spp. and *T. solium*).

Liver diseases and/or disorders include intrahepatic cholestasis (Alagille syndrome, biliary liver cirrhosis), fatty, liver (alcoholic fatty liver, Reye's syndrome), hepatic veiri, thrombosis, hepatolentricular degeneration, hepatomegaly, hepatopulmonary syndrome, hepatorenal, syndrome, portal hypertension (esophageal and gastric varices), liver abscess (amebic liver abscess), liver cirrhosis (alcoholic, biliary and experimental), alcoholic liver diseases (fatty liver, hepatitis, cirrhosis), parasitic (hepatic echinococcosis, fascioliasis, amebic liver abscess), jaundice (hemolytic, hepatocellular, and cholestatic), cholestasis, portal hypertension, liver, enlargement, ascites, hepatitis (alcoholic hepatitis, intra-familial hepatitis, chronic hepatitis (autoimmune, hepatitis B, hepatitis C, hepatitis D, drug induced), toxic hepatitis, viral human hepatitis (hepatitis A, hepatitis B, hepatitis C, hepatitis D, hepatitis E), Wilson's disease, granulomatous hepatitis, secondary biliary cirrhosis, hepaticencephalopathy, portal hypertension, varices, hepatic encebalopathy, primary biliary hemangiomas, bilecirrhosis, primary sclerosing cholangitis, hepatocellular adenoma, stones, liver failure (hepatic encephalopathy, acute liver failure), and liver neoplasms (ancriomyolipoma, calcified liver metastases, cystic liver metastases, epithelial tumors, fibro lamellar hepatocarcinoma, focal nodular hyperplasia, hepatic adenoma, hepatobiliarycystadenoma, hepatoblastoma, hepatocellular carcinoma, hepatoma, liver cancer, liver hemangioendothelioma, mesenchymal hamartoma, mesenchymal tumors of liver, nodular regenerative hyperplasia, benign liver tumors (Hepatic cysts, Simple cysts, Polycystic liver disease, Hepatobiliary cystadenoma, Choledochal cysts, Mesenchymal tumors, Mesenchymal hamartoma, Infantile hemangioendothelioma, Hemangioma, Peliosis hepatis, Lipomas, Inflammatory pseudo tumor, Miscellaneous Epithelial tumors, Bile duct epithelium (Bile duct hamartoma, Bile duct adenoma), Hepatocyte (Adenoma, Focal nodular hyperplasia, Nodular regenerative hyperplasia), malignant liver tumors (hepatocellular, hepatoblastoma, hepatocellular carcinoma, cholangiocellular, cholangiocarcinoma, cystadenocarcinoma, tumors of blood vessels, anaiosarcoma, Karposi's sarcoma, hemangioendothelioma, other tumors, embryonal sarcorria, fibrosarcoma, rhabdomyosarcoma, carcinosarcoma, teratoma, carcinoid, squamous carcinoma, primarylymphorria)), peliosis hepatis, erythrohepatic porphyria, hepatic porphyria (acute interirtittentporphyria; porphyria cutanea tarda), Zelli Neger syndrome).

Pancreatic diseases and/or disorders include acute pancieatitis, chronic pancreatitis (acute necrotizing pancreatitis, alcoholic pancreatitis), neoplasins (adenocarcinoma of the pancreas, cystadenocarcinoma, insulinoma, gastrinoma, and glucacronoma, cysticcitmeoplasms, islet-cell tumors, pancreoblastoma), and other pancreatic diseases (e.g., cysticfibrosis, cyst (pancreatic pseudocyst, pancreatic fistula, insufficiency)).

Gallbladder diseases include gallstones (cholelithiasis and choledocholithiasis), postcholeeystectomy syndrome, diverticulosis of the gallbladder, acute cholecystitis, chronic cholecystitis, bile duct tumors, and mucocele.

Diseases and/or disorders of the large intestine include antibiotic-associated colitis, diverticulitis, ulcerative colitis, acquired megacolon, abscesses, fungal and bacterial infections, anorectal disorders (e.g., fissures, hemorrhoids), colonic diseases (colitis, colonic neoplastris, colon cancer, adenomatous colon polyps (e.g., villous adenoma), coloncarcinoma, colorectal cancer, colonic diverticulitis, colonic diverticulosis, megacolon, Hirschsprung disease, toxic megacolon, sigmoid diseases proctocolitis, sigmoinneoplasmsj, constipation, Crohn's disease, diarrhea (infantile diarrhea, dysentery), duodenal diseases (duodenal neoplasins, duodenal obstruction, duodenal ulcer, duodenitis), enteritis (enterocolitis), HIV enteropathy, leal diseases (leal neoplasins, ileitis), immunoproliferative small intestinal disease, inflammatory bowel disease (ulcerative colitis, Crohn's disease), intestinal atresia, parasitic diseases (anisakiasis, balantidiasis, blastocystis infections, cryptosporidiosis, dientamoebiasis, amebic dysentery, giardiasis), intestinal fistula (rectal fistula), intestinal neoplasms (cecal neoplasms, colonic neolasms, duodenalpneoplasms, leal neoplasms, intestinal polyps, jejunal neoplasins, rectal neoplasms), intestinal obstruction (afferent loop syndrome, duodenal obstruction, impacted feces, intestinal pseudo obstruction cecal volvulus, intussusception), intestinal perforation, intestinal polyps (colonic polyps, gardner syndrome, peutz-jeghers syndrome), jejunal diseases Oejunal neoplasms), mal absorption syndromes (blind loop syndrome, celiac disease, lactose intolerance, short bowl syndrome, tropical sprue, whipple's disease), mesenteric vascular occlusion, pneumatosis cystoides intestinalis, protein losing enteropathies (intestinal lymphagiectasis), rectal diseases (anus diseases, fecal incontinence, hemorrhoids, proctitis, rectal fistula, rectal prolapse, rectocele), peptic ulcer (duodenalulcer, peptic esophagitis, hemorrhage, perforation; stomach ulcer, Zollinger-Ellison syndrome), postgastrectomy syndromes (dumping syndrome), stomach diseases (e.g., achlorhydria, duodenogastric reflux (bile reflux), gastric antral vascular ectasia, gastricfistula, gastric outlet obstruction, gastritis (atrophic or hypertrophic), gastroparesis, stomach dilatation; stomach diverticulum, stomach neoplasms (gastric cancer, gastric polyps, gastric adenocarcinoma, hyperplastic gastric polyp), stomach rupture, stomach ulcer, stomach volvulus), tuberculosis, visceroptosis, vomiting (e.g., hematemesis, hyperemesisgravidanim, postoperative nausea and vomiting) and hemorrhagic colitis.

Further diseases and/or disorders of the gastrointestinal system include biliary tract diseases, such as, gastroschisis, fistula (e.g., biliary fistula, esophageal fistula, gastricfistula, intestinal fistula, pancreatic fistula), neoplasms (e.g., biliary tract neoplasins, esophageal neoplasms; such as adenocarcinoma of the esophagus, esophageal squamous cell carcinoma, gastrointestinal neoplasms, pancreatic neoplasins, such as adenocarcinoma of the pancreas, mucinous cystic neoplasm of the pancreas, pancreatic eystic neoplasms, pancreatoblastoma, and peritoneal neoplasms), esophageal disease (e.g., bullous diseases, candidiasis, glycoaenie acanthosis, ulceration, barrett esophagus varices, atresia, cyst, diverticulum. (e.g., Zenker's diverticulum), fistula (e.g., tracheoesophageal fistula), motility disorders (e.g., CREST syndrome, deglutition disorders, achalasia, spasm, gastroesophageal reflux), neoplasms, perforation (e.g., Boerhaave syndrome, Mallory-Weiss syndrome), stenosis, esophagitis, diaphragmatic hernia (e.g., hiatal hernia); gastrointestinal diseases, such as, gastroenteritis (e.g., cholera morbus, norwalk virus infection), hemorrhage (e.g., hematemesis, melena, peptic ulcer hemorrhage), stomach neoplasms (gastric cancer, gastric polyps, gastric adenocarcinoma, stomach cancer)), hernia (e.g., congenital diaphragmatic hernia, femoral hernia, inguinal hernia, obturator hernia, umbilical hernia, ventral hernia), and intestinal diseases (e.g., cecal diseases (appendicitis, cecal neoplasms)).

Modified transferrin fusion proteins of the invention and/or polynucleotides encoding transferrin fusion proteins of the invention may have chemotaxis activity. A chemotaxic molecule attracts or mobilizes cells (e.g., monocytes, fibroblasts, neutrophils, T-cells, mast cells, eosinophils, epithelial and/or endothelial cells) to a particular site in the body, such as inflammation, infection, or site of hyperproliferation. The mobilized cells can then fight off and/or heal the particular trauma or abnormality.

Modified transferrin fusion proteins of the invention and/or polynucleotides encoding transferrin fusion proteins of the invention may increase chemotaxic activity of particular cells. These chemotactic molecules can then be used to treat inflammation, infection, hyperproliferative disorders, or any immune system disorder by increasing the number of cells targeted to a particular location in the body.

Oral Pharmaceutical Compositions and Delivery Methods

In the present invention, Tf fusion proteins, including but not limited to modified Tf fusion proteins, may be formulated for oral, delivery. In particular, certain fusion proteins of the invention that are used to treat certain classes of diseases or medical conditions may be particularly amenable for oral formulation and delivery. Such classes of diseases or conditions include, but are not limited to, acute, chronic and recurrent diseases. Chronic or recurrent diseases include, but are not limited to, viral disease or infections, cancer, a metabolic diseases, obesity, autoimmune diseases, inflammatory diseases, allergy, graft-vs.-host disease, systemic microbial infection, anemia, cardiovascular disease, psychosis, genetic diseases, neurodegenerative diseases, disorders of hematopoietic cells, diseases of the endocrine system or reproductive systems, gastrointestinal diseases. Examples of these classes of disease include diabetes, multiple sclerosis, asthma, HCV or HIV infections, hypertension, hypercholesterolemia, arterial scherosis, arthritis, and Alzheimer's disease. In many chronic diseases, oral formulations of Tf fusion proteins of the invention and methods of administration are particularly useful because they allow long-term patient care and therapy via home oral administration without reliance on injectable treatment or drug protocols.

Oral formulations and delivery methods comprising Tf fusion proteins of the invention take advantage of, in part, transferrin receptor mediated transcytosis across the gastrointestinal (GI) epithelium. The Tf receptor is found at a very high density in the human GI epithelium, transferrin is highly resistant to tryptic and chymotryptic digestion and Tf chemical conjugates have been used to successfully deliver proteins and peptides across the GI epithelium (Xia et al., (2000) J. Pharmacol. Experiment. Therap., 295:594-600; Xia et al. (2001) Pharmaceutical Res., 18(2):191-195; and Shah et al. (1996) J. Pharmaceutical Sci., S5(12):1306-1311, all of which are herein incorporated by reference in their entirety). Once transported across the GI epithelium, Tf fusion proteins of the invention exhibit extended half-life in serum, that is, the therapeutic protein or peptide(s) attached or inserted into Tf exhibit an extended serum half-life compared to the protein or peptide in its non-fused state.

Oral formulations of Tf fusion proteins of the invention may be prepared so that they are suitable for transport to the GI epithelium and protection of the Tf fusion protein component and other active components in the stomach. Such formulations may include carrier and dispersant components and may be in any suitable form, including aerosols (for oral or pulmonary delivery), syrups, elixirs, tablets, including chewable tablets, hard or soft capsules, troches, lozenges, aqueous or oily suspensions, emulsions, cachets or pellets granulates, and dispersible powders. Preferably, Tf fusion protein formulations are employed in solid dosage forms suitable for simple, and preferably oral, administration of precise dosages. Solid dosage forms for oral administration are preferably tablets, capsules, or the like.

For oral administration in the form of a tablet or capsule, care should be taken to ensure that the composition enables sufficient active ingredient to be absorbed by the host to produce an effective response. Thus, for example, the amount of Tf fusion protein may be increased over that theoretically required or other known measures such as coating or encapsulation may be taken to protect the polypeptides from enzymatic action in the stomach.

Traditionally, peptide and protein drugs have been administered by injection because of the poor bioavailability when administered non-parenterally, and in particular orally. These drugs are prone to chemical and conformational instability and are often degraded by the acidic conditions in the stomach, as well as by enzymes in the stomach and gastrointestinal tract. In response to these delivery problems, certain technologies for oral delivery have been developed, such as encapsulation in nanoparticles composed of polymers with a hydrophobic backbone and hydrophilic branches as drug carriers, encapsulation in microparticles, insertion into liposomes in emulsions, and conjugation to other molecules. All of which may be used with the Tf fusion molecules of the present invention.

Examples of nanoparticles include mucoadhesive nanoparticles coated with chitosan and Carbopol (Takeuchi et al., Adv. Drug Deliv. Rev. 47(1):39-54, 2001) and nanoparticles containing charged combination polyesters, poly(2-sulfobutyl-vinyl alcohol) and poly(D,L-lactic-co-glycolic acid) (Jung et al., Eur. J. Pharm. Biopharm. 50(1):147-160, 2000). Nanoparticles containing surface polymers with poly-N-isopropylacrylamide regions and cationic poly-vinylamine groups showed improved absorption of salmon calcitonin when administered orally to rats.

Drug delivery particles composed of alginate and pectin, strengthened with polylysine, are relatively acid and base resistant and can be used as a carrier for drugs. These particles combine the advantages of bioadhesion, enhanced absorption and sustained release (Liu et al., J. Pharm. Pharmacol. 51(2): 141-149, 1999).

Additionally, lipoamino acid groups and liposaccharide groups conjugated to the N- and C-termini of peptides such as synthetic somatostatin, creating an amphipathic surfactant, were shown to produce a composition that retained biological activity (Toth et al., J. Med. Chem. 42(19):4010-4013, 1999).

Examples of other peptide delivery technologies include carbopol-coated mucoadhesive emulsions containing the peptide of interest and either nitroso-N-acetyl-D,L-penicillamine and carbolpol or taurocholate and carbopol. These were shown to be effective when orally administered to rats to reduce serum calcium concentrations (Ogiso et al., Biol.

Pharm. Bull. 24(6):656-661, 2001). Phosphatidylethanol, derived from phosphatidylcholine, was used to prepare liposomes containing phosphatidylethanol as a carrier of insulin. These liposomes, when administered orally to rats, were shown to be active (Kisel et J. Pharm. 216(1-2):105-114, 2001).

Insulin has also been formulated in poly(vinyl alcohol)-gel spheres containing insulin and a protease inhibitor, such as aprotinin or bacitracin. The glucose-lowering properties of these gel spheres have been demonstrated in rats, where insulin is released largely in the lower intestine (Kimura et al., Biol. Pharm. Bull. 19(6):897-900, 1996.

Oral delivery of insulin has also been studied using nanoparticles made of poly(alkyl cyanoacrylate) that were dispersed with a surfactant in an oily phase (Damge et al., J. Pharm. Sci. 86(12):1403-1409, 1997) and using calcium alginate beads coated with chitosan (Onal et al., Artif. Cells Blood Substit. Immobil. Biotechnol. 30(3):229-237, 2002).

In other methods, the N- and C-termini of a peptide are linked to polyethylene glycol and then to allyl chains to form conjugates with improved resistance to enzymatic degradation and improved diffusion through the GI wall (www.nobexcorp.com).

BioPORTER® is a cationic lipid mixture, which interacts non-covalently with peptides to create a protective coating or layer. The peptide-lipid complex can fuse to the plasma membrane of cells, and the peptides are internalized into the cells (www.genetherapysystems.com).

In a process using liposomes as a starting material, cochleate-shaped particles have been developed as a pharmaceutical vehicle. A peptide is added to a suspension of liposomes containing mainly negatively charged lipids. The addition of calcium causes the collapse and fusion of the liposomes into large sheets composed of lipid bilayers, which then spontaneously roll up or stack into cochleates (U.S. Pat. No. 5,840,707; http://www.biodeliverysciences.com).

Compositions comprising Tf fusion protein intended for oral use may be prepared according to any method known to the art for the manufacture of pharmaceutical compositions and such compositions may contain one or more agents selected from the group consisting of sweetening agents in order to provide a pharmaceutically elegant and palatable preparation. For example, to prepare orally deliverable tablets, Tf fusion protein is mixed with at least one pharmaceutical excipient, and the solid formulation is compressed to form a tablet according to known methods, for delivery to the gastrointestinal tract. The tablet composition is typically formulated with additives, e.g. a saccharide or cellulose carrier, a binder such as starch paste or methyl cellulose, a filler, a disintegrator, or other additives typically usually used in the manufacture of medical preparations. To prepare orally deliverable capsules, DHEA is mixed with at least one pharmaceutical excipient, and the solid formulation is placed in a capsular container suitable for delivery to the gastrointestinal tract. Compositions comprising Tf fusion protein may be prepared as described generally in Remington's Pharmaceutical Sciences, 18th Ed. 1990 (Mack Publishing Co. Easton Pa. 18042) at Chapter 89, which is herein incorporated by reference.

As described above, many of the oral formulations of the invention may contain inert ingredients which allow for protection against the stomach environment, and release of the biologically active material in the intestine. Such formulations, or enteric coatings, are well known in the art. For example, tablets containing Tf fusion protein in admixture with non-toxic pharmaceutically acceptable excipients which are suitable for manufacture of tablets may be used. These excipients may be inert diluents, such as calcium carbonate, sodium carbonate, lactose, calcium phosphate or sodium phosphate; granulating and disintegrating agents, for example, maize starch, gelatin or acacia, and lubricating agents, for example, magnesium stearate, stearic acid, or talc.

The tablets may be uncoated or they may be coated with known techniques to delay disintegration and absorption in the gastrointestinal track and thereby provide a sustained action over a longer period of time. For example, a time delay material such as glyceryl monostearate or glyceryl distearate alone or with a wax may be employed.

Formulations for oral use may also be presented as hard gelatin capsules Wherein the active ingredient is mixed with an inert solid diluent, for example, calcium carbonate, calcium phosphate, or kaolin or as soft gelatin capsules wherein the active ingredient is mixed with an aqueous or an oil medium, for example, arachis oil, peanut oil, liquid paraffin or olive oil.

Aqueous suspensions may contain Tf fusion protein in the admixture with excipients suitable for the manufacture of aqueous suspensions. Such excipients are suspending agents, for example, sodium carboxymethylcellulose, methylcellulose, hydroxypropylmethylcellulose, sodium alginate, polyvinylpyrrolidone, gum tragacanth and gum acacia; dispersing or wetting agents may be a naturally occurring phosphatide, for example, lecithin, or condensation products of an alkylene oxide with fatty acids, for example, polyoxyethylene stearate, or condensation products of ethylene oxide with long chain aliphatic alcohols, for example, heptadecylethyloxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyoxyethylene sorbitan monooleate. The aqueous suspensions may also contain one or more preservatives for example, ethyl or n-propyl p-hydroxybenzoate, one or more coloring agents, one or more flavoring agents and one or more sweetening agents such as sucrose or saccharin.

Oily suspensions may be formulated by suspending the active ingredient in a vegetable oil, for example, arachis oil, olive oil, sesame oil or coconut oil, or in a mineral oil such as liquid paraffin. The oil suspensions may contain a thickening agent, for example, beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules suitable for preparation of an aqueous suspension by the addition of water provide the active ingredient and admixture with dispersing or wetting agent, suspending agent and one or more preservatives. Suitable dispersing or wetting agents and suspending agents are exemplified by those already mentioned above. Additional excipients, for example, sweetening, flavoring and coloring agents, may also be present.

The pharmaceutical compositions containing Tf fusion protein may also be in the form of oil-in-water emulsions. The oil phase may be a vegetable oil, for example, olive oil or arachis oil, or a mineral oil for example, gum acacia or gum tragacanth, naturally-occurring phosphotides, for example soybean lecithin, and esters or partial esters derived from fatty acids and hexitol anhydrides, for example, sorbitan monooleate, and condensation products of the same partial esters with ethylene oxide, for example, polyoxyethylene sorbitan monooleate. The emulsions may also contain sweetening and flavoring agents.

Syrups and elixirs containing Tf fusion protein may be formulated with sweetening agents, for example, glycerol, sorbitol or sucrose. Such formulations may also contain a demulcent, a preservative and flavoring and coloring agents. The pharmaceutical compositions may be in the form of a sterile injectable preparation, for example, as a sterile injectable aqueous or oleaginous suspension. This suspension may be formulated according to the known art using those suitable dispersing or wetting agents and suspending agents which have been mentioned above. The sterile injectable preparations may also be a sterile injectable solution or suspension in a non-toxic parenterally-acceptable diluent or solvate, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this period any bland fixed oil may be employed including synthetic mono- or diglycerides. In addition, fatty acids such as oleic acid find use in the preparation of injectables.

Pharmaceutical compositions may also be formulated for oral delivery using polyester microspheres, zein microspheres, proteinoid microspheres, polycyanoacrylate microspheres, and lipid-based systems (see, for example, DiBase and Morrel, *Oral Delivery of Microencapsulated Proteins*, in Protein Delivery: Physical Systems, Sanders and Hendren (eds.), pages 255-288 (Plenum Press 1997)).

The proportion of pharmaceutically active Tf fusion protein to carrier and/or other substances may vary from about 0.5 to about 100 wt. % (weight percent). For oral use, the pharmaceutical formulation will generally contain from about 5 to about 100% by weight of the active material. For other uses, the formulation will generally have from about 0.5 to about 50 wt. % of the active material.

Tf fusion protein formulations employed in the invention provide an effective amount of Tf fusion protein upon administration to an individual. As used in this context, an "effective amount" of Tf fusion is an amount that is effective to ameliorate a symptom of a disease.

The Tf fusion protein composition of the present invention may be, though not necessarily, administered daily, in an effective amount to ameliorate a symptom. Generally, the total daily dosage will be at least about 50 mg, preferably at least about 100 mg, and more preferably at least about 200 mg, and preferably not more than 500 mg per day, administered orally, e.g., in 4 capsules or tablets, each containing 50 mg Tf fusion protein. Capsules or tablets for oral delivery can conveniently contain up to a full daily oral dose, e.g., 200 mg or more.

In a particularly preferred embodiment, oral pharmaceutical compositions comprising Tf fusion protein are formulated in buffered liquid form which is then encapsulated into soft or hard-coated gelatin capsules which are then coated with an appropriate enteric coating. For the oral pharmaceutical compositions of the invention, the location of release may be anywhere in the GI system, including the small intestine (the duodenum, the jejunum, or the ileum), or the large intestine.

In other embodiments, oral compositions of the invention are formulated to slowly release the active ingredients, including the Tf fusion proteins of the invention, in the GI system using known delayed release formulations.

Tf fusion proteins of the invention for oral delivery are capable of binding the Tf receptor found in the GI epithelium. To facilitate this binding and receptor mediated transport, Tf fusion proteins of the invention are typically produced with iron and in some instances carbonate, bound to the Tf moiety. Processes and methods to load the Tf moiety of the fusion protein compositions of the invention with iron and carbonate are known in the art In some pharmaceutical formulations of the invention, the Tf moiety of the Tf fusion protein may be modified to increase the affinity or avidity of the Tf moiety to iron. Such methods are known in the art. For instance, mutagenesis can be used to produce mutant transferrin moieties that bind iron more avidly than natural transferrin. In human serum transferrin, the amino acids which are ligands for metal ion chelation include, but are not limited to N lobe amino acids Asp63, Tyr 95, Tyr188, Lys206, His207 and His249; and C lobe amino acids Asp392, Tyr426, Tyr517 and His5S5 of SEQ ID NO: 3 (the number beside the amino acid indicates the position of the amino acid residue in the primary amino acid sequence where the valine of the mature protein is designated position 1). See U.S. Pat. No. 5,986,067, which is herein incorporated be reference. In one embodiment, the Lys206 and His207 residues within the N lobe are replaced with Gln and Glu, respectively.

In some pharmaceutical formulations of the invention, the Tf fusion protein is engineered to contain a cleavage site between the therapeutic protein or peptide and the Tf moiety. Such cleavable sites or linkers are known in the art.

Pharmaceutical compositions of the invention and methods of the invention may include the addition of a transcytosis enhancer to facilitate transfer of the fusion protein across the GI epithelium. Such enhancers are known in the art. See Xia et al., (2000) *J. Pharmacol. Experiment. Therap.*, 295:594-600; and Xia et al. (2001) *Pharmaceutical Res.*, 18(2):191-195.

In preferred embodiments of the invention, oral pharmaceutical formulations include Tf fusion proteins comprising a modified Tf moiety exhibiting reduced or no glycosylation fused at the N terminal end to an insulin or GLP-1 protein or peptide as described above. Such pharmaceutical compositions may be used to treat glucose imbalance disorders such as diabetes by oral administration of the pharmaceutical composition comprising an effective dose of fusion protein.

The effective dose of fusion protein may be measured in a numbers of ways, including dosages calculated to alleviate symptoms associated with a specific disease state in a patient, such as the symptoms of diabetes. In other formulations, dosages are calculated to comprise an effective amount of fusion protein to induce a detectable change in blood glucose levels in the patient. Such detectable changes in blood glucose may include a decrease in blood glucose levels of between about 1% and 90%, or between about 5% and about 80%. These decreases in blood glucose levels will be dependent on the disease condition being treated and pharmaceutical compositions or methods of administration may be modified to achieve the desired result for each patient. In other instances, the pharmaceutical compositions are formulated and methods of administration modified to detect an increase in the activity level of the therapeutic protein or peptide in the patient, for instance, detectable increases in the activities of insulin or GLP-1. Such formulations and methods may deliver between about 1 pg to about 100 mg/kg body weight of fusion protein, about 100 ng to about 100 µg/kg body weight of fusion protein, about 100 µg/to about 100 mg/kg body weight of fusion protein, about 1 µg to about 1 g of fusion protein, about 10 µg to about 100 mg of fusion protein or about 10 mg to about 50 mg of fusion protein. Formulations may also be calculated using a unit measurement of therapeutic protein activity, such as about 5 to about 500 units of human insulin or about 10 to about 100 units of human insulin. The measurements by weight or activity can be calculated using known standards for each therapeutic protein or peptide fused to Tf.

The invention also includes methods of orally administering the pharmaceutical compositions of the invention. Such methods may include, but are not limited to, steps of orally administering the compositions by the patient or a caregiver. Such administration steps may include administration on intervals such as once or twice per day depending on the Tf fusion protein, disease or patient condition or individual patient. Such methods also include the administration of various dosages of the individual Tf fusion protein. For instance, the initial dosage of a pharmaceutical composition may be at a higher level to induce a desired effect, such as reduction in blood glucose levels. Subsequent dosages may then be decreased once a desired effect is achieved. These changes or modifications to administration protocols may be done by the attending physician or health care worker. In some instances, the changes in the administration protocol may be done by the individual patient, such as when a patient is monitoring blood glucose levels and administering a mTf-insulin or mTf-GLP-1 oral composition of the invention.

The invention also includes methods of producing oral compositions or medicant compositions of the invention comprising formulating a Tf fusion protein of the invention into an orally administerable form. In other instances, the invention includes methods of producing compositions or medicant compositions of the invention comprising formulating a Tf fusion protein of the invention into a form suitable for oral administration.

Moreover, the present invention includes pulmonary delivery of the Tf fusion protein formulations. Pulmonary delivery is particularly promising for the delivery of macromolecules which are difficult to deliver by other routes of administration. Such pulmonary delivery can be effective both for systemic delivery and for localized delivery to treat diseases of the lungs, since drugs delivered to the lung are readily absorbed through the alveolar region directly into the blood circulation.

The present invention provides compositions suitable for forming a drug dispersion for oral inhalation (pulmonary delivery) to treat various conditions or diseases. The Tf fusion protein formulation could be delivered by different approaches such as liquid nebulizers, aerosol-based metered dose inhalers (MDI's), and dry powder dispersion devices. In formulating compositions for pulmonary delivery, pharmaceutically acceptable carriers including surface active agents or surfactants and bulk carriers are commonly added to provide stability, dispersibility, consistency, and/or bulking characteristics to enhance uniform pulmonary delivery of the composition to the subject.

Surface active agents or surfactants promotes absorption of polypeptide through mucosal membrane or lining. Useful surface active agents or surfactants include fatty acids and salts thereof, bile salts, phospholipid, or an alkyl saccharide. Examples of fatty acids and salts thereof include sodium, potassium and lysine salts of caprylate ($C_8$), caprate ($C_{10}$), laurate ($C_{12}$) and myristate ($C_{14}$). Examples of bile salts include cholic acid, chenodeoxycholic acid, glycocholic acid, taurocholic acid, glycochenodeoxycholic acid, taurochenodeoxycholic acid, deoxycholic acid, glycodeoxycholic acid, taurodeoxycholic acid, lithocholic acid, and ursodeoxycholic acid.
Examples of phospholipids include single-chain phospholipids, such as lysophosphatidylcholine, lysophosphatidylglycerol, lysophosphatidylethanolamine, lysophosphatidylinositol and lysophosphatidylserine; or double-chain phospholipids, such as diacylphosphatidylcholines, diacylphosphatidylglycerols, diacylphosphatidylethanolamines, diacylphosphatidylinositols and diacylphosphatidylserines. Examples of alkyl saccharides include alkyl glucosides or alkyl maltosides, such as decyl glucoside and dodecyl maltoside.

Pharmaceutical excipients that are useful as carriers include stabilizers such as human serum albumin (HSA); bulking agents such as carbohydrates, amino acids and polypeptides; pH adjusters or buffers; salts such as sodium chloride; and the like. These carriers may be in a crystalline or amorphous form or may be a mixture of the two.

Examples of carbohydrates for use as bulking agents include monosaccharides such as galactose, D-mannose, sorbose, and the like; disaccharides, such as lactose, trehalose, and the like; cyclodextrins, such as 2-hydroxypropyl-.beta.-cyclodextrin; and polysaccharides, such as raffinose, maltodextrins, dextrans, and the like; alditols, such as mannitol, xylitol, and the like. Examples of polypeptides for use as bulking agents include aspartame. Amino acids include alanine and glycine, with glycine being preferred.

Additives, which are minor components of the composition, may be included for conformational stability during spray drying and for improving dispersibility of the powder. These additives include hydrophobic amino acids such as tryptophan, tyrosine, leucine, phenylalanine, and the like.

Suitable pH adjusters or buffers include organic salts prepared from organic acids and bases, such as sodium citrate, sodium ascorbate, and the like; sodium citrate is preferred.

The Tf fusion compositions for pulmonary delivery may be packaged as unit doses where a therapeutically effective amount of the composition is present in a unit dose receptacle, such as a blister pack, gelatin capsule, or the like. The manufacture of blister packs or gelatin capsules is typically carried out by methods that are generally well known in the packaging art.

U.S. Pat. No. 6,524,557 discloses a pharmaceutical aerosol formulation comprising (a) a HFA propellant; (b) a pharmaceutically active polypeptide dispersible in the propellant; and (c) a surfactant which is a $C_8$-$C_{16}$ fatty acid or salt thereof, a bile salt, a phospholipid, or an alkyl saccharide, which surfactant enhances the systemic absorption of the polypeptide in the lower respiratory tract. The invention also provides methods of manufacturing such formulations and the use of such formulations in treating patients.

One approach for the pulmonary delivery of dry powder drugs utilizes a hand-held device with a hand pump for providing a source of pressurized gas. The pressurized gas is abruptly released through a powder dispersion device, such as a venturi nozzle, and the dispersed powder made available for patient inhalation.

Dry powder dispersion devices are described in several patents. U.S. Pat. No. 3,921,637 describes a manual pump with needles for piercing through a single capsule of powdered medicine. The use of multiple receptacle disks or strips of medication is described in European Patent Application No. EP 0 467 172; International Patent Publication Nos. WO91/02558; and WO93/09832; U.S. Pat. Nos. 4,627,432; 4,811,731; 5,035,237; 5,048,514; 4,446,862; 5,048,514, and 4,446,862.

The aerosolization of protein therapeutic agents is disclosed in European Patent Application No. EP 0 289 336. Therapeutic aerosol formulations are disclosed in International Patent Publication No. WO 90/09781.

The present invention provides formulating Tf fusion protein for oral inhalation. The formulation comprises Tf fusion protein and suitable pharmaceutical excipients for pulmonary delivery. The present invention also provides administering the Tf fusion protein composition via oral inhalation to subjects in need thereof.

Transgenic Animals

The production of transgenic non-human animals that contain a modified transferrin fusion construct with increased serum half-life increased serum stability or increased bioavailability of the instant invention is contemplated in one embodiment of the present invention. In some embodiments, lactoferrin may be used as the Tf portion of the fusion protein so that the fusion protein is produced and secreted in milk.

The successful production of transgenic, non-human animals has been described in a number of patents and publications, such as, for example U.S. Pat. No. 6,291,740 (issued Sep. 18, 2001); U.S. Pat. No. 6,281,408 (issued Aug. 28, 2001); and U.S. Pat. No. 6,271,436 (issued Aug. 7, 2001) the contents of which are hereby incorporated by reference in their entireties.

The ability to alter the genetic make-up of animals, such as domesticated mammals including cows, pigs, goats, horses, cattle, and sheep, allows a number of commercial applications. These applications include the production of animals which express large quantities of exogenous proteins in an easily harvested form (e.g., expression into the milk or blood), the production of animals with increased weight gain, feed efficiency, carcass composition, milk production or content, disease resistance and resistance to infection by specific microorganisms and the production of animals having enhanced growth rates or reproductive performance. Animals which contain exogenous DNA sequences in their genome are referred to as transgenic animals.

The most widely used method for the production of transgenic animals is the microinjection of DNA into the pronuclei of fertilized embryos (Wall et al., J. Cell. Biochem. 49:113 [1992]). Other methods for the production of transgenic animals include the infection of embryos with retroviruses or with retroviral vectors. Infection of both pre- and post-implantation mouse embryos with either wild-type or recombinant retroviruses has been reported (Janenich, Proc. Natl. Acad. Sci. USA 73:1260 [1976]; Janenich et al., Cell 24:519 [1981]; Stuhlmann et al., Proc. Natl. Acad. Sci. USA 81:7151 [1984]; Jahner et al., Proc. Natl. Acad Sci. USA 82:6927 [1985]; Van der Putten et al., Proc. Natl. Acad Sci. USA 82:6148-6152 [1985]; Stewart et al., EMBO J. 6:383-388 [1987]).

An alternative means for infecting embryos with retroviruses is the injection of virus or virus-producing cells into the blastocoele of mouse embryos (Jahner, D. et al., Nature 298: 623 [1982]). The introduction of transgenes into the germline of mice has been reported using intrauterine retroviral infection of the midgestation mouse embryo Palmer et al., supra [1982]). Infection of bovine and ovine embryos with retroviruses or retroviral vectors to create transgenic animals has been reported. These protocols involve the micro-injection of retroviral particles or growth arrested (i.e., mitomycin C-treated) cells which shed retroviral particles into the perivitelline space of fertilized eggs or early embryos (PCT International Application WO 90/08832 [1990]; and Haskell and Bowen, Mol. Reprod. Dev., 40:386 [1995]. PCT International Application WO 90/08832 describes the injection of wild-type feline leukemia virus B into the perivitelline space of sheep embryos at the 2 to 8 cell stage. Fetuses derived from injected embryos were shown to contain multiple sites of integration.

U.S. Pat. No. 6,291,740 (issued Sep. 18, 2001) describes the production of transgenic animals by the introduction of exogenous DNA into pre-maturation oocytes and mature, unfertilized oocytes (i.e., pre-fertilization oocytes) using retroviral vectors which transduce dividing cells (e.g., vectors derived from murine leukemia virus [MLV]). This patent also describes methods and compositions for cytomegalovirus promoter-driven, as well as mouse mammary tumor LTR expression of various recombinant proteins.

U.S. Pat. No. 6,281,408 (issued Aug. 28, 2001) describes methods for producing transgenic animals using embryonic stem cells. Briefly, the embryonic stem cells are used in a mixed cell co-culture with a morula to generate transgenic animals. Foreign genetic material is introduced into the embryonic stem cells prior to co-culturing by, for example, electroporation, microinjection or retroviral delivery. ES cells transfected in this manner are selected for integrations of the gene via a selection marker such as neomycin.

U.S. Pat. No. 6,271,436 (issued Aug. 7, 2001) describes the production of transgenic animals using methods including isolation of primordial germ cells, culturing these cells to produce primordial germ cell-derived cell lines, transforming both the primordial germ cells and the cultured cell lines, and using these transformed cells and cell lines to generate transgenic animals. The efficiency at which transgenic animals are generated is greatly increased, thereby allowing the use of homologous recombination in producing transgenic non-rodent animal species.

Gene Therapy

The use of modified transferrin fusion constructs for gene therapy wherein a modified transferrin protein or transferrin domain is joined to a therapeutic protein or peptide is contemplated in one embodiment of this invention. The modified transferrin fusion constructs with increased serum half-life or serum stability of the instant invention are ideally suited to gene therapy treatments.

The successful use of gene therapy to express a soluble fusion protein has been described. Briefly, gene therapy via injection of an adenovirus vector containing a gene encoding a soluble fusion protein consisting of cytotoxic lymphocyte antigen 4 (CTLA4) and the Fc portion of human immunoglobulin GI was recently shown in Ijima et al. (Jun. 10, 2001)-Human Gene Therapy (United States) 12/9:1063-77. In this application of gene therapy, a murine model of type II collagen-induced arthritis was successfully treated via intraarticular injection of the vector.

Gene therapy is also described in a number of U.S. patents including U.S. Pat. No. 6,225,290 (issued May 1, 2001); U.S. Pat. No. 6,187,305 (issued Feb. 13, 2001); and U.S. Pat. No. 6,140,111 (issued Oct. 31, 2000).

U.S. Pat. No. 6,225,290 provides methods and constructs whereby intestinal epithelial cells of a mammalian subject are genetically altered to operatively incorporate a gene which expresses a protein which has a desired therapeutic effect. Intestinal cell transformation is accomplished by administration of a formulation composed primarily of naked DNA, and the DNA may be administered orally. Oral or other intragastrointestinal routes of administration provide a simple method of administration, while the use of naked nucleic acid avoids the complications associated with use of viral vectors to accomplish gene therapy. The expressed protein is secreted directly into the gastrointestinal tract and/or blood stream to obtain therapeutic blood levels of the protein thereby treating the patient in need of the protein. The transformed intestinal epithelial cells provide short or long term therapeutic cures for diseases associated with a deficiency in a particular protein or which are amenable to treatment by overexpression of a protein.

U.S. Pat. No. 6,187,305 provides methods of gene or DNA targeting in cells of vertebrate, particularly mammalian, origin. Briefly, DNA is introduced into primary or secondary cells of vertebrate origin through homologous recombination or targeting of the DNA, which is introduced into genomic DNA of the primary or secondary cells at a preselected site.

U.S. Pat. No. 6,140,111 (issued Oct. 31, 2000) describes retroviral gene therapy vectors. The disclosed retroviral vectors include an insertion site for genes of interest and are capable of expressing high levels of the protein derived from the genes of interest in a wide variety of transfected cell types. Also disclosed are retroviral vectors lacking a selectable marker, thus rendering them suitable for human gene therapy in the treatment of a variety of disease states without the co-expression of a marker product, such as an antibiotic. These retroviral vectors are especially suited for use in certain packaging cell lines. The ability of retroviral vectors to insert into the genome of mammalian cells has made them particularly promising candidates for use in the genetic therapy of genetic diseases in humans and animals. Genetic therapy typically involves (1) adding new genetic material to patient cells in vivo, or (2) removing patient cells from the body, adding new genetic material to the cells and reintroducing them into the body, i.e., in vitro gene therapy. Discussions of how to perform gene therapy in a variety of cells using retroviral vectors can be found, for example, in U.S. Pat. No. 4,868,116, issued Sep. 19, 1989, and U.S. Pat. No. 4,980,286, issued Dec. 25, 1990 (epithelial cells), WO89/07136 published Aug. 10, 1989 (hepatocyte cells), EP 378,576 published Jul. 25, 1990 (fibroblast cells), and WO89/05345 published Jun. 15, 1989 and WO/90/06997, published Jun. 28, 1990 (endothelial cells), the disclosures of which are incorporated herein by reference.

Without further description, it is believed that a person of ordinary skill in the art can, using the preceding description and the following illustrative examples, make and utilize the present invention and practice the claimed methods. For example, a skilled artisan would readily be able to determine the biological activity, both in vitro and in vivo, for the fusion protein constructs of the present invention as compared with the comparable activity of the therapeutic moiety in its unfused state. Similarly, a person skilled in the art could readily determine the serum half life and serum stability of constructs according to the present invention. The following working examples therefore, specifically point out the preferred embodiments of the present invention, and are not to be construed as limiting in any way the remainder of the disclosure.

EXAMPLES

Example 1

GLP-1-Transferrin Fusion Proteins

GLP-1 is a peptide that regulates insulin secretion. It possesses anti-diabetic activity in human subjects suffering diabetes, especially type II diabetes. Like other peptides, GLP-1 has a short plasma half-life in humans. The present invention provides fusion proteins with GLP-1 fused to mTf with increased half-life and pharmaceutical compositions of such fusion proteins for the treatment of diseases associated with abnormal glucose levels that can be administered orally.

The present invention also provides fusion proteins comprising an GLP-1 analog and mTF. In one embodiment of the invention, the GLP-1 analog comprises an additional His residue at the N-terminus. The His residue could be added to the N-terminus of GLP-1 or inserted after the His residue at the N-terminus of GLP-1. In another embodiment, the GLP-1 analog comprises an amino acid substitution at position 2. For example, the Ala in GLP-1(7-36) or GLP-1(7-37) peptide (SEQ ID NO: 6) is substituted with another amino acid.

In this example, the steps for producing a GLP-1/mTf fusion protein are described. The same steps may be used to generate transferrin fusion proteins with analogs of the GLP-1 peptides.

To produce the GLP-1/mTf fusion protein, the amino acid sequence of GLP-1(7-36) and GLP-1(7-37) may be used.

```
haegtftsdvssylegqaakefiawlvkgr    (SEQ ID NO: 7)

haegtftsdvssylegqaakefiawlvkgrg   (SEQ ID NO: 8)
```

For example, the peptide sequence of GLP-1(7-36) may be back translated into DNA and codon optimized for yeast:

```
catgctgaaggtacttttacttctgatgtttcttcttatttggaaggtcaagctgctaaagaa
  h   a   e   g   t   f   t   s   d   v   s   s   y   l   e   g   q   a   a   k   e tttattgcttggttggttaaaggtaga (SEQ ID NO: 13)
  f   i   a   w   l   v   k   g   r  (SEQ ID NO: 14)
```

The primers were specifically designed to form 5' XbaI and 3' KpnI sticky ends after annealing and to enable direct ligation into XbaI/KpnI cut pREX0052, just 5' of the end of the leader sequence and at the N-terminus of mTf. Alternatively, other sticky ends may be engineered for ligations into other vectors.

```
        'XbaI
       -+-----
   1   aggtctctag agaaaaggca tgctgaaggt acttttactt ctgatgtttc ttcttatttg
       tccagagatc tcttttccgt acgacttcca tgaaaatgaa gactacaaag aagaataaac
       >>......FL.......>>
         r   s   l   e   k   r  (SEQ ID NO: 17)
                          >>.................GLP-1.....................>
                             h   a   e   g   t   f   t   s   d   v   s   s   y   l KpnI
                                                                  ------+
  61   gaaggtcaag ctgctaaaga atttattgct tggttggtta aaggtagggt acctgata
       cttccagttc gacgatttct taaataacga accaaccaat ttccatccca tggactat
       >......................GLP-1......................>>
         e   g   q   a   a   k   e   f   i   a   w   l   v   k   g   r
                                                           >>...mTf..>>
```

```
                                            v   p   d
Top strand: SEQ ID NO: 15
Bottom strand: SEQ ID NO:16
Top strand primer: P0056 (nucleotides 7-112 of SEQ ID NO: 15)
Bottom strand primer: P0057 (nucleotides 9-108 of SEQ ID NO: 16)
```

After annealing and ligation, the clones were sequenced to confirm correct insertion. This vector was designated pREX0094. The cassette was cut out of pREX0094 with NotI and sub-cloned into NotI cut yeast vector, pSAC35, to make pREX0100.

This plasmid was then electroporated into the host *Saccharomyces* yeast strains and transformants selected for leucine prototrohy on minimal media plates. Expression was determined by growth in liquid minimal media and analysis of supernatant by SDS-PAGE, western blot, and ELISA.

Example 2

Insulin-Transferrin Fusion Proteins

Insulin is a peptide hormone that is secreted by the islets of Langerhans in the pancreas and that regulates the metabolism of carbohydrates and fats, in particular the conversion of glucose to glycogen. It is given to humans suffering from type I and type II diabetes, as well as to diabetic animals. Currently, insulin must be administered by subcutaneous injection and has a short plasma half-life in humans. The present invention provides fusion proteins of insulin fused to mTf that have increased half-life and pharmaceutical compositions of such fusion proteins for the treatment of diseases associated with abnormal glucose levels that can be administered orally.

In this example, the steps for producing an insulin/mTf fusion protein are described. Similar steps may be followed to generate transferrin fusion proteins with analogs of insulin peptides.

For expression in *Saccharomyces* constructs were initially made in the base vector pREX0052, comprising an *E. coli* cloning vector with a cassette for the expression of mTf in yeast, as either inserts between the 5' XbaI/KpnI sites for the N-terminal fusion, or 3' SalI/HindIII sites for the C-terminal fusion.

```
     XbaI           KpnI
    -+-----        -------+
aggtctctag agaagagggt acctgata    (SEQ ID NO: 18)
tccagagatc tcttctccca tggactat
>>......FL........>> >>..mTf..>>
    r  s  l  e  k  r    v  p  d  (SEQ ID NO: 19)
         SalI          HindIII
        -+-----        --+----
actttccgtc gaccttaata agcttaattc  (SEQ ID NO: 20)
tgaaaggcag ctggaattat tcgaattaag
>>........mTf.........>>
    t  f  r    r  p  -  -        (SEQ ID NO: 21)
                  mADH1t >>.....>>
```

These constructs form an expression cassette with (5' to 3') the yeast PRB1 promoter, leader sequence directing secretion into the growth media, (N-terminal fusion), mTf sequence, (C-terminal fusion), stop codons and the ADH1 terminator sequence. Once constructed, the expression cassettes were recovered as NotI fragments and inserted into NotI digested pSAC35, an *E. coli*/yeast shuttle vector.

The insulin sequence used corresponds to that of Genbank Accession No. NM_000207, SEQ ID NOS: 22 (DNA) and 23 (protein), as shown below.

```
  1 gctgcatcag aagaggccat caagcacatc actgtccttc tgccatggcc ctgtggatgc
    cgacgtagtc ttctccggta gttcgtgtag tgacaggaag acggtaccgg gacacctacg
                                                    >>.....INS......>
                                                    >>...leader.....>
                                                               m  a  l  w  m 61 gcctcctgcc cctgctggcg ctgctggccc tctggggacc tgacccagcc gcagcctttg
    cggaggacgg ggacgaccgc gacgaccggg agaccctgg  actgggtcgg cgtcggaaac
    >...........................INS............................>
    >...........................leader..........................>>
       r  l  l   p  l  l  a   l  l  a   l  w  g   p  d  p  a   a
                                                               >>.>
                                                                 f 121 tgaaccaaca cctgtgcggc tcacacctgg tggaagctct ctacctagtg tgcggggaac
    acttggttgt ggacacgccg agtgtggacc accttcgaga gatggatcac acgcccttg
    >...........................INS............................>
    >...........................B..............................>
       v  n  q   h  l  c   g    s  h  l   v  e  a   l  y  l   v  c  g  e 181 gaggcttctt ctacacaccc aagacccgcc gggaggcaga ggacctgcag gtggggcagg
    ctccgaagaa gatgtgtggg ttctgggcgg ccctccgtct cctggacgtc caccccgtcc
    >...........................INS............................>
                                         r  r  e  a   e  d  l  q   v  g  q
    >............B..............>>
       r  g  f   f  y  t   p  k  t 241 tggagctggg cggggccct  ggtgcaggca gcctgcagcc cttggccctg gaggggtccc
    acctcgaccc gccccggga  ccacgtccgt cggacgtcgg gaaccgggac ctccccaggg
    >...........................INS............................>
       v  e  l   g  g  g   p    g  a  g   s  l  q    p  l  a  l   e  g  s 301 tgcagaagcg tggcattgtg gaacaatgct gtaccagcat ctgctccctc taccagctgg
    acgtcttcgc accgtaacac cttgttacga catggtcgta gacgagggag atggtcgacc
```

```
                                  -continued
    >................................INS.........................>
      l   q   k   r
                   >>.......................A..........................>
                       g   i   v   e   q   c   c   t   s   i   c   s   l   y   q   l 361 agaactactg caactagacg cagcccgcag gcagcccccc acccgccgcc tcctgcaccg
    tcttgatgac gttgatctgc gtcgggcgtc cgtcgggggg tgggcggcgg aggacgtggc
    >......INS......>>
    >......A......>>
      e   n   y   c   n 421 agagagatgg aataaagccc ttgaaccagc
    tctctctacc ttatttcggg aacttggtcg
```

The cDNA for the above sequence can be generated in a number of ways, e.g., by RT-PCR, from a cDNA pool, or by overlapping synthetic oligonucleotides. To generate a clone from a cDNA pool, two primers were synthesized and used as PCR primers.

```
5' primer
                                                (SEQ ID NO: 24)
  5'-tttgtgaaccaacacctgtgcggc-3'

3' primer
                                                (SEQ ID NO: 25)
  3'-gacgagggagatggtcgacctcttgatgacgttg-5'
```

To make the N-terminal insert, a 5' mutagenic primer was used to create a second PCR product using the first PCR product as template. This primer inserted the last 5 amino acids of the leader sequence and the XbaI site. The KpnI site could not be inserted by this method, as an amino acid change would have resulted from the creation of the KpnI site. Instead, the PCR product was digested with XbaI/PvuII. A linker was then made of two overlapping oligos with a PvuII 5' end and 3' overhang which would ligate to the KpnI overhang on KpnI digested pREX0052. By annealing and ligating this linker to the digested PCR fragment and ligating the resulting product into XbaI/KpnI digested pREX0052 the plasmid pREX0052 N-insulin (SEQ ID NOS: 26 and 27) was generated.

```
                        XbaI
                        -+----
  1 gcttactcta ggtctctaga taagaggttt gtgaaccaac acctgtgcgg ctcacacctg
    cgaatgagat ccagagatct attctccaaa cacttggttg tggacacgcc gagtgtggac
    >...........FL.............>>
      a   y   s   r   s   l   d   k   r
                             >>...............Ins.................>
                             >>...............B..................>
                                f   v   n   q   h   l   c   g   s   h   l 61 gtggaagctc tctacctagt gtgcggggaa cgaggcttct tctacacacc caagacccgc
    caccttcgag agatggatca cacgcccctt gctccgaaga agatgtgtgg gttctgggcg
    >...............................Ins...............................>
                                                                      r
    >...............B.............................>>
      v   e   a   l   y   l   v   c   g   e   f   g   f   f   y   t   p   k   t 121 cgggaggcag aggacctgca ggtggggcag gtggagctgg gcggggggccc tggtgcaggc
    gccctccgtc tcctggacgt ccacccgtc cacctcgacc cgcccccggg accacgtccg
    >..............................Ins..............................>
      r   e   a   e   d   l   q   v   g   q   v   e   l   g   g   g   p   g   a   g 181 agcctgcagc ccttggccct ggaggggtcc ctgcagaagc gtggcattgt ggaacaatgc
    tcggacgtcg ggaaccggga cctccccagg gacgtcttcg caccgtaaca ccttgttacg
    >...............................Ins............................>
      s   l   q   p   l   a   l   e   g   s   l   q   k   r
                                              >>........A..........>
                                                 g   i   v   e   q   c PvuII
                                  --+---
241 tgtaccagca tctgctccct ctaccagctg gagaactact gcaacgtac
    acatggtcgt agacgaggga gatggtcgac ctcttgatga cgttg
    >.......................Ins........................>>
    >.......................A..........................>>
      c   t   s   i   c   s   l   y   q   l   e   n   y   c   n
                                                              >>mTf
                                                                v
```

```
5' primer: 5'-gcttactctaggtctctagataagaggtttgtgaaccaacacctgtgcg-3' (SEQ ID NO: 28)
Linkers:   5'-ctggagaactactgcaacgtac-3' (SEQ ID NO: 29)
           3'-gacctcttgatgacgttg-5'    (SEQ ID NO: 30)
```

To make the C terminal insert, 5' and 3' mutagenic primers were used to create a second PCR product using the first PCR product as template. This product was then digested with SalI/HindIII and ligated into SalI/HindIII digested pREX0052. This resulted in the plasmid pREX0052 C-insulin (SEQ ID NOS: 31 and 32).

```
            SalI
            -+----
1   tgcactttcc gtcgaccttt tgtgaaccaa cacctgtgcg gctcacacct ggtggaagct
    acgtgaaagg cagctggaaa acacttggtt gtggacacgc cgagtgtgga ccaccttcga
    >>......mTf......>>
      c  t  f   r  r  p
                         >>....................Ins.....................>
                         >>....................B......................>
                         f  v  n  q   h  l  c  g  s  h   l  v  e  a 61  ctctacctag tgtgcgggga acgaggcttc ttctacacac ccaagacccg ccgggaggca
    gagatggatc acacgcccct tgctccgaag aagatgtgtg.ggttctgggc ggccctccgt
    >................................Ins..............................>
                                                   r   r  e  a
    >......................B.....................>>
       l  y  l   v  c  g   e  r  g  f   f  y  t   p  k  t 121 gaggacctgc aggtggggca ggtggagctg ggcggggggcc ctggtgcagg cagcctgcag
    ctcctggacg tccacccccgt ccacctcgac ccgccccggg gaccacgtcc gtcggacgtc
    >................................Ins..............................>
      e  d  l   q  v  g   q  v  e  l   g  g  g   p  g  a   g  s  l  q 181 cccttggccc tggaggggtc cctgcagaag cgtggcattg tggaacaatg ctgtaccagc
    gggaaccggg acctccccag ggacgtcttc gcaccgtaac accttgttac gacatggtcg
    >................................Ins..............................>
      p  l  a   l  e  g   s  l  q  k   r
                                        >>.............A...............>
                                         g  i   v  e  q   c  c  t  s HindIII
                                             -+----
241 atctgctccc tctaccagct ggagaactac tgcaactaat aagcttaatt
    tagacgaggg agatggtcga cctcttgatg acgttgatta ttcgaattaa
    >.................Ins.................>>
    >...................A.................>>
      i  c  s   l  y  q   l  e  n  y   c  n
                                              mADH1t >>....>>
                                                 a  -
5' primer: 5'-tgcactttccgtcgaccttttgtgaaccaacacctgtgcg-3' (SEQ ID NO: 33)
3' primer: 3'-gacctcttgatgacgttgattattcgaattaa-5' (SEQ ID NO: 34)
```

Once the DNA sequence for both the N- and C-terminal inserts had been checked and confirmed, the plasmids pREX0052 N-insulin and pREX0052 C-insulin were digested with NotI and the expression cassettes recovered. These were then ligated into NotI digested pSAC35 to give pSAC35 N-insulin and pSAC35 C-insulin. These plasmids were then electroporated into the host *Saccharomyces* yeast strains and transformants selected for leucine prototrohy on minimal media plates. Expression was determined by growth in liquid minimal media and analysis of superanatant by SDS-PAGE, western blot, ELISA and BIAcore.

These fusion constructs result in the production of proinsulin attached to transferrin. Proteases in yeast may convert the proinsulin to insulin as it is being made and secreted, although the final expression product may contain only proinsulin. In that case, the proinsulin can be converted to insulin post-expression using an appropriate purified protease.

Oral Administration of Insulin/Modified Transferrin Fusion Protein to Rats

To test the insulin activity of the insulin/mTf fusion protein, diabetic rats are first prepared. Female Sprague-Dawley rats are fasted for 24 hours and their blood glucose level determined to establish a baseline. The rats are then injected intraperitoneally with a solution of streptozotocin (STZ), 60 mg/ml, at a dosage of 60 mg/kg. I.p. injections of STZ are continued for four more days, and rats with a fasting blood glucose level above 300 mg/dl are selected as diabetic rats.

Solutions of the fusion protein and of insulin alone are prepared in PBS or sodium bicarbonate to provide dosages of 7 to 80 units of insulin/kg when administered to rats. As a control, rats are also treated with PBS alone. The solutions or PBS are administered by oral gavage to rats following a 12 hour fast, and blood samples are collected from the tail after 0, 30 and 60 minutes, and then at 2-hour intervals. Blood glucose levels at 0, 0.5, 1, 3, 5, 7, 9 and 11 hours after dosing are measured with a blood glucose monitoring device designed for diabetics, and the rats are fed again at 11 hours post-dose.

The activity of the insulin is determined by measuring the decrease in blood glucose level over time, correcting the decrease by any increases or decreases in the PBS-only samples. The insulin activities of the fusion protein versus unfused insulin are compared.

To examine the uptake of the fusion protein by transferrin receptors in the intestinal mucosa, fusion protein and unfused insulin as a control are administered to diabetes induced rats as described above and transport measured using standard sandwich ELISAs and serum samples. Alternatively, $^{125}$I-labeled fusion protein or $^{125}$I-labeled unfused insulin is adminstered to diabetes-induced rats at dosage of 80 U insulin/kg by oral gavage, as described above. Blood samples are collected from the tail after 0, 30 and 60 minutes, then at 2-hour intervals, also as described above, and serum samples are analyzed by HPLC, using, for example a Sephacryl column and eluting samples with PBS. Standards containing $^{125}$I-labeled transferrin, $^{125}$I-labeled insulin and $^{125}$I-labeled fusion protein are also run on the Sephacryl column to determine their peak elution times and fraction numbers. The radioactivity of each fraction is measured with a gamma counter, and the protein content of each fraction is measured by the absorbance at 280 nm. Serum samples from rats treated with the fusion protein may not show the appearance of the fusion protein immediately, as there may be a delay of a few hours.

Example 3

Preparation of Therapeutic mTF Fusion Proteins with Increased Iron Affinity

Therapeutic mTf fusion protein with increased iron affinity may be prepared. As an example for preparing modified transferrin fusion proteins with increased iron binding ability, the procedure in Example 2 above may be carried out with the following modification. These fusion proteins may be used to facilitate uptake and transfer of the fusion protein across the gastrointestinal epithelium.

A cloning vector such as pREX0052, described above, which contains the mTf sequence is cut with a restriction enzyme, or a pair of restriction enzymes, to remove a portion of the mTf gene. Using techniques standard in the art, this fragment is then subjected to site-directed mutagenesis using primers that introduce a mutation at a position corresponding to nucleotide 723 of SEQ ID NO: 1, converting the codon AAG (Lys) to CAG (Gln) or GAG (Glu). Similarly, primers are used that introduce mutations at positions corresponding to nucleotides 726 and 728 of SEQ ID NO: 1, converting the codon CAC (His) to CAG (Gln) or GAG (Glu). Primers may also be used that introduce mutations at all three nucleotide positions, resulting in the substitution of two adjacent amino acids. These nucleotide positions correspond to amino acids 225 and 226 of the protein encoded with the leader sequence and to amino acids 206 and 207 of the mature protein. The mutated fragment is then amplified by RT-PCR and religated into the cloning vector. This vector containing the mutation or mutations is used in a subsequent step for introduction of a DNA molecule coding for the therapeutic protein. As described in Example 2, above, the mTf fusion protein sequence may be introduced into yeast expression vectors and transformed into *Saccharomyces* or other yeasts for protein production.

As discussed previously, other amino acids may also be mutated to obtain therapeutic mTf proteins with increased iron affinity.

Example 4

β-Interferon-Transferrin Fusion Proteins

β-IFN is effective in the treatment of various diseases, such as, but not limited to, multiple sclerosis, brain tumor, skin cancer, and hepatitis B and C. Like most cytokines, β-IFN has a short circulation half-life. The present invention provides fusion proteins comprising β-IFN fused to mTf with increased half-life and efficacy in patients. This example describes the steps in generating a β-IFN/mTf fusion protein that may be administered orally.

In this example, IFNβ-1 is fused to modified transferrin at either the N- or C-termini. The IFNβ-1 clone was obtained from the ATCC (No. 39517). Specifically designed primers were used to confirm the DNA sequence of the IFNβ-1 clone. These primers were external to the IFNβ-1 DNA sequence and designed to read in from the vector such that the full-length sequence of the clone was obtained. The primers used were:

```
P0070  GCTATGACCAACAAGTGTCTC35)   (SEQ ID NO: 35)
and

P0071  CGCACCTGTGGCGCCGGTGATG     (SEQ ID NO: 36)
```

N-Terminal Fusion

Once the DNA sequence was confirmed, primers were designed for fusion of IFNβ-1 to mTf. The N-terminal fusion was a two step process. A straight fusion using primers with XbaI and KpnI sites would have destroyed the KpnI site and clipped the beginning of mTf. A linker, primers P0082 (nucleotides 18-48 of SEQ ID NO: 37) and P0083 (nucleotides 17-39 SEQ ID NO: 38), was designed to create an internal KpnI site at the 3' end of IFNβ-1, by a single silent mutation of by 486 from T to G (bold), and with a 5' XbaI overhang and 3' GTAC which would anneal with a KpnI site. The overhang destroyed the existing KpnI site in pREX0052. The linkers were annealed and ligated into pREX0054 cut with XbaI/KpnI, creating an intermediate vector with mTf untouched and a KpnI site that could be used to fuse the IFNβ-1 gene at the N-terminus of mTf.

```
               XbaI            KpnI
              -+-----         -----+
              >>............P0082..............>>
ctgcttactc taggtctcta gagaaaacag ggtacctccg aaacgtacct gataaaactg
gacgaatgag atccagagat ctcttttgtc ccatggaggc tttgcatgga ctattttgac
                               <<........P0083........<<
>>.........MFa-1...........>>
   a  y   s  r  s  l   e  k  (SEQ ID NO: 39)

>>....IFN-B-1.....>>
                                   t  g  y  l   r  n  (SEQ ID NO: 40)
                                                      >>.....mTf......>
                                                      v  p   d  k  t
                                                         (SEQ ID NO: 41)
Top Strand:    SEQ ID NO: 37
Bottom Strand: SEQ ID NO: 38
```

A second set of primers, P0084 (SEQ ID NO: 42) and P0085 (SEQ ID NO: 43), were designed to tailor the ends of the IFNβ-1 gene by mutagenic PCR for subsequent insertion into the intermediate vector via the XbaI and KpnI sites. A XbaI/KpnI digest of this tailored gene removed the last 5 amino acids of IFNβ-1; however, these were already engineered into the intermediate vector. The resulting construct, pREX0048, was created by ligating the IFNβ-1 gene cut with XbaI/KpnI into the XbaI/KpnI cut intermediate vector.

P0084 (SEQ ID NO: 42)
```
>>-------FL---------->>
                      >>----IFNβ-1-------->>
       XbaI
CTCTAGGTC TCTAGA GAAAAGGAGCTACAACTTGCTTGGATTC
```

P0085 (SEQ ID NO: 43)
```
<<---------IFNβ-1-------<<
          KpnI
GTTTCGGA GGTACC CTGTAAGTCTG
```

After the pREX0048 construct was created, it was sequenced to confirm correct insertion. The expression cassette, as a NotI fragment, was then sub-cloned into NotI cut yeast vector, pSAC35, to make the pREX0050.

C-Terminal Fusion

Specifically designed primers, P0086 (SEQ ID NO: 44) and P0087 (SEQ ID NO: 45), were used to PCR amplify the original clone and, in addition, to tailor the ends of IFNβ-1 to have SalI and HindIII sites at the 5' and 3' ends, respectively. The newly tailored product was ligated into SalI/HindIII cut pREX0052 to create pREX0049.

P0086 (SEQ ID NO.: 44)
```
>>---mTf---->>
          >>------IFNβ-1-------->>
     SalI
ACTTTCC GTCGAC CTAGCTACAACTTGCTTGGATTC
```

P0087 (SEQ ID NO: 45)
```
<<----3'ADH1t-------<< * *
                                      <<-----IFNβ-1-------<<
                                   HindIII
CATAAATCATAAGAATT AAGCTT TATTAGTTTCGGAGGTAACCTGTAAGT
```

After the Prex0049 construct was created, it was sequenced to confirm correct insertion. The expression cassette, as a NotI fragment, is then sub-cloned into NotI cut yeast vector, such as pSAC35, to make pREX0051.

In one embodiment of the invention, β-IFN-1 (GenBank Acc. No. NM_002176, SEQ ID NO: 46) is made more stable and soluble by mutating Cys17 (in the mature protein) to Ser. The mutation of Cys17 to Ser can be performed by routine mutagenic reactions such as a mutagenic PCR reaction using specifically designed primers and the nucleic acid encoding β-IFN-1 as the template.

Further, the β-IFN-1 is modified to prevent glycosylation by modifying the N-linked glycosylation site, NES/T (residues 80 to 82 of SEQ ID NO: 46). As an example, N could be mutagenized to Q and S/T could be mutagenized to Ala or other amino acid acids. Such mutagenesis could be performed with mutagenic PCR reaction using specifically designed primers and the nucleic acid encoding β-IFN-1 as the template.

Although the present invention has been described in detail with reference to examples above, it is understood that various modifications can be made without departing from the spirit of the invention. Accordingly, the invention is limited only by the following claims. All cited patents, patent applications and publications referred to in this application are herein incorporated by reference in their entirety.

What is claimed is:

1. A fusion protein comprising a transferrin (Tf) protein fused at its N-terminus to insulin, wherein the fusion protein is expressed in yeast from a plasmid pREX 0052 comprising the nucleic acid sequence of SEQ ID NO: 26.

2. A fusion protein comprising a Tf protein fused at its C-terminus to insulin, wherein the fusion protein is expressed in yeast from a plasmid pREX0052 comprising the nucleic acid sequence of SEQ ID NO: 31.

* * * * *

SEQUENCE LISTING

```
<160> NUMBER OF SEQ ID NOS: 54

<210> SEQ ID NO 1
<211> LENGTH: 2318
<212> TYPE: DNA
<213> ORGANISM: Homo sapiens
<220> FEATURE:
<221> NAME/KEY: CDS
<222> LOCATION: (51)..(2147)
<223> OTHER INFORMATION: GenBank Acc. No. NM_001063, transferrin gene
      and protein
<220> FEATURE:
<221> NAME/KEY: sig_peptide
<222> LOCATION: (51)..(107)

<400> SEQUENCE: 1
gcacagaagc gagtccgact gtgctcgctg ctcagcgccg cacccggaag atg agg           56
                                                         Met Arg
                                                           1 ctc gcc gtg gga gcc ctg ctg gtc tgc gcc gtc ctg ggg ctg tgt ctg       104
Leu Ala Val Gly Ala Leu Leu Val Cys Ala Val Leu Gly Leu Cys Leu
        5                  10                  15 gct gtc cct gat aaa act gtg aga tgg tgt gca gtg tcg gag cat gag       152
Ala Val Pro Asp Lys Thr Val Arg Trp Cys Ala Val Ser Glu His Glu
    20                  25                  30 gcc act aag tgc cag agt ttc cgc gac cat atg aaa agc gtc att cca       200
Ala Thr Lys Cys Gln Ser Phe Arg Asp His Met Lys Ser Val Ile Pro
35                  40                  45                  50 tcc gat ggt ccc agt gtt gct tgt gtg aag aaa gcc tcc tac ctt gat       248
Ser Asp Gly Pro Ser Val Ala Cys Val Lys Lys Ala Ser Tyr Leu Asp
                55                  60                  65 tgc atc agg gcc att gcg gca aac gaa gcg gat gct gtg aca ctg gat       296
```

-continued

```
                Cys Ile Arg Ala Ile Ala Ala Asn Glu Ala Asp Ala Val Thr Leu Asp
                            70                  75                  80 gca ggt ttg gtg tat gat gct tac ctg gct ccc aat aac ctg aag cct        344
Ala Gly Leu Val Tyr Asp Ala Tyr Leu Ala Pro Asn Asn Leu Lys Pro
            85                  90                  95 gtg gtg gca gag ttc tat ggg tca aaa gag gat cca cag act ttc tat        392
Val Val Ala Glu Phe Tyr Gly Ser Lys Glu Asp Pro Gln Thr Phe Tyr
100                 105                 110 tat gct gtt gct gtg gtg aag aag gat agt ggc ttc cag atg aac cag        440
Tyr Ala Val Ala Val Val Lys Lys Asp Ser Gly Phe Gln Met Asn Gln
115                 120                 125                 130 ctt cga ggc aag aag tcc tgc cac acg ggt cta ggc agg tcc gct ggg        488
Leu Arg Gly Lys Lys Ser Cys His Thr Gly Leu Gly Arg Ser Ala Gly
                135                 140                 145 tgg aac atc ccc ata ggc tta ctt tac tgt gac tta cct gag cca cgt        536
Trp Asn Ile Pro Ile Gly Leu Leu Tyr Cys Asp Leu Pro Glu Pro Arg
            150                 155                 160 aaa cct ctt gag aaa gca gtg gcc aat ttc ttc tcg ggc agc tgt gcc        584
Lys Pro Leu Glu Lys Ala Val Ala Asn Phe Phe Ser Gly Ser Cys Ala
        165                 170                 175 cct tgt gcg gat ggg acg gac ttc ccc cag ctg tgt caa ctg tgt cca        632
Pro Cys Ala Asp Gly Thr Asp Phe Pro Gln Leu Cys Gln Leu Cys Pro
    180                 185                 190 ggg tgt ggc tgc tcc acc ctt aac caa tac ttc ggc tac tcg gga gcc        680
Gly Cys Gly Cys Ser Thr Leu Asn Gln Tyr Phe Gly Tyr Ser Gly Ala
195                 200                 205                 210 ttc aag tgt ctg aag gat ggt gct ggg gat gtg gcc ttt gtc aag cac        728
Phe Lys Cys Leu Lys Asp Gly Ala Gly Asp Val Ala Phe Val Lys His
                215                 220                 225 tcg act ata ttt gag aac ttg gca aac aag gct gac agg gac cag tat        776
Ser Thr Ile Phe Glu Asn Leu Ala Asn Lys Ala Asp Arg Asp Gln Tyr
            230                 235                 240 gag ctg ctt tgc ctg gac aac acc cgg aag ccg gta gat gaa tac aag        824
Glu Leu Leu Cys Leu Asp Asn Thr Arg Lys Pro Val Asp Glu Tyr Lys
        245                 250                 255 gac tgc cac ttg gcc cag gtc cct tct cat acc gtc gtg gcc cga agt        872
Asp Cys His Leu Ala Gln Val Pro Ser His Thr Val Val Ala Arg Ser
    260                 265                 270 atg ggc ggc aag gag gac ttg atc tgg gag ctt ctc aac cag gcc cag        920
Met Gly Gly Lys Glu Asp Leu Ile Trp Glu Leu Leu Asn Gln Ala Gln
275                 280                 285                 290 gaa cat ttt ggc aaa gac aaa tca aaa gaa ttc caa cta ttc agc tct        968
Glu His Phe Gly Lys Asp Lys Ser Lys Glu Phe Gln Leu Phe Ser Ser
                295                 300                 305 cct cat ggg aag gac ctg ctg ttt aag gac tct gcc cac ggg ttt tta       1016
Pro His Gly Lys Asp Leu Leu Phe Lys Asp Ser Ala His Gly Phe Leu
            310                 315                 320 aaa gtc ccc ccc agg atg gat gcc aag atg tac ctg ggc tat gag tat       1064
Lys Val Pro Pro Arg Met Asp Ala Lys Met Tyr Leu Gly Tyr Glu Tyr
        325                 330                 335 gtc act gcc atc cgg aat cta cgg gaa ggc aca tgc cca gaa gcc cca       1112
Val Thr Ala Ile Arg Asn Leu Arg Glu Gly Thr Cys Pro Glu Ala Pro
    340                 345                 350 aca gat gaa tgc aag cct gtg aag tgg tgt gcg ctg agc cac cac gag       1160
Thr Asp Glu Cys Lys Pro Val Lys Trp Cys Ala Leu Ser His His Glu
355                 360                 365                 370 agg ctc aag tgt gat gag tgg agt gtt aac agt gta ggg aaa ata gag       1208
Arg Leu Lys Cys Asp Glu Trp Ser Val Asn Ser Val Gly Lys Ile Glu
                375                 380                 385 tgt gta tca gca gag acc acc gaa gac tgc atc gcc aag atc atg aat       1256
```

-continued

```
                Cys Val Ser Ala Glu Thr Thr Glu Asp Cys Ile Ala Lys Ile Met Asn
                                390                 395                 400 gga gaa gct gat gcc atg agc ttg gat gga ggg ttt gtc tac ata gcg         1304
Gly Glu Ala Asp Ala Met Ser Leu Asp Gly Gly Phe Val Tyr Ile Ala
            405                 410                 415 ggc aag tgt ggt ctg gtg cct gtc ttg gca gaa aac tac aat aag agc         1352
Gly Lys Cys Gly Leu Val Pro Val Leu Ala Glu Asn Tyr Asn Lys Ser
420                 425                 430 gat aat tgt gag gat aca cca gag gca ggg tat ttt gct gta gca gtg         1400
Asp Asn Cys Glu Asp Thr Pro Glu Ala Gly Tyr Phe Ala Val Ala Val
435                 440                 445                 450 gtg aag aaa tca gct tct gac ctc acc tgg gac aat ctg aaa ggc aag         1448
Val Lys Lys Ser Ala Ser Asp Leu Thr Trp Asp Asn Leu Lys Gly Lys
                455                 460                 465 aag tcc tgc cat acg gca gtt ggc aga acc gct ggc tgg aac atc ccc         1496
Lys Ser Cys His Thr Ala Val Gly Arg Thr Ala Gly Trp Asn Ile Pro
            470                 475                 480 atg ggc ctg ctc tac aat aag atc aac cac tgc aga ttt gat gaa ttt         1544
Met Gly Leu Leu Tyr Asn Lys Ile Asn His Cys Arg Phe Asp Glu Phe
            485                 490                 495 ttc agt gaa ggt tgt gcc cct ggg tct aag aaa gac tcc agt ctc tgt         1592
Phe Ser Glu Gly Cys Ala Pro Gly Ser Lys Lys Asp Ser Ser Leu Cys
500                 505                 510 aag ctg tgt atg ggc tca ggc cta aac ctg tgt gaa ccc aac aac aaa         1640
Lys Leu Cys Met Gly Ser Gly Leu Asn Leu Cys Glu Pro Asn Asn Lys
515                 520                 525                 530 gag gga tac tac ggc tac aca ggc gct ttc agg tgt ctg gtt gag aag         1688
Glu Gly Tyr Tyr Gly Tyr Thr Gly Ala Phe Arg Cys Leu Val Glu Lys
                535                 540                 545 gga gat gtg gcc ttt gtg aaa cac cag act gtc cca cag aac act ggg         1736
Gly Asp Val Ala Phe Val Lys His Gln Thr Val Pro Gln Asn Thr Gly
            550                 555                 560 gga aaa aac cct gat cca tgg gct aag aat ctg aat gaa aaa gac tat         1784
Gly Lys Asn Pro Asp Pro Trp Ala Lys Asn Leu Asn Glu Lys Asp Tyr
            565                 570                 575 gag ttg ctg tgc ctt gat ggt acc agg aaa cct gtg gag gag tat gcg         1832
Glu Leu Leu Cys Leu Asp Gly Thr Arg Lys Pro Val Glu Glu Tyr Ala
580                 585                 590 aac tgc cac ctg gcc aga gcc ccg aat cac gct gtg gtc aca cgg aaa         1880
Asn Cys His Leu Ala Arg Ala Pro Asn His Ala Val Val Thr Arg Lys
595                 600                 605                 610 gat aag gaa gct tgc gtc cac aag ata tta cgt caa cag cag cac cta         1928
Asp Lys Glu Ala Cys Val His Lys Ile Leu Arg Gln Gln Gln His Leu
                615                 620                 625 ttt gga agc aac gta act gac tgc tcg ggc aac ttt tgt ttg ttc cgg         1976
Phe Gly Ser Asn Val Thr Asp Cys Ser Gly Asn Phe Cys Leu Phe Arg
            630                 635                 640 tcg gaa acc aag gac ctt ctg ttc aga gat gac aca gta tgt ttg gcc         2024
Ser Glu Thr Lys Asp Leu Leu Phe Arg Asp Asp Thr Val Cys Leu Ala
            645                 650                 655 aaa ctt cat gac aga aac aca tat gaa aaa tac tta gga gaa gaa tat         2072
Lys Leu His Asp Arg Asn Thr Tyr Glu Lys Tyr Leu Gly Glu Glu Tyr
            660                 665                 670 gtc aag gct gtt ggt aac ctg aga aaa tgc tcc acc tca tca ctc ctg         2120
Val Lys Ala Val Gly Asn Leu Arg Lys Cys Ser Thr Ser Ser Leu Leu
675                 680                 685                 690 gaa gcc tgc act ttc cgt aga cct taa aatctcagag gtagggctgc               2167
Glu Ala Cys Thr Phe Arg Arg Pro
                695 caccaaggtg aagatgggaa cgcagatgat ccatgagttt gccctggttt cactggccca      2227
```

-continued

```
agtggtttgt gctaaccacg tctgtcttca cagctctgtg ttgccatgtg tgctgaacaa    2287
aaaataaaaa ttattattga ttttatattt c                                   2318
```

<210> SEQ ID NO 2
<211> LENGTH: 698
<212> TYPE: PRT
<213> ORGANISM: Homo sapiens

<400> SEQUENCE: 2

```
Met Arg Leu Ala Val Gly Ala Leu Leu Val Cys Ala Val Leu Gly Leu
1               5                   10                  15

Cys Leu Ala Val Pro Asp Lys Thr Val Arg Trp Cys Ala Val Ser Glu
            20                  25                  30

His Glu Ala Thr Lys Cys Gln Ser Phe Arg Asp His Met Lys Ser Val
        35                  40                  45

Ile Pro Ser Asp Gly Pro Ser Val Ala Cys Val Lys Lys Ala Ser Tyr
    50                  55                  60

Leu Asp Cys Ile Arg Ala Ile Ala Ala Asn Glu Ala Asp Ala Val Thr
65                  70                  75                  80

Leu Asp Ala Gly Leu Val Tyr Asp Ala Tyr Leu Ala Pro Asn Asn Leu
                85                  90                  95

Lys Pro Val Val Ala Glu Phe Tyr Gly Ser Lys Glu Asp Pro Gln Thr
            100                 105                 110

Phe Tyr Tyr Ala Val Ala Val Val Lys Lys Asp Ser Gly Phe Gln Met
        115                 120                 125

Asn Gln Leu Arg Gly Lys Lys Ser Cys His Thr Gly Leu Gly Arg Ser
    130                 135                 140

Ala Gly Trp Asn Ile Pro Ile Gly Leu Leu Tyr Cys Asp Leu Pro Glu
145                 150                 155                 160

Pro Arg Lys Pro Leu Glu Lys Ala Val Ala Asn Phe Phe Ser Gly Ser
                165                 170                 175

Cys Ala Pro Cys Ala Asp Gly Thr Asp Phe Pro Gln Leu Cys Gln Leu
            180                 185                 190

Cys Pro Gly Cys Gly Cys Ser Thr Leu Asn Gln Tyr Phe Gly Tyr Ser
        195                 200                 205

Gly Ala Phe Lys Cys Leu Lys Asp Gly Ala Gly Asp Val Ala Phe Val
    210                 215                 220

Lys His Ser Thr Ile Phe Glu Asn Leu Ala Asn Lys Ala Asp Arg Asp
225                 230                 235                 240

Gln Tyr Glu Leu Leu Cys Leu Asp Asn Thr Arg Lys Pro Val Asp Glu
                245                 250                 255

Tyr Lys Asp Cys His Leu Ala Gln Val Pro Ser His Thr Val Val Ala
            260                 265                 270

Arg Ser Met Gly Gly Lys Glu Asp Leu Ile Trp Glu Leu Leu Asn Gln
        275                 280                 285

Ala Gln Glu His Phe Gly Lys Asp Lys Ser Lys Glu Phe Gln Leu Phe
    290                 295                 300

Ser Ser Pro His Gly Lys Asp Leu Leu Phe Lys Asp Ser Ala His Gly
305                 310                 315                 320

Phe Leu Lys Val Pro Pro Arg Met Asp Ala Lys Met Tyr Leu Gly Tyr
                325                 330                 335

Glu Tyr Val Thr Ala Ile Arg Asn Leu Arg Glu Gly Thr Cys Pro Glu
            340                 345                 350

Ala Pro Thr Asp Glu Cys Lys Pro Val Lys Trp Cys Ala Leu Ser His
```

```
            355                 360                 365
His Glu Arg Leu Lys Cys Asp Glu Trp Ser Val Asn Ser Val Gly Lys
    370                 375                 380

Ile Glu Cys Val Ser Ala Glu Thr Thr Glu Asp Cys Ile Ala Lys Ile
385                 390                 395                 400

Met Asn Gly Glu Ala Asp Ala Met Ser Leu Asp Gly Gly Phe Val Tyr
                405                 410                 415

Ile Ala Gly Lys Cys Gly Leu Val Pro Val Leu Ala Glu Asn Tyr Asn
            420                 425                 430

Lys Ser Asp Asn Cys Glu Asp Thr Pro Glu Ala Gly Tyr Phe Ala Val
        435                 440                 445

Ala Val Val Lys Lys Ser Ala Ser Asp Leu Thr Trp Asp Asn Leu Lys
    450                 455                 460

Gly Lys Lys Ser Cys His Thr Ala Val Gly Arg Thr Ala Gly Trp Asn
465                 470                 475                 480

Ile Pro Met Gly Leu Leu Tyr Asn Lys Ile Asn His Cys Arg Phe Asp
                485                 490                 495

Glu Phe Phe Ser Glu Gly Cys Ala Pro Gly Ser Lys Lys Asp Ser Ser
            500                 505                 510

Leu Cys Lys Leu Cys Met Gly Ser Gly Leu Asn Leu Cys Glu Pro Asn
        515                 520                 525

Asn Lys Glu Gly Tyr Tyr Gly Tyr Thr Gly Ala Phe Arg Cys Leu Val
    530                 535                 540

Glu Lys Gly Asp Val Ala Phe Val Lys His Gln Thr Val Pro Gln Asn
545                 550                 555                 560

Thr Gly Gly Lys Asn Pro Asp Pro Trp Ala Lys Asn Leu Asn Glu Lys
                565                 570                 575

Asp Tyr Glu Leu Leu Cys Leu Asp Gly Thr Arg Lys Pro Val Glu Glu
            580                 585                 590

Tyr Ala Asn Cys His Leu Ala Arg Ala Pro Asn His Ala Val Val Thr
        595                 600                 605

Arg Lys Asp Lys Glu Ala Cys Val His Lys Ile Leu Arg Gln Gln Gln
    610                 615                 620

His Leu Phe Gly Ser Asn Val Thr Asp Cys Ser Gly Asn Phe Cys Leu
625                 630                 635                 640

Phe Arg Ser Glu Thr Lys Asp Leu Leu Phe Arg Asp Asp Thr Val Cys
                645                 650                 655

Leu Ala Lys Leu His Asp Arg Asn Thr Tyr Glu Lys Tyr Leu Gly Glu
            660                 665                 670

Glu Tyr Val Lys Ala Val Gly Asn Leu Arg Lys Cys Ser Thr Ser Ser
        675                 680                 685

Leu Leu Glu Ala Cys Thr Phe Arg Arg Pro
    690                 695

<210> SEQ ID NO 3
<211> LENGTH: 679
<212> TYPE: PRT
<213> ORGANISM: Homo sapiens
<220> FEATURE:
<221> NAME/KEY: MISC_FEATURE
<223> OTHER INFORMATION: Mature Transferrin Protein

<400> SEQUENCE: 3

Val Pro Asp Lys Thr Val Arg Trp Cys Ala Val Ser Glu His Glu Ala
1               5                   10                  15

Thr Lys Cys Gln Ser Phe Arg Asp His Met Lys Ser Val Ile Pro Ser
```

```
                 20                  25                  30
Asp Gly Pro Ser Val Ala Cys Val Lys Lys Ala Ser Tyr Leu Asp Cys
             35                  40                  45

Ile Arg Ala Ile Ala Ala Asn Glu Ala Asp Ala Val Thr Leu Asp Ala
         50                  55                  60

Gly Leu Val Tyr Asp Ala Tyr Leu Ala Pro Asn Asn Leu Lys Pro Val
 65                  70                  75                  80

Val Ala Glu Phe Tyr Gly Ser Lys Glu Asp Pro Gln Thr Phe Tyr Tyr
                 85                  90                  95

Ala Val Ala Val Val Lys Lys Asp Ser Gly Phe Gln Met Asn Gln Leu
             100                 105                 110

Arg Gly Lys Lys Ser Cys His Thr Gly Leu Gly Arg Ser Ala Gly Trp
         115                 120                 125

Asn Ile Pro Ile Gly Leu Leu Tyr Cys Asp Leu Pro Glu Pro Arg Lys
130                 135                 140

Pro Leu Glu Lys Ala Val Ala Asn Phe Phe Ser Gly Ser Cys Ala Pro
145                 150                 155                 160

Cys Ala Asp Gly Thr Asp Phe Pro Gln Leu Cys Gln Leu Cys Pro Gly
                 165                 170                 175

Cys Gly Cys Ser Thr Leu Asn Gln Tyr Phe Gly Tyr Ser Gly Ala Phe
             180                 185                 190

Lys Cys Leu Lys Asp Gly Ala Gly Asp Val Ala Phe Val Lys His Ser
         195                 200                 205

Thr Ile Phe Glu Asn Leu Ala Asn Lys Ala Asp Arg Asp Gln Tyr Glu
210                 215                 220

Leu Leu Cys Leu Asp Asn Thr Arg Lys Pro Val Asp Glu Tyr Lys Asp
225                 230                 235                 240

Cys His Leu Ala Gln Val Pro Ser His Thr Val Val Ala Arg Ser Met
                 245                 250                 255

Gly Gly Lys Glu Asp Leu Ile Trp Glu Leu Leu Asn Gln Ala Gln Glu
             260                 265                 270

His Phe Gly Lys Asp Lys Ser Lys Glu Phe Gln Leu Phe Ser Ser Pro
         275                 280                 285

His Gly Lys Asp Leu Leu Phe Lys Asp Ser Ala His Gly Phe Leu Lys
290                 295                 300

Val Pro Pro Arg Met Asp Ala Lys Met Tyr Leu Gly Tyr Glu Tyr Val
305                 310                 315                 320

Thr Ala Ile Arg Asn Leu Arg Glu Gly Thr Cys Pro Glu Ala Pro Thr
                 325                 330                 335

Asp Glu Cys Lys Pro Val Lys Trp Cys Ala Leu Ser His His Glu Arg
             340                 345                 350

Leu Lys Cys Asp Glu Trp Ser Val Asn Ser Val Gly Lys Ile Glu Cys
         355                 360                 365

Val Ser Ala Glu Thr Thr Glu Asp Cys Ile Ala Lys Ile Met Asn Gly
370                 375                 380

Glu Ala Asp Ala Met Ser Leu Asp Gly Gly Phe Val Tyr Ile Ala Gly
385                 390                 395                 400

Lys Cys Gly Leu Val Pro Val Leu Ala Glu Asn Tyr Asn Lys Ser Asp
                 405                 410                 415

Asn Cys Glu Asp Thr Pro Glu Ala Gly Tyr Phe Ala Val Ala Val Val
             420                 425                 430

Lys Lys Ser Ala Ser Asp Leu Thr Trp Asp Asn Leu Lys Gly Lys Lys
         435                 440                 445
```

```
Ser Cys His Thr Ala Val Gly Arg Thr Ala Gly Trp Asn Ile Pro Met
    450                 455                 460

Gly Leu Leu Tyr Asn Lys Ile Asn His Cys Arg Phe Asp Glu Phe
465                 470                 475                 480

Ser Glu Gly Cys Ala Pro Gly Ser Lys Lys Asp Ser Ser Leu Cys Lys
                485                 490                 495

Leu Cys Met Gly Ser Gly Leu Asn Leu Cys Glu Pro Asn Asn Lys Glu
            500                 505                 510

Gly Tyr Tyr Gly Tyr Thr Gly Ala Phe Arg Cys Leu Val Glu Lys Gly
        515                 520                 525

Asp Val Ala Phe Val Lys His Gln Thr Val Pro Gln Asn Thr Gly Gly
    530                 535                 540

Lys Asn Pro Asp Pro Trp Ala Lys Asn Leu Asn Glu Lys Asp Tyr Glu
545                 550                 555                 560

Leu Leu Cys Leu Asp Gly Thr Arg Lys Pro Val Glu Glu Tyr Ala Asn
                565                 570                 575

Cys His Leu Ala Arg Ala Pro Asn His Ala Val Val Thr Arg Lys Asp
            580                 585                 590

Lys Glu Ala Cys Val His Lys Ile Leu Arg Gln Gln Gln His Leu Phe
        595                 600                 605

Gly Ser Asn Val Thr Asp Cys Ser Gly Asn Phe Cys Leu Phe Arg Ser
610                 615                 620

Glu Thr Lys Asp Leu Leu Phe Arg Asp Asp Thr Val Cys Leu Ala Lys
625                 630                 635                 640

Leu His Asp Arg Asn Thr Tyr Glu Lys Tyr Leu Gly Glu Glu Tyr Val
                645                 650                 655

Lys Ala Val Gly Asn Leu Arg Lys Cys Ser Thr Ser Ser Leu Leu Glu
            660                 665                 670

Ala Cys Thr Phe Arg Arg Pro
        675

<210> SEQ ID NO 4
<211> LENGTH: 53
<212> TYPE: PRT
<213> ORGANISM: Homo sapiens
<220> FEATURE:
<221> NAME/KEY: misc_feature
<223> OTHER INFORMATION: Amino acids 1-53 of synaptotagmin I

<400> SEQUENCE: 4

Met Val Ser Glu Ser His His Glu Ala Leu Ala Ala Pro Pro Val Thr
1               5                   10                  15

Thr Val Ala Thr Val Leu Pro Ser Asn Ala Thr Glu Pro Ala Ser Pro
            20                  25                  30

Gly Glu Gly Lys Glu Asp Ala Phe Ser Lys Leu Lys Glu Lys Phe Met
        35                  40                  45

Asn Glu Leu His Lys
    50

<210> SEQ ID NO 5
<211> LENGTH: 12
<212> TYPE: PRT
<213> ORGANISM: Artificial sequence
<220> FEATURE:
<223> OTHER INFORMATION: Neutrophil lactoferrin splice variant

<400> SEQUENCE: 5

Glu Asp Cys Ile Ala Leu Lys Gly Glu Ala Asp Ala
1               5                   10
```

```
<210> SEQ ID NO 6
<211> LENGTH: 31
<212> TYPE: PRT
<213> ORGANISM: Homo sapiens
<220> FEATURE:
<221> NAME/KEY: MISC_FEATURE
<223> OTHER INFORMATION: Glucagon-Like Peptide
<220> FEATURE:
<221> NAME/KEY: misc_feature
<222> LOCATION: (31)..(31)
<223> OTHER INFORMATION: Xaa can be any naturally occurring amino acid

<400> SEQUENCE: 6

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Xaa
            20                  25                  30

<210> SEQ ID NO 7
<211> LENGTH: 28
<212> TYPE: PRT
<213> ORGANISM: Artificial sequence
<220> FEATURE:
<223> OTHER INFORMATION: GLP-1 molecule having insulinotropic activity

<400> SEQUENCE: 7

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys
            20                  25

<210> SEQ ID NO 8
<211> LENGTH: 29
<212> TYPE: PRT
<213> ORGANISM: Artificial sequence
<220> FEATURE:
<223> OTHER INFORMATION: GLP-1 molecule having insulinotropic activity

<400> SEQUENCE: 8

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly
            20                  25

<210> SEQ ID NO 9
<211> LENGTH: 29
<212> TYPE: PRT
<213> ORGANISM: Artificial sequence
<220> FEATURE:
<223> OTHER INFORMATION: GLP-1 analog
<220> FEATURE:
<221> NAME/KEY: MISC_FEATURE
<222> LOCATION: (1)..(1)
<223> OTHER INFORMATION: Xaa can be Ala, Gly, Val, Thr, Ile, or
      alpha-methyl-Ala
<220> FEATURE:
<221> NAME/KEY: MISC_FEATURE
<222> LOCATION: (14)..(14)
<223> OTHER INFORMATION: Xaa can be Glu, Gln, Ala, Thr, Ser, or Gly
<220> FEATURE:
<221> NAME/KEY: MISC_FEATURE
<222> LOCATION: (20)..(20)
<223> OTHER INFORMATION: Xaa can be Glu, Gln, Ala, Thr, Ser or Gly

<400> SEQUENCE: 9

Xaa Glu Gly Thr Phe Thr Ser Asp Val Ser Ser Tyr Leu Xaa Gly Gln
1               5                   10                  15
```

```
Ala Ala Lys Xaa Phe Ile Ala Trp Leu Val Lys Gly Arg
            20                  25
```

```
<210> SEQ ID NO 10
<211> LENGTH: 10
<212> TYPE: PRT
<213> ORGANISM: Artificial sequence
<220> FEATURE:
<223> OTHER INFORMATION: EPO domain

<400> SEQUENCE: 10

Cys Arg Ile Gly Pro Ile Thr Trp Val Cys
1               5                   10

<210> SEQ ID NO 11
<211> LENGTH: 20
<212> TYPE: PRT
<213> ORGANISM: Artificial sequence
<220> FEATURE:
<223> OTHER INFORMATION: EMP1 peptide

<400> SEQUENCE: 11

Gly Gly Thr Tyr Ser Cys His Phe Gly Pro Leu Thr Trp Val Cys Lys
1               5                   10                  15

Pro Gln Gly Gly
            20

<210> SEQ ID NO 12
<211> LENGTH: 13
<212> TYPE: PRT
<213> ORGANISM: Artificial sequence
<220> FEATURE:
<223> OTHER INFORMATION: EMP20 peptide

<400> SEQUENCE: 12

Tyr Ser Cys His Phe Gly Pro Leu Thr Trp Val Cys Lys
1               5                   10

<210> SEQ ID NO 13
<211> LENGTH: 90
<212> TYPE: DNA
<213> ORGANISM: Artificial sequence
<220> FEATURE:
<223> OTHER INFORMATION: sequence encoding glucagon-like peptide-1

<400> SEQUENCE: 13
catgctgaag gtactttac  ttctgatgtt tcttcttatt tggaaggtca agctgctaaa      60
gaatttattg cttggttggt taaaggtaga                                       90

<210> SEQ ID NO 14
<211> LENGTH: 30
<212> TYPE: PRT
<213> ORGANISM: Artificial sequence
<220> FEATURE:
<223> OTHER INFORMATION: glucagon-like peptide-1

<400> SEQUENCE: 14

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 15
<211> LENGTH: 118
<212> TYPE: DNA
<213> ORGANISM: Artificial sequence
```

<220> FEATURE:
<223> OTHER INFORMATION: Top Strand Synthetic Oligonucleotide
<220> FEATURE:
<221> NAME/KEY: misc_feature
<222> LOCATION: (7)..(112)
<223> OTHER INFORMATION: Top Strand Primer P0056

<400> SEQUENCE: 15
aggtctctag agaaaaggca tgctgaaggt acttttactt ctgatgtttc ttcttatttg    60
gaaggtcaag ctgctaaaga atttattgct tggttggtta aggtagggt acctgata      118

<210> SEQ ID NO 16
<211> LENGTH: 118
<212> TYPE: DNA
<213> ORGANISM: Artificial sequence
<220> FEATURE:
<223> OTHER INFORMATION: Bottom Strand Synthetic Oligonucleotide
<220> FEATURE:
<221> NAME/KEY: misc_feature
<222> LOCATION: (9)..(108)
<223> OTHER INFORMATION: Bottom Strand Primer P0057

<400> SEQUENCE: 16
tatcaggtac cctacctta accaaccaag caataaattc tttagcagct tgaccttcca    60
aataagaaga acatcagaa gtaaaagtac cttcagcatg cctttctct agagacct      118

<210> SEQ ID NO 17
<211> LENGTH: 6
<212> TYPE: PRT
<213> ORGANISM: Artificial sequence
<220> FEATURE:
<223> OTHER INFORMATION: N-terminal flanking peptide encoded by
      pREX00052

<400> SEQUENCE: 17

Arg Ser Leu Glu Lys Arg
1               5

<210> SEQ ID NO 18
<211> LENGTH: 28
<212> TYPE: DNA
<213> ORGANISM: Artificial Sequence
<220> FEATURE:
<223> OTHER INFORMATION: Description of Artificial Sequence:  XbaI/KpnI
      region of pREX0052

<400> SEQUENCE: 18
aggtctctag agaagagggt acctgata                                      28

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence:  Amino acid
      sequence encoded by XbaI/KpnI region of pREX0052

<400> SEQUENCE: 19

Arg Ser Leu Glu Lys Arg Val Pro Asp
1               5

<210> SEQ ID NO 20
<211> LENGTH: 30
<212> TYPE: DNA
<213> ORGANISM: Artificial Sequence
<220> FEATURE:
<223> OTHER INFORMATION: Description of Artificial Sequence:
      SalI/HindIII region of pREX0052

```
<400> SEQUENCE: 20
actttccgtc gaccttaata agcttaattc                                              30

<210> SEQ ID NO 21
<211> LENGTH: 5
<212> TYPE: PRT
<213> ORGANISM: Artificial Sequence
<220> FEATURE:
<223> OTHER INFORMATION: Description of Artificial Sequence:  Amino acid
      sequence encoded by SalI/HindIII region of pREX0052

<400> SEQUENCE: 21

Thr Phe Arg Arg Pro
1               5

<210> SEQ ID NO 22
<211> LENGTH: 450
<212> TYPE: DNA
<213> ORGANISM: Homo sapiens
<220> FEATURE:
<221> NAME/KEY: CDS
<222> LOCATION: (45)..(377)
<223> OTHER INFORMATION: GenBank Accession No. NM_000207, human insulin

<400> SEQUENCE: 22
gctgcatcag aagaggccat caagcacatc actgtccttc tgcc atg gcc ctg tgg       56
                                                 Met Ala Leu Trp
                                                  1 atg cgc ctc ctg ccc ctg ctg gcg ctg ctg gcc ctc tgg gga cct gac      104
Met Arg Leu Leu Pro Leu Leu Ala Leu Leu Ala Leu Trp Gly Pro Asp
 5                  10                  15                  20 cca gcc gca gcc ttt gtg aac caa cac ctg tgc ggc tca cac ctg gtg      152
Pro Ala Ala Ala Phe Val Asn Gln His Leu Cys Gly Ser His Leu Val
                 25                  30                  35 gaa gct ctc tac cta gtg tgc ggg gaa cga ggc ttc ttc tac aca ccc      200
Glu Ala Leu Tyr Leu Val Cys Gly Glu Arg Gly Phe Phe Tyr Thr Pro
             40                  45                  50 aag acc cgc cgg gag gca gag gac ctg cag gtg ggg cag gtg gag ctg      248
Lys Thr Arg Arg Glu Ala Glu Asp Leu Gln Val Gly Gln Val Glu Leu
         55                  60                  65 ggc ggg ggc cct ggt gca ggc agc ctg cag ccc ttg gcc ctg gag ggg      296
Gly Gly Gly Pro Gly Ala Gly Ser Leu Gln Pro Leu Ala Leu Glu Gly
 70                  75                  80 tcc ctg cag aag cgt ggc att gtg gaa caa tgc tgt acc agc atc tgc      344
Ser Leu Gln Lys Arg Gly Ile Val Glu Gln Cys Cys Thr Ser Ile Cys
 85                  90                  95                 100 tcc ctc tac cag ctg gag aac tac tgc aac tag acgcagcccg caggcagccc      397
Ser Leu Tyr Gln Leu Glu Asn Tyr Cys Asn
                105                 110 cccacccgcc gcctcctgca ccgagagaga tggaataaag cccttgaacc agc            450

<210> SEQ ID NO 23
<211> LENGTH: 110
<212> TYPE: PRT
<213> ORGANISM: Homo sapiens

<400> SEQUENCE: 23

Met Ala Leu Trp Met Arg Leu Leu Pro Leu Leu Ala Leu Leu Ala Leu
1               5                   10                  15

Trp Gly Pro Asp Pro Ala Ala Ala Phe Val Asn Gln His Leu Cys Gly
             20                  25                  30

Ser His Leu Val Glu Ala Leu Tyr Leu Val Cys Gly Glu Arg Gly Phe
```

```
                35                  40                  45
Phe Tyr Thr Pro Lys Thr Arg Arg Glu Ala Glu Asp Leu Gln Val Gly
 50                  55                  60
Gln Val Glu Leu Gly Gly Gly Pro Gly Ala Gly Ser Leu Gln Pro Leu
 65                  70                  75                  80
Ala Leu Glu Gly Ser Leu Gln Lys Arg Gly Ile Val Glu Gln Cys Cys
                 85                  90                  95
Thr Ser Ile Cys Ser Leu Tyr Gln Leu Glu Asn Tyr Cys Asn
                100                 105                 110

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence:  5' primer
      for cloning insulin sequence

<400> SEQUENCE: 24
tttgtgaacc aacacctgtg cggc                                              24

<210> SEQ ID NO 25
<211> LENGTH: 34
<212> TYPE: DNA
<213> ORGANISM: Artificial Sequence
<220> FEATURE:
<223> OTHER INFORMATION: Description of Artificial Sequence:  3' primer
      for cloning insulin sequence

<400> SEQUENCE: 25
gacgagggag atggtcgacc tcttgatgac gttg                                   34

<210> SEQ ID NO 26
<211> LENGTH: 289
<212> TYPE: DNA
<213> ORGANISM: Artificial Sequence
<220> FEATURE:
<223> OTHER INFORMATION: Description of Artificial Sequence:  Plasmid
      pREX0052 N-insulin
<220> FEATURE:
<221> NAME/KEY: CDS
<222> LOCATION: (1)..(288)

<400> SEQUENCE: 26 gct tac tct agg tct cta gat aag agg ttt gtg aac caa cac ctg tgc      48
Ala Tyr Ser Arg Ser Leu Asp Lys Arg Phe Val Asn Gln His Leu Cys
 1               5                  10                  15 ggc tca cac ctg gtg gaa gct ctc tac cta gtg tgc ggg gaa cga ggc      96
Gly Ser His Leu Val Glu Ala Leu Tyr Leu Val Cys Gly Glu Arg Gly
             20                  25                  30 ttc ttc tac aca ccc aag acc cgc cgg gag gca gag gac ctg cag gtg     144
Phe Phe Tyr Thr Pro Lys Thr Arg Arg Glu Ala Glu Asp Leu Gln Val
         35                  40                  45 ggg cag gtg gag ctg ggc ggg ggc cct ggt gca ggc agc ctg cag ccc     192
Gly Gln Val Glu Leu Gly Gly Gly Pro Gly Ala Gly Ser Leu Gln Pro
     50                  55                  60 ttg gcc ctg gag ggg tcc ctg cag aag cgt ggc att gtg gaa caa tgc     240
Leu Ala Leu Glu Gly Ser Leu Gln Lys Arg Gly Ile Val Glu Gln Cys
 65                  70                  75                  80 tgt acc agc atc tgc tcc ctc tac cag ctg gag aac tac tgc aac gta c  289
Cys Thr Ser Ile Cys Ser Leu Tyr Gln Leu Glu Asn Tyr Cys Asn Val
                 85                  90                  95

<210> SEQ ID NO 27
```

```
<211> LENGTH: 96
<212> TYPE: PRT
<213> ORGANISM: Artificial Sequence
<220> FEATURE:
<223> OTHER INFORMATION: Description of Artificial Sequence: Plasmid
      pREX0052 N-insulin

<400> SEQUENCE: 27

Ala Tyr Ser Arg Ser Leu Asp Lys Arg Phe Val Asn Gln His Leu Cys
1               5                   10                  15

Gly Ser His Leu Val Glu Ala Leu Tyr Leu Val Cys Gly Glu Arg Gly
            20                  25                  30

Phe Phe Tyr Thr Pro Lys Thr Arg Arg Glu Ala Glu Asp Leu Gln Val
        35                  40                  45

Gly Gln Val Glu Leu Gly Gly Gly Pro Gly Ala Gly Ser Leu Gln Pro
    50                  55                  60

Leu Ala Leu Glu Gly Ser Leu Gln Lys Arg Gly Ile Val Glu Gln Cys
65                  70                  75                  80

Cys Thr Ser Ile Cys Ser Leu Tyr Gln Leu Glu Asn Tyr Cys Asn Val
                85                  90                  95

<210> SEQ ID NO 28
<211> LENGTH: 49
<212> TYPE: DNA
<213> ORGANISM: Artificial Sequence
<220> FEATURE:
<223> OTHER INFORMATION: Description of Artificial Sequence: 5' insulin
      cloning primer

<400> SEQUENCE: 28
gcttactcta ggtctctaga taagaggttt gtgaaccaac acctgtgcg            49

<210> SEQ ID NO 29
<211> LENGTH: 22
<212> TYPE: DNA
<213> ORGANISM: Artificial Sequence
<220> FEATURE:
<223> OTHER INFORMATION: Description of Artificial Sequence: Linker for
      cloning insulin

<400> SEQUENCE: 29
ctggagaact actgcaacgt ac                                         22

<210> SEQ ID NO 30
<211> LENGTH: 18
<212> TYPE: DNA
<213> ORGANISM: Artificial Sequence
<220> FEATURE:
<223> OTHER INFORMATION: Description of Artificial Sequence: Linker for
      cloning insulin

<400> SEQUENCE: 30
gacctcttga tgacgttg                                              18

<210> SEQ ID NO 31
<211> LENGTH: 290
<212> TYPE: DNA
<213> ORGANISM: Artificial Sequence
<220> FEATURE:
<223> OTHER INFORMATION: Description of Artificial Sequence: Plasmid
      pREX0052 C-insulin
<220> FEATURE:
<221> NAME/KEY: CDS
<222> LOCATION: (1)..(276)

<400> SEQUENCE: 31
```

```
tgc act ttc cgt cga cct ttt gtg aac caa cac ctg tgc ggc tca cac      48
Cys Thr Phe Arg Arg Pro Phe Val Asn Gln His Leu Cys Gly Ser His
1               5                   10                  15 ctg gtg gaa gct ctc tac cta gtg tgc ggg gaa cga ggc ttc ttc tac      96
Leu Val Glu Ala Leu Tyr Leu Val Cys Gly Glu Arg Gly Phe Phe Tyr
                20                  25                  30 aca ccc aag acc cgc cgg gag gca gag gac ctg cag gtg ggg cag gtg     144
Thr Pro Lys Thr Arg Arg Glu Ala Glu Asp Leu Gln Val Gly Gln Val
            35                  40                  45 gag ctg ggc ggg ggc cct ggt gca ggc agc ctg cag ccc ttg gcc ctg     192
Glu Leu Gly Gly Gly Pro Gly Ala Gly Ser Leu Gln Pro Leu Ala Leu
        50                  55                  60 gag ggg tcc ctg cag aag cgt ggc att gtg gaa caa tgc tgt acc agc     240
Glu Gly Ser Leu Gln Lys Arg Gly Ile Val Glu Gln Cys Cys Thr Ser
65                  70                  75                  80 atc tgc tcc ctc tac cag ctg gag aac tac tgc aac taataagctt aatt     290
Ile Cys Ser Leu Tyr Gln Leu Glu Asn Tyr Cys Asn
                85                  90
```

<210> SEQ ID NO 32
<211> LENGTH: 92
<212> TYPE: PRT
<213> ORGANISM: Artificial Sequence
<220> FEATURE:
<223> OTHER INFORMATION: Description of Artificial Sequence:  Plasmid
      pREX0052 C-insulin

<400> SEQUENCE: 32

```
Cys Thr Phe Arg Arg Pro Phe Val Asn Gln His Leu Cys Gly Ser His
1               5                   10                  15

Leu Val Glu Ala Leu Tyr Leu Val Cys Gly Glu Arg Gly Phe Phe Tyr
                20                  25                  30

Thr Pro Lys Thr Arg Arg Glu Ala Glu Asp Leu Gln Val Gly Gln Val
            35                  40                  45

Glu Leu Gly Gly Gly Pro Gly Ala Gly Ser Leu Gln Pro Leu Ala Leu
        50                  55                  60

Glu Gly Ser Leu Gln Lys Arg Gly Ile Val Glu Gln Cys Cys Thr Ser
65                  70                  75                  80

Ile Cys Ser Leu Tyr Gln Leu Glu Asn Tyr Cys Asn
                85                  90
```

<210> SEQ ID NO 33
<211> LENGTH: 40
<212> TYPE: DNA
<213> ORGANISM: Artificial Sequence
<220> FEATURE:
<223> OTHER INFORMATION: Description of Artificial Sequence:  5' insulin
      cloning primer

<400> SEQUENCE: 33
tgcactttcc gtcgaccttt tgtgaaccaa cacctgtgcg                          40

<210> SEQ ID NO 34
<211> LENGTH: 32
<212> TYPE: DNA
<213> ORGANISM: Artificial Sequence
<220> FEATURE:
<223> OTHER INFORMATION: Description of Artificial Sequence:  3' insulin
      cloning primer

<400> SEQUENCE: 34
gacctcttga tgacgttgat tattcgaatt aa                                  32

<210> SEQ ID NO 35
<211> LENGTH: 21
<212> TYPE: DNA
<213> ORGANISM: Artificial sequence
<220> FEATURE:
<223> OTHER INFORMATION: Primer P0070

<400> SEQUENCE: 35
gctatgacca acaagtgtct c                                            21

<210> SEQ ID NO 36
<211> LENGTH: 22
<212> TYPE: DNA
<213> ORGANISM: Artificial sequence
<220> FEATURE:
<223> OTHER INFORMATION: Primer P0071

<400> SEQUENCE: 36
cgcacctgtg gcgccggtga tg                                           22

<210> SEQ ID NO 37
<211> LENGTH: 60
<212> TYPE: DNA
<213> ORGANISM: Artificial sequence
<220> FEATURE:
<223> OTHER INFORMATION: Sequence for fusion of IFN Beta-1 to mTf
<220> FEATURE:
<221> NAME/KEY: misc_feature
<222> LOCATION: (18)..(48)
<223> OTHER INFORMATION: Primer P0082 sequence

<400> SEQUENCE: 37
ctgcttactc taggtctcta gagaaaacag ggtacctccg aaacgtacct gataaaactg 60

<210> SEQ ID NO 38
<211> LENGTH: 60
<212> TYPE: DNA
<213> ORGANISM: Artificial sequence
<220> FEATURE:
<223> OTHER INFORMATION: Sequence for fusion of IFN Beta-1 to mTf
<220> FEATURE:
<221> NAME/KEY: misc_feature
<222> LOCATION: (17)..(39)
<223> OTHER INFORMATION: Primer P0083 sequence

<400> SEQUENCE: 38
cagttttatc aggtacgttt cggaggtacc ctgttttctc tagagaccta gagtaagcag 60

<210> SEQ ID NO 39
<211> LENGTH: 8
<212> TYPE: PRT
<213> ORGANISM: Artificial sequence
<220> FEATURE:
<223> OTHER INFORMATION: MFa-1 sequence

<400> SEQUENCE: 39

Ala Tyr Ser Arg Ser Leu Glu Lys
1 5

<210> SEQ ID NO 40
<211> LENGTH: 6
<212> TYPE: PRT
<213> ORGANISM: Artificial sequence
<220> FEATURE:
<223> OTHER INFORMATION: IFN-B-1 sequence

<400> SEQUENCE: 40

Thr Gly Tyr Leu Arg Asn
1 5

<210> SEQ ID NO 41
<211> LENGTH: 5
<212> TYPE: PRT
<213> ORGANISM: Artificial sequence
<220> FEATURE:
<223> OTHER INFORMATION: mTf sequence

<400> SEQUENCE: 41

Val Pro Asp Lys Thr
1               5

<210> SEQ ID NO 42
<211> LENGTH: 43
<212> TYPE: DNA
<213> ORGANISM: Artificial sequence
<220> FEATURE:
<223> OTHER INFORMATION: Primer P0084

<400> SEQUENCE: 42
ctctaggtct ctagagaaaa ggagctacaa cttgcttgga ttc         43

<210> SEQ ID NO 43
<211> LENGTH: 25
<212> TYPE: DNA
<213> ORGANISM: Artificial sequence
<220> FEATURE:
<223> OTHER INFORMATION: Primer P0085

<400> SEQUENCE: 43
gtctgaatgt cccatggagg ctttg                             25

<210> SEQ ID NO 44
<211> LENGTH: 36
<212> TYPE: DNA
<213> ORGANISM: Artificial sequence
<220> FEATURE:
<223> OTHER INFORMATION: Primer P0086

<400> SEQUENCE: 44
actttccgtc gacctagcta caacttgctt ggattc                 36

<210> SEQ ID NO 45
<211> LENGTH: 50
<212> TYPE: DNA
<213> ORGANISM: Artificial sequence
<220> FEATURE:
<223> OTHER INFORMATION: Primer P0087

<400> SEQUENCE: 45
tgaatgtcca atggaggctt tgattatttc gaattaagaa tactaaatac  50

<210> SEQ ID NO 46
<211> LENGTH: 757
<212> TYPE: DNA
<213> ORGANISM: Homo sapiens
<220> FEATURE:
<221> NAME/KEY: CDS
<222> LOCATION: (1)..(564)
<223> OTHER INFORMATION: interferon-beta 1

<400> SEQUENCE: 46 atg acc aac aag tgt ctc ctc caa att gct ctc ctg ttg tgc ttc tcc    48
Met Thr Asn Lys Cys Leu Leu Gln Ile Ala Leu Leu Leu Cys Phe Ser
1               5                   10                  15 act aca gct ctt tcc atg agc tac aac ttg ctt gga ttc cta caa aga   96
Thr Thr Ala Leu Ser Met Ser Tyr Asn Leu Leu Gly Phe Leu Gln Arg

```
                     20                  25                  30
agc agc aat ttt cag tgt cag aag ctc ctg tgg caa ttg aat ggg agg      144
Ser Ser Asn Phe Gln Cys Gln Lys Leu Leu Trp Gln Leu Asn Gly Arg
         35                  40                  45 ctt gaa tat tgc ctc aag gac agg atg aac ttt gac atc cct gag gag      192
Leu Glu Tyr Cys Leu Lys Asp Arg Met Asn Phe Asp Ile Pro Glu Glu
 50                  55                  60 att aag cag ctg cag cag ttc cag aag gag gac gcc gca ttg acc atc      240
Ile Lys Gln Leu Gln Gln Phe Gln Lys Glu Asp Ala Ala Leu Thr Ile
 65                  70                  75                  80 tat gag atg ctc cag aac atc ttt gct att ttc aga caa gat tca tct      288
Tyr Glu Met Leu Gln Asn Ile Phe Ala Ile Phe Arg Gln Asp Ser Ser
                 85                  90                  95 agc act ggc tgg aat gag act att gtt gag aac ctc ctg gct aat gtc      336
Ser Thr Gly Trp Asn Glu Thr Ile Val Glu Asn Leu Leu Ala Asn Val
            100                 105                 110 tat cat cag ata aac cat ctg aag aca gtc ctg gaa gaa aaa ctg gag      384
Tyr His Gln Ile Asn His Leu Lys Thr Val Leu Glu Glu Lys Leu Glu
        115                 120                 125 aaa gaa gat ttt acc agg gga aaa ctc atg agc agt ctg cac ctg aaa      432
Lys Glu Asp Phe Thr Arg Gly Lys Leu Met Ser Ser Leu His Leu Lys
130                 135                 140 aga tat tat ggg agg att ctg cat tac ctg aag gcc aag gag tac agt      480
Arg Tyr Tyr Gly Arg Ile Leu His Tyr Leu Lys Ala Lys Glu Tyr Ser
145                 150                 155                 160 cac tgt gcc tgg acc ata gtc aga gtg gaa atc cta agg aac ttt tac      528
His Cys Ala Trp Thr Ile Val Arg Val Glu Ile Leu Arg Asn Phe Tyr
                165                 170                 175 ttc att aac aga ctt aca ggt tac ctc cga aac tga agatctccta           574
Phe Ile Asn Arg Leu Thr Gly Tyr Leu Arg Asn
            180                 185 gcctgtccct ctgggactgg acaattgctt caagcattct tcaaccagca gatgctgttt    634
aagtgactga tggctaatgt actgcaaatg aaaggacact agaagatttt gaaattttta    694
ttaaattatg agttattttt atttatttaa atttattttt ggaaaataaa ttattttttgg   754 tgc                                                                  757

<210> SEQ ID NO 47
<211> LENGTH: 187
<212> TYPE: PRT
<213> ORGANISM: Homo sapiens

<400> SEQUENCE: 47

Met Thr Asn Lys Cys Leu Leu Gln Ile Ala Leu Leu Cys Phe Ser
 1               5                  10                  15

Thr Thr Ala Leu Ser Met Ser Tyr Asn Leu Leu Gly Phe Leu Gln Arg
            20                  25                  30

Ser Ser Asn Phe Gln Cys Gln Lys Leu Leu Trp Gln Leu Asn Gly Arg
        35                  40                  45

Leu Glu Tyr Cys Leu Lys Asp Arg Met Asn Phe Asp Ile Pro Glu Glu
 50                  55                  60

Ile Lys Gln Leu Gln Gln Phe Gln Lys Glu Asp Ala Ala Leu Thr Ile
 65                  70                  75                  80

Tyr Glu Met Leu Gln Asn Ile Phe Ala Ile Phe Arg Gln Asp Ser Ser
                 85                  90                  95

Ser Thr Gly Trp Asn Glu Thr Ile Val Glu Asn Leu Leu Ala Asn Val
            100                 105                 110

Tyr His Gln Ile Asn His Leu Lys Thr Val Leu Glu Glu Lys Leu Glu
```

```
                 115                 120                 125
Lys Glu Asp Phe Thr Arg Gly Lys Leu Met Ser Ser Leu His Leu Lys
            130                 135                 140

Arg Tyr Tyr Gly Arg Ile Leu His Tyr Leu Lys Ala Lys Glu Tyr Ser
145                 150                 155                 160

His Cys Ala Trp Thr Ile Val Arg Val Glu Ile Leu Arg Asn Phe Tyr
                165                 170                 175

Phe Ile Asn Arg Leu Thr Gly Tyr Leu Arg Asn
            180                 185

<210> SEQ ID NO 48
<211> LENGTH: 676
<212> TYPE: PRT
<213> ORGANISM: Oryctolagus cuniculus

<400> SEQUENCE: 48

Val Thr Glu Lys Thr Val Arg Trp Cys Ala Val Asn Asp His Glu Ala
1               5                   10                  15

Ser Lys Cys Ala Asn Phe Arg Asp Ser Met Lys Lys Val Leu Pro Glu
            20                  25                  30

Asp Gly Pro Arg Ile Ile Cys Val Lys Lys Ala Ser Tyr Leu Asp Cys
        35                  40                  45

Ile Lys Ala Ile Ala Ala His Glu Ala Asp Ala Val Thr Leu Asp Ala
    50                  55                  60

Gly Leu Val His Glu Ala Gly Leu Thr Pro Asn Asn Leu Lys Pro Val
65                  70                  75                  80

Val Ala Glu Phe Tyr Gly Ser Lys Glu Asn Pro Lys Thr Phe Tyr Tyr
                85                  90                  95

Ala Val Ala Leu Val Lys Lys Gly Ser Asn Phe Gln Leu Asn Glu Leu
            100                 105                 110

Gln Gly Lys Lys Ser Cys His Thr Gly Leu Gly Arg Ser Ala Gly Trp
        115                 120                 125

Asn Ile Pro Ile Gly Leu Leu Tyr Cys Asp Leu Pro Glu Pro Arg Lys
    130                 135                 140

Pro Leu Glu Lys Ala Val Ala Ser Phe Phe Ser Gly Ser Cys Val Pro
145                 150                 155                 160

Cys Ala Asp Gly Ala Asp Phe Pro Gln Leu Cys Gln Leu Cys Pro Gly
                165                 170                 175

Cys Gly Cys Ser Ser Val Gln Pro Tyr Phe Gly Tyr Ser Gly Ala Phe
            180                 185                 190

Lys Cys Leu Lys Asp Gly Leu Gly Asp Val Ala Phe Val Lys Gln Glu
        195                 200                 205

Thr Ile Phe Glu Asn Leu Pro Ser Lys Asp Glu Arg Asp Gln Tyr Glu
    210                 215                 220

Leu Leu Cys Leu Asp Asn Thr Arg Lys Pro Val Asp Glu Tyr Glu Gln
225                 230                 235                 240

Cys His Leu Ala Arg Val Pro Ser His Ala Val Val Ala Arg Ser Val
                245                 250                 255

Asp Gly Lys Glu Asp Leu Ile Trp Glu Leu Leu Asn Gln Ala Gln Glu
            260                 265                 270

His Phe Gly Lys Asp Lys Ser Gly Asp Phe Gln Leu Phe Ser Ser Pro
        275                 280                 285

His Gly Lys Asn Leu Leu Phe Lys Asp Ser Ala Tyr Gly Phe Phe Lys
    290                 295                 300

Val Pro Pro Arg Met Asp Ala Asn Leu Tyr Leu Gly Tyr Glu Tyr Val
```

```
                305                 310                 315                 320
Thr Ala Val Arg Asn Leu Arg Glu Gly Ile Cys Pro Asp Pro Leu Gln
            325                 330                 335

Asp Glu Cys Lys Ala Val Lys Trp Cys Ala Leu Ser His His Glu Arg
            340                 345                 350

Leu Lys Cys Asp Glu Trp Ser Val Thr Ser Gly Gly Leu Ile Glu Cys
            355                 360                 365

Glu Ser Ala Glu Thr Pro Glu Asp Cys Ile Ala Lys Ile Met Asn Gly
370                 375                 380

Glu Ala Asp Ala Met Ser Leu Asp Gly Gly Tyr Val Tyr Ile Ala Gly
385                 390                 395                 400

Gln Cys Gly Leu Val Pro Val Leu Ala Glu Asn Tyr Glu Ser Thr Asp
                405                 410                 415

Cys Lys Lys Ala Pro Glu Glu Gly Tyr Leu Ser Val Ala Val Val Lys
                420                 425                 430

Lys Ser Asn Pro Asp Ile Asn Trp Asn Asn Leu Glu Gly Lys Lys Ser
                435                 440                 445

Cys His Thr Ala Val Asp Arg Thr Ala Gly Trp Asn Ile Pro Met Gly
            450                 455                 460

Leu Leu Tyr Asn Arg Ile Asn His Cys Arg Phe Asp Glu Phe Phe Arg
465                 470                 475                 480

Gln Gly Cys Ala Pro Gly Ser Gln Lys Asn Ser Ser Leu Cys Glu Leu
                485                 490                 495

Cys Ile Gly Pro Ser Val Cys Ala Pro Asn Asn Arg Glu Gly Tyr Tyr
                500                 505                 510

Gly Tyr Thr Gly Ala Phe Arg Cys Leu Val Glu Lys Gly Asp Val Ala
            515                 520                 525

Phe Val Lys Ser Gln Thr Val Leu Gln Asn Thr Gly Gly Arg Asn Ser
530                 535                 540

Glu Pro Trp Ala Lys Asp Leu Lys Glu Asp Phe Glu Leu Leu Cys
545                 550                 555                 560

Leu Asp Gly Thr Arg Lys Pro Val Ser Glu Ala His Asn Cys His Leu
                565                 570                 575

Ala Lys Ala Pro Asn His Ala Val Val Ser Arg Lys Asp Lys Ala Ala
                580                 585                 590

Cys Val Lys Gln Lys Leu Leu Asp Leu Gln Val Glu Tyr Gly Asn Thr
            595                 600                 605

Val Ala Asp Cys Ser Ser Lys Phe Cys Met Phe His Ser Lys Thr Lys
610                 615                 620

Asp Leu Leu Phe Arg Asp Asp Thr Lys Cys Leu Val Asp Leu Arg Gly
625                 630                 635                 640

Lys Asn Thr Tyr Glu Lys Tyr Leu Gly Ala Asp Tyr Ile Lys Ala Val
                645                 650                 655

Ser Asn Leu Arg Lys Cys Ser Ser Arg Leu Leu Glu Ala Cys Thr
                660                 665                 670

Phe His Lys His
        675

<210> SEQ ID NO 49
<211> LENGTH: 676
<212> TYPE: PRT
<213> ORGANISM: Rattus norvegicus

<400> SEQUENCE: 49

Val Pro Asp Lys Thr Val Lys Trp Cys Ala Val Ser Glu His Glu Asn
```

```
              1               5                  10                 15
Thr Lys Cys Ile Ser Phe Arg Asp His Met Lys Thr Val Leu Pro Ala
                 20                  25                 30
Asp Gly Pro Arg Leu Pro Cys Val Lys Lys Thr Ser Tyr Gln Asp Cys
                 35                  40                 45
Ile Lys Ala Ile Ser Gly Gly Glu Ala Asp Ala Ile Thr Leu Asp Gly
                 50                  55                 60
Gly Trp Val Tyr Asp Ala Gly Leu Thr Pro Asn Asn Leu Lys Pro Val
65                   70                  75                 80
Ala Ala Glu Phe Tyr Gly Ser Leu Glu His Arg Gln Thr His Tyr Leu
                      85                  90                 95
Ala Val Ala Val Val Lys Lys Gly Thr Asp Phe Gln Leu Asn Gln Leu
                 100                 105                110
Gln Gly Lys Lys Ser Cys His Thr Gly Leu Gly Arg Ser Ala Gly Trp
                 115                 120                125
Ile Ile Pro Ile Gly Leu Leu Phe Cys Asn Leu Pro Glu Pro Arg Lys
                 130                 135                140
Pro Leu Glu Lys Ala Val Ala Ser Phe Phe Ser Gly Ser Cys Val Pro
145                  150                 155                160
Cys Ala Asp Pro Val Ala Phe Pro Gln Leu Cys Gln Leu Cys Pro Gly
                 165                 170                175
Cys Gly Cys Ser Pro Thr Gln Pro Phe Phe Gly Tyr Val Gly Ala Phe
                 180                 185                190
Lys Cys Leu Arg Asp Gly Gly Gly Asp Val Ala Phe Val Lys His Thr
                 195                 200                205
Thr Ile Phe Glu Val Leu Pro Gln Lys Ala Asp Arg Asp Gln Tyr Glu
                 210                 215                220
Leu Leu Cys Leu Asp Asn Thr Arg Lys Pro Val Asp Gln Tyr Glu Asp
225                  230                 235                240
Cys Tyr Leu Ala Arg Ile Pro Ser His Ala Val Val Ala Arg Asn Gly
                 245                 250                255
Asp Gly Lys Glu Asp Leu Ile Trp Glu Ile Leu Lys Val Ala Gln Glu
                 260                 265                270
His Phe Gly Lys Gly Lys Ser Lys Asp Phe Gln Leu Phe Gly Ser Pro
                 275                 280                285
Leu Gly Lys Asp Leu Leu Phe Lys Asp Ser Arg Phe Gly Leu Leu Arg
                 290                 295                300
Ala Pro Lys Asp Gly Leu Gln Ala Val Pro Arg Pro Gln Leu Cys His
305                  310                 315                320
Cys His Ser Lys Ser Ala Gly Ser Cys Pro Asp Ala Ile Asp Ser Ala
                 325                 330                335
Pro Val Lys Trp Cys Ala Leu Ser His Gln Glu Arg Ala Lys Cys Asp
                 340                 345                350
Glu Trp Ser Val Thr Gly Asn Gly Gln Ile Glu Cys Glu Ser Ala Glu
                 355                 360                365
Ser Thr Glu Asp Cys Ile Asp Lys Ile Val Asn Gly Glu Ala Asp Ala
                 370                 375                380
Met Ser Leu Asp Gly Gly His Ala Tyr Ile Ala Gly Gln Cys Gly Leu
385                  390                 395                400
Val Pro Val Met Ala Glu Asn Tyr Asp Ile Ser Ser Cys Thr Asn Pro
                 405                 410                415
Gln Ser Asp Val Phe Pro Lys Gly Tyr Tyr Ala Val Ala Val Val Lys
                 420                 425                430
```

```
Ala Ser Asp Ser Ser Ile Asn Trp Asn Asn Leu Lys Gly Lys Lys Ser
            435                 440                 445

Cys His Thr Gly Val Asp Arg Thr Ala Gly Trp Asn Ile Pro Met Gly
450                 455                 460

Leu Leu Phe Ser Arg Ile Asn His Cys Lys Phe Asp Glu Phe Phe Ser
465                 470                 475                 480

Gln Gly Cys Ala Pro Gly Tyr Lys Lys Asn Ser Thr Leu Cys Asp Leu
            485                 490                 495

Cys Ile Gly Pro Ala Lys Cys Ala Pro Asn Asn Arg Glu Gly Tyr Asn
            500                 505                 510

Gly Tyr Thr Gly Ala Phe Gln Cys Leu Val Glu Lys Gly Asp Val Ala
            515                 520                 525

Phe Val Lys His Gln Thr Val Leu Glu Asn Thr Asn Gly Lys Asn Thr
530                 535                 540

Ala Ala Trp Ala Lys Asp Leu Lys Gln Glu Asp Phe Gln Leu Leu Cys
545                 550                 555                 560

Pro Asp Gly Thr Lys Lys Pro Val Thr Glu Phe Ala Thr Cys His Leu
            565                 570                 575

Ala Gln Ala Pro Asn His Val Val Val Ser Arg Lys Gly Lys Ala Ala
            580                 585                 590

Arg Val Ser Thr Val Leu Thr Ala Gln Lys Asp Leu Phe Trp Lys Gly
            595                 600                 605

Asp Lys Asp Cys Thr Gly Asn Phe Cys Leu Phe Arg Ser Ser Thr Lys
610                 615                 620

Asp Leu Leu Phe Arg Asp Asp Thr Lys Cys Leu Thr Lys Leu Pro Glu
625                 630                 635                 640

Gly Thr Thr Tyr Glu Glu Tyr Leu Gly Ala Glu Tyr Leu Gln Ala Val
            645                 650                 655

Gly Asn Ile Arg Lys Cys Ser Thr Ser Arg Leu Leu Glu Ala Cys Thr
            660                 665                 670

Phe His Lys Ser
        675

<210> SEQ ID NO 50
<211> LENGTH: 677
<212> TYPE: PRT
<213> ORGANISM: Mus musculus

<400> SEQUENCE: 50

Val Pro Asp Lys Thr Val Lys Trp Cys Ala Val Ser Glu His Glu Asn
1               5                   10                  15

Thr Lys Cys Ile Ser Phe Arg Asp His Met Lys Thr Val Leu Pro Pro
            20                  25                  30

Asp Gly Pro Arg Leu Ala Cys Val Lys Lys Thr Ser Tyr Pro Asp Cys
        35                  40                  45

Ile Lys Ala Ile Ser Ala Ser Glu Ala Asp Ala Met Thr Leu Asp Gly
    50                  55                  60

Gly Trp Val Tyr Asp Ala Gly Leu Thr Pro Asn Asn Leu Lys Pro Val
65                  70                  75                  80

Ala Ala Glu Phe Tyr Gly Ser Val Glu His Pro Gln Thr Tyr Tyr Tyr
            85                  90                  95

Ala Val Ala Val Val Lys Lys Gly Thr Asp Phe Gln Leu Asn Gln Leu
        100                 105                 110

Glu Gly Lys Lys Ser Cys His Thr Gly Leu Gly Arg Ser Ala Gly Trp
    115                 120                 125
```

```
Val Ile Pro Ile Gly Leu Leu Phe Cys Lys Leu Ser Glu Pro Arg Ser
    130                 135                 140

Pro Leu Glu Lys Ala Val Ser Ser Phe Phe Ser Gly Ser Cys Val Pro
145                 150                 155                 160

Cys Ala Asp Pro Val Ala Phe Pro Lys Leu Cys Gln Leu Cys Pro Gly
                165                 170                 175

Cys Gly Cys Ser Ser Thr Gln Pro Phe Phe Gly Tyr Val Gly Ala Phe
                180                 185                 190

Lys Cys Leu Lys Asp Gly Gly Asp Val Ala Phe Val Lys His Thr
        195                 200                 205

Thr Ile Phe Glu Val Leu Pro Glu Lys Ala Asp Arg Asp Gln Tyr Glu
    210                 215                 220

Leu Leu Cys Leu Asp Asn Thr Arg Lys Pro Val Asp Gln Tyr Glu Asp
225                 230                 235                 240

Cys Tyr Leu Ala Arg Ile Pro Ser His Ala Val Val Ala Arg Lys Asn
                245                 250                 255

Asn Gly Lys Glu Asp Leu Ile Trp Glu Ile Leu Lys Val Ala Gln Glu
            260                 265                 270

His Phe Gly Lys Gly Lys Ser Lys Asp Phe Gln Leu Phe Ser Ser Pro
        275                 280                 285

Leu Gly Lys Asp Leu Leu Phe Lys Asp Ser Ala Phe Gly Leu Leu Arg
    290                 295                 300

Val Pro Pro Arg Met Asp Tyr Arg Leu Tyr Leu Gly His Asn Tyr Val
305                 310                 315                 320

Thr Ala Ile Arg Asn Gln Gln Glu Gly Val Cys Pro Glu Gly Ser Ile
                325                 330                 335

Asp Asn Ser Pro Val Lys Trp Cys Ala Leu Ser His Leu Glu Arg Thr
            340                 345                 350

Lys Cys Asp Glu Trp Ser Ile Ile Ser Glu Gly Lys Ile Glu Cys Glu
        355                 360                 365

Ser Ala Glu Thr Thr Glu Asp Cys Ile Glu Lys Ile Val Asn Gly Glu
    370                 375                 380

Ala Asp Ala Met Thr Leu Asp Gly Gly His Ala Tyr Ile Ala Gly Gln
385                 390                 395                 400

Cys Gly Leu Val Pro Val Met Ala Glu Tyr Tyr Glu Ser Ser Asn Cys
                405                 410                 415

Ala Ile Pro Ser Gln Gln Gly Ile Phe Pro Lys Gly Tyr Tyr Ala Val
            420                 425                 430

Ala Val Val Lys Ala Ser Asp Thr Ser Ile Thr Trp Asn Asn Leu Lys
        435                 440                 445

Gly Lys Lys Ser Cys His Thr Gly Val Asp Arg Thr Ala Gly Trp Asn
    450                 455                 460

Ile Pro Met Gly Met Leu Tyr Asn Arg Ile Asn His Cys Lys Phe Asp
465                 470                 475                 480

Glu Phe Phe Ser Gln Gly Cys Ala Pro Gly Tyr Glu Lys Asn Ser Thr
                485                 490                 495

Leu Cys Asp Leu Cys Ile Gly Pro Leu Lys Cys Ala Pro Asn Asn Lys
            500                 505                 510

Glu Glu Tyr Asn Gly Tyr Thr Gly Ala Phe Arg Cys Leu Val Glu Lys
        515                 520                 525

Gly Asp Val Ala Phe Val Lys His Gln Thr Val Leu Asp Asn Thr Glu
    530                 535                 540

Gly Lys Asn Pro Ala Glu Trp Ala Lys Asn Leu Lys Gln Glu Asp Phe
545                 550                 555                 560
```

Glu Leu Leu Cys Pro Asp Gly Thr Arg Lys Pro Val Lys Asp Phe Ala
              565                 570                 575

Ser Cys His Leu Ala Gln Ala Pro Asn His Val Val Ser Arg Lys
          580                 585                 590

Glu Lys Ala Ala Arg Val Lys Ala Val Leu Thr Ser Gln Glu Thr Leu
          595                 600                 605

Phe Gly Gly Ser Asp Cys Thr Gly Asn Phe Cys Leu Phe Lys Ser Thr
          610                 615                 620

Thr Lys Asp Leu Leu Phe Arg Asp Asp Thr Lys Cys Phe Val Lys Leu
625                 630                 635                 640

Pro Glu Gly Thr Thr Pro Glu Lys Tyr Leu Gly Ala Glu Tyr Met Gln
              645                 650                 655

Ser Val Gly Asn Met Arg Lys Cys Ser Thr Ser Arg Leu Leu Glu Ala
              660                 665                 670

Cys Thr Phe His Lys
              675

<210> SEQ ID NO 51
<211> LENGTH: 688
<212> TYPE: PRT
<213> ORGANISM: Equus caballus

<400> SEQUENCE: 51

Ala Glu Gln Thr Val Arg Trp Cys Thr Val Ser Asn His Glu Val Ser
1               5                   10                  15

Lys Cys Ala Ser Phe Arg Asp Ser Met Lys Ser Ile Val Pro Ala Pro
              20                  25                  30

Pro Leu Val Ala Cys Val Lys Arg Thr Ser Tyr Leu Glu Cys Ile Lys
          35                  40                  45

Ala Ile Ala Asp Asn Glu Ala Asp Ala Val Thr Leu Asp Ala Gly Leu
      50                  55                  60

Val Phe Glu Ala Gly Leu Ser Pro Tyr Asn Leu Lys Pro Val Val Ala
65                  70                  75                  80

Glu Phe Tyr Gly Ser Lys Thr Glu Pro Gln Thr His Tyr Tyr Ala Val
              85                  90                  95

Ala Val Val Lys Lys Asn Ser Asn Phe Gln Leu Asn Gln Leu Gln Gly
              100                 105                 110

Lys Lys Ser Cys His Thr Gly Leu Gly Arg Ser Ala Gly Trp Asn Ile
          115                 120                 125

Pro Ile Gly Leu Leu Tyr Trp Gln Leu Pro Glu Pro Arg Glu Ser Leu
      130                 135                 140

Gln Lys Ala Val Ser Asn Phe Phe Ala Gly Ser Cys Val Pro Cys Ala
145                 150                 155                 160

Asp Arg Thr Ala Val Pro Asn Leu Cys Gln Leu Cys Val Gly Lys Gly
              165                 170                 175

Thr Asp Lys Cys Ala Cys Ser Asn His Glu Pro Tyr Phe Gly Tyr Ser
          180                 185                 190

Gly Ala Phe Lys Cys Leu Ala Asp Gly Ala Gly Asp Val Ala Phe Val
      195                 200                 205

Lys His Ser Thr Val Leu Glu Asn Leu Pro Gln Glu Ala Asp Arg Asp
  210                 215                 220

Glu Tyr Gln Leu Leu Cys Arg Asp Asn Thr Arg Lys Ser Val Asp Glu
225                 230                 235                 240

Tyr Lys Asp Cys Tyr Leu Ala Ser Ile Pro Ser His Ala Val Val Ala
              245                 250                 255

```
Arg Ser Val Asp Gly Lys Glu Asp Leu Ile Trp Gly Leu Leu Asn Gln
            260                 265                 270

Ala Gln Glu His Phe Gly Thr Glu Lys Ser Lys Asp Phe His Leu Phe
        275                 280                 285

Ser Ser Pro His Gly Lys Asp Leu Leu Phe Lys Asp Ser Ala Leu Gly
290                 295                 300

Phe Leu Arg Ile Pro Pro Ala Met Asp Thr Trp Leu Tyr Leu Gly Tyr
305                 310                 315                 320

Glu Tyr Val Thr Ala Ile Arg Asn Leu Arg Glu Asp Ile Arg Pro Glu
                325                 330                 335

Val Pro Lys Asp Glu Cys Lys Lys Val Lys Trp Cys Ala Ile Gly His
            340                 345                 350

His Glu Lys Val Lys Cys Asp Glu Trp Ser Val Asn Ser Gly Gly Asn
        355                 360                 365

Ile Glu Cys Glu Ser Ala Gln Ser Thr Glu Asp Cys Ile Ala Lys Ile
    370                 375                 380

Val Lys Gly Glu Ala Asp Ala Met Ser Leu Asp Gly Gly Phe Ile Tyr
385                 390                 395                 400

Ile Ala Gly Lys Cys Gly Leu Val Pro Val Leu Ala Glu Asn Tyr Glu
                405                 410                 415

Thr Arg Ser Gly Ser Ala Cys Val Asp Thr Pro Glu Glu Gly Tyr His
            420                 425                 430

Ala Val Ala Val Val Lys Ser Ser Asp Pro Asp Leu Thr Trp Asn
        435                 440                 445

Ser Leu Lys Gly Lys Lys Ser Cys His Thr Gly Val Asp Arg Thr Ala
    450                 455                 460

Gly Trp Asn Ile Pro Met Gly Leu Leu Tyr Ser Glu Ile Lys His Cys
465                 470                 475                 480

Glu Phe Asp Lys Phe Phe Arg Glu Gly Cys Ala Pro Gly Tyr Arg Arg
                485                 490                 495

Asn Ser Thr Leu Cys Asn Leu Cys Ile Gly Ser Ala Ser Gly Pro Gly
            500                 505                 510

Arg Glu Cys Glu Pro Asn Asn His Glu Arg Tyr Tyr Gly Tyr Thr Gly
        515                 520                 525

Ala Phe Arg Cys Leu Val Glu Lys Gly Asp Val Ala Phe Val Lys His
    530                 535                 540

Gln Thr Val Glu Gln Asn Thr Asp Gly Arg Asn Pro Asp Asp Trp Ala
545                 550                 555                 560

Lys Asp Leu Lys Ser Glu Asn Phe Lys Leu Leu Cys Pro Asp Gly Thr
                565                 570                 575

Arg Lys Ser Val Thr Glu Phe Lys Ser Cys Tyr Leu Ala Arg Ala Pro
            580                 585                 590

Asn His Ala Val Val Ser Arg Lys Glu Lys Ala Ala Cys Val Cys Gln
        595                 600                 605

Glu Leu His Asn Gln Gln Ala Ser Tyr Gly Lys Asn Gly Ser His Cys
    610                 615                 620

Pro Asp Lys Phe Cys Leu Phe Gln Ser Ala Thr Lys Asp Leu Leu Phe
625                 630                 635                 640

Arg Asp Asp Thr Gln Cys Leu Ala Asn Leu Gln Pro Thr Thr Thr Tyr
                645                 650                 655

Lys Thr Tyr Leu Gly Glu Lys Tyr Leu Thr Ala Val Ala Asn Leu Arg
            660                 665                 670

Gln Cys Ser Thr Ser Arg Leu Leu Glu Ala Cys Thr Phe His Arg Val
```

```
                  675                 680                 685

<210> SEQ ID NO 52
<211> LENGTH: 685
<212> TYPE: PRT
<213> ORGANISM: Bos taurus

<400> SEQUENCE: 52

Asp Pro Glu Arg Thr Val Arg Trp Cys Thr Ile Ser Thr His Glu Ala
1               5                   10                  15

Asn Lys Cys Ala Ser Phe Arg Glu Asn Val Leu Arg Ile Leu Glu Ser
            20                  25                  30

Gly Pro Phe Val Ser Cys Val Lys Lys Thr Ser His Met Asp Cys Ile
        35                  40                  45

Lys Ala Ile Ser Asn Asn Glu Ala Asp Ala Val Thr Leu Asp Gly Gly
    50                  55                  60

Leu Val Tyr Glu Ala Gly Leu Lys Pro Asn Asn Leu Lys Pro Val Val
65                  70                  75                  80

Ala Glu Phe His Gly Thr Lys Asp Asn Pro Gln Thr His Tyr Tyr Ala
                85                  90                  95

Val Ala Val Val Lys Lys Asp Thr Asp Phe Lys Leu Asn Glu Leu Arg
            100                 105                 110

Gly Lys Lys Ser Cys His Thr Gly Leu Gly Arg Ser Ala Gly Trp Asn
        115                 120                 125

Ile Pro Met Ala Lys Leu Tyr Lys Glu Leu Pro Asp Pro Gln Glu Ser
    130                 135                 140

Ile Gln Arg Ala Ala Ala Asn Phe Phe Ser Ala Ser Cys Val Pro Cys
145                 150                 155                 160

Ala Asp Gln Ser Ser Phe Pro Lys Leu Cys Gln Leu Cys Ala Gly Lys
                165                 170                 175

Gly Thr Asp Lys Cys Ala Cys Ser Asn His Glu Pro Tyr Phe Gly Tyr
            180                 185                 190

Ser Gly Ala Phe Lys Cys Leu Met Glu Gly Ala Gly Asp Val Ala Phe
        195                 200                 205

Val Lys His Ser Thr Val Phe Asp Asn Leu Pro Asn Pro Glu Asp Arg
    210                 215                 220

Lys Asn Tyr Glu Leu Leu Cys Gly Asp Asn Thr Arg Lys Ser Val Asp
225                 230                 235                 240

Asp Tyr Gln Glu Cys Tyr Leu Ala Met Val Pro Ser His Ala Val Val
                245                 250                 255

Ala Arg Thr Val Gly Gly Lys Glu Asp Val Ile Trp Glu Leu Leu Asn
            260                 265                 270

His Ala Gln Glu His Phe Gly Lys Asp Lys Pro Asp Asn Phe Gln Leu
        275                 280                 285

Phe Gln Ser Pro His Gly Lys Asp Leu Leu Phe Lys Asp Ser Ala Asp
    290                 295                 300

Gly Phe Leu Lys Ile Pro Ser Lys Met Asp Phe Glu Leu Tyr Leu Gly
305                 310                 315                 320

Tyr Glu Tyr Val Thr Ala Leu Gln Asn Leu Arg Glu Ser Lys Pro Pro
                325                 330                 335

Asp Ser Ser Lys Asp Glu Cys Met Val Lys Trp Cys Ala Ile Gly His
            340                 345                 350

Gln Glu Arg Thr Lys Cys Asp Arg Trp Ser Gly Phe Ser Gly Gly Ala
        355                 360                 365

Ile Glu Cys Glu Thr Ala Glu Asn Thr Glu Glu Cys Ile Ala Lys Ile
```

```
                370             375             380
Met Lys Gly Glu Ala Asp Ala Met Ser Leu Asp Gly Gly Tyr Leu Tyr
385                 390                 395                 400

Ile Ala Gly Lys Cys Gly Leu Val Pro Val Leu Ala Glu Asn Tyr Lys
                405                 410                 415

Thr Glu Gly Glu Ser Cys Lys Asn Thr Pro Glu Lys Gly Tyr Leu Ala
                420                 425                 430

Val Ala Val Val Lys Thr Ser Asp Ala Asn Ile Asn Trp Asn Asn Leu
                435                 440                 445

Lys Asp Lys Lys Ser Cys His Thr Ala Val Asp Arg Thr Ala Gly Trp
450                 455                 460

Asn Ile Pro Met Gly Leu Leu Tyr Ser Lys Ile Asn Asn Cys Lys Phe
465                 470                 475                 480

Asp Glu Phe Phe Ser Ala Gly Cys Ala Pro Gly Ser Pro Arg Asn Ser
                485                 490                 495

Ser Leu Cys Ala Leu Cys Ile Gly Ser Glu Lys Gly Thr Gly Lys Glu
                500                 505                 510

Cys Val Pro Asn Ser Asn Glu Arg Tyr Tyr Gly Tyr Thr Gly Ala Phe
                515                 520                 525

Arg Cys Leu Val Glu Lys Gly Asp Val Ala Phe Val Lys Asp Gln Thr
                530                 535                 540

Val Ile Gln Asn Thr Asp Gly Asn Asn Asn Glu Ala Trp Ala Lys Asn
545                 550                 555                 560

Leu Lys Lys Glu Asn Phe Glu Val Leu Cys Lys Asp Gly Thr Arg Lys
                565                 570                 575

Pro Val Thr Asp Ala Glu Asn Cys His Leu Ala Arg Gly Pro Asn His
                580                 585                 590

Ala Val Val Ser Arg Lys Asp Lys Ala Thr Cys Val Glu Lys Ile Leu
                595                 600                 605

Asn Lys Gln Gln Asp Asp Phe Gly Lys Ser Val Thr Asp Cys Thr Ser
                610                 615                 620

Asn Phe Cys Leu Phe Gln Ser Asn Ser Lys Asp Leu Leu Phe Arg Asp
625                 630                 635                 640

Asp Thr Lys Cys Leu Ala Ser Ile Ala Lys Lys Thr Tyr Asp Ser Tyr
                645                 650                 655

Leu Gly Asp Asp Tyr Val Arg Ala Met Thr Asn Leu Arg Gln Cys Ser
                660                 665                 670

Thr Ser Lys Leu Leu Glu Ala Cys Thr Phe His Lys Pro
                675                 680                 685

<210> SEQ ID NO 53
<211> LENGTH: 696
<212> TYPE: PRT
<213> ORGANISM: Sus scrofa
<220> FEATURE:
<221> NAME/KEY: misc_feature
<222> LOCATION: (308)..(308)
<223> OTHER INFORMATION: Xaa can be any naturally occurring amino acid

<400> SEQUENCE: 53

Val Ala Gln Lys Thr Val Arg Trp Cys Thr Ile Ser Asn Gln Glu Ala
1               5                   10                  15

Asn Lys Cys Ser Ser Phe Arg Glu Asn Met Ser Lys Ala Val Lys Asn
                20                  25                  30

Gly Pro Leu Val Ser Cys Val Lys Ser Ser Tyr Leu Asp Cys Ile
                35                  40                  45
```

```
Lys Ala Ile Arg Asp Lys Glu Ala Asp Ala Val Thr Leu Asp Ala Gly
 50                  55                  60

Leu Val Phe Glu Ala Gly Leu Ala Pro Tyr Asn Leu Lys Pro Val Val
 65                  70                  75                  80

Ala Glu Phe Tyr Gly Gln Lys Asp Asn Pro Gln Thr His Tyr Tyr Ala
                     85                  90                  95

Val Ala Val Val Lys Lys Gly Ser Asn Phe Gln Trp Asn Gln Leu Gln
                100                 105                 110

Gly Lys Arg Ser Cys His Thr Gly Leu Gly Arg Ser Ala Gly Trp Ile
            115                 120                 125

Ile Pro Met Gly Leu Leu Tyr Asp Gln Leu Pro Glu Pro Arg Lys Pro
        130                 135                 140

Ile Glu Lys Ala Val Ala Ser Phe Phe Ser Ser Ser Cys Val Pro Cys
145                 150                 155                 160

Ala Asp Pro Val Asn Phe Pro Lys Leu Cys Gln Gln Cys Ala Gly Lys
                165                 170                 175

Gly Ala Glu Lys Cys Ala Cys Ser Asn His Glu Pro Tyr Phe Gly Tyr
            180                 185                 190

Ala Gly Ala Phe Asn Cys Leu Lys Glu Asp Ala Gly Asp Val Ala Phe
        195                 200                 205

Val Lys His Ser Thr Val Leu Glu Asn Leu Pro Asp Lys Ala Asp Arg
    210                 215                 220

Asp Gln Tyr Glu Leu Leu Cys Arg Asp Asn Thr Arg Arg Pro Val Asp
225                 230                 235                 240

Asp Tyr Glu Asn Cys Tyr Leu Ala Gln Val Pro Ser His Ala Val Val
                245                 250                 255

Ala Arg Ser Val Asp Gly Gln Glu Asp Ser Ile Trp Glu Leu Leu Asn
            260                 265                 270

Gln Ala Gln Glu His Phe Gly Arg Asp Lys Ser Pro Asp Phe Gln Leu
        275                 280                 285

Phe Ser Ser His Gly Lys Asp Leu Leu Phe Lys Asp Ser Ala Asn
    290                 295                 300

Gly Phe Leu Xaa Ile Pro Ser Lys Met Asp Ser Ser Leu Tyr Leu Gly
305                 310                 315                 320

Tyr Gln Tyr Val Thr Ala Leu Arg Asn Leu Arg Glu Glu Ile Ser Pro
                325                 330                 335

Asp Ser Ser Lys Asn Glu Cys Lys Lys Val Arg Trp Cys Ala Ile Gly
            340                 345                 350

His Glu Thr Gln Lys Cys Asp Ala Trp Ser Ile Asn Ser Gly Gly
        355                 360                 365

Lys Ile Glu Cys Val Ser Ala Glu Asn Thr Glu Asp Cys Ile Ala Lys
    370                 375                 380

Ile Val Lys Gly Glu Ala Asp Ala Met Ser Leu Asp Gly Gly Tyr Ile
385                 390                 395                 400

Tyr Ile Ala Gly Lys Cys Gly Leu Val Pro Val Leu Ala Glu Asn Tyr
                405                 410                 415

Lys Thr Glu Gly Glu Asn Cys Val Asn Thr Pro Glu Lys Gly Tyr Leu
            420                 425                 430

Ala Val Ala Val Val Lys Lys Ser Ser Gly Pro Asp Leu Asn Trp Asn
        435                 440                 445

Asn Leu Lys Gly Lys Lys Ser Cys His Thr Ala Val Asp Arg Thr Ala
    450                 455                 460

Gly Trp Asn Ile Pro Met Gly Leu Leu Tyr Asn Lys Ile Asn Ser Cys
465                 470                 475                 480
```

```
Lys Phe Asp Gln Phe Phe Gly Glu Gly Cys Ala Pro Gly Ser Gln Arg
                485                 490                 495

Asn Ser Ser Leu Cys Ala Leu Cys Ile Gly Ser Glu Arg Ala Pro Gly
            500                 505                 510

Arg Glu Cys Leu Ala Asn His Glu Arg Tyr Tyr Gly Tyr Thr Gly
        515                 520                 525

Ala Phe Arg Cys Leu Val Glu Lys Gly Asp Val Ala Phe Val Lys Asp
        530                 535                 540

Gln Val Val Gln Asn Thr Asp Gly Lys Asn Lys Asp Asp Trp Ala
545                 550                 555                 560

Lys Asp Leu Lys Gln Met Asp Phe Glu Leu Leu Cys Gln Asn Gly Ala
                565                 570                 575

Arg Glu Pro Val Asp Asn Ala Glu Asn Cys His Leu Ala Arg Ala Pro
            580                 585                 590

Asn His Ala Val Val Ala Arg Asp Asp Lys Val Thr Cys Val Ala Glu
        595                 600                 605

Glu Leu Leu Lys Gln Gln Ala Gln Phe Gly Arg His Val Thr Asp Cys
610                 615                 620

Ser Ser Ser Phe Cys Met Phe Lys Ser Asn Thr Lys Asp Leu Leu Phe
625                 630                 635                 640

Arg Asp Asp Thr Gln Cys Leu Ala Arg Val Gly Lys Thr Thr Tyr Glu
                645                 650                 655

Ser Tyr Leu Gly Ala Asp Tyr Ile Thr Ala Val Ala Asn Leu Arg Lys
            660                 665                 670

Cys Ser Thr Ser Lys Leu Leu Glu Ala Cys Thr Phe His Ser Ala Lys
        675                 680                 685

Asn Pro Arg Val Glu Thr Thr Thr
        690                 695

<210> SEQ ID NO 54
<211> LENGTH: 686
<212> TYPE: PRT
<213> ORGANISM: Gallus gallus

<400> SEQUENCE: 54

Ala Pro Pro Lys Ser Val Ile Arg Trp Cys Thr Ile Ser Ser Pro Glu
1               5                   10                  15

Glu Lys Lys Cys Asn Asn Leu Arg Asp Leu Thr Gln Gln Glu Arg Ile
            20                  25                  30

Ser Leu Thr Cys Val Gln Lys Ala Thr Tyr Leu Asp Cys Ile Lys Ala
        35                  40                  45

Ile Ala Asn Asn Glu Ala Asp Ala Ile Ser Leu Asp Gly Gly Gln Ala
    50                  55                  60

Phe Glu Ala Gly Leu Ala Pro Tyr Lys Leu Lys Pro Ile Ala Ala Glu
65                  70                  75                  80

Val Tyr Glu His Thr Glu Gly Ser Thr Thr Ser Tyr Tyr Ala Val Ala
                85                  90                  95

Val Val Lys Lys Gly Thr Glu Phe Thr Val Asn Asp Leu Gln Gly Lys
            100                 105                 110

Thr Ser Cys His Thr Gly Leu Gly Arg Ser Ala Gly Trp Asn Ile Pro
        115                 120                 125

Ile Gly Thr Leu Leu His Arg Gly Ala Ile Glu Trp Glu Gly Ile Glu
    130                 135                 140

Ser Gly Ser Val Glu Gln Ala Val Ala Lys Phe Ser Ala Ser Cys
145                 150                 155                 160
```

```
Val Pro Gly Ala Thr Ile Glu Gln Lys Leu Cys Arg Gln Cys Lys Gly
            165                 170                 175
Asp Pro Lys Thr Lys Cys Ala Arg Asn Ala Pro Tyr Ser Gly Tyr Ser
            180                 185                 190
Gly Ala Phe His Cys Leu Lys Asp Gly Lys Gly Asp Val Ala Phe Val
            195                 200                 205
Lys His Thr Thr Val Asn Glu Asn Ala Pro Asp Gln Lys Asp Glu Tyr
210                 215                 220
Glu Leu Leu Cys Leu Asp Gly Ser Arg Gln Pro Val Asp Asn Tyr Lys
225                 230                 235                 240
Thr Cys Asn Trp Ala Arg Val Ala Ala His Ala Val Val Ala Arg Asp
            245                 250                 255
Asp Asn Lys Val Glu Asp Ile Trp Ser Phe Leu Ser Lys Ala Gln Ser
            260                 265                 270
Asp Phe Gly Val Asp Thr Lys Ser Asp Phe His Leu Phe Gly Pro Pro
            275                 280                 285
Gly Lys Lys Asp Pro Val Leu Lys Asp Leu Leu Phe Lys Asp Ser Ala
            290                 295                 300
Ile Met Leu Lys Arg Val Pro Ser Leu Met Asp Ser Gln Leu Tyr Leu
305                 310                 315                 320
Gly Phe Glu Tyr Tyr Ser Ala Ile Gln Ser Met Arg Lys Asp Gln Leu
            325                 330                 335
Thr Pro Ser Pro Arg Glu Asn Arg Ile Gln Trp Cys Ala Val Gly Lys
            340                 345                 350
Asp Glu Lys Ser Lys Cys Asp Arg Trp Ser Val Val Ser Asn Gly Asp
            355                 360                 365
Val Glu Cys Thr Val Val Asp Glu Thr Lys Asp Cys Ile Ile Lys Ile
            370                 375                 380
Met Lys Gly Glu Ala Asp Ala Val Ala Leu Asp Gly Gly Leu Val Tyr
385                 390                 395                 400
Thr Ala Gly Val Cys Gly Leu Val Pro Val Met Ala Glu Arg Tyr Asp
            405                 410                 415
Asp Glu Ser Gln Cys Ser Lys Thr Asp Glu Arg Pro Ala Ser Tyr Phe
            420                 425                 430
Ala Val Ala Val Ala Arg Lys Asp Ser Asn Val Asn Trp Asn Asn Leu
            435                 440                 445
Lys Gly Lys Lys Ser Cys His Thr Ala Val Gly Arg Thr Ala Gly Trp
450                 455                 460
Val Ile Pro Met Gly Leu Ile His Asn Arg Thr Gly Thr Cys Asn Phe
465                 470                 475                 480
Asp Glu Tyr Phe Ser Glu Gly Cys Ala Pro Gly Ser Pro Pro Asn Ser
            485                 490                 495
Arg Leu Cys Gln Leu Cys Gln Gly Ser Gly Gly Ile Pro Pro Glu Lys
            500                 505                 510
Cys Val Ala Ser Ser His Glu Lys Tyr Phe Gly Tyr Thr Gly Ala Leu
            515                 520                 525
Arg Cys Leu Val Glu Lys Gly Asp Val Ala Phe Ile Gln His Ser Thr
            530                 535                 540
Val Glu Glu Asn Thr Gly Gly Lys Asn Lys Ala Asp Trp Ala Lys Asn
545                 550                 555                 560
Leu Gln Met Asp Asp Phe Glu Leu Leu Cys Thr Asp Gly Arg Arg Ala
            565                 570                 575
Asn Val Met Asp Tyr Arg Glu Cys Asn Leu Ala Glu Val Pro Thr His
```

```
                580                 585                 590
Ala Val Val Val Arg Pro Glu Lys Ala Asn Lys Ile Arg Asp Leu Leu
        595                 600                 605

Glu Arg Gln Glu Lys Arg Phe Gly Val Asn Gly Ser Glu Lys Ser Lys
        610                 615                 620

Phe Met Met Phe Glu Ser Gln Asn Lys Asp Leu Leu Phe Lys Asp Leu
625                 630                 635                 640

Thr Lys Cys Leu Phe Lys Val Arg Glu Gly Thr Thr Tyr Lys Glu Phe
                645                 650                 655

Leu Gly Asp Lys Phe Tyr Thr Val Ile Ser Ser Leu Lys Thr Cys Asn
                660                 665                 670

Pro Ser Asp Ile Leu Gln Met Cys Ser Phe Leu Glu Gly Lys
        675                 680                 685
```